United States Patent
Power et al.

(10) Patent No.: US 9,833,486 B2
(45) Date of Patent: Dec. 5, 2017

(54) COMPOSITIONS COMPRISING SELENIUM AND USE OF SAME FOR THE TREATMENT AND PREVENTION OF DISEASE OR CONDITIONS ASSOCIATED WITH MITOCHONDRIAL DYSFUNCTION

(71) Applicants: Ronan Power, Lexington, KY (US); Casey Egan, Lexington, KY (US); Alexander Yiannikouris, Lexington, KY (US); Zi-Jian Lan, Lexington, KY (US); Rijin Xiao, Lexington, KY (US); Lewis Collen Jackson, Lexington, KY (US); Stefan Kwiatkowski, Lexington, KY (US)

(72) Inventors: Ronan Power, Lexington, KY (US); Casey Egan, Lexington, KY (US); Alexandros Yiannikouris, Lexington, KY (US); Zi-Jian Lan, Lexington, KY (US); Rijin Xiao, Lexington, KY (US); Jackson Colleen Lewis, Lexington, KY (US); Stefan Kwiatkowski, Lexington, KY (US)

(73) Assignee: ALLTECH, INC., Nicholasville, KY (US)

( * ) Notice: Subject to any disclaimer, the term of this patent is extended or adjusted under 35 U.S.C. 154(b) by 0 days.

(21) Appl. No.: 14/776,307

(22) PCT Filed: Mar. 14, 2014

(86) PCT No.: PCT/US2014/029328
§ 371 (c)(1),
(2) Date: Sep. 14, 2015

(87) PCT Pub. No.: WO2014/144776
PCT Pub. Date: Sep. 18, 2014

(65) Prior Publication Data
US 2016/0113977 A1    Apr. 28, 2016

Related U.S. Application Data

(60) Provisional application No. 61/788,133, filed on Mar. 15, 2013.

(51) Int. Cl.
| | |
|---|---|
| *A61K 36/06* | (2006.01) |
| *A61K 31/7076* | (2006.01) |
| *A61K 31/198* | (2006.01) |
| *A61K 45/06* | (2006.01) |
| *A61K 33/04* | (2006.01) |

(52) U.S. Cl.
CPC ............ *A61K 36/06* (2013.01); *A61K 31/198* (2013.01); *A61K 31/7076* (2013.01); *A61K 33/04* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 2006/0078629 A1* | 4/2006 | Serfontein | A23L 33/165 424/702 |
| 2007/0026090 A1 | 2/2007 | Tirosh et al. | |
| 2010/0247679 A1 | 9/2010 | Power | |
| 2010/0269183 A1 | 10/2010 | Olson et al. | |
| 2014/0044828 A1 | 2/2014 | Mine et al. | |

FOREIGN PATENT DOCUMENTS

| | | |
|---|---|---|
| EP | 1774972 A1 | 4/2007 |
| WO | 2005013951 A2 | 2/2005 |
| WO | WO 2012/141316 A1 | 10/2012 |

OTHER PUBLICATIONS

Marshall et al., Methyl Selenocysteine: single-dose pharmacokinetics in men, Cancer Prevention Research (Phil.), Nov. 2011, 4(11): pp. 1938-1944.*
Solgar Vitamin and Herb, Se-methylselenocysteine 200 mcg, 2010, Available Online at: www.solgar.com/pub/solgarscience/20100831100412_semethylselenocysteine_consumerflyer.pdf.*
Wikipedia, Human body weight, Accessed Jul. 18, 2017, Available Online at: en.wikipedia.org/wiki/Human_body_.*
International Search Report and Written Opinion for corresponding International Application No. PCT/US2014/029328, dated Aug. 12, 2014.
Chang et al.: "A Field of Myocardial-Endocardial NFAT Signaling Underlies Heart Valve Morphogenesis", Cell, vol. 118, pp. 649-663, Sep. 3, 2004 (Sep. 30, 2004).
IWIG: "Investigation of the Catalytic Mechanism of the Reaction Catalyzed by *Escherichia coli* Cyclopropane Fatty Acid Synthase," Dissertation, pp. 1-267. 2006. [Retrieved on Jul. 17, 2014] Retrieved from internet: https://www.google.com/search?q=INVESTIGATION+OF+THE+CATALYTIC+MECHANISM+OF+THE+REACTION+CATALYZED+BY+ESCHERICHIA+COLI+CYCLOPROPANE+FATTY+ACID&ie=utf-8&oe=utf-8&aq=t&rls=org.mozilla:en-US:official&client=firefox-a&channel=np&source=hp.
Juhaszova et al: "Role of Glycogen Synthase Kinase-3β in Cardioprotection", Circulation Research, 104, No. 11, pp. 1240-1252, Jun. 5, 2009 (Jun. 5, 2009).

(Continued)

*Primary Examiner* — Karen Cochrane Carlson
*Assistant Examiner* — Jennifer M. H. Tichy
(74) *Attorney, Agent, or Firm* — Kilyk & Bowersox, P.L.L.C.; Valerie Calloway

(57) ABSTRACT

The present application relates to compositions comprising selenium (e.g., selenium enriched yeast) and methods of using the same to treat and inhibit obesity, diabetes and related conditions. In particular, the present application provides compositions comprising selenium enriched yeast (e.g., selenium enriched yeast comprising 2% or less inorganic selenium), and methods of using the same to enhance mitochondrial activity and function (e.g., in skeletal muscle and liver) in a subject (e.g., as a therapeutic and/or prophylactic treatment for diabetes, obesity and related conditions).

6 Claims, 63 Drawing Sheets

(56) References Cited

OTHER PUBLICATIONS

Padmaja et al.: "Protective Effect of Curcumin During selenium Induced Toxicity on Dehydrogenases in hepatic Tissue", Indian Journal of Physiology and Pharmacology, vol. 49, No. 1, pp. 111-114, 2005.
Pinto et al.: "Supranutritional selenium induces alterations in molecular targets related to energy metabolism in skeletal muscle and visceral adipose tissue of pigs," Journal of inorganic Biochemistry, vol. 114, pp. 47-54, Apr. 30, 2012 (Apr. 30, 2012).
SCHIPS: "FoxO3 induces reversible cardiac atrophy and autophagy in a transgenic mouse a model," Cardiovascular Research, vol. 91, pp. 587-597, 2011.
Snyder: "Genomic Analysis of the Influence of Selenium Sources in Broiler Chickens Challenged with an Enteric Avian Reovirus," Master's Thesis, North Carolina State University, pp. 1-243, 2009. [Retrieved on Jul. 17, 2014]. Retrieved from internet: http://repository.lib.ncsu.edu/ir/bitstream/1840.16/2336/1/etd.pdf.
Extended European Search Report in corresponding European application No. 14762675.8, dated Dec. 7, 2016, 11 pages.

\* cited by examiner

FIGURE 6
A
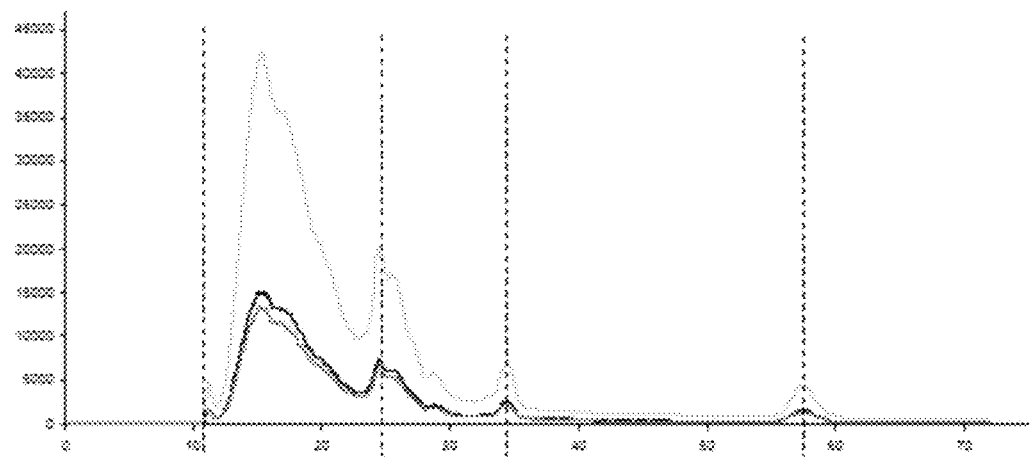
B
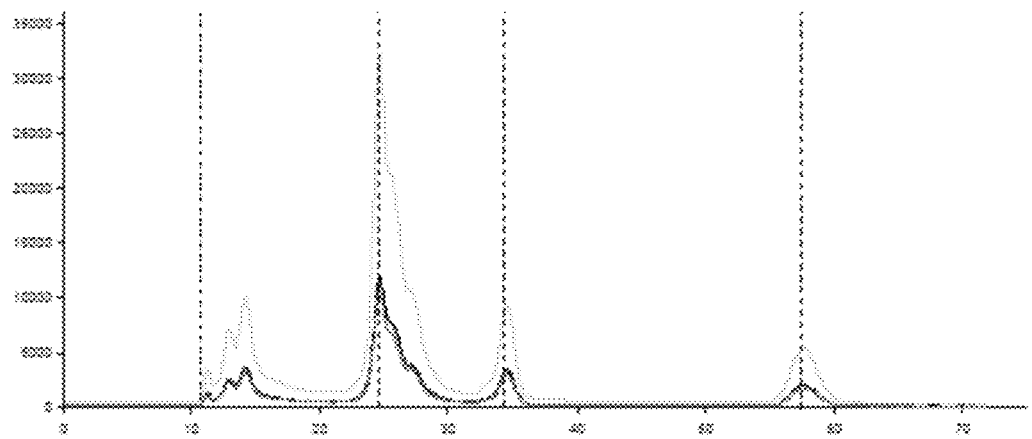

| Experimental mass | Theoretical mass | Formula | Name |
|---|---|---|---|
| 346.04025 | 346.04129 | $C_{11}H_{15}N_5O_3Se$ | Se-methyl-Se-adenosine |
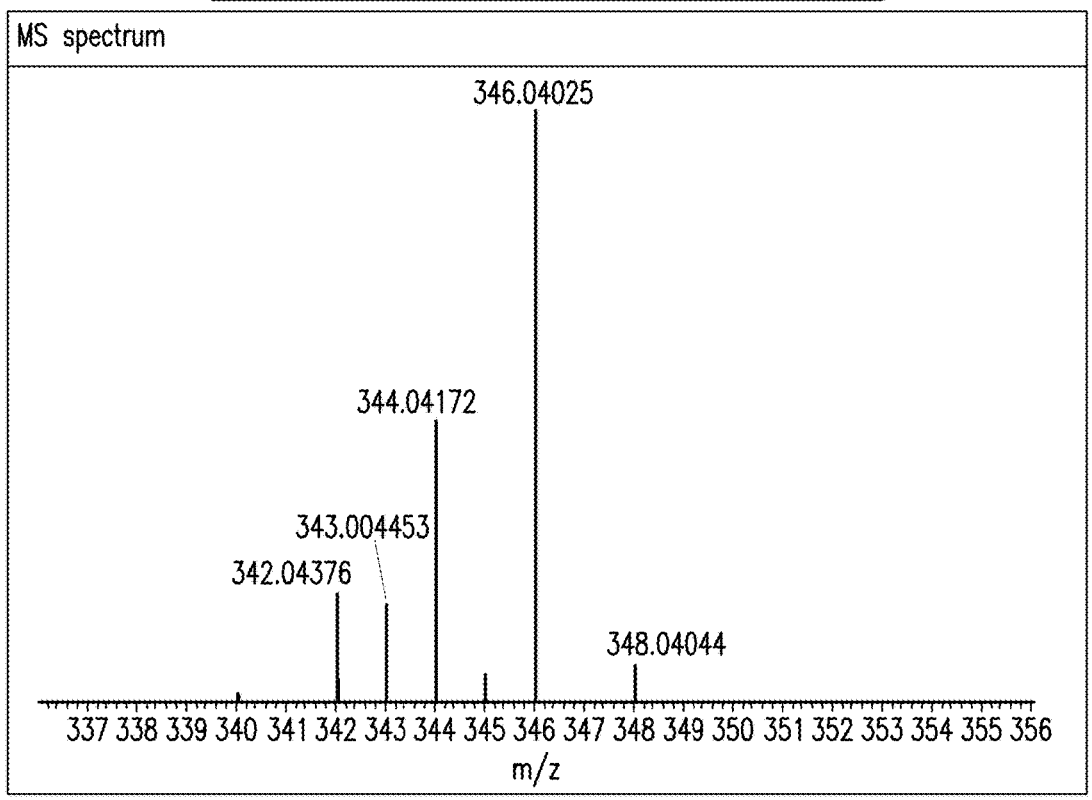
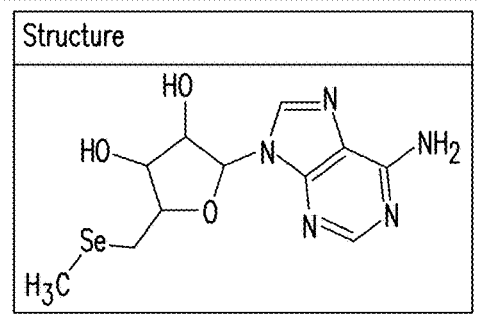
FIG. 9

FIGURE 12
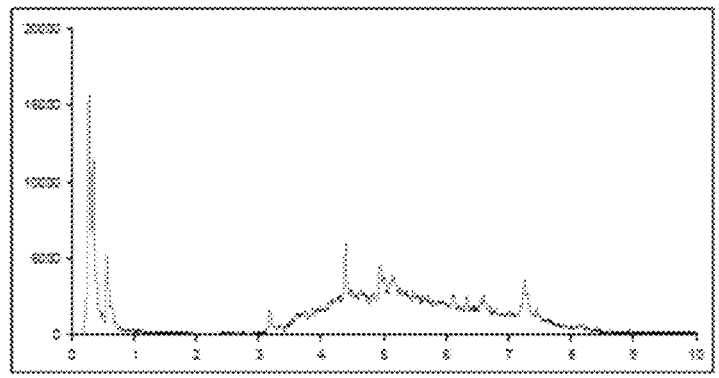
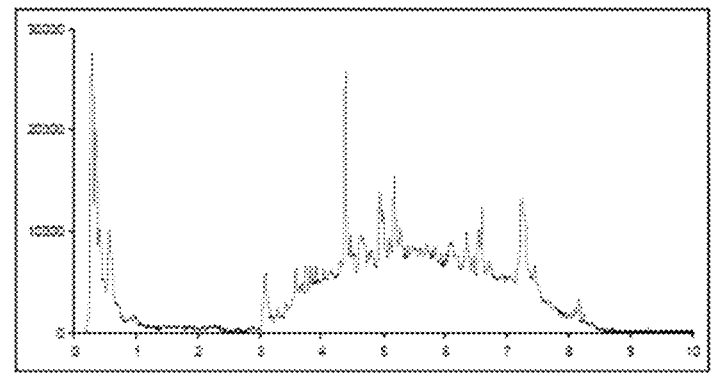
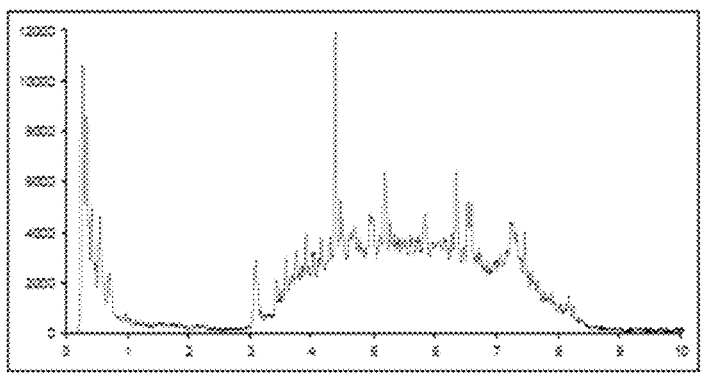

FIGURE 12 CONTINUED
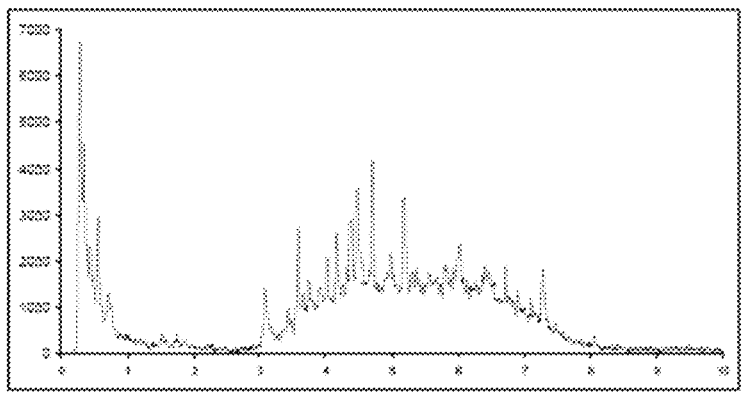
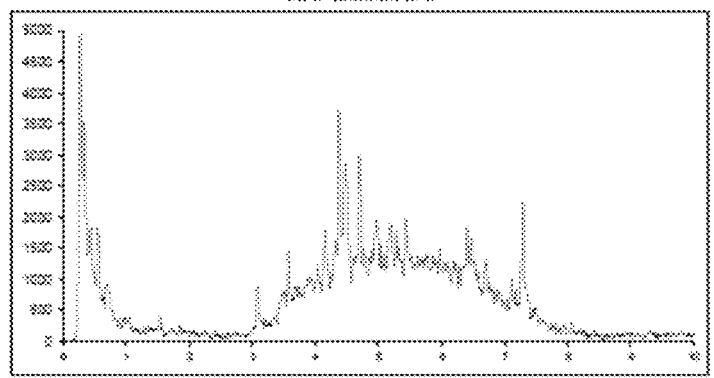
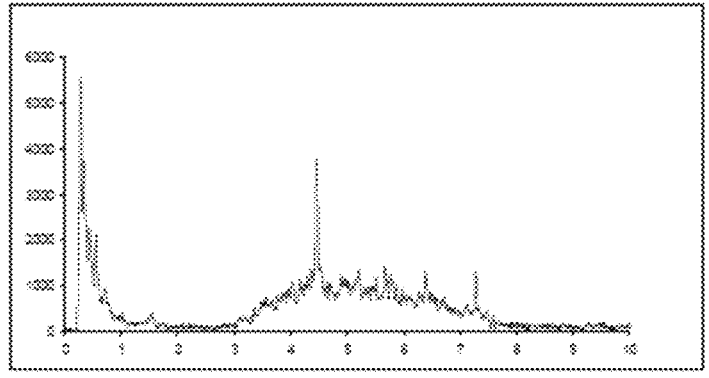
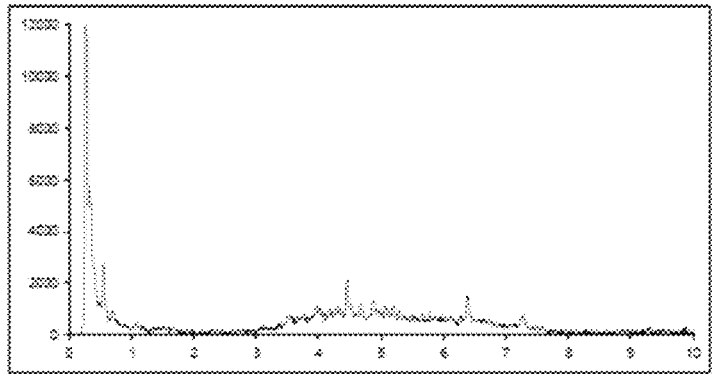

FIGURE 13

| | MW (theoretical) | MW (experimental) | Peptide sequence | z | Protein identification | Compound present in sub fraction |
|---|---|---|---|---|---|---|
| 1 | 825.32400 | 825.32615 | MVAEAEK | 1 | HSP70 (heat shock protein 70) | T2, T3, T5, T6 |
| 2 | 803.28210 | 803.28448 | DYMGAAK | 1 | HSP12 (heat shock protein 12) | T2, T3, T4, T5, T8 |
| 3 | 888.25525 | 888.25853 | YNGAAK | 1 | HSP12 | T5, T8 |
| 4 | 703.82559 | 703.82829 | ELQDIANPIMSK | 2 | HSP70 Ssa1p (Heat shock protein 70) | T2, T3 |
| 5 | 1655.6931 | 1655.6972 | NQAAMNPSNTVFDAK | 2 | HSP70 Ssa1p (Heat shock protein 70) | T6 |
| 6 | 799.8605 | 799.87097 | NFTPEQISSMVLGK | 2 | HSP SSA1 (heat shock protein SSA1) | T2, T3 |
| 7 | 1598.7332 | 1598.7338 | NFTPEQISSMVLGK | 2 | HSP SSA1 (heat shock protein SSA1) | T2, T3, T4 |
| 8 | 841.31890 | 841.32074 | MVSEAEK | 1 | HSP SSA2 (heat shock protein SSA2) | T2, T3 |
| 9 | 931.36090 | 931.36835 | PEVQGDMK | 1 | SSA1 or SSA2 | T2, T3 |
| 10 | 1406.8433 | 1406.8456 | ELQDIANPIMSK | | Ssa1p | T2, T3 |
| 11 | 599.29539 | 599.29422 | AMSSR | 1 | Ssb3p | T2 |
| 12 | 770.04864 | 770.04810 | NQGSVGIDLGTTNSAVAIMDG K | 3 | Ssc1p | T2 |
| 13 | 822.32430 | 822.32599 | AAAEGPMK | 1 | TDH1 (glyceraldehyde-3-phosphate dehydrogenase 1) | T2, T3, T4, T5 |
| 14 | 843.36100 | 843.36316 | LTGMAFR | 1 | TDH (Glyceraldehyde-3-phosphate dehydrogenase) | T2, T3, T4 |
| 15 | 1552.6590 | 1552.6589 | PFVSNDYAAYMVK | 2 | TDH1 (glyceraldehyde-3-phosphate dehydrogenase 1) | T6 |

FIGURE 13 CONTINUED

| 16 | 1091.51880 | 1091.52002 | APGHEEGLMTTVHSLTATQK | 2 | GPD3 (glyceraldehyde-3-phosphate dehydrogenase) | T5, T6 |
|---|---|---|---|---|---|---|
| 17 | 1828.6903 | 1828.6921 | PFITNDYAAYMFK | 2 | GPD3 (glyceraldehyde-3-phosphate dehydrogenase) | T6 |
| 18 | 1239.64200 | 1239.64514 | PGMVVTFAPAGVTTEVK | 2 | EF1α (translation elongation factor 1-alpha) | T2 |
| 19 | 2478.2761 | 2478.2824 | VETDVIKGNVTFAPAGVTTEVK | 2 | EF1α (translation elongation factor 1-alpha) | T2, T3 |
| 20 | 883.37710 | 883.37913 | AAATAAMTK | 1 | elongation factor 3A | T5 |
| 21 | 944.93743 | 944.93878 | SIVPSGASTGVHEALEMR | 2 | Eno1p (enolase 1) | T2, T3 |
| 22 | 569.1990 | 569.1987 | WMGK | 1 | Eno1p (enolase 1) | T3, T6 |
| 23 | 1888.8679 | 1888.8693 | SIVPSGASTGVHEALEMR | 3 | Eno1p (enolase 1) | T2, T3, T4, T6 |
| 24 | 622.24460 | 622.24628 | AMPQK | 1 | Yna1p | T2 |
| 25 | 539.20750 | 539.20911 | AAMAK | 1 | Yna1p | T2 |
| 26 | 582.29729 | 582.29691 | RVGDMEIR* | 2 | Nop5p* | T2 |
| 27 | 748.34379 | 748.34375 | VIEEPITSETAMK | 2 | 60S RP L23 (ribosomal protein) | T2 |
| 28 | 956.43449 | 956.43091 | VLQALEEKGIVEISPK+iodine | 2 | Rps19ap | T2 |
| 29 | 778.37185 | 778.37103 | LPAASLGDMVMATVK | 2 | Rpl13ap | T2 |
| 30 | 896.41077 | 896.40948 | AGMTTIVR | 1 | RPL3 (Ribosomal protein L3) | T5 |
| 31 | 896.4107 | 896.4087 | AGMTTIVR | 1 | RPL3 (Ribosomal protein L3) | T2, T4 |
| 32 | 667.27359 | 667.27321 | MLMFK | 1 | 40S ribosomal protein S18-A | T5 |
| 33 | 555.28437 | 555.28378 | TMGAK | 1 | Pnx1p | T2, T3, T4, T5, T6 |
| 34 | 596.29880 | 596.29404 | MNAGK | 1 | SIP18 | T2, T4, T6 |

| 35 | 833.29079 | 833.29449 | TYENMK | 1 | SIP18 | T5 |
|---|---|---|---|---|---|---|
| 36 | 564.68551 | 564.68597 | MGHDQSGTK | 2 | SIP18 | T5 |
| 37 | 864.37337 | 864.37231 | GEAMAFK | 1 | Hsd3p | T2, T3 |
| 38 | 785.36790 | 785.36802 | Ac-MNVFGK | 1 | Ctt1p | T5 |
| 39 | 1039.4326 | 1039.43223 | AMEVVASER | 1 | Lsn1p | T3 |
| 40 |  | 955.90926 |  | 2 | to be identified |  |
| 41 | 568.25480 | 568.25519 | IVMR | 1 | to be identified |  |
| 42 | 538.22350 | 538.22510 | MA(I,L)R | 1 | to be identified | T2, T3, T4 |
| 43 | 581.2564 | 581.2565 | AMKAK | 1 | Bsc1p | T3 |
| 44 | 1236.5378 | 1236.5374 | DLETLTMHTK | 2 | Rpl12p | T3 |

| Formula | Theoretical mass: [M+H]+ | Experimental mass: [M+H]+ | Structures | Isotopic pattern |
|---|---|---|---|---|
| $C_9H_{17}N_2O_7Se^+$ | 345.0196 | 345.0204 | 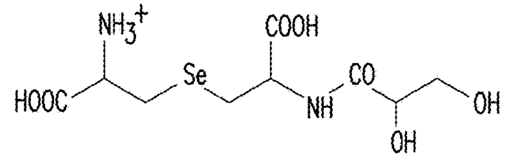 | |
| $C_{13}H_{23}N_4O_8SSe^+$ | 475.0396 | 475.0410 | 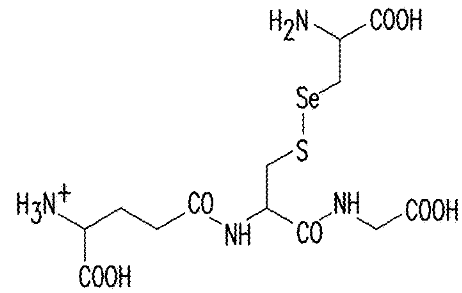 | |
| $C_{14}H_{24}N_3O_{10}Se_2^+$ | 553.9787 | 553.9802 | 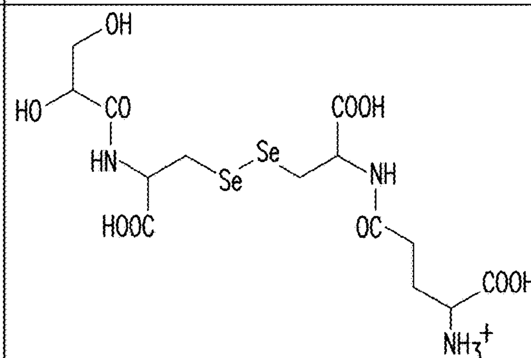 | |

FIG. 15

| Formula | Theoretical mass: [M+H]+ | Experimental mass: [M+H]+ | Structures | Isotopic pattern |
|---|---|---|---|---|
| $C_{10}H_{17}N_2O_7Se^+$ | 357.0196 | 357.0218 (359−2H+) | (structure with Se+, COOH, NH, CO, OH, NH2) | 353.0248, 354.0257, 355.0227, 356.0263, 357.0218, 358.0257, 359.0373 (352–360) |
| $C_{16}H_{27}N_4O_{10}SSe^+$ | 547.0608 | 547.0621 | (structure with S–Se, COOH, NH, CO, NH2, NH3+) | 543.9233, 545.0627, 547.0621, 547.9830 (542–550) |
| $C_{16}H_{27}N_4O_{11}Se_2^+$ | 611.0005 | 611.0023 | (structure with Se–Se, COOH, NH, CO, NH3+, OH) | |

FIG. 15 Continued

| Formula | Theoretical mass: [M+H]+ | Experimental mass: [M+H]+ | Structures | Isotopic pattern |
|---|---|---|---|---|
| $C_{18}H_{30}N_5O_{11}Se_2^+$ | 652.0271 | 652.0288 | 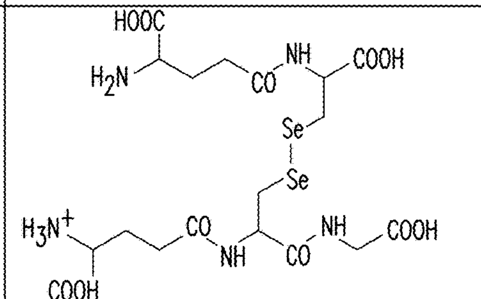 | |
| $C_{11}H_{20}N_2O_8SSe^+$ | 434.0131 | 434.0152 | | |
| $C_{20}H_{33}N_6O_{12}Se_2^+$ | 709.0486 | 709.0503 | 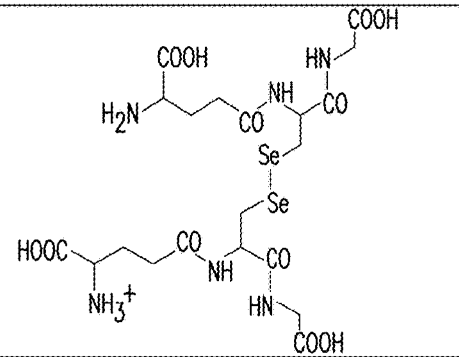 | |

FIG. 15 Continued

| Formula | Theoretical mass: [M+H]+ | Experimental mass: [M+H]+ | Structures | Isotopic pattern |
|---|---|---|---|---|
| $C_{17}H_{29}N_4O_{11}Se_2^+$ | 625.0162 | 625.1174 | 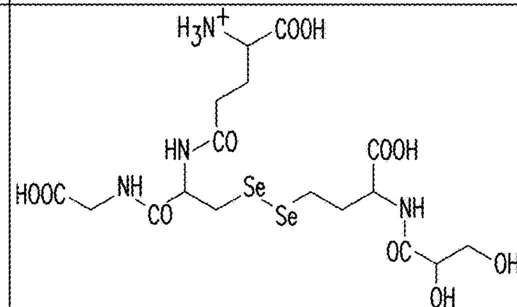 | |
| $C_{12}H_{21}N_2O_{10}Se_2^+$ | 512.9521 | 512.9537 | 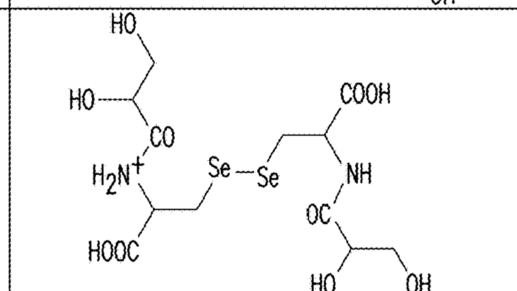 | |
| $C_{17}H_{29}N_4O_{11}SSe^+$ | 577.0714 | 577.0728 | 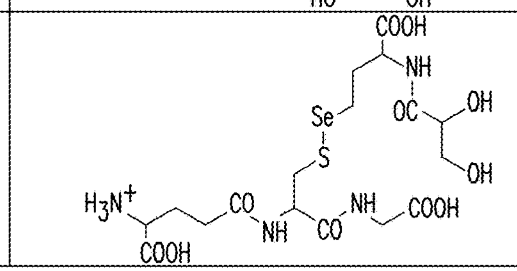 | |

|   | Sequence | Charge | Exp. mass | Theor. mass | Protein |
|---|---|---|---|---|---|
| 1 | LVMR | 1 | 566.25800 | 566.2568 | Glyceraldehyde-3-phosphate dehydrogenase 3; (GAPDH3) |
| 2 | VMR | 1 | 453.17352 | 453.1727 | |
| 3 | LTGMAFR | 2 | 422.18521 | 422.18545 | |
| 4 | SRPNVEVVALNDPFIT NDYAAYMFK | 3 | 974.79626 | 974.7912 | |
| 5 | VINDAFGIEEGLMTT VHSLTATQK | 3 | 875.09418 | 875.08923 | |

FIGURE 32
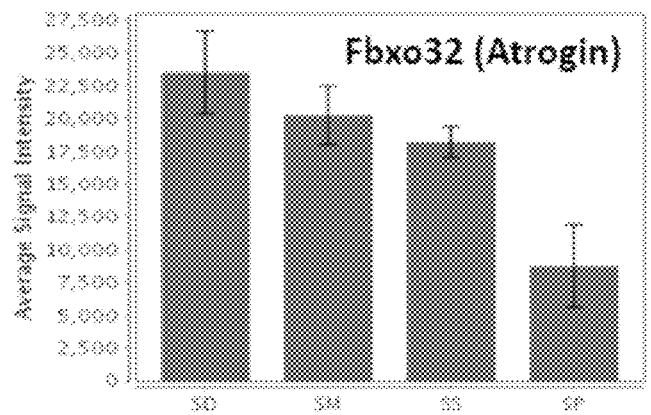
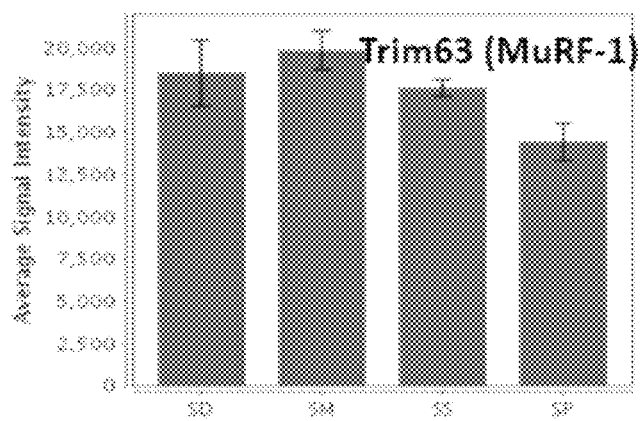
FIGURE 33
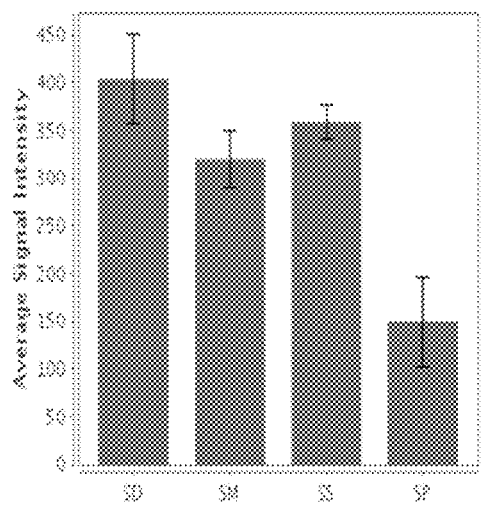

*p<0.05

*p<0.05

FIGURE 40
A
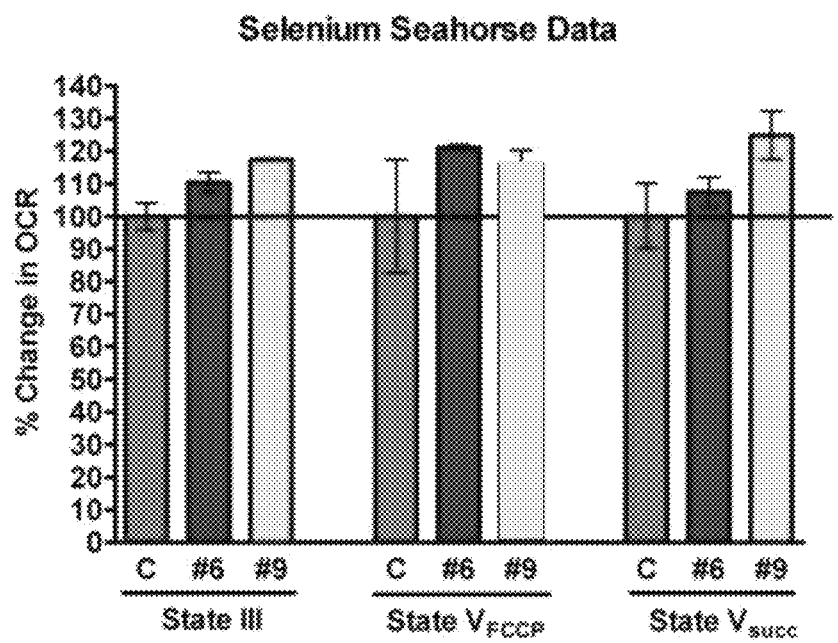
B
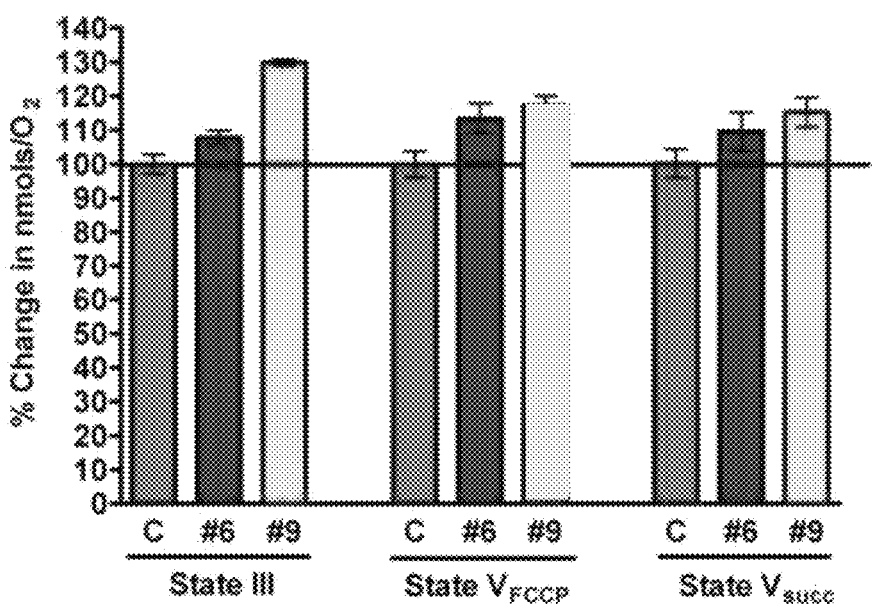

SEQUENCE LISTING

```
<160> NUMBER OF SEQ ID NOS: 46

<210> SEQ ID NO 1
<211> LENGTH: 7
<212> TYPE: PRT
<213> ORGANISM: Saccharomyces cerevisiae

<400> SEQUENCE: 1

Met Val Ala Glu Ala Glu Lys
1               5

<210> SEQ ID NO 2
<211> LENGTH: 7
<212> TYPE: PRT
<213> ORGANISM: Saccharomyces cerevisiae

<400> SEQUENCE: 2

Asp Tyr Met Gly Ala Ala Lys
1               5

<210> SEQ ID NO 3
<211> LENGTH: 6
<212> TYPE: PRT
<213> ORGANISM: Saccharomyces cerevisiae

<400> SEQUENCE: 3

Tyr Met Gly Ala Ala Lys
1               5

<210> SEQ ID NO 4
<211> LENGTH: 12
<212> TYPE: PRT
<213> ORGANISM: Saccharomyces cerevisiae

<400> SEQUENCE: 4

Glu Leu Gln Asp Ile Ala Asn Pro Ile Met Ser Lys
1               5                   10

<210> SEQ ID NO 5
<211> LENGTH: 15
<212> TYPE: PRT
<213> ORGANISM: Saccharomyces cerevisiae

<400> SEQUENCE: 5

Asn Gln Ala Ala Met Asn Pro Ser Asn Thr Val Phe Asp Ala Lys
1               5                   10                  15

<210> SEQ ID NO 6
<211> LENGTH: 14
<212> TYPE: PRT
<213> ORGANISM: Saccharomyces cerevisiae

<400> SEQUENCE: 6

Asn Phe Thr Pro Glu Gln Ile Ser Ser Met Val Leu Gly Lys
1               5                   10

<210> SEQ ID NO 7
<211> LENGTH: 7
<212> TYPE: PRT
```

-continued

<213> ORGANISM: Saccharomyces cerevisiae

<400> SEQUENCE: 7

Met Val Ser Glu Ala Glu Lys
1               5

<210> SEQ ID NO 8
<211> LENGTH: 8
<212> TYPE: PRT
<213> ORGANISM: Saccharomyces cerevisiae

<400> SEQUENCE: 8

Pro Glu Val Gln Gly Asp Met Lys
1               5

<210> SEQ ID NO 9
<211> LENGTH: 12
<212> TYPE: PRT
<213> ORGANISM: Saccharomyces cerevisiae

<400> SEQUENCE: 9

Glu Leu Gln Asp Ile Ala Asn Pro Ile Met Ser Lys
1               5                   10

<210> SEQ ID NO 10
<211> LENGTH: 5
<212> TYPE: PRT
<213> ORGANISM: Saccharomyces cerevisiae

<400> SEQUENCE: 10

Ala Met Ser Ser Arg
1               5

<210> SEQ ID NO 11
<211> LENGTH: 23
<212> TYPE: PRT
<213> ORGANISM: Saccharomyces cerevisiae

<400> SEQUENCE: 11

Val Gln Gly Ser Val Ile Gly Ile Asp Leu Gly Thr Thr Asn Ser Ala
1               5                   10                  15

Val Ala Ile Met Glu Gly Lys
            20

<210> SEQ ID NO 12
<211> LENGTH: 8
<212> TYPE: PRT
<213> ORGANISM: Saccharomyces cerevisiae

<400> SEQUENCE: 12

Ala Ala Ala Glu Gly Pro Met Lys
1               5

<210> SEQ ID NO 13
<211> LENGTH: 7
<212> TYPE: PRT
<213> ORGANISM: Saccharomyces cerevisiae

<400> SEQUENCE: 13

Leu Thr Gly Met Ala Phe Arg
1               5

<210> SEQ ID NO 14
<211> LENGTH: 13

```
<212> TYPE: PRT
<213> ORGANISM: Saccharomyces cerevisiae

<400> SEQUENCE: 14

Pro Phe Val Ser Asn Asp Tyr Ala Ala Tyr Met Val Lys
1               5                   10

<210> SEQ ID NO 15
<211> LENGTH: 20
<212> TYPE: PRT
<213> ORGANISM: Saccharomyces cerevisiae

<400> SEQUENCE: 15

Ala Phe Gly Ile Glu Glu Gly Leu Met Thr Thr Val His Ser Leu Thr
1               5                   10                  15

Ala Thr Gln Lys
            20

<210> SEQ ID NO 16
<211> LENGTH: 13
<212> TYPE: PRT
<213> ORGANISM: Saccharomyces cerevisiae

<400> SEQUENCE: 16

Pro Phe Ile Thr Asn Asp Tyr Ala Ala Tyr Met Phe Lys
1               5                   10

<210> SEQ ID NO 17
<211> LENGTH: 17
<212> TYPE: PRT
<213> ORGANISM: Saccharomyces cerevisiae

<400> SEQUENCE: 17

Pro Gly Met Val Val Thr Phe Ala Pro Ala Gly Val Thr Thr Glu Val
1               5                   10                  15

Lys

<210> SEQ ID NO 18
<211> LENGTH: 24
<212> TYPE: PRT
<213> ORGANISM: Saccharomyces cerevisiae

<400> SEQUENCE: 18

Val Glu Thr Gly Val Ile Lys Pro Gly Met Val Val Thr Phe Ala Pro
1               5                   10                  15

Ala Gly Val Thr Thr Glu Val Lys
            20

<210> SEQ ID NO 19
<211> LENGTH: 9
<212> TYPE: PRT
<213> ORGANISM: Saccharomyces cerevisiae

<400> SEQUENCE: 19

Ala Ala Ala Thr Ala Ala Met Thr Lys
1               5

<210> SEQ ID NO 20
<211> LENGTH: 18
<212> TYPE: PRT
<213> ORGANISM: Saccharomyces cerevisiae

<400> SEQUENCE: 20
```

```
Ser Ile Val Pro Ser Gly Ala Ser Thr Gly Val His Glu Ala Leu Glu
1               5                   10                  15

Met Arg

<210> SEQ ID NO 21
<211> LENGTH: 4
<212> TYPE: PRT
<213> ORGANISM: Saccharomyces cerevisiae

<400> SEQUENCE: 21

Trp Met Gly Lys
1

<210> SEQ ID NO 22
<211> LENGTH: 18
<212> TYPE: PRT
<213> ORGANISM: Saccharomyces cerevisiae

<400> SEQUENCE: 22

Ser Ile Val Pro Ser Gly Ala Ser Thr Gly Val His Glu Ala Leu Glu
1               5                   10                  15

Met Arg

<210> SEQ ID NO 23
<211> LENGTH: 5
<212> TYPE: PRT
<213> ORGANISM: Saccharomyces cerevisiae

<400> SEQUENCE: 23

Ala Met Pro Gln Lys
1               5

<210> SEQ ID NO 24
<211> LENGTH: 5
<212> TYPE: PRT
<213> ORGANISM: Saccharomyces cerevisiae

<400> SEQUENCE: 24

Ala Ala Met Ala Lys
1               5

<210> SEQ ID NO 25
<211> LENGTH: 8
<212> TYPE: PRT
<213> ORGANISM: Saccharomyces cerevisiae

<400> SEQUENCE: 25

His Val Gly Asp Met Glu Ile Arg
1               5

<210> SEQ ID NO 26
<211> LENGTH: 13
<212> TYPE: PRT
<213> ORGANISM: Saccharomyces cerevisiae

<400> SEQUENCE: 26

Val Ile Glu Glu Pro Ile Thr Ser Glu Thr Ala Met Lys
1               5                   10

<210> SEQ ID NO 27
<211> LENGTH: 16
<212> TYPE: PRT
<213> ORGANISM: Saccharomyces cerevisiae
```

```
<400> SEQUENCE: 27

Val Leu Gln Ala Leu Glu Glu Ile Gly Ile Val Glu Ile Ser Pro Lys
1               5                   10                  15

<210> SEQ ID NO 28
<211> LENGTH: 15
<212> TYPE: PRT
<213> ORGANISM: Saccharomyces cerevisiae

<400> SEQUENCE: 28

Leu Pro Ala Ala Ser Leu Gly Asp Met Val Met Ala Thr Val Lys
1               5                   10                  15

<210> SEQ ID NO 29
<211> LENGTH: 8
<212> TYPE: PRT
<213> ORGANISM: Saccharomyces cerevisiae

<400> SEQUENCE: 29

Ala Gly Met Thr Thr Ile Val Arg
1               5

<210> SEQ ID NO 30
<211> LENGTH: 5
<212> TYPE: PRT
<213> ORGANISM: Saccharomyces cerevisiae

<400> SEQUENCE: 30

Met Leu Met Pro Lys
1               5

<210> SEQ ID NO 31
<211> LENGTH: 5
<212> TYPE: PRT
<213> ORGANISM: Saccharomyces cerevisiae

<400> SEQUENCE: 31

Thr Met Gly Ala Lys
1               5

<210> SEQ ID NO 32
<211> LENGTH: 5
<212> TYPE: PRT
<213> ORGANISM: Saccharomyces cerevisiae

<400> SEQUENCE: 32

Met Asn Ala Gly Arg
1               5

<210> SEQ ID NO 33
<211> LENGTH: 6
<212> TYPE: PRT
<213> ORGANISM: Saccharomyces cerevisiae

<400> SEQUENCE: 33

Thr Tyr Glu Asn Met Lys
1               5

<210> SEQ ID NO 34
<211> LENGTH: 9
<212> TYPE: PRT
<213> ORGANISM: Saccharomyces cerevisiae

<400> SEQUENCE: 34
```

```
Met Gly His Asp Gln Ser Gly Thr Lys
1               5

<210> SEQ ID NO 35
<211> LENGTH: 8
<212> TYPE: PRT
<213> ORGANISM: Saccharomyces cerevisiae

<400> SEQUENCE: 35

Gly Glu Ala Ile Met Ala Pro Lys
1               5

<210> SEQ ID NO 36
<211> LENGTH: 6
<212> TYPE: PRT
<213> ORGANISM: Saccharomyces cerevisiae

<400> SEQUENCE: 36

Met Asn Val Phe Gly Lys
1               5

<210> SEQ ID NO 37
<211> LENGTH: 9
<212> TYPE: PRT
<213> ORGANISM: Saccharomyces cerevisiae

<400> SEQUENCE: 37

Ala Met Glu Val Val Ala Ser Glu Arg
1               5

<210> SEQ ID NO 38
<211> LENGTH: 4
<212> TYPE: PRT
<213> ORGANISM: Saccharomyces cerevisiae

<400> SEQUENCE: 38

Ile Val Met Arg
1

<210> SEQ ID NO 39
<211> LENGTH: 4
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (3)..(3)
<223> OTHER INFORMATION: X=I or L

<400> SEQUENCE: 39

Met Ala Xaa Arg
1

<210> SEQ ID NO 40
<211> LENGTH: 5
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (3)..(3)
<223> OTHER INFORMATION: X should be any amino acid

<400> SEQUENCE: 40

Ala Met Xaa Ala Lys
```

-continued

```
<210> SEQ ID NO 41
<211> LENGTH: 10
<212> TYPE: PRT
<213> ORGANISM: Saccharomyces cerevisiae

<400> SEQUENCE: 41

Asp Leu Glu Thr Leu Thr Met His Thr Lys
1               5                   10

<210> SEQ ID NO 42
<211> LENGTH: 4
<212> TYPE: PRT
<213> ORGANISM: Saccharomyces cerevisiae

<400> SEQUENCE: 42

Leu Val Met Arg
1

<210> SEQ ID NO 43
<211> LENGTH: 7
<212> TYPE: PRT
<213> ORGANISM: Saccharomyces cerevisiae

<400> SEQUENCE: 43

Leu Thr Gly Met Ala Phe Arg
1               5

<210> SEQ ID NO 44
<211> LENGTH: 25
<212> TYPE: PRT
<213> ORGANISM: Saccharomyces cerevisiae

<400> SEQUENCE: 44

Ser Arg Pro Asn Val Glu Val Val Ala Leu Asn Asp Pro Phe Ile Thr
1               5                   10                  15

Asn Asp Tyr Ala Ala Tyr Met Phe Lys
            20                  25

<210> SEQ ID NO 45
<211> LENGTH: 24
<212> TYPE: PRT
<213> ORGANISM: Saccharomyces cerevisiae

<400> SEQUENCE: 45

Val Ile Asn Asp Ala Phe Gly Ile Glu Glu Gly Leu Met Thr Thr Val
1               5                   10                  15

His Ser Leu Thr Ala Thr Gln Lys
            20

<210> SEQ ID NO 46
<211> LENGTH: 4
<212> TYPE: PRT
<213> ORGANISM: Saccharomyces cerevisiae

<400> SEQUENCE: 46

Met Arg Phe Ala
1
```

COMPOSITIONS COMPRISING SELENIUM AND USE OF SAME FOR THE TREATMENT AND PREVENTION OF DISEASE OR CONDITIONS ASSOCIATED WITH MITOCHONDRIAL DYSFUNCTION

CROSS-REFERENCE TO RELATED APPLICATION(S)

This application is a National Stage Application of International Application No. PCT/US2014/029328, filed Mar. 14, 2014, which claims priority to U.S. Patent Application Ser. No. 61/788,133 filed on March 2013, the disclosures of which are incorporated herein by reference in their entirety.

FIELD OF THE PRESENT APPLICATION

The present application relates to compositions comprising selenium (e.g., selenium enriched yeast and selenium containing compounds) and methods of using the same to treat mitochondrial dysfunction. In particular, the present application provides compositions comprising selenium enriched yeast (e.g., selenium enriched yeast comprising 2% or less inorganic selenium), selenium containing compounds present therein and/or derived therefrom, and methods of using the same to treat diseases and conditions associated with mitochondrial malfunction.

BACKGROUND OF THE PRESENT APPLICATION

The organelle known as the mitochondrion is the main energy source in cells of higher organisms. Mitochondria provide direct and indirect biochemical regulation of a wide array of cellular respiratory, oxidative and metabolic processes. These include electron transport chain (ETC) activity, which drives oxidative phosphorylation to produce metabolic energy in the form of adenosine triphosphate (ATP), and which also underlies a central mitochondrial role in intracellular calcium homeostasis.

Mitochondrial respiration occurs on the inner mitochondrial membrane and is achieved by the flow of electrons through the electron transport system, which contains four complexes (complex I, II, III, and IV) with a further complex (complex V) serving as a site for ATP synthesis (ATP synthase). Impairment or reduction of activity of any complex disrupts electron flow and may cause mitochondrial respiratory dysfunction (See, e.g., Schildgen et al., *Exp Hematol* 2011; 39:666-67510, 11; Arthur et al., Mol Neurodegener 2009; 4:37). Analysis of mitochondrial metabolic dysfunction may be monitored by oxygen electrode analysis (See, e.g., Chance and Williams, J Biol Chem 1955; 217: 383-393). Analysis has permitted an intimate understanding of mitochondrial respiratory function. The association between mitochondrial respiratory malfunction (e.g., leading to cell death, reactive oxygen species production, increased oxidative DNA damage, increased autophagy, loss of mitochondrial membrane potential (e.g., via aberrant Complex I expression and/or activity) and associated decreased ATP production) and a multitude of diseases and conditions (e.g., diabetes, obesity, aging related neurodegeneration including Alzheimer's disease, stroke, insulin resistance, atherosclerosis, etc.) has been extensively documented (See, e.g., Miguel et al., Exp Gerontol 1980; 15:575-591; McLean et al., Pharmacol Rev 2004; 56:163-184; Kujoth et al., Science 2005; 309:481-484; Guarente, Cell 2008; 132:171-176; Lopez-Lluch et al., Exp Gerontol 2008; 43:813-819; Shigenaga et al., Proc Natl Acad Sci USA 1994; 91:10771-10778; Schaefer et al., Biochim Biophys Acta 2004; 1659:115-120).

SUMMARY OF THE PRESENT APPLICATION

The present application relates to compositions comprising selenium (e.g., selenium enriched yeast and selenium containing compounds obtained or derived therefrom) and methods of using the same to treat mitochondrial dysfunction. In particular, the present application provides compositions comprising selenium enriched yeast (e.g., selenium enriched yeast comprising 2% or less inorganic selenium), selenium containing compounds present therein and/or derived therefrom, and methods of using the same to treat diseases and conditions associated with mitochondrial malfunction.

Accordingly, in some embodiments, the present application provides a composition comprising an isolated selenium containing compound, wherein the selenium containing compound is selected from 2,3-DHP-selenocysteine-cysteine, N-acetylselenocysteine-selenohomocysteine, methylthioselenoglutathione, 2,3-DHP-selenocysteine-selenocysteine, 2,3-DHP-selenocysteine-cysteinylglycine, 2,3-DHP-selenocysteine-selenohomocysteine, 2,3-DHP-selenocysteine-selenohomocysteine, 2,3-DHP-selenohomocysteine-cysteinylglycine, selenomethylselenoglutathione, selenoglutathione-cysteine, glutathione-selenohomocysteine, 2,3-DHP-selenocysteine-γ-glutamoylcysteine, di-2,3-DHP-selenocysteine, N-acetylcysteine-selenoglutathione, Selenoglutathione-selenocysteine, 2,3-DHP-selenocysteine-2,3 DHP selenohomocysteine, glutathione-N-acetylselenohomocysteine, glutathione-selenocysteinylglycine, γ-glutamoyl selenocysteine-γ-glutamoyl cysteine, γ-glutamoylcysteine-2,3-DHP-selenocysteine, glutathione-2,3-DHP-selenocysteine, glutathione-2,3-DHP-selenohomocysteine, di-γ-glutamoylselenocysteine, selenoglutathione-γ-glutamoylcysteine, selenoglutathione-2,3-DHP-selenocysteine, selenoglutathione-2,3-DHP-selenohomocysteine, selenoglutathionthio-2,3-DHP-selenocysteine, selenoglutathione-γ-glutamoylselenocysteine, selenoglutathione-glutathione, selenodiglutathione, diselenoglutathione, thio-diselenoglutathione, methyl dehydrohomocysteine, selenomethionine, selenohomolanthionine, N-acetylselenocystathionine, dehydroxy 5'-methylselenoadenosine, N-acetylcysteine-selenohomocysteine, 2,3-DHP-selenolanthionine, ethylselenoadenosine, N-propionylselenocystathionine, 2,3-DHP-selenocystathionine, methylselenoglutathione, γ-glutamoylselenocystathione, and selenoglutathione.

In some embodiments of the present application, a selenium containing compound includes, but is not limited to, seleno(hydroxyl)-selenophene-(3'-deoxy-adenosine), N-acetylcysteine-selenohomocysteine, allylselenoadenosyl homocysteine, seleno-adenosyl homocysteine, seleno-hydroxy adenosyl homocysteine, selno adenosine, seleno-adenosyl-Se(methyl)-selenoxide, adenosyl-hydroxy selenoxide, ethyl selenoadenosine, seleno-(hydroxy)-selenophene-(3'-desoxy-adenosine), adenosyl-hydroxy selnoxide, selno-adenosyl-Se(methyl)-selenoxide and combinations thereof.

In embodiments, a composition comprises a compound selected from the group consisting methyl seleno adenosine, seleno(hydroxyl)-selenophene-(3'-deoxy-adenosine), N-acetylcysteine-selenohomocysteine, allylselenoadenosyl homocysteine, seleno-adenosyl homocysteine, seleno-hydroxy adenosyl homocysteine, selno adenosine, seleno-adenosyl-Se(methyl)-selenoxide, adenosyl-hydroxy selenoxide, ethyl selenoadenosine, seleno-(hydroxy)-selenophene-(3'-desoxy-adenosine), adenosyl-hydroxy selnoxide, selnoadenosyl-Se(methyl)-selenoxide and combinations thereof. In a specific embodiment, a composition comprises the compound methylselenoadenosine. In embodiments, one or more compounds are isolated and/or purified. In embodiments, compositions are useful for increasing mitochondrial function in a cell or increasing the activity of pyruvate dehydrogenase complex.

In some embodiments of the present application, a selenium containing compound comprises a selenium containing peptide. Examples of compounds comprising a selenium peptide include, but are not limited to, MVAEAEK, DYMGAAK, YMGAAK, ELQDIANPIMSK, NQAAMNPSNTVFDAK, NFTPEQISSMVLGK, NFTPEQISSMVLGK, MVSEAEK, PEVQGDMK, ELQDIANPIMSK, AMSSR, VQGSVIGIDLGTTNSAVAIMEGK, AAAEGPMK, LTGMAFR, PFVSNDYAAYMVK, AFGIEEGLMTTVHSLTATQK, PFITNDYAAYMFK, PGMVVTFAPAGVTTEVK, VETGVIKPGMVVTFAPAGVTTEVK, AAATAAMTK, SIVPSGASTGVHEALEMR, WMGK, SIVPSGASTGVHEALEMR, AMPQK, AAMAK, HVGDMEIR, VIEEPITSETAMK, VLQALEEIGVEISPK, LPAASLGDMVMATVK, AGMTTIVR, AGMTTIVR, MLMPK, TMGAK, MNAGR, TYENMK, MGHDQSGTK, GEAIMAPK, Ac-MNVFGK, AMEVVASER, IVMR, MA(I/L)R, AMXAK, DLETLTMHTK, LVMR, VMR, LTGMAFR, SRPNVEVVALNDPFITNDYAAYMFK, and VINDAFGIEEGLMTTVHSLTATQK, wherein each peptide fragment contains a selenium molecule, and use of the same in the manufacture of a medicament for the treatment or prevention of a disease or condition associated with mitochondrial dysfunction.

The present application also provides a method for increasing mitochondrial activity in a subject comprising administering an effective amount of a composition comprising selenium (e.g., described herein) to the subject. In some embodiments, increasing mitochondrial activity comprises increasing mitochondrial ATP production. In some embodiments, increasing mitochondrial activity comprises increasing mitochondrial metabolism. In some embodiments, increasing mitochondrial activity results in a decrease in reactive oxygen species production in the subject (e.g., in the skeletal muscle, liver, cortex or ovarian tissue of the subject). In some embodiments, increasing mitochondrial activity results in enhanced glucose metabolism in the subject (e.g., in the skeletal muscle and/or liver tissue of the subject). In some embodiments, increased mitochondrial activity comprises increased mitochondrial Complex I activity. In some embodiments, increased mitochondrial function occurs in mitochondria present in skeletal muscle of the subject. In some embodiments, increased mitochondrial function occurs in mitochondria present in the liver of the subject.

In some embodiments, the composition comprising selenium is selected from selenium enriched yeast comprising 2% or less inorganic selenium, a selenoether, a conjugate of SeCys containing di- and/or tri-peptides, a selonol, and a selenoxide. In some embodiments, a selenium containing component is obtained or derived from selenium enriched yeast comprising 2% or less inorganic selenium. In embodiments, a selenium containing component is selected from the group consisting of a SeCys or SeMet peptide, a selenium containing adenosyl molecule, and combinations thereof. In a specific embodiment, the selenium containing compound is methylselenoadenosine or leucine-valine-selenomethionine-arginine.

In embodiments, a method of increasing mitochondrial function in a cell comprises administering an effective amount of a composition comprising isolated 5' methylselenoadenosine, LVSe-MR or combinations thereof, wherein the effective amount increases mitochondrial function in a cell as compared to a cell not exposed to the composition.

In other embodiments, a method of increasing pyruvate dehydrogenase complex in a cell comprises administering an effective amount of a composition comprising 5' methylselenoadenosine, wherein the effective amount increases the activity of pyruvate dehydrogenase complex in a cell as compared to a cell not exposed to the composition.

In some embodiments, the subject has or is at risk for a disease or condition associated with mitochondrial dysfunction. The present application is not limited by the type of disease or condition associated with mitochondrial dysfunction. Indeed, compositions and methods of the present application find use for a variety of diseases and conditions (e.g., those disclosed herein). In some embodiments, the subject has cardiomyopathy. In some embodiments, the subject has sarcopenia. In some embodiments, the subject has a loss of muscle protein.

The present application further provides a method for increasing glucose metabolism in a subject comprising administering to a subject in need thereof an effective amount of a composition comprising selenium (e.g., described herein) wherein the administering results in increased mitochondrial activity in the subject. In some embodiments, the enhanced glucose metabolism takes place in the skeletal muscle of the subject. In some embodiments, the enhanced glucose metabolism takes place in the liver.

The present application provides a method for treating a subject having a disease or condition associated with altered mitochondrial function comprising administering to the subject a therapeutically effective amount of a composition comprising selenium (e.g., as described herein) wherein the administering results in increased mitochondrial activity in the subject thereby treating the subject for the disease or condition.

The present application is not limited by the composition comprising selenium administered. In some embodiments, the composition comprising selenium comprises selenium enriched yeast comprising 2% or less inorganic selenium. In some embodiments, the present application provides the use and administration of selenium containing fractions prepared from selenium enriched yeast (e.g., selenium enriched yeast comprising 2% or less inorganic selenium). For example, in some embodiments, the composition comprising selenium comprises a water soluble fraction of selenium enriched yeast comprising 2% or less inorganic selenium. In other embodiments, the composition comprising selenium comprises a water insoluble fraction of selenium enriched yeast comprising 2% or less inorganic selenium. In some embodiments, a composition comprising selenium administered to a subject comprises a single, liquid phase comprising the extract of selenium enriched yeast (e.g., soluble under acidic conditions (e.g., a fraction of soluble selenium containing compounds (e.g., soluble selenoglycoproteins) extracted and/or precipitated at a first pH (e.g., pH of 1.85), a second fraction precipitated at a second pH (e.g., pH of 3.0), a third fraction precipitated at a third pH (e.g., pH of 4.0), and a fourth fraction precipitated at a fourth pH (e.g., pH of 6.0))).

In some embodiments, the present application provides the use and administration of selenium containing compounds (e.g., obtained or derived from selenium enriched yeast (e.g., selenium enriched yeast comprising 2% or less inorganic selenium) or derivatives thereof. The present application is not limited by the one or more selenium containing compounds utilized. In some embodiments, the one or more selenium containing compounds are selenoethers, conjugates of SeCys containing di- and/or tri-peptides, selonols or selenoxides (or derivatives thereof), selenium containing proteins and/or selenium containing peptides described herein.

For example, in some embodiments, a composition comprising selenium containing component that is administered to a subject (e.g., in a method of the present application) comprises one or more of the following: 2,3-DHP-selenocysteine-cysteine, N-acetylselenocysteine-selenohomocysteine, methylthioselenoglutathione, 2,3-DHP-selenocysteine-selenocysteine, 2,3-DHP-selenocysteine-cysteinylglycine, 2,3-DHP-selenocysteine-selenohomocysteine, 2,3-DHP-selenocysteine-selenohomocysteine, 2,3-DHP-selenohomocysteine-cysteinylglycine, selenomethyl-selenoglutathione, selenoglutathione-cysteine, glutathione-selenohomocysteine, 2,3-DHP-selenocysteine-γ-glutamoylcysteine, di-2,3-DHP-selenocysteine, N-acetylcysteine-selenoglutathione, Selenoglutathione-selenocysteine, 2,3-DHP-selenocysteine-2,3 DHP selenohomocysteine, glutathione-N-acetylselenohomocysteine, glutathione-selenocysteinylglycine, γ-glutamoyl selenocysteine-γ-glutamoyl cysteine, γ-glutamoylcysteine-2,3-DHP-selenocysteine, glutathione-2,3-DHP-selenocysteine, glutathione-2,3-DHP-selenohomocysteine, di-γ-glutamoylselenocysteine, selenoglutathione-γ-glutamoylcysteine, selenoglutathione-2,3-DHP-selenocysteine, selenoglutathione-2,3-DHP-selenohomocysteine, selenoglutathion-thio-2,3-DHP-selenocysteine, selenoglutathione-γ-glutamoylselenocysteine, selenoglutathione-glutathione, selenodiglutathione, diselenoglutathione, thio-diselenoglutathione, methyl dehydrohomocysteine, selenomethionine, selenohomolanthionine, N-acetylselenocystathionine, N-acetylcysteine-selenohomocysteine, 2,3-DHP-selenolanthionine, N-propionylselenocystathionine, 2,3-DHP-selenocystathionine, methylselenoglutathione, γ-glutamoylselenocystathione, or selenoglutathione, In embodiments, the selenium containing compound comprises one or more of dehydroxy 5'-methylselenoadenosine, seleno(hydroxyl)-selenophene-(3'-deoxy-adenosine), ethyl-selenoadenosine, allylselenoadenosyl homocysteine, seleno-adenosyl homocysteine, seleno-hydroxy adenosyl homocysteine, selno adenosine, seleno-adenosyl-Se(methyl)-selenoxide, adenosyl-hydroxy selenoxide, ethyl selenoadenosinee, seleno-(hydroxy)-selenophene-(3'-desoxy-adenosine), or selno-adenosyl-Se(methyl)-selenoxide.

In some embodiments, a composition comprising selenium that is administered to a subject (e.g., in a method of the present application) comprises one or more proteins or peptide fragments, wherein one or more sulfur molecules present within one or more amino acid residues of the protein or peptide is substituted with a selenium molecule. The present application is not limited to a specific selenium containing protein or peptide. In some embodiments, a composition comprising selenium that is administered to a subject comprises one or more peptide fragments wherein one or more sulfur molecules present within one or more amino acid residues of the peptide is substituted with a selenium molecule from the following: MVAEAEK, DYMGAAK, YMGAAK, ELQDIANPIMSK, NQAAMNPSNTVFDAK, NFTPEQISSMVLGK, NFTPEQISSMVLGK, MVSEAEK, PEVQGDMK, ELQDIANPIMSK, AMSSR, VQGSVIGIDLGTTNSAVAIMEGK, AAAEGPMK, LTGMAFR, PFVSNDYAAYMVK, AFGIEEGLMTTVHSLTATQK, PFITNDYAAYMFK, PGMVVTFAPAGVTTEVK, VETGVIKPGMVVTFAPAGVTTEVK, AAATAAMTK, SIVPSGASTGVHEALEMR, WMGK, SIVPSGASTGVHEALEMR, AMPQK, AAMAK, HVGDMEIR, VIEEPITSETAMK, VLQALEEIGIVEISPK, LPAASLGDMVMATVK, AGMTTIVR, AGMTTIVR, MLMPK, TMGAK, MNAGR, TYENMK, MGHDQSGTK, GEAIMAPK, Ac-MNVFGK, AMEVVASER, IVMR, MA(I/L)R, AMXAK, DLETLTMHTK, LVMR, VMR, LTGMAFR, SRPNVEVVALNDPFITNDYAAYMFK, and VINDAFGIEEGLMTTVHSLTATQK.

In some embodiments, compositions (e.g., pharmaceutical compositions) comprise 2 or more (e.g., 3 or more, 4 or more, 5 or more, 6 or more, 7 or more, 8 or more, 9 or more, 10 or more, 15 or more, 20 or more, 30 or more, 40 or more, or 50 or more) distinct selenium containing compounds (e.g., those described herein). In some embodiments, the present application provides a composition comprising a combination of 2 or more (e.g., 3 or more, 4 or more, 5 or more, 6 or more, 7 or more, 8 or more, 9 or more, 10 or more, 15 or more, 20 or more, 30 or more, 40 or more, or 50 or more) selenium containing compounds (e.g., isolated, chemically synthesized, or recombinant selenium containing compound) tailored for a specific use (e.g., that, when combined, display a desired level of bioactivity (e.g., stimulatory and/or inhibitory activity)).

For example, in some embodiments, a first composition comprising a combination of two or more selenium containing compounds is utilized to enhance mitochondrial activity (e.g., ATP production and/or respiration) in muscle tissue, whereas a second composition comprising a combination of two or more different selenium containing compounds (e.g., displaying bioactivity that is different than the first composition) is utilized to alter mitochondrial activity in liver tissue. In some embodiments, a composition comprising two or more selenium containing compounds is customized to the specific genetic profile of an individual (e.g., to target a particular gene or protein).

Yeast extracts or fractions can be customized in a similar manner for use in treating a particular disease or condition in an individual. In such a way, a custom formulation is developed for the individual subject in need of treatment. In some embodiments, the subject administered a composition comprising selenium of the present application has or is at risk for a condition or disease associated with mitochondrial dysfunction. The present application is not limited by the type of subject at risk for or having mitochondrial dysfunction. Indeed, the art knows well that a variety of subjects are at risk for or have mitochondrial dysfunction including, but not limited to, a subject genetically predisposed to mitochondrial dysfunction.

In embodiments, the subject has a condition or disease including, but not limited to, cardiomyopathy, sarcopenia, or loss of muscle protein.

In an embodiment, a method of increasing the protein content of a muscle cell comprises administering an effective amount of a composition comprising a selenium enriched yeast comprising 2% or less inorganic selenium to the muscle cell, wherein the effective amount increases protein in a muscle cell. In other embodiments, a method of treating sarcopenia comprises administering an effective amount of a composition comprising a selenium enriched yeast comprising 2% or less inorganic selenium to a subject, wherein the effective amount ameliorates the symptoms of sarcopenia.

In embodiments, a method of treating cardiomyopathy comprises administering an effective amount of a composition comprising a selenium enriched yeast comprising 2% or less inorganic selenium to a subject, wherein the effective amount ameliorates the symptoms of cardiomyopathy.

In another aspect, the present application provides for modulating (e.g increasing or decreasing) gene expression in cardiac muscle cells, skeletal muscle cells, and/or liver cells.

In other embodiments, a method of modulating transcriptional activity in a cardiac muscle cell comprises administering of an effective amount of a composition comprising selenium enriched yeast comprising 2% or less inorganic selenium to the cardiac muscle cell, wherein the effective amount is effective to modulate NFATc2/c3 and/or Foxo3 transcriptional activity in a cardiac muscle cell. In further embodiments, NFATc2/c3 transcriptional activity is decreased in a cardiac muscle cell contacted with a selenium enriched yeast comprising 2% or less inorganic selenium as compared to a muscle cell not exposed to the composition. In other embodiments, phosphorylation of NFATc2/c3 is increased in a cardiac muscle cell contacted with a selenium enriched yeast comprising 2% or less inorganic selenium as compared to a muscle cell not exposed to the composition. In embodiments, Foxo3 transcriptional activity is increased in the cardiac muscle cell contacted with a selenium enriched yeast comprising 2% or less inorganic selenium as compared to a cardiac muscle cell not exposed to the composition.

In embodiments, a method of decreasing gene expression in a cardiac muscle cell comprises administering an effective amount of a composition comprising a selenium enriched yeast comprising 2% or less inorganic selenium to the cardiac muscle cell, wherein the effective amount decreases expression of Myh7, Ankrd1, Lcn2, pS6K1, and combinations thereof. In another embodiment, a method of increasing gene expression in a cardiac muscle cell comprises administering an effective amount of a composition comprising a selenium enriched yeast comprising 2% or less inorganic selenium to the cardiac muscle wherein the effective amount increases expression of gene selected from the group consisting of Atm, Gadd45g, Gsk3b, UCP2, and combinations thereof is increased in the cardiac muscle cell contacted with a selenium enriched yeast comprising 2% or less inorganic selenium as compared to a cardiac muscle cell not exposed to the composition.

In other embodiments, a method of decreasing expression of one or more genes in a skeletal muscle cell comprises administering an effective amount of a composition comprising a selenium enriched yeast comprising 2% or less inorganic selenium to the skeletal muscle cell, wherein the effective amount decreases expression of one or more or all of myostatin, Avcr2b, mTOR, S6K1, Gsk3b, Fxbo32, Trim 63, and Nr2f2 in the cardiac muscle cell contacted with a selenium enriched yeast comprising 2% or less inorganic selenium as compared to a cardiac muscle cell not exposed to the composition. In embodiments, a method of increasing expression of one or more genes in a skeletal muscle cell comprises administering an effective amount of a composition comprising a selenium enriched yeast comprising 2% or less inorganic selenium to the skeletal muscle cell, wherein the effective amount increases expression of one or more or all Prkaa2, Myf6, Des, and PGC1a, is increased in the skeletal muscle cell contacted with a selenium enriched yeast comprising 2% or less inorganic selenium as compared to a muscle cell not exposed to the composition.

In other embodiments, the expression of gene selected from the group consisting of Nr2F2, PGC1a and combinations thereof is increased in a liver cells in an animal fed a diet with a selenium enriched yeast comprising 2% or less inorganic selenium as compared to gene expression in liver cells in animal fed a selenium deficient diet.

In other embodiments, a method of increasing mitochondrial function in a cell comprises administering an effective amount of a composition comprising isolated 5' methylselenoadenosine, LVSe-MR or combinations thereof, wherein the effective amount increases mitochondrial function in a cell as compared to a cell not exposed to the composition. Other embodiments include, a method of increasing pyruvate dehydrogenase complex in a cell comprising administering an effective amount of a composition comprising isolated 5' methylselenoadenosine, wherein the effective amount increases the activity of pyruvate dehydrogenase complex in a cell as compared to a cell not exposed to the composition.

In further embodiments of the present application, a composition comprising an isolated compound selected from the group consisting methyl seleno adenosine, seleno (hydroxyl)-selenophene-(3'-deoxy-adenosine), N-acetylcysteine-selenohomocysteine, allylselenoadenosyl homocysteine, seleno-adenosyl homocysteine, seleno-hydroxy adenosyl homocysteine, selno adenosine, seleno-adenosyl-Se(methyl)-selenoxide, adenosyl-hydroxy selenoxide, ethyl selenoadenosine, seleno-(hydroxy)-selenophene-(3'-desoxy-adenosine), adenosyl-hydroxy selnoxide, selno-adenosyl-Se(methyl)-selenoxide and combinations thereof is provided. In embodiments, isolated compound is methylselenoadenosine. In other embodiments, the compositions are for use in increasing mitochondrial function in a cell.

In some embodiments, the amount of a composition comprising selenium that is administered to a subject is an effective amount to slow, stop or reverse the progression of mitochondrial dysfunction and/or disease or condition associated with the same in a subject in need thereof while minimizing toxicity. In some embodiments, a composition comprising selenium of the present application (e.g., organic selenium (e.g., selenized yeast (e.g., SEL-PLEX) or a selenium containing compound present therein or derived therefrom)) is administered at a daily dose so as to provide between 25 and 800 μg of selenium to a subject per day (e.g., SEL-PLEX is administered to a subject in such a way so as to provide between 25 and 800 μg of selenium to the subject each day). However, the present application is not so limited. Indeed, in some embodiments, a composition comprising selenium of the present application is administered at a daily dose so as to provide between less than 25 (e.g., 24, 23, 22, 21, 20, or less) or more than 800 (e.g., 825, 850, 900, 950, 1000, 1050, 1100, or more) μg of selenium to a subject per day. In some embodiments, the selenium (e.g., organic selenium (e.g., selenized yeast (e.g., SEL-PLEX))) is administered at a daily dose of between 200 and 500 μg per day. In other embodiments, selenium is administered at a daily dose of between 200 and 400 μg per day. In some embodiments, a single dose of selenium (e.g., organic selenium (e.g., selenized yeast (e.g., SEL-PLEX))) is administered once daily. In other embodiments, 2, 3, 4, or more doses are administered each day. In some embodiments, the daily dose is between 25-75 μg of selenium. In other embodiments, the daily dose is 200 μg of selenium (e.g., organic selenium (e.g., selenized yeast (e.g., SEL-PLEX))).

The present application also provides a method of treating mitochondrial dysfunction comprising administering to a subject in need thereof an effective amount of a pharmaceutical composition comprising a composition comprising selenium selected from the group consisting of a selenium enriched yeast comprising 2% or less inorganic selenium, a water soluble fraction of a selenium enriched yeast comprising 2% or less inorganic selenium, and a water insoluble fraction of a selenium enriched yeast comprising 2% or less inorganic selenium; and a pharmaceutically acceptable carrier.

The present application also provides a method of treating a disease or condition associated with mitochondrial dysfunction in a subject comprising the step of administering an effective amount of a selenium enriched yeast comprising 2% or less inorganic selenium to a subject in need thereof.

BRIEF DESCRIPTION OF THE DRAWINGS

FIG. 6 shows size exclusion-ICP MS chromatograms of the water extracts post SUPERDEX peptide column (76Se—dark grey line, 77Se—black line, 78Se light grey line).

FIG. 9 shows the identification of the selenocompound eluting at 58 min from the SEC column shown in FIG. 8B utilizing mass spectroscopy and reversed phase chromatography coupled with Orbitrap

FIG. 13 shows a list of selenium containing peptides found in the tryptic digestates of the sub-fractions of water soluble extract from selenium enriched yeast (MW—molecular weight, Z—ionization state).

FIG. 21 provides a list of selenium containing peptides identified from water insoluble extract of selenium enriched yeast using 1D gel electrophoresis, Blot digestion prior to HPLC analysis, ICP MS analysis of blot samples and MS/MS (Orbitrap) analysis of blot samples.

FIG. 32 shows significantly reduced expression of atrophic genes Trim63 and Fbxo32 in skeletal muscle of normal mice fed for three months with a diet supplemented with selenium in the form selenium enriched yeast comprising 2% or less inorganic selenium (SP) compared to control diets supplemented with selenium in the form of selenomethionine (SM), supplemented with selenium in the form of sodium selenite (SS) or a diet not supplemented with selenium. Data are presented as mean±sd (n=6).

FIG. 33 shows significantly reduced expression of Acvr2b in skeletal muscle of normal mice fed for three months with a diet supplemented with selenium in the form selenium enriched yeast comprising 2% or less inorganic selenium (SP) compared to control diets supplemented with selenium in the form of selenomethionine (SM), supplemented with selenium in the form of sodium selenite (SS) or a diet not supplemented with selenium. Data are presented as mean±sd (n=6).

FIG. 40 shows (A) mitochondrial oxygen consumption rates (OCR) parameters measured in three different respiratory states (including ATP synthesis (State III), complex I dependent (NADH-driven) maximum respiratory capacity (State V fccp), and complex II (FADH-driven) dependent maximum respiratory capacity (State Vsucc) in the presence of control (C), LVSe-MR ($C_{22}H_{44}N_7O_5Se$) (#6) and methylselenoadenosine ($C_{11}H_{15}N_5O_3Se$) (#9). (B) Shows that the selenium containing peptide LVSe-MR increased State III (7.7%), State $V_{FCCP}$ (13.3%) and State $V_{succ}$ (9.6%) compared to control. Methylselenoadenosine ($C_{11}H_{15}N_5O_3Se$) (#9) increased State III (29.9%), State $V_{FCCP}$ (17.3%) and State $V_{succ}$ (15.3%) compared to control using oxytherm.

DEFINITIONS

Figure 1:
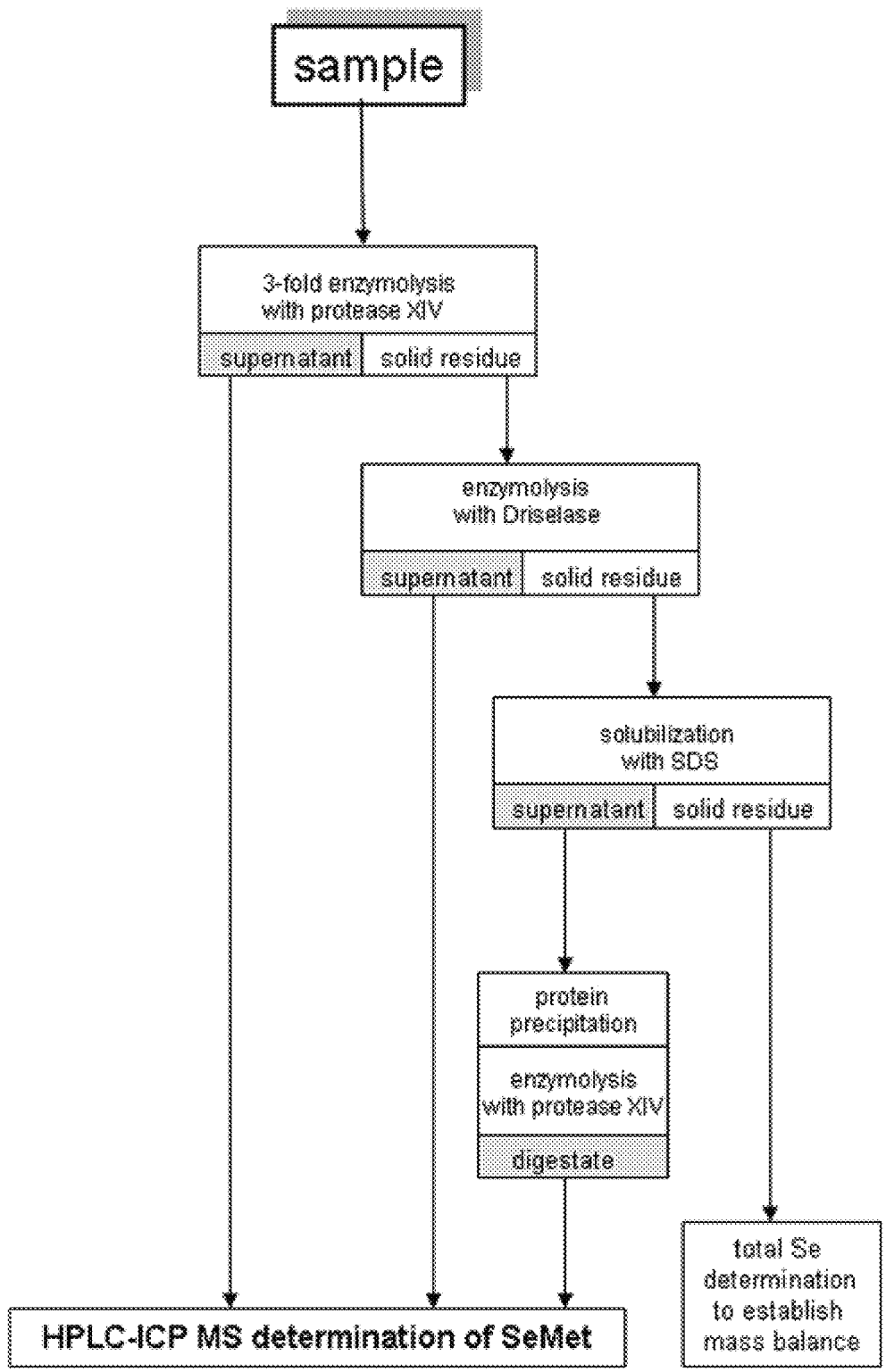
FIG. 1 shows a sequential extraction procedure allowing the complete solubilization of a sample and the determination of selenomethionine in the individual fractions of one embodiment of the present application.

As used herein, the term "yeast" and "yeast cells" refers to eukaryotic microorganisms classified in the kingdom Fungi, having a cell wall, cell membrane and intracellular components. Yeasts do not form a specific taxonomic or phylogenetic grouping. Currently about 1,500 species are know; it is estimated that only 1% of all yeast species have been described. The term "yeast" is often taken as a synonym for *S. cerevisiae*, but the phylogenetic diversity of yeasts is shown by their placement in both divisions Ascomycota and Basidiomycota. The budding yeasts ("true yeasts") are classified in the order Saccharomycetales. Most species of yeast reproduce asexually by budding, although some reproduce by binary fission. Yeasts are unicellular, although some species become multicellular through the formation of a string of connected budding cells known as pseudohyphae, or false hyphae. Yeast size can vary greatly depending on the species, typically measuring 3-4 μm in diameter, although some yeast can reach over 40 μm.

As used herein, the terms "peptide," "polypeptide" and "protein" all refer to a primary sequence of amino acids that are joined by covalent "peptide linkages." In general, a peptide consists of a few amino acids, typically from 2-50 amino acids, and is shorter than a protein. The term "polypeptide" encompasses peptides and proteins. In some embodiments, the peptide, polypeptide or protein is synthetic, while in other embodiments, the peptide, polypeptide or protein are recombinant or naturally occurring. A synthetic peptide is a peptide that is produced by artificial means in vitro (i.e., was not produced in vivo).

The terms "sample" and "specimen" are used in their broadest sense and encompass samples or specimens obtained from any source. As used herein, the term "sample" is used to refer to biological samples obtained from animals (including humans), and encompasses fluids, solids, tissues, and gases. In some embodiments of this present application, biological samples include cerebrospinal fluid (CSF), serous fluid, urine, saliva, blood, and blood products such as plasma, serum and the like. However, these examples are not to be construed as limiting the types of samples that find use with the present application.

As used herein, the terms "selenium-enriched yeast" and "selenized yeast" refer to any yeast (e.g., *Saccharomyces cerevisiae*) that is cultivated in a medium containing inorganic selenium salts. The present application is not limited by the selenium salt used. Indeed, a variety of selenium salts are contemplated to be useful in the present application including, but not limited to, sodium selenite, sodium selenate, cobalt selenite or cobalt selenate. Free selenomethionine (e.g., not associated with a cell or yeast) can also be used as the selenium source for selenium enriched yeast as yeast does incorporate this form of selenium. During cultivation, because of the chemical similarity between selenium and sulfur, yeast incorporate selenium in place of sulfur in what are normally sulfur-containing organic compounds within the cell. A selenium-containing compound in such yeast preparations is selenomethionine which will be present in a form that is incorporated into polypeptides/proteins. The amount of total cellular selenium present in the form of selenomethionine in such preparations will vary, but can be between 10 and 100%, 20-60%, 50-75% and between 60 and 75%. The remainder of the organic selenium in selenized yeast preparations is predominantly made up of intermediates in the pathway for selenomethionine biosynthesis. These include, but are not limited to, selenocysteine, selenocystathionine, selenohomocysteine and seleno-adenosylselenomethionine. The amount of residual inorganic selenium salt in the finished product is generally quite low (e.g., <2%). However, the present application is not limited by this percentage, as preparations that contain more (e.g., between 2 and 70%) or less (e.g., between 0.1 and 2%) than this percentage are also encompassed by the present application.

As used herein, the term "SELPLEX" refers to a dried, nonviable selenium-enriched yeast (e.g., *Saccharomyces cerevisiae* of accession number CNCM I-3060, Collection Nationale De Cultures De Microorganisms (CNCM), Institut Pasteur, Paris, France) cultivated in a fed-batch fermentation that provides incremental amounts of cane molasses and selenium salts in a manner that minimizes the detrimental effects of selenium salts on the growth rate of the yeast and allows for optimal incorporation of inorganic selenium into cellular organic material. Residual inorganic selenium is eliminated (e.g., using a rigorous washing process) and does not exceed 2% of the total selenium content.

As used herein, the term "organic selenium" refers to any organic compound wherein selenium replaces sulfur. Thus, organic selenium can refer to any such compound biosynthesized by yeast, or it can refer to free organic selenocompounds that are chemically synthesized. An example of the latter is free selenomethionine.

As used herein, the term "inorganic selenium" generally refers to any selenium salt (e.g., sodium selenite, sodium selenate, cobalt selenite and cobalt selenate). There are also a variety of other inorganic selenium sources (See e.g., those listed in the Merck index). Selenized yeast may be generated using a source of inorganic selenium including, but not limited to, sodium selenite, sodium selenate, cobalt selenite, cobalt selenate, selenic acid, selenious acid, selenium bromide, selenium chloride, selenium hexafluoride, selenium oxide, selenium oxybromide, selenium oxychloride, selenium oxyfluoride, selenium sulfides, selenium tetrabromide, selenium tetrachloride and selenium tetrafluoride.

As used herein, the terms "selenium compound" "selenium containing compound" and "selenium containing component" refer to any compound containing selenium that is capable of providing a bioavailable source of selenium. The selenium compound may include inorganic compounds, such as minerals containing selenites and selenates, and organic compounds such as selenoethers, conjugates of SeCys containing di and tri peptides, selonols, selenoxides, selenium containing proteins and peptides, an amino acid (e.g., isoleucine, alanine leucine, asparagine, lysine, aspartate, methionine, cysteine, phenylalanine, glutamate, threonine, glutamine, tryptophan, glycine, valine, proline, serine, tyrosine, arginine, histidine.) containing selenium (e.g., replacing a sulphur therein) or a divalent or tetravalent selenium compound, selenium enriched yeast or a fraction thereof, as well as selenium containing molecules described herein. The selenium compound may be sourced as a yeast or plant extract or from commercial synthesis. In a particular embodiment, the selenium compound provides a bioavailable source of selenium that is readily absorbed by the body into blood plasma or inter-cellular fluids. In a preferred embodiments, a selenium containing compound is a selenium enriched yeast or a molecule containing selenium present therein or derived therefrom.

As used herein, the term "oxidative stress" refers to the cytotoxic effects of oxygen radicals (e.g., superoxide anion ($O_2^-$), hydroxy radical (OH), and hydrogen peroxide ($H_2O_2$)), generated, for example, as byproducts of metabolic processes that utilize molecular oxygen (See e.g., Coyle et al., Science 262:689-695 (1993)).

As used herein, the terms "host," "subject" and "patient" refer to any animal, including but not limited to, human and non-human animals (e.g., dogs, cats, cows, horses, sheep, poultry, fish, crustaceans, etc.) that is studied, analyzed, tested, diagnosed or treated. As used herein, the terms "host," "subject" and "patient" are used interchangeably, unless indicated otherwise.

As used herein, the term "in vivo" refers to studies and/or experiments conducted within a living organism, occurring within a biological organism.

As used herein, the term "in vitro" refers to an artificial environment outside the living organism and to biological processes or reactions that would normally occur within an organism but are made to occur in an artificial environment. In vitro environments can comprise of, but are not limited to, test tubes and cell culture.

The terms "Western blot," "Western immunoblot" "immunoblot" and "Western" refer to the immunological analysis of protein(s), polypeptides or peptides that have been immobilized onto a membrane support. The proteins are first resolved by polyacrylamide gel electrophoresis (i.e., SDS-PAGE) to separate the proteins, followed by transfer of the protein from the gel to a solid support, such as nitrocellulose or a nylon membrane. The immobilized proteins are then exposed to an antibody having reactivity towards an antigen of interest. The binding of the antibody (i.e., the primary antibody) is detected by use of a secondary antibody that specifically binds the primary antibody. The secondary antibody is typically conjugated to an enzyme that permits visualization of the antigen-antibody complex by the production of a colored reaction product or catalyzes a luminescent enzymatic reaction (e.g., the ECL reagent, Amersham).

As used herein, the term "ELISA" refers to enzyme-linked immunosorbent assay (or EIA). Numerous ELISA methods and applications are known in the art, and are described in many references (See, e.g., Crowther, "Enzyme-Linked Immunosorbent Assay (ELISA)," in Molecular Biomethods Handbook, Rapley et al. (eds.), pp. 595-617, Humana Press, Inc., Totowa, N.J. (1998); Harlow and Lane (eds.), Antibodies: A Laboratory Manual, Cold Spring Harbor Laboratory Press (1988); Ausubel et al. (eds.), Current Protocols in Molecular Biology, Ch. 11, John Wiley & Sons, Inc., New York (1994)). In addition, there are numerous commercially available ELISA test systems.

As used herein, the terms "reporter reagent," "reporter molecule," "detection substrate" and "detection reagent" are used in reference to reagents that permit the detection and/or quantitation of an antibody bound to an antigen. For example, in some embodiments, the reporter reagent is a colorimetric substrate for an enzyme that has been conjugated to an antibody. Addition of a suitable substrate to the antibody-enzyme conjugate results in the production of a colorimetric or fluorimetric signal (e.g., following the binding of the conjugated antibody to the antigen of interest). Other reporter reagents include, but are not limited to, radioactive compounds. This definition also encompasses the use of biotin and avidin-based compounds (e.g., including but not limited to neutravidin and streptavidin) as part of the detection system.

As used herein, the term "signal" is used generally in reference to any detectable process that indicates that a reaction has occurred, for example, binding of antibody to antigen. It is contemplated that signals in the form of radioactivity, fluorimetric or colorimetric products/reagents will all find use with the present application. In various embodiments of the present application, the signal is assessed qualitatively, while in alternative embodiments, the signal is assessed quantitatively.

As used herein, the term "solid support" is used in reference to any solid or stationary material to which reagents such as antibodies, antigens, and other test components are attached. For example, in an ELISA method, the wells of microliter plates provide solid supports. Other examples of solid supports include microscope slides, coverslips, beads, particles, cell culture flasks, as well as many other suitable items.

As used herein, the term "characterizing tissue in a subject" refers to the identification of one or more properties of a tissue sample. In some embodiments, tissues are characterized by the identification of the expression, or lack thereof, of various genes described in detail herein.

As used herein, the term "reagent(s) capable of specifically detecting gene expression" refers to reagents capable of or sufficient to detect the expression of various genes described in detail herein. Examples of suitable reagents include, but are not limited to, nucleic acid probes capable of specifically hybridizing to mRNA or cDNA, and antibodies (e.g., monoclonal or polyclonal antibodies).

As used herein, the term "effective amount" refers to the amount of a composition (e.g., comprising selenium—e.g., SELPLEX) sufficient to effect beneficial or desired results. An effective amount can be administered in one or more administrations, applications or dosages and is not intended to be limited to a particular formulation or administration route.

As used herein, the terms "administration" and "administering" refer to the act of giving a drug, prodrug, or other agent, or therapeutic treatment (e.g., compositions of the present application) to a subject (e.g., a subject or in vivo, in vitro, or ex vivo cells, tissues, and organs). Exemplary routes of administration to the human body can be through the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

As used herein, the terms "co-administration" and "co-administering" refer to the administration of at least two agent(s) (e.g., composition comprising SEL-PLEX or one or more selenium containing compounds present therein or derived therefrom) and one or more other agents (e.g., a therapeutic) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term "treatment" or grammatical equivalents encompasses the improvement and/or reversal of the symptoms of disease. A compound which causes an improvement in any parameter associated with disease when used in the screening methods of the instant present application may thereby be identified as a therapeutic compound. As used herein, the term "at risk for disease" (e.g., at risk for hypertrophic cardiomyopathy, diabetes, cancer, etc.) refers to a subject (e.g., a human) that is predisposed to experiencing a particular disease (e.g., hypertrophic cardiomyopathy, diabetes, cancer, etc.). This predisposition may be genetic (e.g., a particular genetic tendency to experience the disease, such as heritable disorders), or due to other factors (e.g., hypertension, age, weight, environmental conditions, exposures to detrimental compounds present in the environment, etc.). Thus, it is not intended that the present application be limited to any particular risk, nor is it intended that the present application be limited to any particular disease.

As used herein, the term "suffering from disease" (e.g., suffering from hypertrophic cardiomyopathy, diabetes, cancer, etc.) refers to a subject (e.g., a human) that is experiencing a particular disease (e.g., hypertrophic cardiomyopathy, diabetes, cancer, etc.). It is not intended that the present application be limited to any particular signs or symptoms, nor disease. Thus, it is intended that the present application encompass subjects that are experiencing any range of disease (e.g., from sub-clinical manifestation to full-blown disease) wherein the subject exhibits at least some of the indicia (e.g., signs and symptoms) associated with the particular disease.

As used herein, the terms "disease" and "pathological condition" are used interchangeably to describe a state, signs, and/or symptoms that are associated with any impairment of the normal state of a living animal or of any of its organs or tissues that interrupts or modifies the performance of normal functions, and may be a response to environmental factors (such as malnutrition, industrial hazards, or climate), to specific infective agents (such as worms, bacteria, or viruses), to inherent defect of the organism (such as various genetic anomalies, or to combinations of these and other factors.

The term "compound" refers to any chemical entity, pharmaceutical, drug, and the like that can be used to treat or prevent a disease, illness, sickness, or disorder of bodily function. Compounds comprise both known and potential therapeutic compounds. A compound can be determined to be therapeutic by screening using the screening methods of the present application. A "known therapeutic compound" refers to a therapeutic compound that has been shown (e.g., through animal trials or prior experience with administration to humans) to be effective in such treatment. In other words, a known therapeutic compound is not limited to a compound efficacious in the treatment of disease (e.g., neurodegenerative disease).

As used herein, the term "kit" is used in reference to a combination of reagents and other materials. It is contemplated that the kit may include reagents such as nutrients and drugs as well as administration means. It is not intended that the term "kit" be limited to a particular combination of reagents and/or other materials.

As used herein, the term "toxic" refers to any detrimental or harmful effects on a subject, a cell, or a tissue as compared to the same cell or tissue prior to the administration of the toxicant.

As used herein, the term "pharmaceutical composition" refers to the combination of an active agent (e.g., composition comprising SEL-PLEX and/or one or more selenium containing compounds present therein or derived therefrom) with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "topically" refers to application of the compositions of the present application to the surface of the skin and mucosal cells and tissues (e.g., alveolar, buccal, lingual, masticatory, or nasal mucosa, and other tissues and cells that line hollow organs or body cavities).

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintrigrants (e.g., potato starch or sodium starch glycolate), and the like. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. (1975), incorporated herein by reference).

As used herein, the term "pharmaceutically acceptable salt" refers to any salt (e.g., obtained by reaction with an acid or a base) of a compound of the present application that is physiologically tolerated in the target subject (e.g., a mammalian subject, and/or in vivo or ex vivo, cells, tissues, or organs). "Salts" of the compounds of the present application may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the present application and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present application compounded with a suitable cation such as $Na^+$, $NH_4^+$, and $NW_4^+$ (wherein W is a $C_{1-4}$ alkyl group), and the like. For therapeutic use, salts of the compounds of the present application are contemplated as being pharmaceutically acceptable. However, salts of acids and bases that are non-pharmaceutically acceptable may also find use, for example, in the preparation or purification of a pharmaceutically acceptable compound.

For therapeutic use, salts of the compounds of the present application are contemplated as being pharmaceutically acceptable. However, salts of acids and bases that are non-pharmaceutically acceptable may also find use, for example, in the preparation or purification of a pharmaceutically acceptable compound.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

As used herein, the term "high-performance liquid chromatography" and the term "HPLC" refer to a form of liquid chromatography to separate compounds. The compounds are dissolved in solution. Compounds are separated by injecting a plug of the sample mixture onto the column. HPLC instruments comprise a reservoir of mobile phase, a pump, an injector, a separation column, and a detector. The presence of analytes in the column effluent is recorded by quantitatively detecting a change in refractive index, UV-VIS absorption at a set wavelength, fluorescence after excitation with a suitable wavelength, or electrochemical response.

As used herein, the term "scanning electron microscopy" and the term "SEM" refer to a type of electron microscope that images the sample surface by scanning it with a high-energy beam of electrons in a raster scan pattern. The electrons interact with the atoms that make up the sample producing signals that contain information about the sample's surface topography, composition and other properties such as electrical conductivity.

As used herein, the term "fixation agent" refers to a chemical that is capable of fixing one substance to another in order to "fix", stabilize, or otherwise preserve the substance in its current form to prevent the substance from degrading or otherwise changing. Often, fixation agents are used in scanning electron microscopy (SEM) to prepare the sample. Primary fixation agent: as used herein, the terms "primary fixation agent" refers to the first fixation agent used to "fix" a substance. Secondary fixation agent: as used herein, the terms "secondary fixation agent" refers to the second fixation agent used to "fix" a substance. Tertiary fixation agent: as used herein, the terms "tertiary fixation agent" refers to the third fixation agent used to "fix" a substance.

As used herein, the term "analyte" refers to an atom, a molecule, a grouping of atoms and/or molecules, a substance, or chemical constituent. An analyte, in and of itself cannot be measured, rather, aspects or properties (physical, chemical, biological, etc.) of the analyte can be determined using an analytical procedure, such as HPLC. For example, one cannot measure a "chair" (analyte-component) in and of itself, but, the height, width, etc. of a chair can be measured. Likewise, one cannot measure a mycotoxin but can measure the mycotoxin fluorescence that is related to its concentration.

As used herein, the term "signal" is used generally in reference to any detectable process that indicates that a reaction has occurred (for example, binding of antibody to antigen). Signals can be assessed qualitatively as well as quantitatively. Examples of types of "signals" include, but are not limited to, radioactive signals, fluorimetric signals or colorimetric product/reagent signals.

As used herein, the term "bioavailability" refers to the fraction of a molecule or component that is available to an organism or reaches the systemic circulation. When a molecule or component is administered intravenously, its bioavailability is 100%. However, when a molecule or component is administered via other routes (such as orally), its bioavailability decreases (due to incomplete absorption and first-pass metabolism).

DETAILED DESCRIPTION OF THE PRESENT APPLICATION

Energy obtained through the transfer of electrons down the electron transfer chain (ETC) is used to pump protons from the mitochondrial matrix into the intermembrane space, creating an electrochemical proton gradient across the mitochondrial inner membrane (IMM) called $\Delta\Psi$. This electrochemical proton gradient allows ATP synthase (ATPase) to use the flow of $H^+$ through the enzyme back into the matrix to generate ATP from adenosine diphosphate (ADP) and inorganic phosphate. Four membrane-bound complexes have been identified in mitochondria. Each is a transmembrane structure that is embedded in the inner membrane. Three of them are proton pumps. The structures are electrically connected by lipid-soluble electron carriers and water-soluble electron carriers. Complex I (NADH coenzyme Q reductase; labeled I) accepts electrons from the Krebs cycle electron carrier nicotinamide adenine dinucleotide (NADH), and passes them to coenzyme Q (ubiquinone; (UQ)), which also receives electrons from complex II (succinate dehydrogenase; (II)). UQ passes electrons to complex III (cytochrome $bc_1$ complex; (III)), which passes them to cytochrome c (cyt c). Cyt c passes electrons to Complex IV (cytochrome c oxidase; (IV)), which uses the electrons and hydrogen ions to reduce molecular oxygen to water.

In Complex I (NADH dehydrogenase, also called NADH:ubiquinone oxidoreductase;) two electrons are removed from NADH and transferred to a lipid-soluble carrier, ubiquinone (Q). The reduced product, ubiquinol ($QH_2$) freely diffuses within the membrane, and Complex I translocates four protons ($H^+$) across the membrane, thus producing a proton gradient. Complex I is one of the main sites at which premature electron leakage to oxygen occurs, thus being one of the main sites of production of harmful superoxide. Thus, along with Complex III, it produces most of the reactive oxygen species (mainly superoxide radicals) generated by the electron transport chain. Apart from genetic mutations, mitochondrial dysfunction is thought to primarily arise from damage caused by reactive oxygen species (ROS) to its sub-components (See, e.g., Kirkinezos and Moraes, 2001). Indeed, there exists wide agreement that the aging process and the onset of metabolic diseases (e.g., type 2 diabetes) originate with ROS-induced cellular damage. Mitochondria are the primary producers of ROS within the cell and this distinction means that they are also the first organelles to suffer the damage caused by ROS and so-called oxidative stress (See, e.g., Kaneto et al., 2012). A significant number of mitochondrial diseases are specifically linked to Complex I dysfunction or insufficiency.

The pathway of electrons occurs as follows: NADH is oxidized to $NAD^+$, by reducing Flavin mononucleotide to $FMNH_2$ in one two-electron step. $FMNH_2$ is then oxidized in two one-electron steps, through a semiquinone intermediate. Each electron thus transfers from the $FMNH_2$ to an Fe—S cluster, from the Fe—S cluster to ubiquinone (Q). Transfer of the first electron results in the free-radical (semiquinone) form of Q, and transfer of the second electron reduces the semiquinone form to the ubiquinol form, $QH_2$. During this process, four protons are translocated from the mitochondrial matrix to the intermembrane space.

In Complex II (succinate dehydrogenase) additional electrons are delivered into the quinone pool (Q) originating from succinate and transferred (via FAD) to Q. Complex II includes four protein subunits: SDHA, SDHB, SDHC, and SDHD. Other electron donors (e.g., fatty acids and glycerol 3-phosphate) also direct electrons into Q (via FAD).

In Complex III (cytochrome $bc_1$ complex), the Q-cycle contributes to the proton gradient by an asymmetric absorption/release of protons. Two electrons are removed from $QH_2$ at the $Q_O$ site and sequentially transferred to two molecules of cytochrome c, a water-soluble electron carrier located within the intermembrane space. The two other electrons sequentially pass across the protein to the $Q_i$ site where the quinone part of ubiquinone is reduced to quinol. A proton gradient is formed by two quinol (4H+4e−) oxidations at the $Q_o$ site to form one quinol (2H+2e−) at the $Q_i$ site. (in total six protons are translocated: two protons reduce quinone to quinol and four protons are released from two ubiquinol molecules).

In Complex IV (cytochrome c oxidase), sometimes called cytochrome A3, four electrons are removed from four molecules of cytochrome c and transferred to molecular oxygen ($O_2$), producing two molecules of water. At the same time, four protons are removed from the mitochondrial matrix (although only two are translocated across the membrane), contributing to the proton gradient. The activity of cytochrome c oxidase is inhibited by cyanide.

The electron transport chain and oxidative phosphorylation are coupled by a proton gradient across the inner mitochondrial membrane. The efflux of protons from the mitochondrial matrix creates an electrochemical gradient (proton gradient). This gradient is used by the $F_OF_1$ ATP synthase complex to make ATP via oxidative phosphorylation. ATP synthase is sometimes described as Complex V of the electron transport chain. The $F_O$ component of ATP synthase acts as an ion channel that provides for a proton flux back into the mitochondrial matrix. This reflux releases free energy produced during the generation of the oxidized forms of the electron carriers ($NAD^+$ and Q). The free energy is used to drive ATP synthesis, catalyzed by the $F_1$ component of the complex.

Thus, Complex I (NADH:ubiquinone oxidoreductase) is the first enzyme in the mitochondrial respiratory chain. It extracts energy from NADH, produced by the oxidation of sugars and fats, and traps the energy in a potential difference or voltage across the mitochondrial inner membrane. The potential difference is used to power the synthesis of ATP. Because complex I is central to energy production in the cell, its malfunction results in a wide range of neuromuscular diseases. Some of them are due to mutations in the mitochondrial genome, but others, which result from a decrease in the activity of complex I, or an increase in the production of reactive oxygen species, Noninsulin-dependent (Type II) diabetes mellitus (DM) is a disease characterized by insulin resistance in skeletal muscle, liver and fat, combined with defects in insulin secretion due to pancreatic β-cell function. Insulin resistance is a central feature of Type II diabetes. It is known, for example, that the vast majority of Type II diabetics are insulin-resistant. Likewise, insulin resistance in the offspring of Type II diabetics is the best predictor for later development of the disease (See, e.g., Warram et al., 1990). Interventions that reduce insulin resistance also prevent the development of diabetes. Mitochondrial function is required for normal glucose-stimulated insulin secretin from pancreatic beta cells.

Skeletal muscle and liver are the two key insulin-responsive organs in the maintenance of glucose homeostasis. The transition of these organs to an insulin-resistant state accounts for most of the changes in glucose metabolism seen in patients with Type II diabetes (See, e.g., Lowell and Shulman, 2005). Of these two organs, skeletal muscle is the more important in terms of consequences accruing from insulin resistance development. This is because skeletal muscle has been found to dispose of or metabolize 80 to 90% of daily ingested glucose (See, e.g., DeFronzo et al., 1985).

It has been documented by genome wide expression analysis that mitochondrial oxidative phosphorylation (OXPHOS) genes exhibit reduced expression in pre-diabetic and diabetic individuals when compared to healthy controls and that these genes are, in many cases, targets of the transcriptional coactivator proliferator-activated receptor gamma coactivator 1-alpha (PGC1-α, See, e.g., Mootha et al., 2003). In these studies, the typical decrease in expression for OXPHOS genes was modest (approximately 20%) but extremely consistent, with 89% of the genes studied showing lower expression in individuals with either impaired glucose tolerance or Type II diabetes relative to those with normal glucose tolerance.

It is generally understood and appreciated in the art that drugs or agents that boost OXPHOS activity in muscle exist as valuable therapeutics for type 2 diabetes. To bolster this hypothesis, it has long been known that aerobic exercise is the best non-pharmacological intervention for treating diabetes as it increases mitochondrial activity and number and promotes OXPHOS gene expression.

In addition to Type 2 diabetes, there exist multiple diseases and conditions associated with mitochondrial dysfunction. Because mitochondria are the main energy source in cells of higher organisms, mitochondria provide direct and indirect biochemical regulation of a wide array of cellular respiratory, oxidative and metabolic processes. These include electron transport chain (ETC) activity, which drives oxidative phosphorylation to produce metabolic energy in the form of adenosine triphosphate (ATP), and which also underlies a central mitochondrial role in intracellular calcium homeostasis.

In addition to their role in energy production in growing cells, mitochondria (or, at least, mitochondrial components) participate in programmed cell death (PCD), also known as apoptosis (See, e.g., Newmeyer et al., Cell 1994, 79:353-364; Liu et al., Cell 1996, 86:147-157). Apoptosis is required for normal development of the nervous system, and for proper functioning of the immune system. Moreover, some disease states are thought to be associated with either insufficient or excessive levels of apoptosis (e.g., cancer and autoimmune diseases, and stroke damage and neurodegeneration in Alzheimer's disease in the latter case, respectively). The role of mitochondria in apoptosis has been documented (See, e.g., Green and Reed, Science, 1998, 281:1309-1312; Green, Cell, 1998, 94:695-698; and Kromer, Nature Medicine, 1997, 3:614-620). Altered or defective mitochondrial activity, including but not limited to failure at any step of the ETC, may result in the generation of highly reactive free radicals that have the potential of damaging cells and tissues. These free radicals may include reactive oxygen species (ROS) such as superoxide, peroxynitrite and hydroxyl radicals, and potentially other reactive species that may be toxic to cells. For example, oxygen free radical induced lipid peroxidation is a well established pathogenetic mechanism in central nervous system (CNS) injury such as that found in a number of degenerative diseases, and in ischemia (e.g., stroke).

In addition to free radical mediated tissue damage, there are at least two deleterious consequences of exposure to reactive free radicals arising from mitochondrial dysfunction that adversely impact the mitochondria themselves. First, free radical mediated damage may inactivate one or more of the proteins of the ETC. Second, free radical mediated damage may result in mitochondrial collapse that has been termed "permeability transition" (PT) or "mitochondrial permeability transition" (MPT). According to generally accepted theories of mitochondrial function, and as described herein, proper ETC respiratory activity requires maintenance of an electrochemical potential in the inner mitochondrial membrane by a coupled chemiosmotic mechanism. Free radical oxidative activity may dissipate this membrane potential, thereby preventing ATP biosynthesis and halting the production of a vital biochemical energy source. In addition, mitochondrial proteins such as cytochrome c may leak out of the mitochondria after permeability transition and may induce the genetically programmed cell suicide sequence known as apoptosis or programmed cell death.

Mitochondria associated diseases (e.g., caused by dysfunctional mitochondria) may also be related to loss of mitochondrial membrane electrochemical potential by mechanisms other than free radical oxidation, and permeability transition may result from direct or indirect effects of mitochondrial genes, gene products or related downstream mediator molecules and/or extramitochondrial genes, gene products or related downstream mediators, or from other known or unknown causes. Loss of mitochondrial potential therefore may be a critical event in the progression of diseases associated with altered mitochondrial function, including degenerative diseases as well as diseases/conditions associated with aging (e.g., cancer, cardiovascular disease and cardiac failure, type 2 diabetes, Alzheimer's and Parkinson's diseases, fatty liver disease, cataracts, osteoporosis, muscle wasting, sleep disorders and inflammatory diseases such as psoriasis, arthritis and colitis).

Cardiomyopathy

Figure 25:
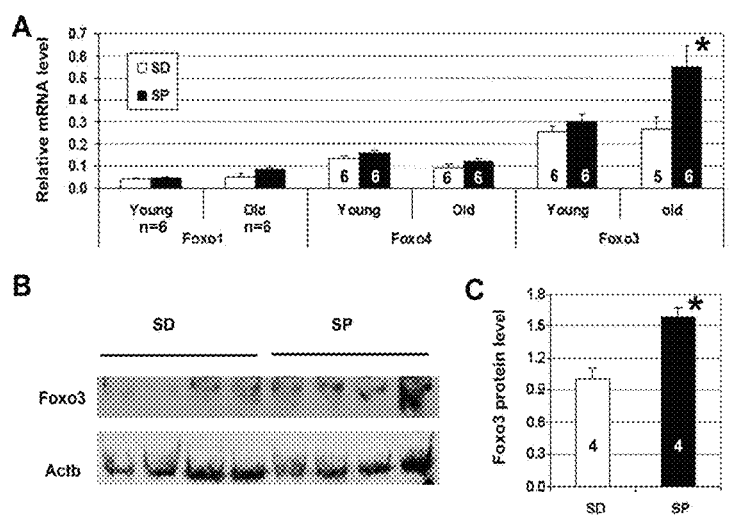
FIG. 25 shows enhanced cardiac expression of Foxo3, an anti-hypertrophic gene, in PolG mice administered diets containing selenium in the form of selenium rich yeast for 374 days. (A). QRT-PCR of Foxo family member genes showing the dominant Foxo3 expression in polG hearts, and the elevated cardiac Foxo3 expression in treated (SP) PolG mice compared to control (SD) PolG mice. (B-C). Elevated Foxo3 protein levels in the hearts of polG mice after selenium (SP) treatments for 374 days. In A and C, data are presented as mean±sem of indicated numbers of mice. *P<0.05 vs. SD control.

Nucleus-encoded DNA polymerase c (POLG) is the only known DNA polymerase in animal cell mitochondria. Mutations in the human POLG gene are connected to numerous diseases associated with a variety of symptoms, including ophthalmoplegia, cataracts, progressive muscle weakness, parkinsonism, premature ovarian failure, male infertility, hearing loss (presbycusis), and cardiac dysfunction (See, e.g., Kujoth et al., PLoS Genetics, 2007. 3(2)). The PolG$^{(D257A)}$ mouse model displays progressive decline in respiratory function of mitochondrially encoded complexes at 12 weeks, resulting in decreased oxygen consumption and reduced ATP production (See, e.g., Kujoth et al., PLoS Genetics, 2007. 3(2)). It has been reported that PolG mice display accelerated cardiac aging phenotypes with marked cardiac hypertrophy indicated by enlarged heart size and cardiomyocytes by the ages of 13-14 months (See, e.g., Dai et al 2010, Kujoth et al., 2005 and FIG. 25A).

Hypertrophic cardiomyopathy (HCM) is the most-common monogenically inherited form of heart disease and is the most-common cause of sudden cardiac death in individuals younger than 35 years of age (See, e.g., Frey et al., Nat Rev Cardiol, 2012. 9(2): p. 91-100). Genetic mutations that are the basis for HCM have been well characterized, with a majority of mutations encoding sarcomeric proteins, such as myosin-7 (also known as cardiac muscle β-myosin heavy chain; MYH7) (See, e.g., Frey et al., Nat Rev Cardiol, 2012. 9(2): p. 91-100).

Cardiac ankyrin repeat protein (CARP) is encoded by the ANKRD1 gene and expression of the ANKRD1 gene and CARP nuclear factor is involved in left ventricular hypertrophy, human heart failure, dilated cardiomyopathy (DCM), and adriamycin-induced cardiomyopathy (See, e.g., Duboscq-Bidot et al., Archives of Cardiovascular Diseases, 2009. 102, Supplement 1(0): p. S73). Consistent with documented phenotypes, age-dependent expression of cardiac hypertrophy markers Myh7 and Ankrd1 were elevated in heart tissue of POLG old mice when compared to POLG young mice.

Thus, empirical data generated throughout experiments conducted during development of embodiments of the present application determined that the PolG mouse line was an excellent experimental model for cardiac hypertrophy. For example, it was discovered and determined that the PolG mice provided a live animal model of heart aging that in turn permitted the analysis/testing of specific molecules involved in heart aging and hypertrophy (e.g., at the genetic and protein level). Moreover, it was also discovered that the PolG model permitted the assessment and characterization of compounds that alter specific molecules involved in heart aging and hypertrophy (e.g., at the genetic and protein level). Thus, in some embodiments, the present application provides a method of identifying test compounds (e.g., for the treatment and/or prevention of hypertrophic cardiomyopathy) comprising exposing PolG mice that exhibit marked cardiac hypertrophy indicated by enlarged heart size and cardiomyocytes at the ages of 13-14 months, to one or more compounds and detecting a change in heart size or cardiomyocytes and/or expression of molecules involved in hypertrophic cardiomyopathy in the presence of the test compound (e.g., compared to an animal not given the test compound (e.g., administered a control substance). As used herein, the term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present application. A "known therapeutic compound" refers to a therapeutic compound that has been shown (e.g., through animal trials or prior experience with administration to humans) to be effective in such treatment or prevention. In some embodiments, the test compound is a single drug candidate.

The present application provides compositions comprising selenium (e.g., selenium enriched yeast and selenium containing compounds obtained or derived therefrom) and methods of using the same to treat and inhibit cardiomyopathy. In particular, the present application provides compositions comprising selenium enriched yeast (e.g., comprising 2% or less inorganic selenium), selenium containing compounds present therein and/or derived therefrom, and methods of using the same to treat and inhibit cardiac hypertrophy in a subject (e.g., as a therapeutic and/or prophylactic treatment for cardiomyopathy). For example, in some embodiments, the present application provides compositions comprising selenium enriched yeast (e.g., SELPLEX), selenium containing compounds present therein and/or derived therefrom, and methods of using the same to inhibit or attenuate the expression of hypertrophic proteins myosin heavy chain beta (Myh7) and/or cardiac ankyrin repeat protein (Ankrd1) (e.g., as a therapeutic and/or prophylactic treatment for cardiac muscle hypertrophy). Although an understanding of a mechanism is not needed to practice the present application, and while the present application is not limited to any particular mechanism of action, in some embodiments, selenium in the form of selenium enriched yeast comprising 2% or less inorganic selenium (or one or more selenium containing compounds present therein), when administered to a subject, regulates the transcription factor Foxo3 to inhibit the expression of Myh7 and Ankrd1 molecules (e.g., thereby inhibiting cardiac muscle hypertrophy).

Experiments conducted during development of embodiments of the present application have discovered and shown that selenium enriched yeast (e.g., selenium enriched yeast comprising 2% or less inorganic selenium), when administered to a subject, inhibits the accumulation of hypertrophic proteins myosin heavy chain beta (Myh7) and cardiac ankyrin repeat protein (Ankrd1), thereby inhibiting and/or preventing cardiac muscle aging and hypertrophy. Although an understanding of a mechanism is not needed to practice the present application, and while the present application is not limited to any particular mechanism of action, in some embodiments, selenium in the form of selenium enriched yeast comprising 2% or less inorganic selenium (or one or more selenium containing compounds present therein), when administered to a subject, regulates Nfat signaling (e.g., by increasing phosphorylation of Nfatc2/3 resulting in a decrease of nuclear Nfatc2/3 activity related gene transcription (e.g., thereby inhibiting cardiac accumulation of hypertrophic proteins Myh7 and Ankrd1)).

Further experiments conducted during development of embodiments of the present application have discovered and shown that selenium in the form of selenium enriched yeast comprising 2% or less inorganic selenium (or one or more selenium containing compounds present therein), when administered to a subject, significantly reduces cardiac expression of pS6K1 (e.g., thereby inhibiting and/or reducing cardiac muscle aging and hypertrophy Atm/Gadd45 signaling is a critical pathway in cell cycle arrest and DNA repair, both in skeletal as well as cardiac muscle. Experiments were conducted during development of embodiments of the present application in order to characterize Atm and Gadd45 expression in heart from control and selenium treated PolG mice. It was discovered that there was an age-dependent decrease of Atm expression in PolG mouse heart. However, administration of selenium in the form of selenium enriched yeast comprising 2% or less inorganic selenium abolished the age-dependent decrease of Atm expression in the PolG mice. In addition, the expression of heart Gadd45, a downstream target of the Atm was significantly up-regulated in PolG mice administered selenium in the form of selenium enriched yeast comprising 2% or less inorganic selenium. Although an understanding of a mechanism is not needed to practice the present application, and while the present application is not limited to any particular mechanism of action, in some embodiments, selenium in the form of selenium enriched yeast comprising 2% or less inorganic selenium (or one or more selenium containing compounds present therein), when administered to a subject (e.g., an aged subject) neutralizes and/or abolishes age associated reduced expression of Atm in heart tissue (e.g., thereby augmenting and/or enhancing expression of molecules downstream of Atm (e.g., Gadd45) and/or improving the health of the heart via protecting cardiomyocytes against DNA damage (e.g., thereby inhibiting and/or preventing cardiac muscle hypertrophy (e.g., in aged subjects))).

Uncouple proteins (Ucp) in mitochondria (MT) are important for thermogenesis and maintenance of mitochondrial potential or integrity. Loss of Ucp2 has been documented to cause shorter lifespan and elevated production of reactive oxygen species (ROS) in mitochondria. Experiments conducted during development of embodiments of the present application have discovered and shown that Ucp2 is a major Ucps expressed in cardiac muscle. Administration of selenium in the form of selenium enriched yeast comprising 2% or less inorganic selenium did not alter Ucp1 or Ucp3 expression, however, Ucp2 expression was significantly elevated in selenium-treated PolG mice. Although an understanding of a mechanism is not needed to practice the present application, and while the present application is not limited to any particular mechanism of action, in some embodiments, selenium in the form of selenium enriched yeast comprising 2% or less inorganic selenium (or one or more selenium containing compounds present therein), when administered to a subject (e.g., an aged subject) upregulates expression of Ucp2 in the heart (e.g., thereby controlling reactive oxygen species production (e.g., thereby improving the health of the heart via protecting cardiomyocytes against DNA damage (e.g., thereby inhibiting and/or preventing cardiac muscle hypertrophy (e.g., in aged subjects))).

Lcn2 is a biomarker of heart failure, and is critical for cardiac muscle contraction. When a human ages, the heart becomes stiff with enlarged cardiomyocytes and reduced muscle cell contractility, both leading causes of heart failure and cardiac hypertrophy. Experiments were conducted during development of embodiments of the present application in order to characterize Lcn2 expression in heart from control and selenium treated PolG mice. A significant and dramatic increase in Lcn2 expression was discovered in aged PolG heart. Even more surprising was the observation that administration of selenium in the form of selenium enriched yeast comprising 2% or less inorganic selenium resulted in a significant reduction of Lcn2 expression in old PolG mice compared to control. These findings support other finding disclosed herein with regard to increased pNfat2/3 levels (e.g., inactivation of Nfat activity in gene transcription) in selenium-treated polG heart. In addition, it has been documented that Lcn2 is a Nfat target. Thus, although an understanding of a mechanism is not needed to practice the present application, and while the present application is not limited to any particular mechanism of action, in some embodiments, selenium in the form of selenium enriched yeast comprising 2% or less inorganic selenium (or one or more selenium containing compounds present therein), when administered to a subject (e.g., an aged subject) neutralizes and/or abolishes age-associated enhanced expression of Lcn2 in heart tissue (e.g., thereby inhibiting and/or preventing cardiac muscle hypertrophy (e.g., in aged subjects)).

Thus, in a preferred embodiment, the present application provides compositions (e.g., pharmaceutical compositions) comprising selenium in the form of selenium enriched yeast comprising 2% or less inorganic selenium (or a water soluble fraction thereof (e.g., described herein) or a water insoluble fraction thereof (e.g., described herein) or one or more selenium containing compounds present therein or obtained therefrom (e.g., described herein)), that are utilized to reduce the cardiac expression of hypertrophic protein (e.g., in order to prophylactically or therapeutically treat cardiac hypertrophy) in a subject (e.g., so as to inhibit cardiac hypertrophy and/or the expression of molecules involved in the thickening of the myocardium in a subject administered the composition comprising selenium compared to cardiac muscle thickness and/or the expression of molecules involved in the thickening of the myocardium in a control subject not receiving the composition comprising selenium).

In another preferred embodiment, the present application provides compositions (e.g., pharmaceutical compositions) comprising selenium in the form of selenium enriched yeast comprising 2% or less inorganic selenium (or a water soluble fraction thereof (e.g., described herein) or a water insoluble fraction thereof (e.g., described herein) or one or more selenium containing compounds present therein or obtained therefrom (e.g., described herein)), that are utilized for administration to a subject to prevent the expression of molecules involved in the thickening of the myocardium (e.g., so as to prevent cardiac hypertrophy in a human or animal subject administered the composition comprising selenium compared to presence or severity of cardiac hypertrophy of a control subject not receiving the composition comprising selenium). The present application is not limited by the type of cardiomyopathy prophylactically or therapeutically treated in a subject. Indeed, the compositions and methods of the present application find use in the prophylactic and/or therapeutic treatment of any cardiomyopathy that benefits from the reduction of the cardiac expression of hypertrophic protein including, but not limited to, hypertrophic cardiomyopathy (e.g., due to familial hypertrophic cardiomyopathy, myocardial infarction, or valvular heart disease (e.g., related to myxomatous degeneration of the valve, papillary muscle dysfunction or rheumatic fever)), dilated cardiomyopathy, restrictive cardiomyopathy, and arrhythmogenic right ventricular cardiomyopathy (ARVC).

Although an understanding of a mechanism is not needed to practice the present application, and while the present application is not limited to any particular mechanism of action, in preferred embodiments, administration of selenium in the form of selenium enriched yeast comprising 2% or less inorganic selenium (or a water soluble fraction thereof (e.g., described herein) or a water insoluble fraction thereof (e.g., described herein) or one or more selenium containing compounds present therein or obtained therefrom (e.g., described herein)) decreases cardiac expression of hypertrophic proteins (e.g., beta ($\beta$)-myosin heavy chain and/or ankyrin repeat protein) thereby inhibiting and/or preventing cardiac muscle aging and hypertrophy. In one non-limiting embodiment, a decrease in cardiac expression of hypertrophic proteins (e.g., beta ($\beta$)-myosin heavy chain and/or ankyrin repeat protein) in a subject administered a composition comprising selenium in the form of selenium enriched yeast and/or one or more selenium containing compounds present therein or obtained therefrom to a subject is obtained via the reduction of cardiac nuclear Nfatc2/3 activity related gene transcription in the subject. In another non-limiting embodiment, a decrease in cardiac expression of hypertrophic proteins (e.g., beta ($\beta$)-myosin heavy chain, ankyrin repeat protein) in a subject administered a composition comprising selenium in the form of selenium enriched yeast and/or one or more selenium containing compounds present therein or obtained therefrom to the subject occurs via the reduction of cardiac ribosomol protein kinase (pS6K1) expression and/or activity in the subject.

In some embodiments, a decrease in cardiac expression of hypertrophic proteins (e.g., beta ($\beta$)-myosin heavy chain, ankyrin repeat protein) in a subject administered a composition comprising selenium in the form of selenium enriched yeast and/or one or more selenium containing compounds present therein or obtained therefrom to the subject is obtained via the enhanced cardiac expression and/or activity of forkhead box O3 (foxo3) in the subject.

In some embodiments, a decrease in cardiac expression of hypertrophic proteins (e.g., beta ($\beta$)-myosin heavy chain, ankyrin repeat protein) in a subject administered a composition comprising selenium in the form of selenium enriched yeast and/or one or more selenium containing compounds present therein or obtained therefrom to the subject occurs via reduction or elimination of age-associated, enhanced cardiac expression of lipcalin-2 (Lcn2) in the subjection.

The present application is not limited by the type of subject administered the compositions and methods of the present application. Indeed, a variety of subjects find benefit from administration of the compositions and methods of the present application including, but not limited to, subjects in which the progression of cardiac hypertrophy is sought to be slowed, subjects in which the progression of cardiac hypertrophy is to be stopped and subjects in which the progression of cardiac hypertrophy is to be reversed. A non-limiting example of slowing the progression of cardiac hypertrophy in a subject is reducing the cardiac expression of hypertrophic proteins (e.g., beta (β)-myosin heavy chain and/or ankyrin repeat protein) in the subject via administration of a composition comprising selenium in the form of selenium enriched yeast and/or one or more selenium containing compounds present therein or obtained therefrom in an amount effective to reduce cardiac expression of hypertrophic proteins in the subject (e.g., compared to a control subject not receiving the composition comprising selenium).

The subject may display signs, symptoms or other indication of cardiac hypertrophy, or be at risk for (e.g., genetically predisposed to) displaying signs, symptoms or other indication of cardiac hypertrophy (e.g., not currently displaying signs, symptoms or other indication of cardiac hypertrophy but medically diagnosed with a genetic predisposition to be at an elevated risk for cardiac hypertrophy). In other embodiments, the subject has or is at risk for cardiomyopathy (e.g., hypertrophic cardiomyopathy (e.g., due to familial hypertrophic cardiomyopathy, myocardial infarction, valvular heart disease (e.g., related to myxomatous degeneration of the valve, papillary muscle dysfunction or rheumatic fever), etc.), dilated cardiomyopathy, restrictive cardiomyopathy, and arrhythmogenic right ventricular cardiomyopathy (ARVC)).

Changes in gene expression can be detected by comparing levels of mRNA expression in treated subjects verses untreated. Primers, and probes can be obtained and designed based on identifiable sequences. Primers or probes are typically about 200, 150, 100, 75, 50, 25, 15, 10 or 5 nucleotides or any integer in between 5 and 200 nucleotides. Primers or probes specifically hybridize to a nucleic acid sequence encoding a protein having the sequence shown below. Primers or probes can be detectably labeled with a reporter molecule.

TABLE 1

| Gene Symbol | Accession (NCBI) | GI (NCBI) | Accession (NCBI) | GI (NCBI) |
|---|---|---|---|---|
| Myh7 | NP_000248 | 115496169 | NM_000257 | 115496168 |
| AnKrd1 | NP_055206 | 38327522 | NM_014391 | 38327521 |
| Foxo3 | NP_001446 | 4503739 | NM_001455 | 146260266 |
| Pgc1a | NP_037393 | 7019499 | NM_013261 | 116284374 |
| Nr2F2 | NP_005645 | 5032173 | NM_005654 | 53749664 |
| Prkaa2 | NP_006243 | 46877068 | NM_006252 | 157909838 |
| Trim63 | NP_115977 | 19924163 | NM_032588 | 378744182 |
| Fbxo32 | NP_001229392 | 335057520 | NM_001242463 | 335057519 |
| Acvr2b | NP_001097 | 116734708 | NM_001106 | 116734707 |
| Gadd45g | NP_006696 | 5729836 | NM_006705 | 209413759 |
| UCP2 | NP_003346 | 13259541 | NM_003355 | 13259540 |
| UCP1 | NP_068605 | 11225256 | NM_021833 | 194733736 |
| UCP3 | NP_003347 | 4507807 | NM_003356 | 215272349 |
| Atm | NP_000042 | 71902540 | NM_000051 | 71902539 |
| mTOR | NP_004949 | 4826730 | NM_004958 | 206725550 |
| Gsk3b | NP_001139628 | 225903437 | NM_001146156 | 225903436 |
| S6K1 | NP_991385 | 45430051 | NM_205816 | 45430050 |
| MAP2k2 | NP_109587 | 13489054 | NM_030662 | 187171274 |
| NFAT1 | NP_001265598 | 522021835 | NM_001278669 | 522021834 |
| NFAT2 | NP_001129493 | 209862843 | NM_001136021 | 385137138 |
| Lcn2 | NP_005555 | 38455402 | NM_005564 | 108936956 |

Nucleic acid and protein sequence for genes disclosed herein can be determined by one of skill in the art. Exemplary sequences are shown in Table 1.

Sarcopenia

Sarcopenia, the age-related loss of skeletal muscle mass, is characterized by a deterioration of muscle quantity and quality leading to a gradual slowing of movement, a decline in strength and power, frailty and increased risk of fall-related injury. Sarcopenia has been defined as appendicular skeletal muscle mass (kg/height$^2$ (m$^2$)) being less than two standard deviations below the mean of a reference group (See, e.g., Baumgartner et al. (Am J Epidemiol 1998; 147:755-63; 149: 1161). Estimates of the prevalence of sarcopenia range from 13% to 24% in adults over 60 years of age to more than 50% in persons aged 80 and older. Growth hormone secretion declines progressively from mid puberty, and growth hormone is known to increase muscle mass. Patients with growth hormone deficiency have reduced muscle mass and increased fat mass. Growth hormone replacement increases the muscle mass and leads to a reduction in fat mass.

The normal mechanism involved in muscle tissue regeneration initially involves the recruitment of satellite cells. Muscle satellite cells are a distinct lineage of myogenic progenitors which are located between the basal lamina and sarcolemma of mature myofibers (See, e.g., Bischoff, 1994; Grounds and Yablonka-Reuveni, 1993). During the regeneration cycle, satellite cells are activated and migrate from the myofibres to the site of regeneration to produce myoblasts. Most proliferating myoblasts differentiate into myotubes. The myotubes mature and are incorporated into muscle fibres. Myoblasts that do not differentiate into myotubes return to the myfibers to renew the satellite cell population.

The muscle regeneration cycle occurs continuously throughout human and animal lifespan (e.g., to replace worn out or damaged muscle tissue). As the body ages the muscle regeneration cycle becomes less efficient. Sarcopenia, resulting in a decline in muscle mass and performance, is associated with normal aging. While the skeletal muscle remains capable of regenerating itself during aging, unknown factors in old aged muscles create an environment that is not supportive towards muscle satellite cell activation, proliferation and differentiation, resulting in a net loss of muscle tissue (See, e.g., Greenlund and Nair, 2003). Some growth factors, including Hepatocyte Growth Factor (HGF), Fibroblast Growth Factor (FF) and Mechano Growth Factor (MGF), have been shown to positively affect muscle regeneration by regulating satellite cell activation (Floss et al., 1997; Miller et al., 2000, Goldspink and Harridge; 2004).

The present application provides compositions comprising selenium (e.g., selenium enriched yeast and selenium containing compounds obtained or derived therefrom) and methods of using the same to treat and inhibit sarcopenia. In particular, the present application provides compositions comprising selenium enriched yeast (e.g., SELPLEX), selenium containing compounds present therein and/or derived therefrom, and methods of using the same to increase and/or maintain skeletal muscle mass in a subject (e.g., as a therapeutic and/or prophylactic treatment for sarcopenia). Experiments conducted during development of embodiments of the present application have discovered and shown that selenium enriched yeast (e.g., selenium enriched yeast comprising 2% or less inorganic selenium), when administered to a subject, enhances skeletal muscle protein synthesis and also inhibits proteasome protein degradation in skeletal muscle. Administration of selenium enriched yeast comprising 2% or less inorganic selenium to a subject also activated skeletal muscle satellite (stem) cells. Moreover, the administration of selenium enriched yeast to a subject activated expression of calcineurin thereby promoting hypertrophic gene expression in skeletal muscle.

Thus, in a preferred embodiment, the present application provides compositions (e.g., pharmaceutical compositions) comprising selenium in the form of selenium enriched yeast comprising 2% or less inorganic selenium (or one or more selenium containing compounds present therein or obtained therefrom), that are utilized to treat sarcopenia in a subject (e.g., so as to increase and/or maintain muscle mass in a human or animal subject administered the composition comprising selenium compared to the muscle mass of a control subject not receiving the composition comprising selenium). In another preferred embodiment, the present application provides compositions (e.g., pharmaceutical compositions) comprising selenium in the form of selenium enriched yeast comprising 2% or less inorganic selenium (or one or more selenium containing compounds present therein or obtained therefrom), that are utilized to prevent sarcopenia in a subject (e.g., so as to increase and/or maintain muscle mass in a human or animal subject administered the composition comprising selenium compared to the muscle mass of a control subject not receiving the composition comprising selenium).

Although an understanding of a mechanism is not needed to practice the present application, and while the present application is not limited to any particular mechanism of action, in some embodiments, the increase in total protein mass in a subject administered selenium in the form of selenium enriched yeast and/or one or more selenium containing compounds present therein or obtained therefrom is due to the stimulation of protein synthesis and/or the inhibition of protein degradation. In one non-limiting embodiment, the increase in total protein mass in subjects administered selenium (in the form of selenium enriched yeast comprising 2% or less inorganic selenium or a selenium containing compound present therein or derived therefrom) is due to the ability of selenium containing compounds present in selenium enriched yeast comprising 2% or less inorganic selenium to regulate Gsk3β and/or Ampk expression and alter mTOR/MAPK/S6K1 signaling, thus enhancing protein synthesis in skeletal muscle. Although an understanding of a mechanism is not needed to practice the present application, and while the present application is not limited to any particular mechanism of action, in some embodiments, selenium in the form of selenium enriched yeast comprising 2% or less inorganic selenium (or one or more selenium containing compounds present therein) stimulates hypertrophic gene expression (e.g., calcineurin and protein elongation factors) thereby increasing protein synthesis and combating atrophy in skeletal muscle.

In another non-limiting embodiment, an increase in total protein mass in a subject administered a composition comprising selenium in the form of selenium enriched yeast and/or one or more selenium containing compounds present therein or obtained therefrom to a subject is obtained via enhanced protein synthesis resulting from reducing the inhibitory effect of myostatin/Acvr signaling on protein synthesis (e.g., thereby inhibiting sarcopenia and/or leading to skeletal muscle hypertrophy). In some embodiments, an increase in total protein mass in a subject administered a composition comprising selenium in the form of selenium enriched yeast and/or one or more selenium containing compounds present therein or obtained therefrom to a subject is obtained via activation of skeletal muscle satellite cells. In some embodiments, an increase in total protein mass in a subject administered a composition comprising selenium in the form of selenium enriched yeast and/or one or more selenium containing compounds present therein or obtained therefrom to a subject is obtained via stimulation of signaling molecules calcineurin and/or NFAT.

Although an understanding of a mechanism is not needed to practice the present application, and while the present application is not limited to any particular mechanism of action, in some embodiments, inhibition of protein degradation and the prevention of skeletal muscle atrophy in subjects administered selenium (in the form of selenium enriched yeast comprising 2% or less inorganic selenium) is due to the ability of selenium containing compounds present in selenium enriched yeast comprising 2% or less inorganic selenium to reduce/attenuate expression of the atrophic genes Trim63 and Fbxo32 as a result of the reduced expression of mTOR, and/or attenuate activities involving Foxo transcription factors.

Accordingly, in some embodiments, the present application provides a method of treating sarcopenia comprising administering an effective amount of a composition comprising selenium in the form of selenium enriched yeast comprising 2% or less inorganic selenium or one or more selenium containing compounds present therein or obtained therefrom to a subject (e.g., a human or animal subject) in need thereof. In some embodiments, the present application provides use of a composition comprising selenium in the form of selenium enriched yeast comprising 2% or less inorganic selenium or one or more selenium containing compounds present therein or obtained therefrom in a method of increasing the activation of skeletal muscle satellite cells in a subject. In some embodiments, the present application provides use of a composition comprising selenium in the form of selenium enriched yeast comprising 2% or less inorganic selenium or one or more selenium containing compounds present therein or obtained therefrom in a method of reducing myostatin and/or Acvr inhibition of protein synthesis in a subject. In some embodiments, the present application provides use of a composition comprising selenium in the form of selenium enriched yeast comprising 2% or less inorganic selenium or one or more selenium containing compounds present therein or obtained therefrom in a method of inhibiting myostatin/Acvr signaling (e.g., via downregulation of expression of myostatin and/or Acvr (e.g., Acvr2b)) in a subject (e.g. to increase skeletal muscle mass in a subject).

Changes in gene expression can be detected by determining levels of mRNA expression as compared to a reference gene such as actinomycin b (Act b) or by detecting increased levels of protein using assays such as immune assays. Primers, and probes can be obtained and designed based on an exemplary reference sequence as shown below for the genes described herein. Such protein and nucleic acid sequences are publicly available. Primers or probes are typically about 200, 150, 100, 75, 50, 25, 15, 10 or 5 nucleotides or any integer in between 5 and 200 nucleotides. Primers or probes specifically hybridize to a nucleic acid sequence encoding a protein having the sequence shown below. Primers or probes can be detectably labeled with a reporter molecule. Such labels include Alexa flour, biotin, FAM, TAMRA, HEX, NED, ROX, and the like.

In some embodiments, the present application provides a method of maintaining or increasing muscle mass in a subject in need thereof comprising administering an effective amount of a composition comprising selenium in the form of selenium enriched yeast comprising 2% or less inorganic selenium or one or more selenium containing compounds present therein or obtained therefrom to the subject (e.g., to treat sarcopenia in the subject).

The present application is not limited by the type of subject for which skeletal muscle mass maintenance and/or increase is sought. As described above, sarcopenia as defined is the appendicular skeletal muscle mass (kg/height$^2$ (m$^2$)) being less than two standard deviations below the mean of a young reference group (the t-score). A t-score is determined by measuring the axial skeletal muscle mass of a subject, typically by dxa (dual energy xray absorptiometry) or a similar and reproducible measure. The measurement of axial skeletal muscle mass can be used to follow the progress of a subject (prior to, during and/or subsequent to use of a method of treating the subject described herein) to determine if treatment is slowing, preventing, or reversing skeletal muscle mass decline.

One object of the present application is to treat and/or inhibit sarcopenia including slowing its progression, stopping its progression, and partially reversing it. An example of slowing the progression of sarcopenia is changing the length of time a subject would go from a t-score of −1.5 to −2 (e.g., if such a progression would normally take 5 years, then treating as used herein could slow this change to 10 years). Examples of partial reversal include reducing a t-score 0.1, 0.2, 0.3, 0.4, 0.5, 0.6, 0.7, 0.8, 0.9, 1.0 or more units (e.g., moving from a t-score of −2 to a t-score of −1.9, −1.8, −1.7, −1.6, −1.5, −1.4, −1.3, −1.2, −1.1, etc.). Treating sarcopenia also includes delaying the onset of sarcopenia. For example, if a typical male age 50 would begin to see signs of sarcopenia by age 55, treatment according to the present application could delay the onset 1, 2, 3, 4, 5, 6, 7, 8, 9, 10, or more years. Thus, treating sarcopenia includes treating subjects that have not yet been diagnosed with sarcopenia, but that would be vulnerable or expected to be vulnerable to developing sarcopenia. Non-limiting examples of subjects that are vulnerable or expected to be vulnerable also include, but are not limited to, subjects being administered hormonal therapy including glucocorticoid steroids, subjects with a neurodegenerative disease, subjects with chronic infections, subjects with AIDS, subjects with a chronic inflammatory conditions and subjects with cancer.

Other subjects that benefit from the compositions and methods of the present application include those that have suffered loss of muscle mass but that do not suffer from a condition that interferes with acts of daily living and/or prevents the subject from living an independent life (e.g., a patient who might soon need assisted living).

For example, a subject that benefits from the compositions and methods of the present application includes a subject with a t score from, but not limited to, 3, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, 0.1, 0, −0.1, −0.2, −0.3, −0.4, −0.5, −0.6, −0.7, −0.8, −0.9, −1.0, −1.1, −1.2, −1.3, −1.4, −1.5, −1.6, −1.7, −1.8, −1.9, −2.0, −2.1, −2.2, −2.3, −2.4, −2.5, −2.6, −2.7, −2.8, −2.9, −3.0, −3.1, −3.2, −3.3, −3.4, −3.5, −3.6, −3.7, −3.8, −3.9, −4.0, −4.1, −4.2, −4.3, −4.4, −4.5, −4.6, −4.7, −4.8, −4.9, −5.0, −5.1, −5.2, −5.3, −5.4, −5.5, −5.6, −5.7, −5.8, −5.9, and −6.0. However, the present application is not so limited. For example, in some embodiments, a subject that benefits from the compositions and methods of the present application includes a subject with a t score higher than 3 or less than −6.0.

In some embodiments, a subject that benefits from the compositions and methods of the present application includes a subject of an age in years between, 40-45, 45-50, 50-55, 55-60, 60-65, 65-70, 70-75, 75-80, 80-85, 85-90, or older. However, the present application is not so limited. For example, in some embodiments, a subject that benefits from the compositions and methods of the present application includes a subject with an age younger than 40 (e.g., a subject with cancer, a subject with neurodegenerative disease, a subject with chronic inflammatory disease, etc.).

In a preferred embodiment, the present application provides a method of treating sarcopenia comprising administering an effective amount of a composition comprising selenium in the form of selenium enriched yeast comprising 2% or less inorganic selenium or one or more selenium containing compounds present therein or obtained therefrom to a subject (e.g., a human or animal subject) in need thereof.

Obesity, Type 2 Diabetes, and Related Conditions

Sarcopenia and obesity are two independent yet interconnected conditions that have a growing impact on life expectancy and health care costs in developed nations. The combination of diminished muscle mass with increased fat mass is referred to as "sarcopenic obesity" (See, e.g., Parr, E., Maturitas, 2013. 74: p. 109-113). Obesity exacerbates sarcopenia as it promotes an increase in fat mass and lipid accumulation that prevents amino acid incorporation and reduces protein synthesis in skeletal muscle (See, e.g., Parr, E., Maturitas, 2013. 74: p. 109-113). In turn, because skeletal muscle mass is critical to metabolic health with fundamental roles in whole-body glucose disposal and insulin sensitivity, sarcopenia exacerbates obesity (See, e.g., Parr, E., Maturitas, 2013. 74: p. 109-113). In addition to sarcopenia, obesity is often a side effect associated with other metabolic diseases such as, type II diabetes, hyperglycemia, and others. It is well understood that genetic predisposition and the expression of obesity associated molecules are also a contributing factor.

Obesity has a growing impact on life expectancy and health care costs in developed nations (See, e.g., Parr, E., Maturitas, 2013. 74: p. 109-113). Obesity is associated with several metabolic diseases such as type II diabetes, hyperglycemia metabolic syndrome, insulin resistance and many others. It is understood that genetics and the expression of specific genes associated with increased obesity play a contributing role to these conditions.

One such example is the fat mass and obesity related gene (FTO), also referred to as the "obesity gene." FTO is powerfully associated with increased body mass index and predisposition to obesity in children and adults (See, e.g., Gulati et al, PNAS, 2013. 110(7): p. 2557-2562). The FTO gene is ubiquitously expressed, but in the brain, mRNA levels are particularly high within the hippocampus, cerebellum and hypothalamus suggesting a potential role of brain FTO in the control of food intake, whole body metabolism and obesity (See, e.g., Church, PLoS Genetics, 2009).

Further experiments conducted during development of embodiments of the present application were performed in order to determine if administration of selenium to a subject might alter the expression of FTO. Utilizing the animal model described in Example 2, it was determined that subjects administered selenium in the form of selenium enriched yeast comprising 2% or less inorganic selenium displayed markedly reduced levels of FTO gene expression, not only in cortex tissue, (fold change=−1.70) but also in gastrocnemius tissue (fold change=−3.33) compared to control subjects.

There exists a strong association between increased FTO expression and reduced mitochondrial oxidative function in subjects with type 2 diabetes (See, e.g., Bravard et al, 2011). Several selenium containing compounds identified and isolated from selenium enriched yeast were discovered to significantly improve mitochondrial bioenergetics with increased mitochondrial ATP synthesis ability as well as increased maximum respiratory capacity using Complex I or II dependent substrates. Thus, the present application provides, in some embodiments, a method of treating a subject (e.g., a subject with diabetes and/or an obese subject) comprising administering an effective amount of a composition comprising selenium (selenium enriched yeast comprising 2% or less inorganic selenium, a water soluble fraction of selenium enriched yeast comprising 2% or less inorganic selenium, a water insoluble fraction of selenium enriched yeast comprising 2% or less inorganic selenium, an extract of selenium enriched yeast (e.g., soluble under acidic conditions), soluble selenoglycoprotein, a selenium containing compounds (e.g., obtained or derived from selenium enriched yeast (e.g., selenium enriched yeast comprising 2% or less inorganic selenium) or derivatives thereof, an isolated or synthesized selenium containing compound (e.g., selenoethers, conjugates of SeCys containing di- and/or tripeptides, selonols or selenoxides (or derivatives thereof), selenium containing proteins and/or selenium containing peptides described herein (e.g., in Example 1) to the subject (e.g., thereby enhancing mitochondrial ATP production, increasing mitochondrial respiration, increasing glucose metabolism, and/or reducing the expression of molecules associated with obesity (e.g., FTO)).

Experiments were also conducted during development of embodiments of the present application in order to investigate if administration of selenium to subjects could alter OXPHOS activity in the subject's liver and/or skeletal muscle (e.g., as a therapeutic for type 2 diabetes). Empirical data generated during development of embodiments of the present application discovered that administration of selenium in the form of selenium enriched yeast comprising 2% or less inorganic selenium resulted in significant enhancement of PGC1-α expression in skeletal muscle compared to control subjects.

PGC1-α is a powerful transcriptional coactivator which enhances mitochondrial activity in skeletal muscle. However, expression of elevated PGC1-α levels in tissues other than skeletal muscle may have a deleterious and/or harmful effect in a subject. For example, in liver, PGC1-α performs a different role than the role it performs in skeletal muscle. In particular, elevated PGC1-α levels in liver leads to increased gluconeogenesis (glucose production; See, e.g., Liang and Ward, 2006), an extremely unfavorable event to occur in a diabetic subject with impaired insulin sensitivity that is unable to metabolize glucose.

Unexpectedly, it was discovered that administration of selenium in the form of selenium enriched yeast comprising 2% or less inorganic selenium resulted in significant reduction of PGC1-α expression in liver tissue compared to control subjects. This discovery was surprising based upon the observation that administration of selenium in the form of selenium enriched yeast comprising 2% or less inorganic selenium resulted in significant enhancement of PGC1-α expression in skeletal muscle compared to control subjects. Thus, in some embodiments, the present application provides compositions comprising selenium enriched yeast comprising 2% or less inorganic selenium (or one or more selenium containing compounds present therein or derived therefrom (e.g., described in Example 1) for use in methods of enhancing PGC1-α expression in skeletal muscle of a subject while concurrently decreasing PGC1-α expression in liver in the subject (e.g., thereby providing a subject with enhanced glucose metabolism and disposal in skeletal muscle (e.g., via enhanced OXPHOS) and suppressed glucose production in liver).

COUP-TFII (COUP transcription factor 2), also known as Nr2F2 (nuclear receptor subfamily 2, group F, member 2) is a putative direct inhibitor of PGC1-α (See, e.g., Lin et al., 2011). Experiments were conducted to analyze expression of Nr2F2 in subjects administered a composition comprising selenium. Again, it was surprising to find that administration of selenium in the form of selenium enriched yeast comprising 2% or less inorganic selenium resulted in a significant reduction of Nr2F2 expression in skeletal muscle compared to control subjects whereas there was a significant enhancement of Nr2F2 in liver tissue compared to control. Thus, the present application provides the first evidence regarding the utility of a composition comprising selenium in the form of selenium enriched yeast comprising 2% or less inorganic selenium (or one or more water soluble fractions thereof or one or more water insoluble fractions thereof or one or more selenium containing compounds present therein or derived therefrom (See Example 1)) for use in regulating glucose homeostasis in multiple tissues (e.g., skeletal muscle tissue and liver tissue) in a subject.

Accordingly, the present application provides, in some embodiments, a method of treating (therapeutically or prophylactically) a subject (e.g., a subject with type 2 diabetes) comprising administering an effective amount of a composition comprising selenium enriched yeast comprising 2% or less inorganic selenium (or one or more water soluble fractions thereof or one or more water insoluble fractions thereof or one or more selenium containing compounds present therein or derived therefrom) to enhance PGC1-α expression in skeletal muscle of the subject while concurrently decreasing PGC1-α expression in liver in the subject (e.g., thereby enhancing glucose metabolism and/or disposal in the skeletal muscle of the subject and suppressing glucose production in liver in the subject). Although an understanding of a mechanism is not needed to practice the present application, and while the present application is not limited to any particular mechanism of action, in some embodiments, enhancement of glucose metabolism/disposal in skeletal muscle of a subject with concurrent suppression of glucose production in liver in the subject occurs via the ability of selenium, when administered to a subject, to reduce expression of Nr2f2 in the skeletal muscle of a subject (e.g., thereby enhancing PGC1-α expression in the skeletal muscle) and to enhance the expression of Nr2f2 in liver of a subject (e.g., thereby reducing PGC1-α expression in the liver).

The present application also provides that it is possible to preferentially and differentially regulate liver specific mitochondrial activity via administration of selenium enriched yeast comprising 2% or less inorganic selenium, whereas administration of selenium selenite or selenomethionine were significantly less effective. Accordingly, the present application provides administration of selenium (e.g., selenium enriched yeast comprising 2% or less inorganic selenium, sodium selenite, etc.) to a subject may be used to elicit/enhance the liver specific expression of glucose-burning (OXPHOS) genes and/or glucose metabolism. Accordingly, in some embodiments, the present application provides methods of enhancing glucose utilization in the liver of subjects via administration of selenium (e.g., selenium enriched yeast (e.g., comprising 2% or less inorganic selenium) or one or more water soluble fractions thereof or one or more water insoluble fractions thereof or one or more selenium containing compounds present therein or derived therefrom, sodium selenite, etc.) to a subject in need thereof (e.g., a type 2 diabetic subject).

Experiments conducted during development of embodiments of the present application documented that the increase in OXPHOS gene expression in the liver of subjects administered the selenium compositions described herein exhibited a modest, albeit significant, increase in expression (about 20-25%) compared to controls. This increase is in accordance with the documented and corresponding gene expression decreases seen in insulin-resistant and diabetic subjects (See, e.g., Mootha et al., 2004). Accordingly, in some embodiments, compositions and methods of the present application are utilized to treat type 2 diabetes in a subject (e.g., although an understanding of a mechanism is not needed to practice the present application, and while the present application is not limited to any particular mechanism of action, in some embodiments, the present application provides compositions and methods that increase in liver specific mitochondrial activity (e.g., that restore the decreased mitochondrial activity observed in type 2 diabetic subjects).

Further experiments were conducted during development of embodiments of the present application in order to determine if specific selenium containing compounds identified in Example 1 possessed biological activity(ies) (e.g., to determine whether a selenium containing compound would display biological activity and/or whether a selenium containing compound might be more (or less) biologically active if isolated and purified from the constraints of the yeast cell and/or the internal mélange of other, non-selenium-containing, cellular components). A number of the most abundant selenium containing compounds and molecules identified from selenium enriched yeast in Example 1 were synthesized.

One focus of the experiments was on the water-soluble extract which as described in Example 1 accounted for up to 25% of the total selenium present in the selenium enriched yeast. It was postulated that selenium containing compounds from the water soluble extract would be the first to be liberated/digested from the selenium enriched yeast upon consumption by a subject and its passage through the intestinal tract. Also described in Example 1 above, selenium-containing proteins present in the selenium enriched yeast were identified using computer-assisted prediction modeling. Moreover, experiments identified small, selenium containing peptides that are liberated by the action of digestive enzymes (e.g., trypsin).

Multiple selenium-containing compounds were generated for analysis and characterization. In order to determine what potential effects, if any, the individual selenium containing compounds had on mitochondrial bioenergetics, the selenium containing compounds were tested directly using isolated mitochondria. Several of the selenium containing compounds demonstrated positive increase in mitochondrial activity in all three states of respiration and increased mitochondrial bioenergetics profiles. Thus, the present application provides the identification and characterization of selenium containing compounds (e.g., LVSe-MR ($C_{22}H_{44}N_7O_5Se$), methylselenoadenosine ($C_{11}H_{15}N_5O_3Se$), Selenoadenosylhomocysteine ($C_{14}H_{20}N_6O_5Se$)) and other compounds identified in Example 1) and compositions comprising the same for use in modulating mitochondrial activity/bioenergetics in a subject (e.g., a subject in need thereof (e.g., a type 2 diabetic subject)).

For example, in some embodiments, the present application provides a composition (e.g., a pharmaceutical composition) comprising a selenium containing compound described herein (e.g., in Example 1 (e.g., for use in the manufacture of a medicament for the treatment of a condition or disease (e.g., obesity, diabetes, insulin resistance, metabolic syndrome, chronic inflammation (e.g., of the liver, adipose tissue, etc.) hepatic steatosis, etc.). In some embodiments, the present application provides a method of treating a subject in need thereof (e.g., an obese subject) comprising administering an effective amount of a composition (e.g., a pharmaceutical composition) comprising a selenium containing compound described herein (e.g., in Example 1) to the subject to increase mitochondrial activity (e.g., skeletal muscle specific or liver specific mitochondrial activity (e.g., resulting in enhanced glucose metabolism in the subject)). In some embodiments, the present application provides a method of treating a subject in need thereof (e.g., a diabetic subject) comprising administering an effective amount of a composition (e.g., a pharmaceutical composition) comprising a selenium containing compound described herein (e.g., in Example 1) to the subject to increase mitochondrial activity (e.g., skeletal muscle specific or liver specific mitochondrial activity). Although an understanding of a mechanism is not needed to practice the present application, and while the present application is not limited to any particular mechanism of action, in some embodiments, increasing mitochondrial activity (e.g., skeletal muscle specific or liver specific mitochondrial activity) in a subject occurs via increasing ATP synthesis in the mitochondria. In some embodiments, increasing mitochondrial activity (e.g., skeletal muscle specific or liver specific mitochondrial activity) in a subject occurs via increasing respiratory capacity (e.g., maximum respiratory capacity (e.g., using Complex I or II dependent substrates)).

Another surprising finding was the fact that while certain selenium containing compounds displayed mitochondrial activity-enhancing properties when incubated with mitochondria, this was not the case for a number of the other selenium containing compounds identified and characterized. For example, several selenium containing compounds displayed a negative effect on mitochondrial activity. In particular, it was surprising to find that several selenium containing compounds that share some similarity in overall structure displayed vastly different biological properties with regard to the ability to alter mitochondrial activity. For example, glutamylselenocysteine ($C_{16}H_{26}N_{24}O_{10}Se_2$)(#10) decreased ATP synthesis (State III) by almost 19% even though its overall structure is similar to/not vastly different from methylselenoadenosine ($C_{11}H_{15}N_5O_3Se$) (#9) which increased ATP synthesis by 17.3%. This is a greater than 36% swing in effect on mitochondrial activity between these two selenium containing compounds present in selenium enriched yeast.

Due to the fact that several of the selenium containing compositions of the present application displayed the ability to enhance the activity of mitochondrial Complex I, experiments were conducted in order to determine if mitochondrial stimulation might take place through removal of damaging reactive oxygen species (ROS) by the selenium containing compounds. Thus, experiments were conducted during development of embodiments of the present application in order to assess the antioxidant potential of selenium containing compounds.

It was discovered that some of the selenium containing compounds possess/display antioxidant capacity. Moreover, some of the selenium containing compounds possess/display antioxidant capacity that is additive or mildly synergistic, mildly antagonistic, or synergistic (e.g., in terms of oxygen radical-scavenging ability).

The data and information generated during development of embodiments of the present application are unique and unprecedented findings. In particular, the present application provides new compositions and methods for the treatment (e.g., prophylactic and/or therapeutic treatment) of mitochondrial dysfunction or insufficiency (e.g., related to diabetes (e.g., type II diabetes), obesity, insulin resistance, diabetic cardiomyopathy, etc.). In some embodiments, the present application provides a composition comprising two or more selenium containing compounds (e.g., a water soluble fraction of selenium enriched yeast, a water insoluble fraction of selenium enriched yeast, a selenium containing compound present in selenium enriched yeast and/or derived therefrom) that are combined to generate a composition comprising a desired, specific mitochondrial activity enhancing ability.

For example, in some embodiments, compositions (e.g., pharmaceutical compositions) comprise 2 or more (e.g., 3 or more, 4 or more, 5 or more, 6 or more, 7 or more, 8 or more, 9 or more, 10 or more, 15 or more, 20 or more, 30 or more, 40 or more, or 50 or more) distinct selenium containing compounds (e.g., those described herein). In some embodiments, the present application provides a composition comprising a combination of 2 or more (e.g., 3 or more, 4 or more, 5 or more, 6 or more, 7 or more, 8 or more, 9 or more, 10 or more, 15 or more, 20 or more, 30 or more, 40 or more, or 50 or more) selenium containing compounds (e.g., isolated, chemically synthesized, or recombinant selenium containing compound) tailored for a specific use (e.g., that, when combined, display a desired level of bioactivity (e.g., stimulatory and/or inhibitory activity)).

For example, in some embodiments, a first composition comprising a combination of two or more selenium containing compounds is utilized to enhance mitochondrial activity (e.g., ATP production and/or glucose metabolism) in muscle tissue, whereas a second composition comprising a combination of two or more different selenium containing compounds (e.g., displaying bioactivity that is different than the first composition) is utilized to alter mitochondrial activity (e.g., ATP production and/or glucose metabolism) in liver tissue. In some embodiments, the present application provides a composition (e.g., a pharmaceutical composition) comprising a selenium containing compound (e.g., identified in Example 1). In some embodiments, the present application provides a method of increasing PDHC enzyme activity and/or increasing mitochondrial Complex I activity in a subject comprising administering to a subject in need thereof (e.g., a type II diabetic subject) an effective amount of a composition (e.g., a pharmaceutical composition) comprising a selenium containing compound (e.g., described in Example 1) to the subject that increases mitochondrial Complex I and/or PDHC activity (e.g., thereby increasing mitochondrial respiration in the subject (e.g., in skeletal muscle and or liver).

In some embodiments, provided herein are methods of treatment comprising: administering a pharmaceutically effective amount of a composition comprising selenium (e.g., selenium enriched yeast comprising 2% or less inorganic selenium, a water soluble fraction of selenium enriched yeast comprising 2% or less inorganic selenium, a water insoluble fraction of selenium enriched yeast comprising 2% or less inorganic selenium, an extract of selenium enriched yeast (e.g., soluble under acidic conditions), soluble selenoglycoprotein, a selenium containing compounds (e.g., obtained or derived from selenium enriched yeast (e.g., selenium enriched yeast comprising 2% or less inorganic selenium) or derivatives thereof, an isolated or synthesized selenium containing compound (e.g., selenoethers, conjugates of SeCys containing di- and/or tri-peptides, selonols or selenoxides (or derivatives thereof), selenium containing proteins and/or selenium containing peptides described herein (e.g., in Example 1), alone or in combination with another agent, to a subject with a condition associated with obesity or insulin resistance. In some embodiments, the administration causes one or more of a reduction in or elimination of one or more symptoms of the condition, prevention of increased severity of one or more symptoms of the condition, and/or reduction, prevention, or elimination of further diseases or conditions.

In certain embodiments, the insulin resistance is in the subject's adipocyte cells, liver cells, or muscle cells. In particular embodiments, the insulin resistance causes the subject to have impaired glucose metabolism. In further embodiments, administration of a selenium containing composition of the present application causes an increase in glucose metabolism in the subject (e.g., by adipocytes, liver and/or skeletal muscle). In some embodiments, the increase in glucose metabolism is caused by increased mitochondrial ATP synthesis, mitochondrial respiration, and/or insulin receptor signaling.

In particular embodiments, administration of a selenium containing composition of the present application causes a reduction of body fat in the subject (e.g., the size and/or number of adipocytes in the subject is reduced). In certain embodiments, the administering causes a subject to lose at least 10 pounds (e.g., 10, 15, 20, 35, 60, 100, 200 or more pounds). In some embodiments, the administration causes at least a 5% reduction in the subject's body weight (e.g., at least 7%, 10%, 20%, 30%, 50%, 75% reduction or more). In some embodiments, the condition treated is obesity. In other embodiments, the condition treated is diabetes (e.g., type II or both types I and II). In further embodiments, the condition treated is insulin resistance.

In some embodiments, the subject is experiencing or is at risk of experiencing a condition such as obesity, diabetes, and insulin resistance. In some embodiments, the treatment results in an outcome of increased glucose metabolism, reduction in body fat, lack of increase in body fat, increased insulin receptor signaling, increased/enhanced mitochondrial activity, reduction in or prevention of chronic inflammation in the liver, reduction in or prevention of chronic inflammation in adipose tissue, reduction in or prevention of hepatic steatosis, promotion of metabolic energy expenditure, reduction in circulating free fatty acids, and/or reduction in cholesterol.

Conditions and disease states that may be treated by the methods and pharmaceutically acceptable compositions provided herein include, but are not limited to, obesity, diabetes, type II diabetes, metabolic syndrome, insulin resistance syndrome, lipid metabolic conditions, and hepatic steatosis disease (also referred to as fatty liver disease). Fatty liver disease can range from fatty liver alone (steatosis) to fatty liver associated with inflammation (steatohepatitis).

Fertility

Conditions and disease states that may be treated by the methods and pharmaceutically acceptable compositions provided herein include, but are not limited to, obesity, diabetes, type II diabetes, metabolic syndrome, insulin resistance syndrome, lipid metabolic conditions, and hepatic steatosis disease (also referred to as fatty liver disease). Fatty liver disease can range from fatty liver alone (steatosis) to fatty liver associated with inflammation (steatohepatitis).

The recent social pattern of having children at an advanced maternal age (≥35 years) has had an increasing impact on the demand for health care services. In addition to decreased fertility, women over 35 are at higher risk for birth complications and defects (See, e.g., Noda et al., Biology of Reproduction, 2012. 86(1): p. 1-8). A study conducted in the U.S. concluded that advanced maternal age was one of the most prevalent risk factors related to the stillbirths and despite higher rates of obstetric intervention, advanced age women have higher rates of preterm birth, caesarean delivery, and low birth weight (LBW) (See, e.g., Noda et al., Biology of Reproduction, 2012. 86(1): p. 1-8).

Moreover, preexisting maternal medical conditions such as obesity and diabetes, increase with advanced maternal age, as do pregnancy-related maternal complications such as pre-eclampsia and gestational diabetes (See, e.g., Hoque, M., *Advanced maternal age and outcomes of pregnancy: A retrospective study from South Africa.* 2012. Obesity not only decreases ovulation in females, it also significantly reduces the chance for pregnancy in women who ovulate regularly. A mouse model of maternal obesity also demonstrated high incidence of spindle abnormalities as well as increased reactive oxygen species (ROS) generation in oocyte mitochondria (See, e.g., Mills et al., Obstetrics, Gynaecology & Reproductive Medicine, 2011. 21(4): p. 107-111). Toxic conditions (e.g., increased ROS) to which oocytes are exposed in diabetic mothers induce significant mitochondrial damage (See, e.g., Shaum, Maturitas, 2013). Additionally, murine models of diabetes have demonstrated an increase in granulosa cell apoptosis and impaired oocyte maturation (See, e.g., Shaum, Maturitas, 2013). These and other animal model studies have highlighted the role of oocyte dysfunction in obesity and diabetes.

The linkage between obesity, diabetes, and fertility is of particular concern given the ongoing obesity epidemic, the prevalence of diabetes, and the trend of delayed childbirth in women over 35 years of age (See, e.g., Chang et al., Endocrinology, 2005. 146(5): p. 2445-53).

Recent data suggest a central role for mitochondria and the accumulation of point mutations and deletions of mitochondrial DNA (mtDNA) on the process of aging. Dysfunctional mitochondria and the subsequent low ATP production is one of the major factors that compromise oocyte quality (See, e.g., Bentov et al., Fertility and Sterility 2013. 99(1)). During the process of mitochondrial replication and expansion, oocytes dramatically amplify their population of mitochondria and have by far, the largest number of mitochondria and mitochondrial DNA (mtDNA) copies of any cell.

Oocytes of women with ovarian insufficiency have been reported to contain a lower mtDNA copy number than women with a normal ovarian profile. Interestingly, female mtDNA-mutator mice (POLG, described herein) that prematurely expresses phenotypic characteristics similar to that of an individual of advanced age suffer a profound reduction in fertility and could not conceive after the age of 20 weeks despite being exposed to males for several months (See, e.g., Yu et al., J Cell Physiol., 2010. 3: p. 672-80). These, and other studies indicated that reproductive aging is not the result of a preferential selection of oocytes, but rather the effect of the aging process and, more specifically, the aging effect on the function of the mitochondria.

High levels of reactive oxygen species ROS are strongly associated with mtDNA damage and about 90% of cellular ROS is produced by the mitochondria at complexes I and III.

Levels of ROS in follicular fluid can be used for predicting the success of in vitro fertilization and elevated levels of ROS in peritoneal fluid are suspected to be the culprit of infertility in some women who do not have any other obvious cause (See, e.g., Trifunovic et al., Nature, 2004. 429(6990): p. 417-423). In addition, baseline total antioxidant capacity (TAC) levels have shown to be higher in follicles whose oocytes fertilized successfully (See, e.g., Cupta et al., Reprod Fertil Dev, 2011. 23(5): p. 673-80).

Thus, in some embodiments, the present application provides compositions and methods of enhancing and/or maintaining fertility (e.g., in oocytes (e.g., aged oocytes)). In some embodiments, a composition comprising selenium (e.g., a selenium containing compound described herein) is administered to a subject in need thereof (e.g., a subject wishing to become pregnant) in an effective amount to maintain or enhance fertility. The present application also provides, in some embodiments, use of a composition comprising selenium (e.g., described herein) in the manufacture of a medicament or nutritional supplement for the maintenance and/or enhancement of fertility. In some embodiments, compositions and methods of the present application are utilized to improve oocyte quality, quantity, and/or functionality (e.g., via reduction of reactive oxygen species and/or increase in total antioxidant capacity (e.g., within mitochondria)).

Thus, the present application provides that a variety of mitochondrial diseases can be treated utilizing the compositions and methods of the present application including diseases that display signs or symptoms caused by dysfunction of mitochondria in cells. Examples of mitochondrial disease include, but are not limited to, mitochondrial encephalomyopathy, lactic acidosis, and stroke-like episodes (termed MELAS), chronic progressive external ophthalmoplegia, myoclonus epilepsy associated with ragged-red fibers; Fukuhara syndrome, Leber's disease, Leigh encephalopathia and Pearson's disease are widely known.

In some embodiments, the present application provides methods for regulating skeletal muscle metabolism or skeletal muscle energy homeostasis, or liver metabolism or liver energy homeostasis in a subject. In such methods, an effective amount of a composition comprising selenium (e.g., described herein) is administered to a subject in need thereof. Methods for regulating skeletal muscle metabolism or skeletal muscle energy homeostasis in a subject include administering to a subject in need thereof a composition comprising selenium (e.g., described herein) that modulates mitochondrial activity (e.g., as described herein). Compositions and methods of the present application may also be used to counterbalance the effects of certain drugs on liver and/or muscle activity (e.g., during and/or after treatment with a chemotherapeutic drug (e.g., used for treating cancer and/or autoimmune disease). Compositions and methods of the present application may also be used to enhance the performance (e.g., physical performance) of healthy subjects.

In some embodiments, a composition comprising selenium (e.g., described herein) is administered to a subject in need thereof in order to increase mitochondrial function and/or activity in the subject (e.g., in order to treat (e.g., prophylactically or therapeutically) a condition or disease associated with mitochondrial dysfunction). In some embodiments, administration of a composition comprising selenium described herein decreases mitochondrial cell death in the subject. In some embodiments, administration of a composition comprising selenium described herein decreases reactive oxygen species production in the subject. In some embodiments, administration of a composition comprising selenium described herein decreases hypoxia related signs, symptoms or conditions in the subject. In some embodiments, administration of a composition comprising selenium described herein increases mitochondrial ATP production in the subject. In some embodiments, administration of a composition comprising selenium described herein increases mitochondrial respiration in the subject.

Cardiovascular diseases that can be treated using compositions and methods of the present application include cardiomyopathy or myocarditis; such as idiopathic cardiomyopathy, metabolic cardiomyopathy, alcoholic cardiomyopathy, drug-induced cardiomyopathy, ischemic cardiomyopathy, and hypertensive cardiomyopathy. Also treatable or preventable using the compositions and methods described herein are atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries. Other vascular diseases that can be treated or prevented include those related to the retinal arterioles, the glomerular arterioles, the vasa nervorum, cardiac arterioles, and associated capillary beds of the eye, the kidney, the heart, and the central and peripheral nervous systems.

In like manner, compositions and methods of the present application may be used to treat (e.g., prophylactically and/or therapeutically) muscular diseases. Muscular diseases include, but are not limited to, muscular dystrophy and myopathy.

Compositions and methods of the present application may be utilized to treat insulin resistance disorders (e.g., any disease or condition that is caused by or contributed to by insulin resistance). Examples include, but are not limited to, diabetes, obesity, metabolic syndrome, insulin-resistance syndromes, syndrome X, insulin resistance, high blood pressure, hypertension, high blood cholesterol, dyslipidemia, hyperlipidemia, dyslipidemia, atherosclerotic disease including stroke, coronary artery disease or myocardial infarction, hyperglycemia, hyperinsulinemia and/or hyperproinsulinemia, impaired glucose tolerance, delayed insulin release, diabetic complications, including coronary heart disease, angina pectoris, congestive heart failure, stroke, cognitive functions in dementia, retinopathy, peripheral neuropathy, nephropathy, glomerulonephritis, glomerulosclerosis, nephrotic syndrome, hypertensive nephrosclerosis, complications of pregnancy, poor female reproductive health (such as menstrual irregularities, infertility, irregular ovulation, polycystic ovarian syndrome (PCOS)), lipodystrophy, cholesterol related disorders, such as gallstones, cholescystitis and cholelithiasis, gout, obstructive sleep apnea and respiratory problems, osteoarthritis, and prevention and treatment of bone loss, e.g. osteoporosis.

The present application is not limited by the type of selenium administered to a subject. The source of selenium may be a synthetic or natural source, and the selenium may be organic or inorganic. As described herein, and depending on the target sought to be treated in a subject, multiple forms of selenium may be used, independently or in combination with one another. In a preferred embodiment, a subject is administered selenium in the form of selenium enriched yeast comprising 2% or less inorganic selenium (e.g., SEL-PLEX). In some embodiments, the present application also provides the use and administration of selenium containing compounds (e.g., obtained or derived from selenium enriched yeast) or derivatives thereof. In some embodiments, the present application provides the use and administration of selenium containing fractions prepared from selenium enriched yeast. For example, in some embodiments, a composition comprising selenium administered to a subject comprises a water soluble fraction of selenium enriched yeast. In some embodiments, a composition comprising selenium administered to a subject comprises a water insoluble fraction of selenium enriched yeast.

In some embodiments, a composition comprising selenium administered to a subject comprises a single, liquid phase comprising the extract of selenium enriched yeast (e.g., soluble under acidic conditions (e.g., a fraction of soluble selenium containing compounds (e.g., soluble selenoglycoproteins) extracted and/or precipitated at a first pH (e.g., pH of 1.85), a second fraction precipitated at a second pH (e.g., pH of 3.0), a third fraction precipitated at a third pH (e.g., pH of 4.0), and a fourth fraction precipitated at a fourth pH (e.g., pH of 6.0))). In some embodiments, a composition comprising selenium administered to a subject comprises an extract of selenium enriched yeast prepared as described in U.S. Patent Publication No. 20120164234A1, published 28 Jun. 2012, hereby incorporated by reference in its entirety.

In some embodiments, the present application provides one or more selenium containing compounds (e.g., selenoethers, conjugates of SeCys containing di- and/or tri-peptides, selonols and selenoxides (or derivatives thereof), selenium containing proteins and/or selenium containing peptides, compositions comprising the same and methods of using the same (e.g., for human and/or animal use as described herein) (See Example 1).

For example, in some embodiments, a composition comprising selenium that is administered to a subject (e.g., in a method of the present application) comprises one or more of the following: 2,3-DHP-selenocysteine-cysteine, N-acetylselenocysteine-selenohomocysteine, methylthioselenoglutathione, 2,3-DHP-selenocysteine-selenocysteine, 2,3-DHP-selenocysteine-cysteinylglycine, 2,3-DHP-selenocysteine-selenohomocysteine, 2,3-DHP-selenocysteine-selenohomocysteine, 2,3-DHP-selenohomocysteine-cysteinylglycine, selenomethylselenoglutathione, selenoglutathione-cysteine, glutathione-selenohomocysteine, 2,3-DHP-selenocysteine-γ-glutamoylcysteine, di-2,3-DHP-selenocysteine, N-acetylcysteine-selenoglutathione, Selenoglutathione-selenocysteine, 2,3-DHP-selenocysteine-2,3 DHP selenohomocysteine, glutathione-N-acetylselenohomocysteine, glutathione-selenocysteinylglycine, γ-glutamoyl selenocysteine-γ-glutamoyl cysteine, γ-glutamoylcysteine-2,3-DHP-selenocysteine, glutathione-2,3-DHP-selenocysteine, glutathione-2,3-DHP-selenohomocysteine, di-γ-glutamoylselenocysteine, selenoglutathione-γ-glutamoylcysteine, selenoglutathione-2,3-DHP-selenocysteine, selenoglutathione-2,3-DHP-selenohomocysteine, selenoglutathion-thio-2,3-DHP-selenocysteine, selenoglutathione-γ-glutamoylselenocysteine, selenoglutathione-glutathione, selenodiglutathione, diselenoglutathione, thio-diselenoglutathione, methyl dehydrohomocysteine, selenomethionine, selenohomolanthionine, N-acetylselenocystathionine, dehydroxy 5'-methylselenoadenosine, N-acetylcysteine-selenohomocysteine, 2,3-DHP-selenolanthionine, ethylselenoadenosine, N-propionylselenocystathionine, 2,3-DHP-selenocystathionine, methylselenoglutathione, γ-glutamoylselenocystathione, selenoglutathione, seleno(hydroxyl)-selenophene-(3'-deoxy-adenosine), N-acetylcysteine-selenohomocysteine, allylselenoadenosyl homocysteine, seleno-adenosyl homocysteine, seleno-hydroxy adenosyl homocysteine, selno adenosine, seleno-adenosyl-Se(methyl)-selenoxide, adenosyl-hydroxy selenoxide, ethyl selenoadenosine, seleno-(hydroxy)-selenophene-(3'-desoxy-adenosine), adenosyl-hydroxy selnoxide, and selno-adenosyl-Se(methyl)-selenoxide. In some embodiments, the present application provides methods of identifying selenium containing compounds present within selenium enriched yeast (e.g., methods described in Example 1).

In some embodiments, a composition comprising selenium that is administered to a subject (e.g., in a method of the present application) comprises one or more proteins or peptide fragments, wherein one or more sulfur molecules present within one or more amino acid residues of the protein or peptide is substituted with a selenium molecule. The present application is not limited to a specific selenium containing protein or peptide. In a preferred embodiment, a composition comprising selenium that is administered to a subject (e.g., in a method of the present application) comprises one or more peptide fragments wherein one or more sulfur molecules present within one or more amino acid residues of the peptide is substituted with a selenium molecule from the following: MVAEAEK, DYMGAAK, YMGAAK, ELQDIANPIMSK, NQAAMNPSNTVFDAK, NFTPEQISSMVLGK, NFTPEQISSMVLGK, MVSEAEK, PEVQGDMK, ELQDIANPIMSK, AMSSR, VQGSVIG-IDLGTTNSAVAIMEGK, AAAEGPMK, LTGMAFR, PFVSNDYAAYMVK, AFGIEEGLMTTVHSLTATQK, PFITNDYAAYMFK, PGMVVTFAPAGVTTEVK, VETG-VIKPGMVVTFAPAGVTTEVK, AAATAAMTK, SIVPS-GASTGVHEALEMR, WMGK, SIVPSGAST-GVHEALEMR, AMPQK, AAMAK, HVGDMEIR, VIEEPITSETAMK, VLQALEEIGIVEISPK, LPAASLGD-MVMATVK, AGMTTIVR, AGMTTIVR, MLMPK, TMGAK, MNAGR, TYENMK, MGHDQSGTK, GEAIM-APK, Ac-MNVFGK, AMEVVASER, IVMR, MA(I/L)R, AMXAK, DLETLTMHTK, LVMR, VMR, LTGMAFR, SRPNVEVVALNDPFITNDYAAYMFK, and VINDAF-GIEEGLMTTVHSLTATQK.

Other forms of selenium containing compounds that find use in various embodiments of the present application are described in U.S. Pat. Nos. 6,911,550 6,197,295, 5,221,545, 6 and 6,576,233, and U.S. Pat. App. Nos. 20010043925, 20050069594, and 20050089530, herein incorporated by reference in their entireties.

In some embodiments, compositions (e.g., pharmaceutical compositions) comprise 2 or more (e.g., 3 or more, 4 or more, 5 or more, 6 or more, 7 or more, 8 or more, 9 or more, 10 or more, 15 or more, 20 or more, 30 or more, 40 or more, or 50 or more) distinct selenium containing compounds (e.g., those described herein). In some embodiments, the present application provides a composition comprising a combination of 2 or more (e.g., 3 or more, 4 or more, 5 or more, 6 or more, 7 or more, 8 or more, 9 or more, 10 or more, 15 or more, 20 or more, 30 or more, 40 or more, or 50 or more) selenium containing compounds (e.g., isolated, chemically synthesized, or recombinant selenium containing compound) tailored for a specific use (e.g., that, when combined, display a desired level of bioactivity (e.g., stimulatory and/or inhibitory activity)). For example, in some embodiments, a first composition comprising a combination of two or more selenium containing compounds is utilized to enhance mitochondrial activity (e.g., ATP production and/or respiration) in muscle tissue, whereas a second composition comprising a combination of two or more different selenium containing compounds (e.g., displaying bioactivity that is different than the first composition) is utilized to alter mitochondrial activity in liver tissue. In some embodiments, a composition comprising two or more selenium containing compounds is customized to the specific genetic profile of an individual (e.g., to target a particular gene or protein). Yeast extracts or fractions can be customized in a similar manner for use in treating a particular disease or condition in an individual. In such a way, a custom formulation is developed for the individual subject in need of treatment.

In some embodiments, the present application provides a composition comprising selenium in the form of selenium enriched yeast comprising 2% or less inorganic selenium, or one or more selenium containing compounds present therein or obtained therefrom, in the form of, or together with, a nutraceutical (e.g., an over-the-counter composition that is promoted, for example, as improving health or general well-being).

In further embodiments, the present application provides pharmaceutical compositions that comprise one or more forms of selenium (e.g., as described above), alone or in combination with at least one other agent, such as an anti-diabetic, a fatty acid (e.g., eicosapentaenoic acid (EPA)), etc., and may be administered in any sterile, biocompatible pharmaceutical carrier, including, but not limited to, saline, buffered saline, dextrose, and water.

The methods of the present application find use in treating (e.g., prophylactically or therapeutically) a subject (e.g., a subject with diabetes and/or an obese subject). Compositions comprising selenium (e.g., SEL-PLEX) can be administered to a subject (e.g., a patient) intravenously in a pharmaceutically acceptable carrier such as physiological saline. Standard methods for intracellular delivery of compounds can be used (e.g., delivery via liposome). Such methods are well known to those of ordinary skill in the art. Compositions comprising selenium are useful for intravenous administration as well as parenteral administration, such as intravenous, subcutaneous, intramuscular, and intraperitoneal.

As is well known in the medical arts, dosages for any one subject may depend upon many factors, including the patient's size, body surface area, age, the particular compound to be administered, sex, time and route of administration, general health, and interaction with other drugs being concurrently administered.

Accordingly, in some embodiments of the present application, compositions and/or formulations comprising selenium can be administered to a subject alone, or in combination with other forms of selenium, drugs, small molecules, or in pharmaceutical compositions where it is mixed with excipient(s) or other pharmaceutically acceptable carriers. In one embodiment of the present application, the pharmaceutically acceptable carrier is pharmaceutically inert. In another embodiment of the present application, compositions comprising selenium may be administered alone to individuals subject to, at risk of, or suffering from diabetes and/or obesity. Compositions comprising selenium (e.g., SEL-PLEX or selenium containing compounds present therein or derived therefrom, alone or in combination with one or more other forms of selenium) may be added to a nutritional drink or food (e.g., ENSURE, POWERBAR, or the like), a multi-vitamin, nutritional products, food products, etc. for daily consumption.

Depending on the target sought to be altered by treatment, pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, a composition comprising selenium (e.g., a pharmaceutical composition) of the present application may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions of the present application are formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present application include compositions wherein the active ingredients (e.g., selenium enriched yeast or selenium containing compounds) are contained in an effective amount to achieve the intended purpose. For example, in a preferred embodiment, an effective amount of a pharmaceutical composition comprises an amount of selenium enriched yeast comprising 2% or less inorganic selenium, or a selenium containing compound present therein or derived therefrom) that increase mitochondrial activity (e.g., ATP production and/or respiration). Determination of effective amounts is well within the capability of those skilled in the art, especially in light of the disclosure provided herein.

In addition to the active ingredients pharmaceutical compositions may contain suitable pharmaceutically acceptable carriers comprising excipients and auxiliaries which facilitate processing of active compounds into preparations which can be used pharmaceutically. The preparations formulated for oral administration may be in the form of tablets, dragees, capsules, or solutions.

The pharmaceutical compositions of the present application may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethyl-cellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound.

Pharmaceutical preparations which are used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Selenium containing compositions of the present application, alone or formulated in a pharmaceutical acceptable carrier, may be prepared, placed in an appropriate container, and labeled for treatment of an indicated condition. For compositions or formulations comprising selenium, conditions indicated on the label may include treatment of conditions related to prophylactic or therapeutic treatment of diabetes and/or obesity as well as other diseases or conditions that benefit from stimulation of mitochondrial activity (e.g., skeletal muscle and/or liver mitochondrial activity).

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

For any compound used in the methods of the present application, the therapeutically effective dose can be estimated initially from cell culture assays. Then, preferably, dosage can be formulated in animal models (particularly murine models) to achieve a desirable circulating concentration range.

An effective amount (e.g., therapeutically effective dose) refers to that amount of which ameliorates or prevents signs, symptoms and/or conditions associated with diabetes and/or obesity in a subject. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage may be chosen by a subject or by a physician in view of the patient to be treated. Dosage and administration are adjusted to provide sufficient levels of the active moiety or to maintain the desired effect (e.g., alteration of gene expression in a subject). Additional factors that may be taken into account include the severity of the disease state; age, weight, and gender of the patient; diet, time and frequency of administration, drug combination(s), reaction sensitivities, and tolerance/response to therapy. Long acting pharmaceutical compositions may be administered every 3 to 4 days, every week, or once every two weeks depending on half-life and clearance rate of the particular formulation. Thus, the present application is not limited by the length of time a subject is administered a composition of the present application. In some embodiments, a subject is administered/receives a composition of the present application for between 3-12 months (e.g., 3, 4, 5, 6, 7, 8, 9, 10, 11 or 12 months). However, the present application is not limited to this time frame. In some embodiments, a subject is administered/receives a composition of the present application for less than 3 months (e.g., 1 or 2 months) or for more than 12 months (e.g., 15, 18, 21, or 24 months, 2.5 years, 3 years, 4 years, 5 years, 6 years, 7 years, 8 years, 9 years, 10 years or more).

In some embodiments, a composition comprising selenium of the present application (e.g., organic selenium (e.g., selenized yeast (e.g., SEL-PLEX) or a selenium containing compound present therein or derived therefrom)) is administered at a daily dose so as to provide between 25 and 800 µg of selenium to a subject per day (e.g., SEL-PLEX is administered to a subject in such a way so as to provide between 25 and 800 µg of selenium to the subject each day). However, the present application is not so limited. Indeed, in some embodiments, a composition comprising selenium of the present application is administered at a daily dose so as to provide between less than 25 (e.g., 24, 23, 22, 21, 20, or less) or more than 800 (e.g., 825, 850, 900, 950, 1000, 1050, 1100, or more) µg of selenium to a subject per day. In preferred embodiments, the selenium (e.g., organic selenium (e.g., selenized yeast (e.g., SEL-PLEX))) is administered at a daily dose of between 200 and 500 µg per day. In other preferred embodiments, selenium is administered at a daily dose of between 200 and 400 µg per day. In some embodiments, a single dose of selenium (e.g., organic selenium (e.g., selenized yeast (e.g., SEL-PLEX))) is administered once daily. In other embodiments, 2, 3, 4, or more doses are administered each day (e.g., once in the morning and once at night, or once every 4 to 6 hours). For example, in some embodiments, selenium is administered to a subject in three separate, more than three separate, two separate, or less than two separate doses. In some preferred embodiments, the daily dose is administered in a time release capsule. In some embodiments, the daily dose is between 25-75 µg of selenium. In other embodiments, the daily dose is 200 µg of selenium (e.g., organic selenium (e.g., selenized yeast (e.g., SEL-PLEX))). In some embodiments, a dose is formulated for administration to a subject of a specific age (e.g., younger than 50, older than 50, younger than 70, older than 70, younger than 80, older than 80 years of age, etc.).

The pharmaceutical compositions of the present application may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Compositions and formulations comprising selenium are believed to be particularly useful for oral administration.

Pharmaceutical compositions and formulations for topical administration may include transdermal patches, gels, ointments, lotions, creams, gels, drops, suppositories, sprays, liquids and powders. Conventional pharmaceutical carriers, aqueous, powder or oily bases, thickeners and the like may be used.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Thus, in some embodiments, pharmaceutical compositions of the present application include, but are not limited to, solutions, emulsions, and liposome-containing formulations. These compositions may be generated from a variety of components that include, but are not limited to, preformed liquids, self-emulsifying solids and self-emulsifying semi-solids.

The pharmaceutical formulations of the present application, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

Thus, in some embodiments, the compositions of the present application may be formulated into any of many possible dosage forms such as, but not limited to, tablets, capsules, liquid syrups, soft gels, suppositories, and enemas. The compositions of the present application may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present application the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

The compositions of the present application may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present application, such as dyes, flavoring agents, preservatives, antioxidants, opacifiers, thickening agents and stabilizers. However, such materials, when added, should not unduly interfere with the biological activities of the components of the compositions of the present application. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

In some embodiments, the present application provide pharmaceutical compositions containing (a) one or more forms of selenium (e.g., SEL-PLEX and/or a selenium containing compound present therein and/or derived therefrom) and (b) one or more other agents (e.g., an anti-diabetic, anti-oxidant, etc.). In some embodiments, two or more combined agents may be used together or sequentially.

The present application also includes methods involving co-administration of compounds comprising selenium described herein with one or more additional active agents (e.g., anti-diabetic, anti-oxidant, etc.). Indeed, it is a further aspect of this present application to provide methods for enhancing prior art therapies and/or pharmaceutical compositions by co-administering a composition comprising selenium of this present application. In co-administration procedures, the agents may be administered concurrently or sequentially. In one embodiment, the compounds described herein are administered prior to the other active agent(s) (e.g., beta-blocker). The pharmaceutical formulations and modes of administration may be any of those described above. In addition, the two or more co-administered agents may each be administered using different modes or different formulations.

The agent or agents to be co-administered depends on the type of condition being treated. For example, when the condition being treated obesity, the additional agent can be and anti-obesity medication or weight loss drug or the like. When the condition being treated is the prevention or treatment of diabetes, the additional agent may be any one of the anti-diabetic medications known in the art. The additional agents to be co-administered can be any of the well-known agents in the art, including, but not limited to, those that are currently in clinical use.

In some embodiments of the present application, antioxidants are co-administered with compositions or formulations containing selenium of the present application. The present application is not limited by the type of antioxidant utilized. Indeed, a variety of antioxidants are contemplated to be useful in the present application including, but not limited to, alkylated diphenylamines, N-alkylated phenylenediamines, phenyl-α-naphthylamine, alkylated phenyl-α-naphthylamine, dimethyl quinolines, trimethyldihydroquinolines, hindered phenolics, alkylated hydroquinones, hydroxylated thiodiphenyl ethers, alkylidenebisphenols, thiopropionates, metallic dithiocarbamates, 1,3,4-dimercaptothiadiazole, an oil soluble copper compound, NAUGALUBE 438, NAUGALUBE 438 L, NAUGALUBE 640, NAUGALUBE 635, NAUGALUBE 680, NAUGALUBE AMS, NAUGALUBE APAN, Naugard PANA, NAUGALUBE TMQ, NAUGALUBE 531, NAUGALUBE 431, NAUGALUBE BHT, NAUGALUBE 403, NAUGALUBE 420, ascorbic acid, tocopherols, alpha-tocopherol, a sulfhydryl compound, sodium metabisulfite, N-acetyl-cysteine, lipoic acid, dihydrolipoic acid, lactoferrin, ascorbic acid, ascorbyl palmitate, ascorbyl polypeptide, butylated hydroxytoluene, retinoids, retinol, retinol palmitate, tocotrienols, ubiquinone, a flavonoid, an isoflavonoid, genistein, diadzein, resveratrol, grape seed, green tea, pine bark, propolis, IRGANOX, Antigene P, SUMILIZER GA-80, beta-carotene, lycopene, vitamin C, vitamin E, and vitamin A.

EXPERIMENTAL

The following examples are provided in order to demonstrate and further illustrate certain preferred embodiments and aspects of the present application and are not to be construed as Example 1

Identification and Characterization of Selenium Containing Compounds in Selenium Enriched Yeast Selenium (Se) is an essential element in human and animal diets. The low levels of Se in many countries have been generating the increasing interest in the supplementation of food and feed with selenium (See, e.g., Rayman, Br. J. Nutr., 92 (2004), p. 557). Yeast grown in selenium (Se)-rich media may be used as a source of organic Se for human and animal supplementation. The most popular form of supplemented Se is yeast grown in the presence of selenate and/or selenite, which is able to accumulate up to 3000 mg Se/kg. The attraction of Se-rich yeast, available on the market since 1974, is due to its relatively low cost and high content of selenomethionine (SeMet) acting as a precursor for selenoprotein synthesis. Se-rich yeast is a natural product which has long been difficult to characterize in terms of Se speciation. A number of questions have remained unanswered, including variability in the reported values for SeMet concentration; high variability of the composition in terms of Se species; and, the gap between the sum of the identified Se compounds and the total Se concentration.

Its insufficient characterization made the European Union exclude Se yeast from the permitted food supplements of Directive 2002/46/EC.

Thus, experiments were conducted during development of embodiments of the present application in order to characterize the Se metabolome and proteome of selenium rich yeast. Accordingly, as described herein, the present application provides the identification and characterization of Se-containing metabolites and proteins whose identification and characterization (e.g., biological activity) have heretofore remained unknown.

Total Se Determination and Isotopic Composition

Commercial yeast samples usually contain 1000 ppm or 2000 ppm of Se, with maximum values exceeding 3000 ppm. Se-rich yeast is said to be indistinguishable in appearance, flavor and odor from normal dried food yeast (See, e.g., Schrauzer, Pure Appl. Chem., 78 (2006), p. 105) but the morphologies of different preparations can be different. Poor quality Se-rich yeast samples are reddish or brownish in color as a result of the formation of $Se^0$ and selenides.

The determination of the total amount of Se in Se-rich yeast can be straightforward. For example, yeast are digested with a mixture of $HNO_3$ and $H_2O_2$ on a hot-plate or using microwave heating. Se content can subsequently be determined by hydride-generation (HG) atomic absorption spectrometry (AAS) or atomic fluorescence spectrometry (AFS). However, the completeness of the digestion (no dissolved carbon) is essential, otherwise low and/or inconsistent results are obtained. In some embodiments, inductively coupled plasma mass spectrometry (ICP-MS) is used to characterize selenium containing compounds (e.g., which is more tolerant of dissolved carbon). However, when ICP-MS is used, the isotope(s) used are optimized (e.g., because the most abundant $^{80}Se$ isotope is not suitable for work with older quadrupole instruments, it is not usable with quadrupole characterization). In a preferred embodiment, instruments equipped with a collision cell using $H_2$ as collision gas is used to provoke creation of <<M+1>> interferences for $^{77}Se$ and $^{78}Se$. In a further preferred embodiment, He is used as a collision gas. The use of the CRM SELM-1 may be used for quality control/assurance.

Se-rich yeast is often used as the active component of premixes (3-5 ppm as Se) and feeds (0.3-0. ppm as Se). However, severe inhomogeneity of premix samples is commonplace in the marketplace making the total digestion of samples, or consistency between batch processing, difficult to impossible. For example, it is common that the solid residue after hot-plate leaching with a $HNO_3$—$H_2O_2$ mixture does not contain Se. Thus, in some embodiments, ICP-MS analysis is used (e.g., when complete digestion of premix samples is not possible or inconsistent). Additionally, the precise determination of the Se isotopic composition by HG-ICP-multiple collector-MS (HG-MC-ICP-MS) has revealed significant variations in the isotope ratios ($\delta^{82/77}$Se, $\delta^{82/76}$Se and $\delta^{82/74}$Se) in Se-rich yeast from different manufacturers (See, e.g., Far et al., J Anal At Spectrom, 25 (2010) 1695). Knowledge and understanding regarding the origin of variations in the isotope ratios (different source of Se or different isotope fractionation during the biochemical incorporation in different biotechnologies) has remained elusive.

Determination of SeMet

Whether or not an accurate description, the total SeMet concentration has conventionally been referred to as an indication of the "organic" character of Se-rich yeast. SeMet is a constituent of proteins, most of which are insoluble in water. SeM content has therefore been determined via its release from proteins. Accordingly, in some embodiments, the present application provides methods of characterizing SeMet that lead to the complete breakdown of the yeast proteins into amino acids. In some embodiments, the present application provides methods of characterizing SeMet that prevent degradation of SeMet (e.g., resulting in a loss of Se or oxidation).

Many results in the field have referred to SeMet present in a water extract and were largely responsible for the confusion about the SeMet level in Se-rich yeast. Confusion has also been magnified by the fact that the conditions of the canonical acid digestion used in amino-acid analysis (6 N HCl digestion at 120 C in closed ampoules) are too harsh to preserve SeMet in a controlled way. Two procedures can be utilized for the recovery of SeMet: one based on 16-h digestion with methanesulfonic acid under reflux and the other based on the multiple proteolytic digestion with protease (See, e.g., Mester et al, Anal Bioanal Chem, 385 (2006) p 168). Thus, in some embodiments the present application provides that with regard to determination of SeMet content, retention time and presence of Se are required parameters for confirmation of the identify and the purity of Se-Met present in a sample. In some embodiments, reversed-phase (RP) or anion-exchange (AE) HPLC-ICP-MS chromatography analysis is utilized to characterize selenium species in a sample.

Sample Digestion

Experiments conducted during development of embodiments of the present application have shown that commercial yeast products present on the market differ in terms of morphology and texture and may give much lower SeMet recovery than expected (e.g., based upon reference material analysis). In addition, experiments conducted during development of embodiments of the present application have revealed the presence of protease-batch variability (e.g., thereby leading to poor reproducibility of extraction yield). Thus, in some embodiments, the present application provides steps and methods that minimize the risk of low recoveries. For example, in some embodiments, only freshly prepared and highly active protease is used. In further embodiments, the extraction is carried out multiple times (e.g., three times), each time with a fresh portion of the enzyme. In a preferred embodiment, the final extraction/extract contains less than 1% Se. In further embodiments, complete solubilization of the sample is obtained by enzymolysis. In some embodiments, if complete solubilization of the sample by enzymolysis is not possible, a sequential extraction using a mixture of cellulases and hemicellulases and chaotropic agents is used and the absence of SeMet in each of the extracts verified. The present application is not limited by the method of verifying the absence of SeMet in the extracts (See, e.g., Encinar et al., Anal Chem Acta, 500 (2003), 171). Extraction mass balance methods and data may be used to supplement the analytical results. An example of sample solubilization according to one aspect of the present application is shown in FIG. 1.

Experiments conducted during development of embodiments of the present application identified and characterized undigested proteolytic residues from a series of commercially-available yeasts and further revealed the presence of residual SeMet after additional treatment with cellulase-pectinase mixture. For some samples, residual SeMet accounted for up to 10% of the total Se although the typical values were ~3-5%. Treatment of the residues with sodium dodecyl sulfonate (SDS), followed by proteolytic digestion, allowed a further increase in the SeMet yield by, typically, 2-8% with one sample as high as 15%. The presence of residue (e.g., $Se^0$ extractable with $CS_2$) was an indication of poor-quality yeast.

HPLC-ICP-MS Analysis

Figure 2:
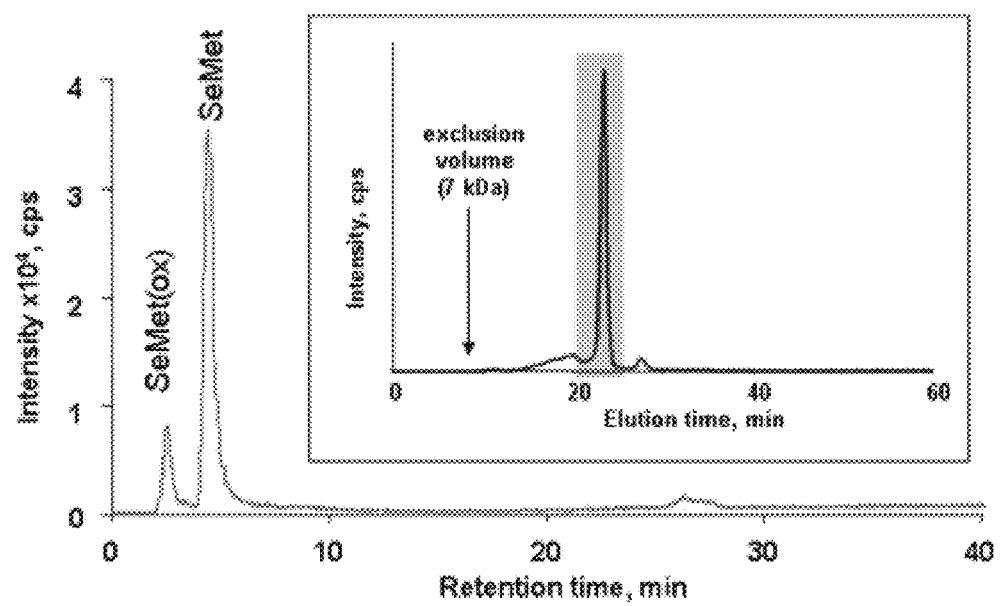
FIG. 2 shows the determination of selenomethionine in selenium (Se)-rich yeast by anion-exchange HPLC-ICP-MS. The inset shows the verification of the completeness of the digestion by SEC-ICP-MS (no Se present in the high molecular weight fraction and the quantitative recovery from the column).

Experiments conducted during development of embodiments of the present application identified and characterized selenium containing compounds present in solution obtained after enzymolysis (e.g., as containing SeMet but also oxidized SeMet, different forms of SeCys, different Se metabolites, and incompletely digested proteins). It was determined that the presence of incompletely digested proteins lead to the underestimation of total SeMet concentration. Incompletely digested proteins were identified to be present in a fine slurry (e.g., thereby remaining on the column filter) or in solution. Accordingly, in some embodiments, a validation step involving analyzing the digest by size-exclusion LC-ICP-MS is utilized (e.g., in order to verify the absence of high molecular-weight compounds and the completeness of elution of Se (See, e.g., FIG. 2, inset).

SeMet can be quantified by AE-HPLC-ICP-MS (See FIG. 2) or RP-HPLC-ICP-MS using the method of standard additions. The choice of the chromatographic stationary phase is important (e.g., in order to minimize loss due to on-column sorption of Se containing species). However, identification, quantification and analysis of selenocompounds (e.g., selenoprotein, seleoaminoacids, selenopeptides, etc.) may be accompanied by mass balance, excluding or accounting for its elution before and after the peak used for quantification. This made the identification and quantification of selenium containing compounds (e.g., SeMet) a complicated task. Isotope-dilution quantification could not be regarded as properly characterizing a sample (e.g., because the incomplete digestion and retention of incompletely-digested SeMet-containing species was a principal cause of inaccurate results) as the spike added was unlikely to behave in the same way as SeMet in the sample.

Another common source of error has been due to the occurrence of oxidized SeMet. Part of SeMet appears as a separate SeMetOx peak, leading to the underestimation of SeMet concentration. The oxidation of SeMet during the procedure could be prevented or even reversed by the addition of a redox reagent (e.g., dithiothreithol) but the SeMet oxide originally present cannot be converted to SeMet.

Experiments conducted during development of embodiments of the present application indicated that the replacement of ICP-MS by triple-quadrupole MS used in the (single or multiple) reaction-monitoring mode is likely to offer an alternative, increasing the selectivity and the reliability of the quantification of other SeMet forms (e.g., ox-SeMet) in parallel.

Determination of SeMet in Premixes and Feeds

The determination of SeMet in premixes, animal feeds and supplement tablets is more difficult than that in Se-rich yeast. The release of SeMet is hampered by the presence of some additives that may act as protease inhibitors. An extraction step is recommended to remove these additives prior to enzymatic extraction of SeMet. In some embodiments, SeMet concentration in animal feed is too low to be determined directly in the extract and requires preconcentration. Freeze drying of the enzymatic digest leads to the co-preconcentration of the residual enzyme, and, consequently, a matrix perturbing the subsequent RP-HPLC or AE-HPLC. Thus, the present application provides the isolation of low-molecular Se fraction by size-exclusion chromatography (SEC) prior to freeze-drying and HPLC-ICP-MS.

Analysis for Water-Soluble Se Containing Compounds and Metabolites

Figure 3:
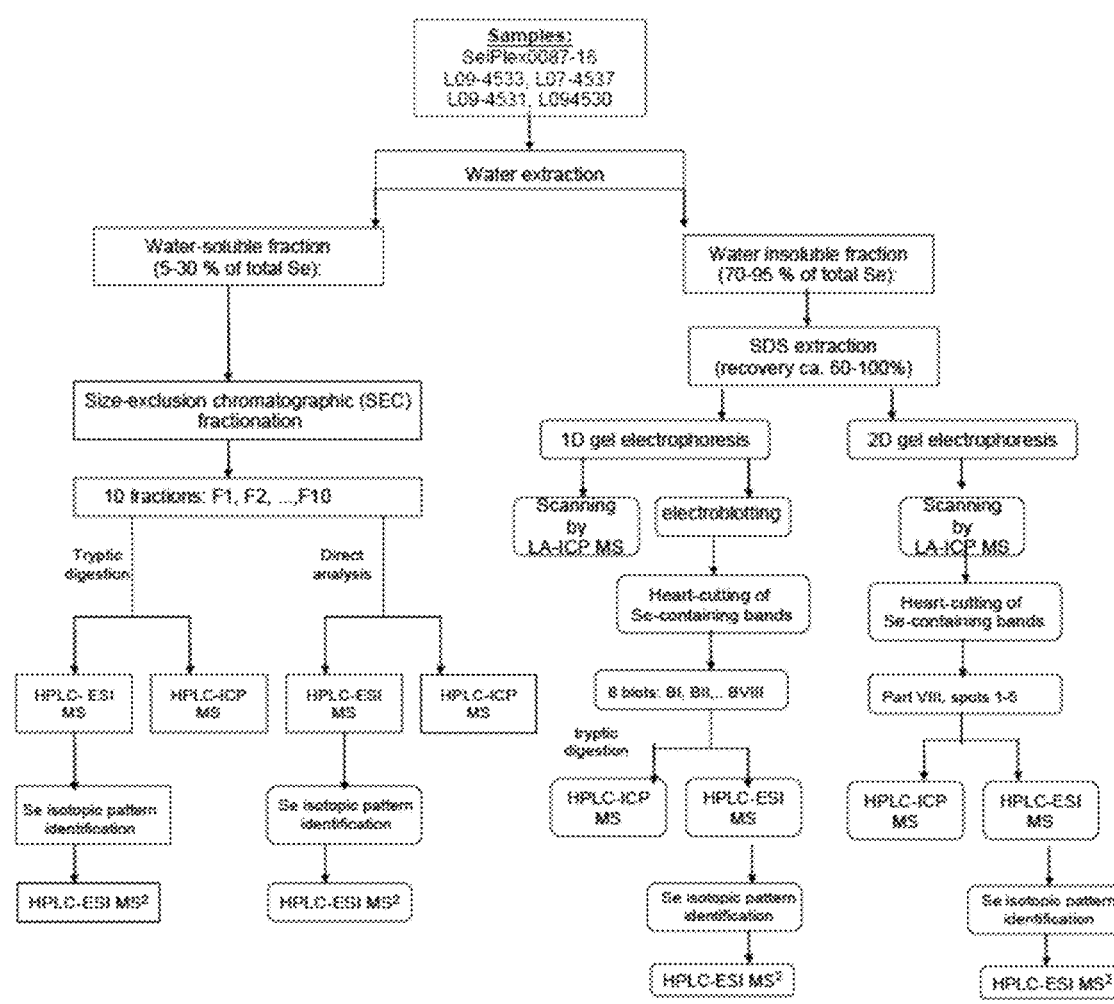
FIG. 3 shows an exemplary method for obtaining and identifying water-soluble and water-insoluble fractions present in selenized yeast according to one embodiment of the present application.

Experiments conducted during development of embodiments of the present application indicated Se-rich yeast are characterizable by the Se-metabolic profile (selenometabolome), which is a characteristic of yeast strain and fermentation parameters. The selenometabolome can serve as a fingerprint of the origin of the preparations available on the market and of the reproducibility of the production process. As described herein, experiments conducted during development of embodiments of the present application provide that the selenometabolome contain one or more Se-containing compounds (e.g., that display therapeutic activity and/or anti-therapeutic properties (e.g., toxicity)). An exemplary procedure according to one embodiment of the present application for obtaining and identifying both the water-soluble and water-insoluble fraction of Se containing compounds present in selenized yeast is shown in FIG. 3.

It was determined that extraction with water allows the recovery of 15-25% of Se. A typical chromatogram (100% recovery) obtained by SEC-ICP-MS is shown in FIG. 4A. The water extract contains ~5% of water-soluble proteins, of either high molecular mass eluting in the void of a SuperdexPeptide column, or low molecular mass (5-15 kDa), including multiply selenized (1-7) SIP18, monoselenized HSP12 or YMZ protein. These proteins contain Se exclusively present as SeMet.

Accordingly, the present application also provides that the remaining water-soluble Se occurring in the form of low-molecular-weight (<1500 Da) compounds/metabolites constitute the selenometabolome of yeast. Prior to experiments conducted during the development of embodiments of the present application, the identification and characterization of these metabolites has been a very challenging task (e.g., these metabolites have remained generally unknown since the first formal "de novo" identification of Se-adenosyl-Se-homocysteine by Casiot et al. using electrospray triple-quad MS (See, e.g., Casiot et al, Anal Commun, 36 (1999), p 77)). For example, the complexity of the water extract in terms of Se speciation was characterized and is illustrated in FIG. 4b. As shown, more than 25 different peaks were observed, with each peak potentially hiding any number of other less intense peaks (e.g., with each peak representing one or more different Se-containing compounds).

Figure 4:
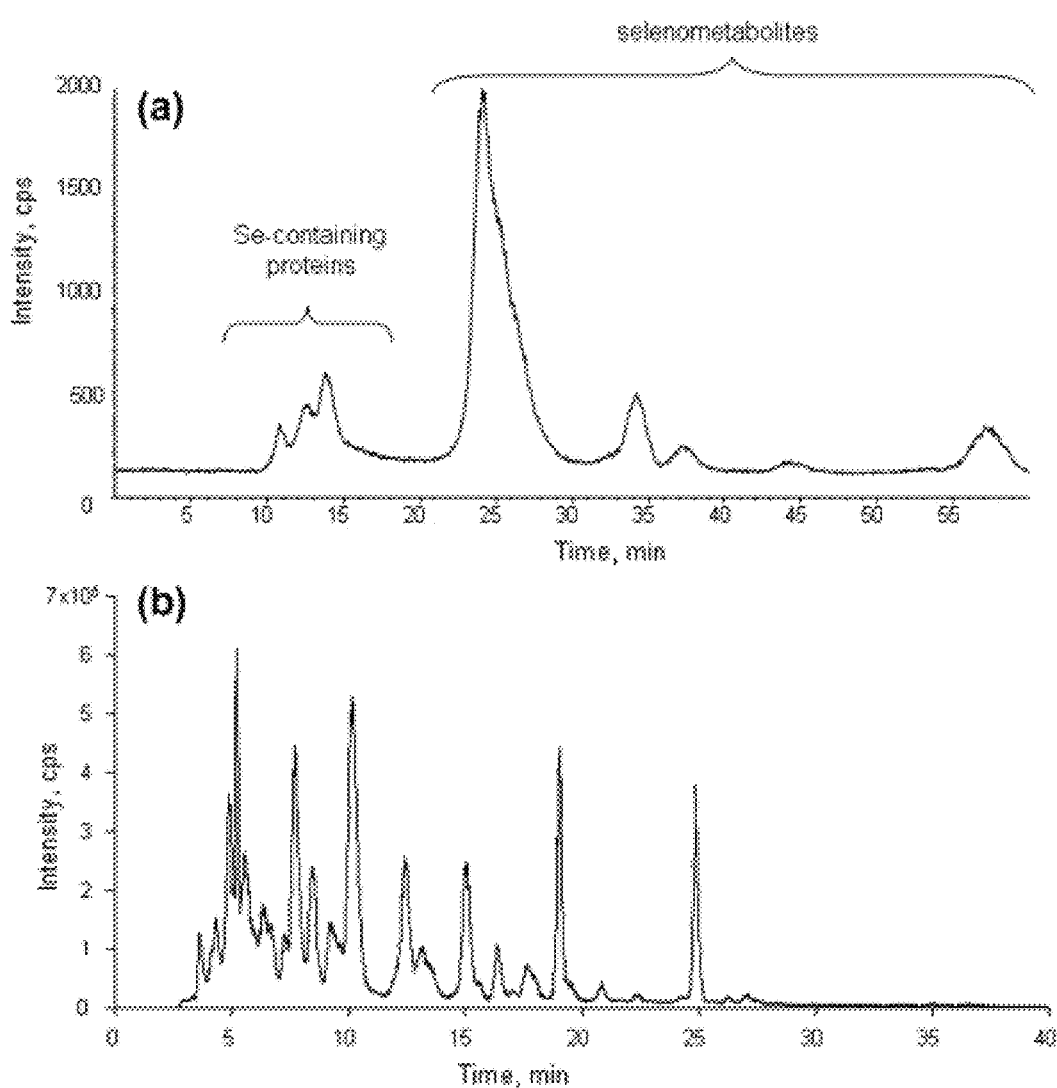
FIG. 4 shows HPLC-ICP-MS analysis for selenium metabolites. (a) size-exclusion chromatography (SEC)-ICP-MS; (b) ion-pairing (HFBA) reversed-phase HPLC-ICP-MS.

Experiments conducted during development of embodiments of the present application have taken advantage of certain advances in multi-dimensional purification techniques and progress in MS that in turn have allowed a large increase in the knowledge of the selenometabolome in yeast (See FIG. 4). In particular, the availability of an FT orbital ion-trap instrument offering a larger intrascan dynamic range, and the possibility of accurate mass determination and of multistage fragmentation, have be utilized to facilitate identification and characterization of the Se metabolome (e.g., identification of each selenium containing compound (e.g., metabolite, peptide, protein, nucleic acid, and/or precursors of each) as well as characterization of the biological properties of individual compounds as well as combinations of the same (e.g., as described herein).

Selenium enriched yeast (Se-rich yeast, *Saccharomyces cerevisiae*) was obtained and characterized. LCMS grade chemicals obtained from Sigma-Aldrich (Saint-Quentin Fallavier, France) were used. Water was purified using a Milli-Q system (MILLIPORE, Guyancourt, France). In one exemplary procedure, the total concentration of selenium in the Se-rich yeast was 2399 µg/g (+/−40). A 0.2-g sample was extracted with 5 ml of water in an ultrasonic bath for 1 h. The extract was centrifuged at 4000 rpm for 15 min. The supernatant was freeze-dried and stored, if necessary, at −20° C. The total selenium concentration in the water extract was 756 µg which accounted for about thirty percent of total selenium. Additional extractions of selenium enriched yeast run in parallel also produced a water extract with concentrations ranging between about 170-750 µg (corresponding to about 5-30% of total selenium).

Next, size exclusion-ICP MS was performed using the water extract. Size exclusion chromatography-ICP-MS was achieved using an AGILENT 1200 HPLC system (AGILENT, Tokyo, Japan) connected to an AGILENT 7500ce ICP mass spectrometer equipped with a Scott spray chamber and a collision cell. Liquid chromatography was performed with an Ultimate 3000 UPLC pump (DIONEX, Paris, France). The exit of the column was connected to an LTQ30 Orbitrap Velos mass spectrometer (Thermo-Fisher Scientific, Bremen, Germany) with an ESI ion source and to an AGILENT 7700 ICP-MS equipped with a Scott spray chamber and a collision cell.

Figure 5:
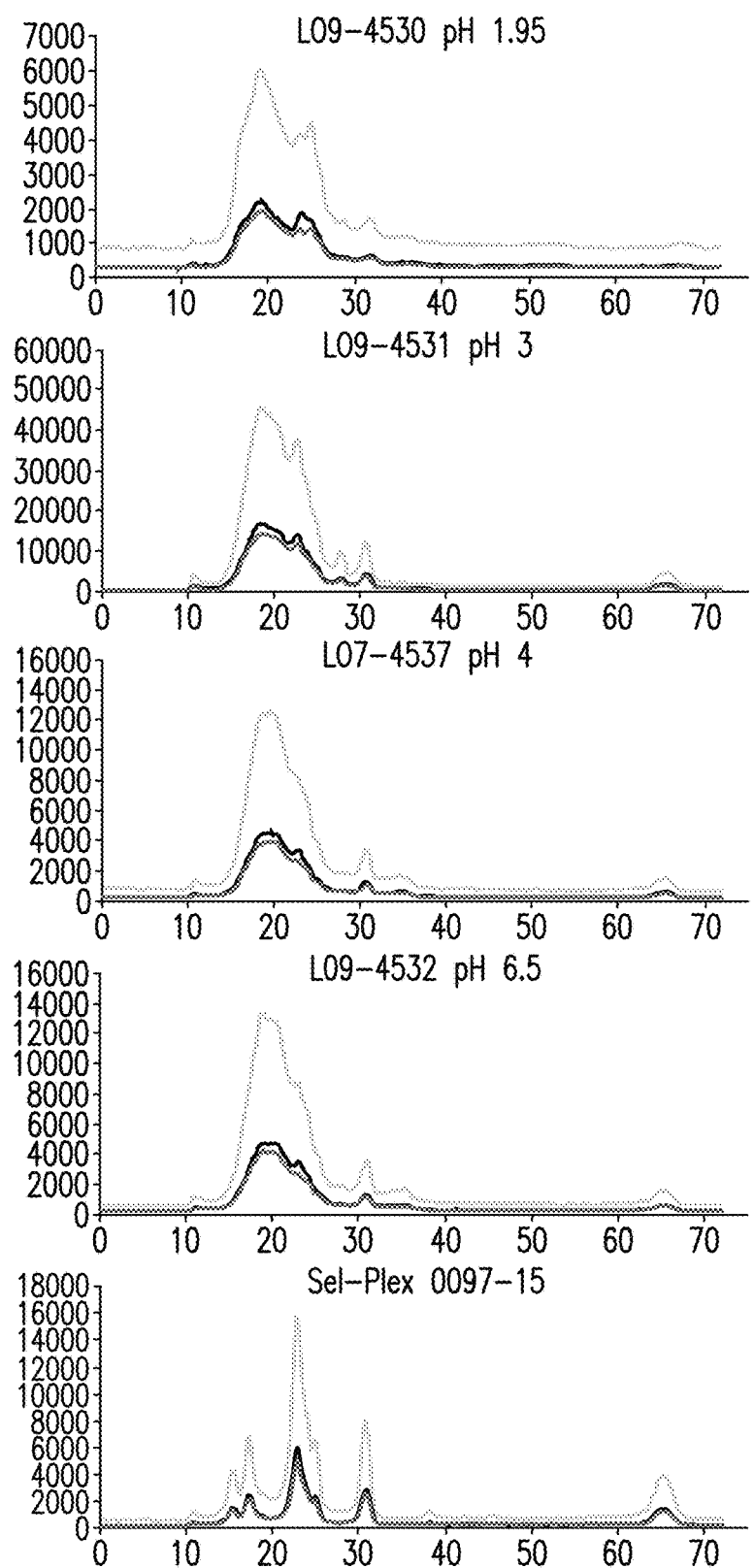
FIG. 5 shows size exclusion-ICP MS chromatograms of the water extracts (76Se—dark grey line, 77Se—black line, 78Se light grey line).

Size exclusion-ICP MS chromatograms of five separate water extracts are shown in FIG. 5 (76Se—dark grey line, 77Se-black line, 78Se light grey line). The chromatogram of the Se-rich yeast extract (FIG. 5, bottom panel) shows a typical pattern obtained using SELPLEX (ALLTECH, Inc., Lexington, Ky.). In addition, a relatively intense late eluting (at ca. 66 min) peak, unknown from previous research appeared. The profiles of remaining samples (FIG. 1, upper panels) are significantly different from the Sel-Plex one and similar to each other. They are dominated by a highly abundant broad peak, apparently containing a number of species, eluting early in the chromatogram. As a result of this observation, several samples (FIG. 5, second panel from top, and bottom panel) were chosen for further characterization using a size-exclusion column with more appropriate separation range (SUPERDEX peptide column) (FIGS. 6, A and B, respectively). The broad peak present in the previous chromatogram (FIG. 5, second panel from the top) was separated into two, each of them having 2-3 shoulders, showing presence of highly abundant selenocompounds with molecular weight in the range 5-1.5 kDa. It was further identified that the sample shown in FIG. 5 bottom panel also has a late eluting peak at about 25 min.

Identification and Characterization of Selenium Containing Compounds from Water Soluble Fractions The series of experiments described above identified the presence of a large fraction of selenium containing compounds (ca. 1.5-5 kDa) in the treated samples which was absent in the original yeast. Thus, experiments were performed during development of embodiments of the present application in order to characterize this fraction.

Figure 7:
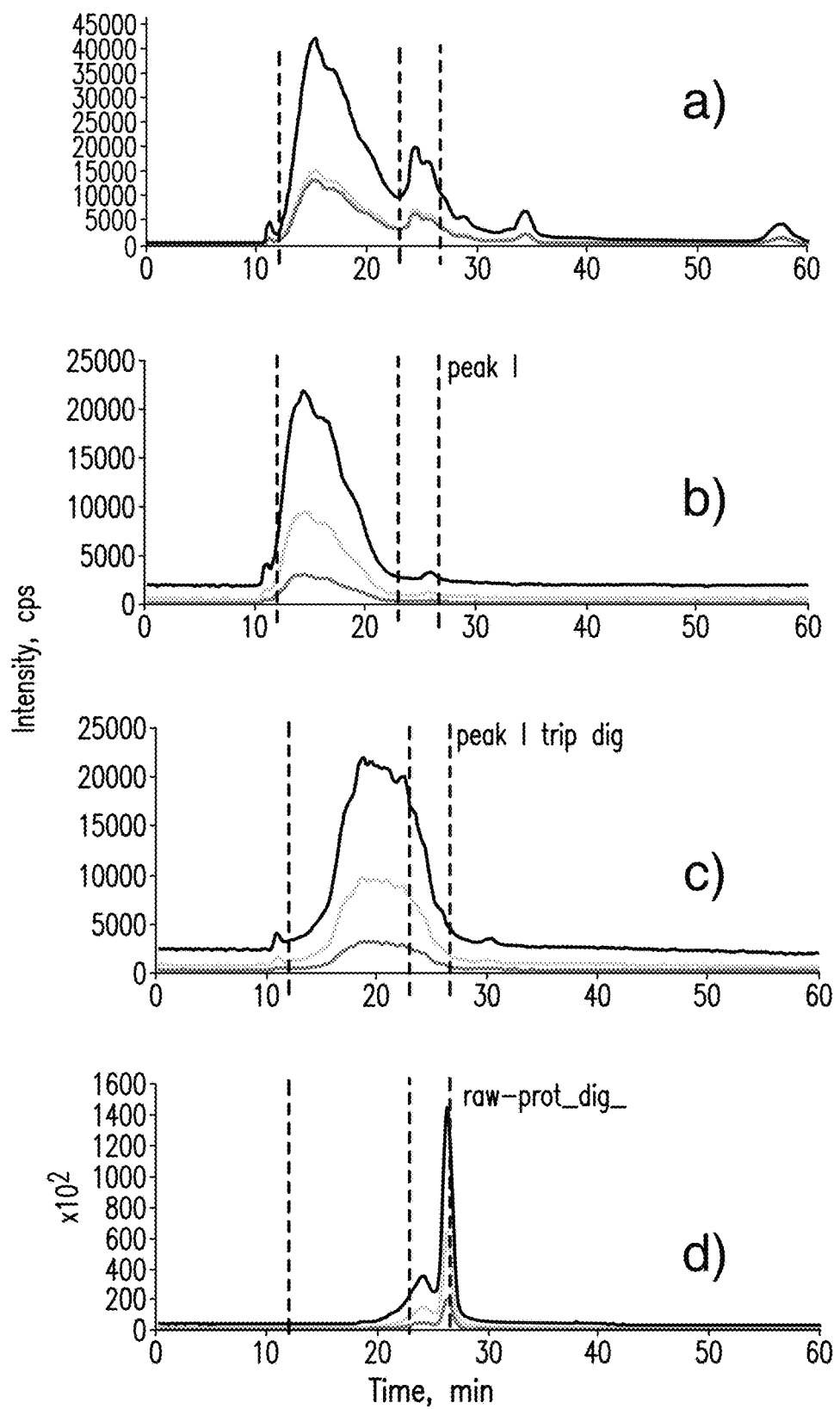
FIG. 7 shows a SEC peptide chromatogram of samples: a) water extract, b) separated peak I, c) peak I digested with trypsin, d) water extract digested with protease; black line—80Se, light grey line 78Se, dark grey line—77Se.

The fraction of interest (arbitrarily named "peak I") was heartcut from a size-exclusion chromatogram (SEC) (See FIG. 7A) and preconcentrated by freeze-drying. As shown in FIG. 7B, this allowed the recovery of the intact fraction of interest free of other Se-compounds present in the untreated yeast. The SEC peptide chromatogram of samples: a) water extract, b) separated peak I, c) peak I digested with trypsin, d) water extract digested with protease; black line—80Se, light grey line 78Se, dark grey line—77Se are shown in FIG. 7.

Several attempts to fractionate further the fraction of interest by reversed phase HPLC failed. The recovery from RP-HPLC columns tested was very low and separation poor. Therefore, proteolytic enzyme digestion (trypsin and protease XIV) of this fraction was attempted in an effort to further characterize the fraction and to identify components contained therein. As shown in FIG. 7C, trypsin (cleaving at arginine and lysine residues) reduced the average molecular mass of the Se-compounds in the mixture. Thus, as described herein, in some embodiments, the present application provides that one or more water soluble fractions of a Sel-rich yeast are proteolytically digested (e.g., with trypsin, protease XIV, or other enzyme) prior to isolation and/or characterization of selenium containing compounds with reversed-phase HPLC-ICP MS and/or Orbitrap MS.

For example, as shown in FIG. 7D, protease digestion of the peptides gives mostly selenomethionine (FIG. 7D, tall black line ca. 27 minutes). There also exist other selenium containing compounds eluting before ca 25 minutes.

Figure 8:
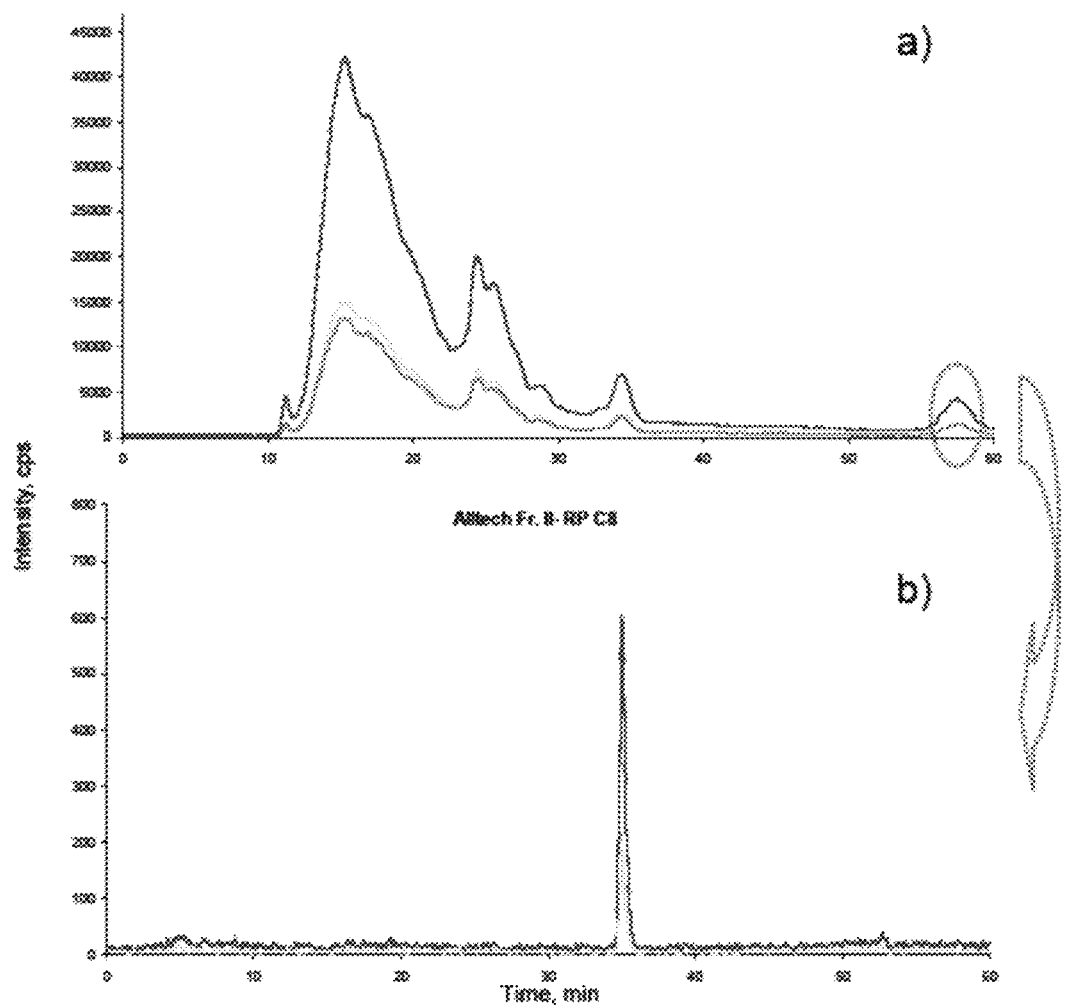
FIG. 8 shows (A) the peptide chromatogram of the water extract of FIG. 7A and (B) the reverse phase (RP) chromatogram of the peak eluting at 58 min from the SEC column shown in FIG. 7A

Additional experiments were conducted during development of embodiments of the present application in order to isolate, purify and characterize the peak eluting at 58 min from the SEC column shown in FIG. 7A. In order to identify the compounds present in the size exclusion chromatogram elution time of 58 min—See FIG. 7A, the peak was separated and concentrated. The elution process for reversed phase chromatography was optimized. The RP chromatogram of the peak eluting at 58 min from the SEC column shown in FIG. 7A (also shown in FIG. 8A) shows just one, sharp and well resolved peak (See FIG. 8B). Next, further analysis including mass spectroscopy was performed in order to identify the selenocompound. Reversed phase chromatography was coupled with Orbitrap. The selenocoumpond at mass 346.04025 was identified as Se-methyl-Se-adenosine (See FIG. 9).

Experiments were conducted during development of embodiments of the present application in order to further identify and characterize selenium containing compounds in the water soluble fractions isolated from selenium enriched yeast.

The water extract from the Se-rich yeast described above (containing 756 µg accounting for about thirty percent of total selenium), that contained approximately 70% of the water soluble selenium containing compounds, was used. The extract was concentrated and injected onto size exclusion chromatography (SEC) column and 10 sub-fractions (starting from the first broad peak shown in FIG. 2A) were collected at even time intervals. Again, these fractions represent species not present in the raw yeast aqueous extract. Each fraction was divided into two separate samples, with one sample being used for fraction dramatization and the other sample being treated with tryptic digestion.

Figure 10:
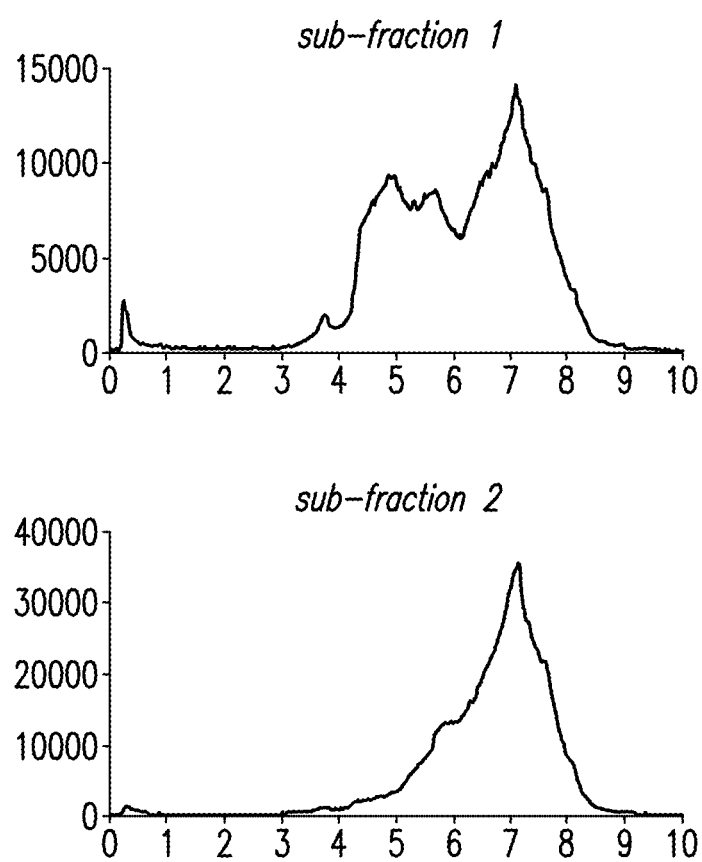
FIG. 10 shows reversed-phase HPLC-ICP MS chromatograms of the sub-fractions of the water soluble extract of selenium rich yeast presented in elution order. Subfractions 1-10 are shown.
Figure 10:
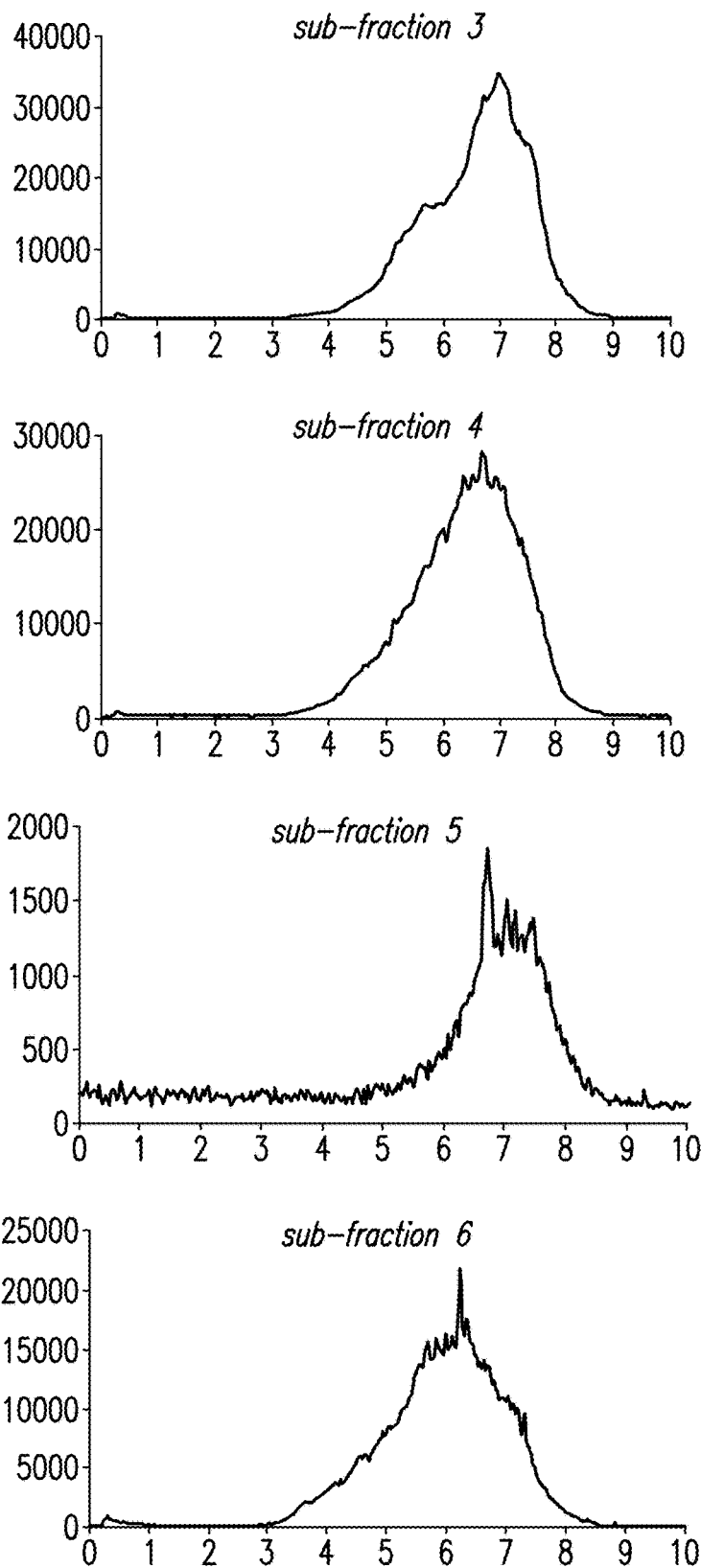
Figure 10:
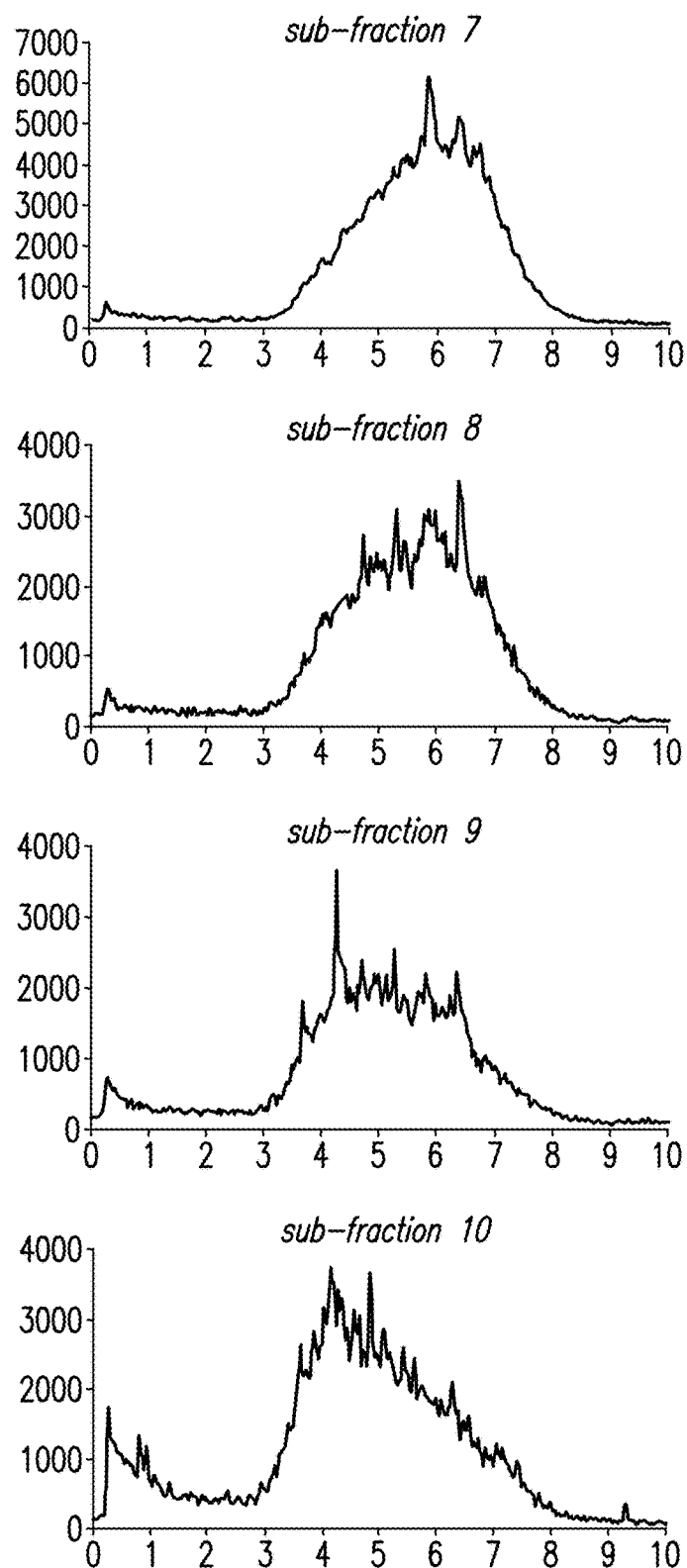

The samples were analyzed first with ICP MS (See FIG. 10) using RP C18 column. The resolution was sufficient for the UPLC-Orbitrap MS analysis.

Figure 11:
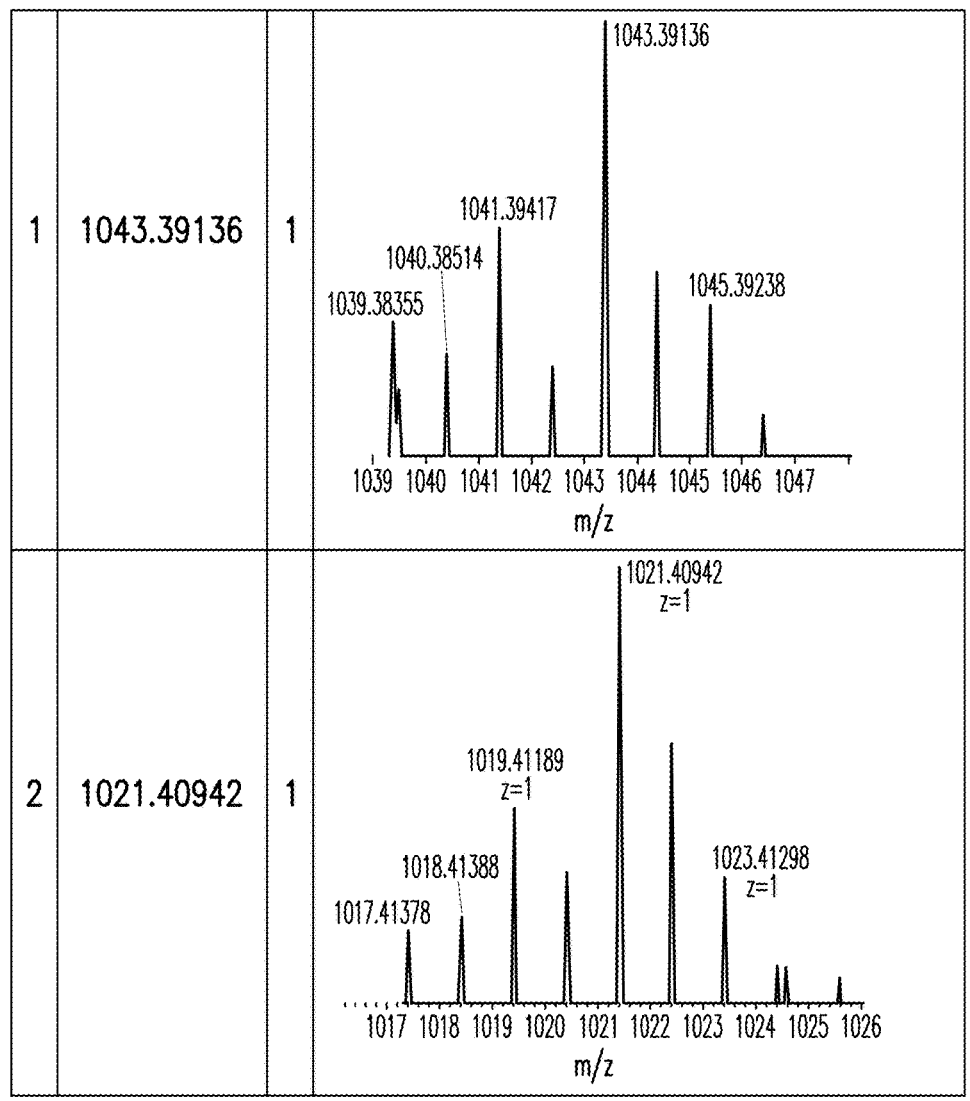
FIG. 11 shows mass spectroscopy of selenium containing peptides identified in subfraction 8 of the sample.
Figure 11:
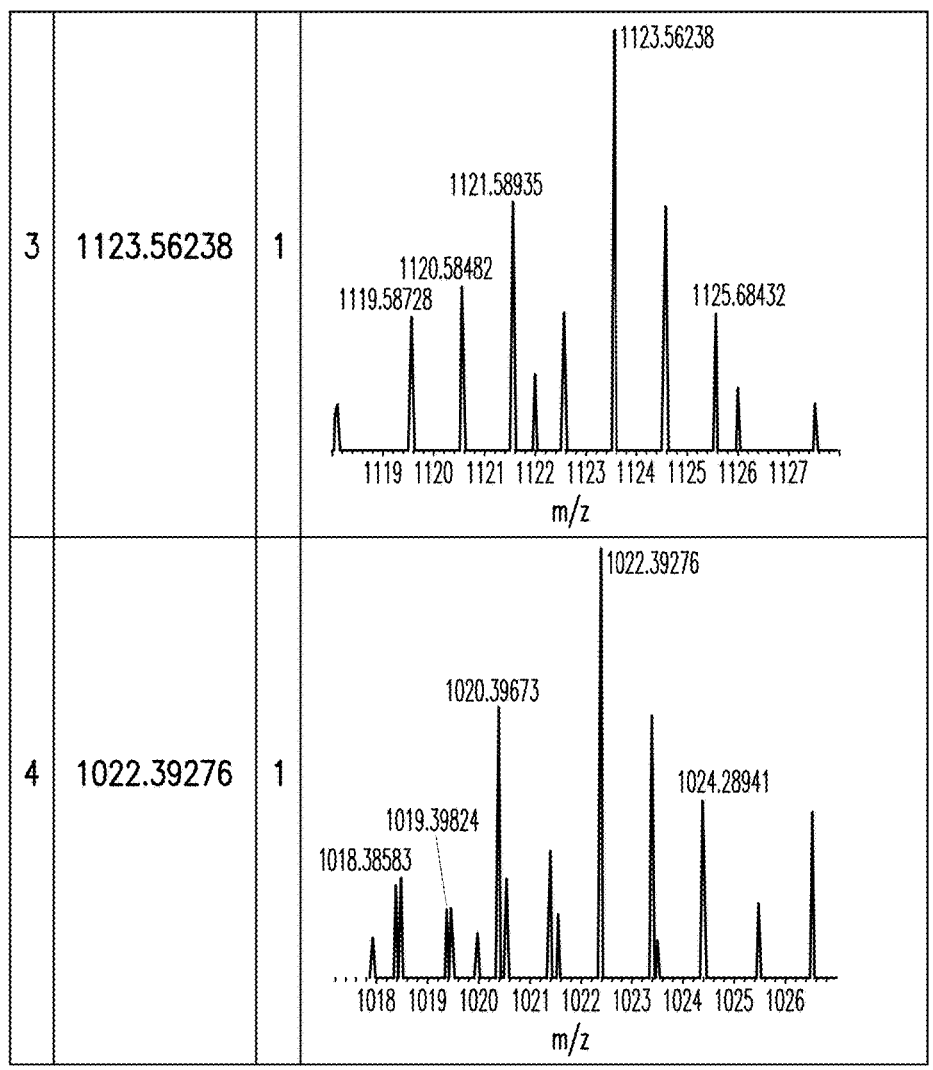
Figure 11:
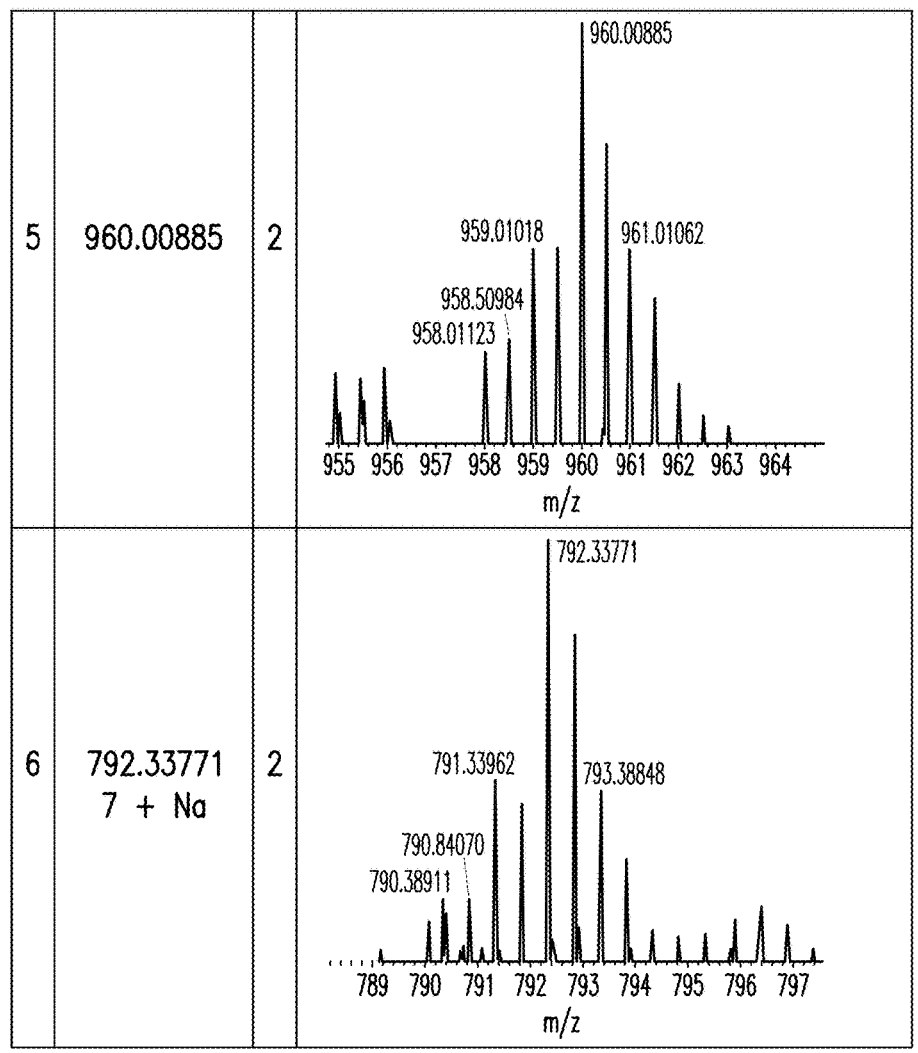
Figure 11:
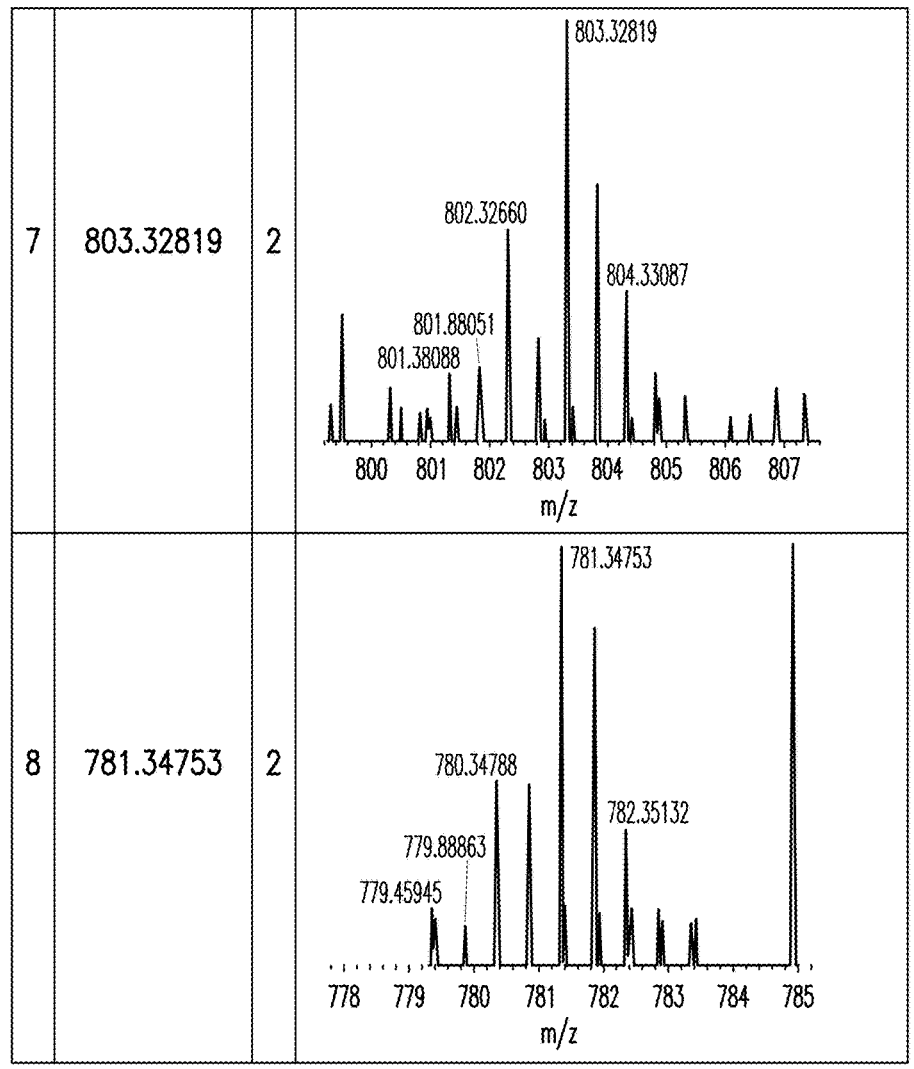
Figure 11:
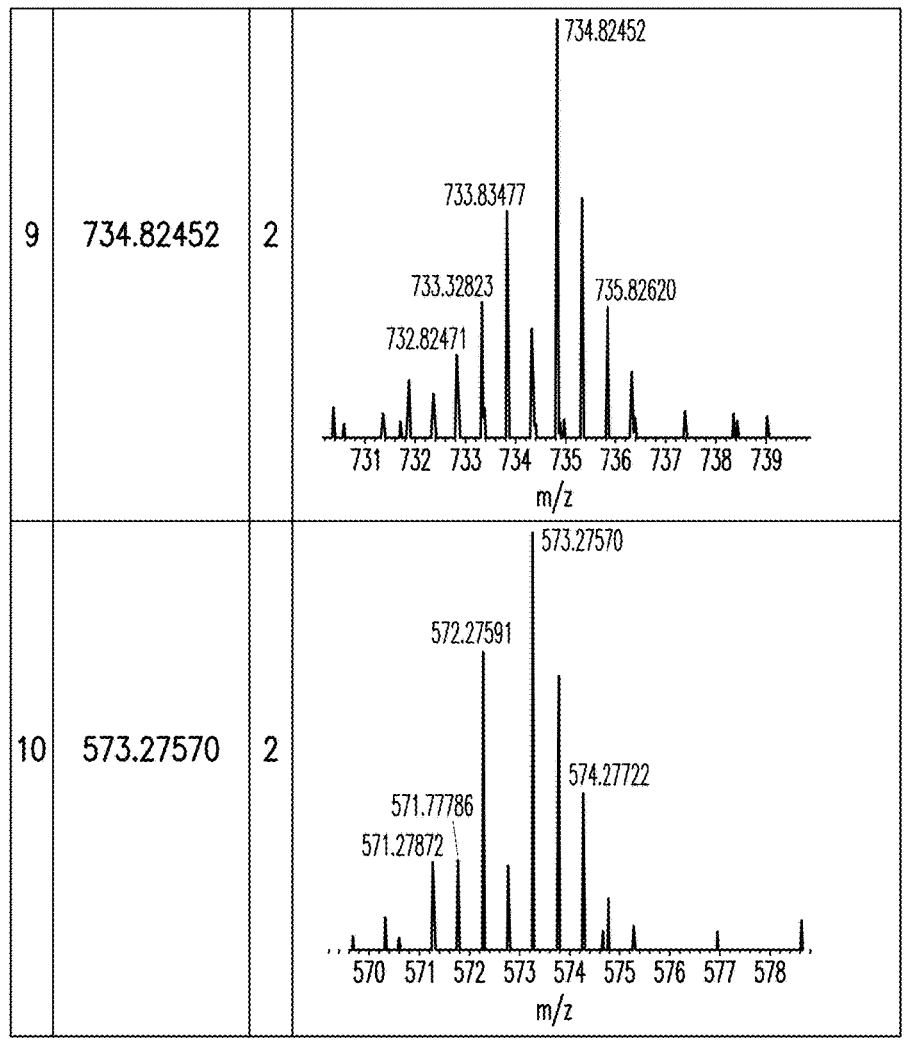
Figure 11:
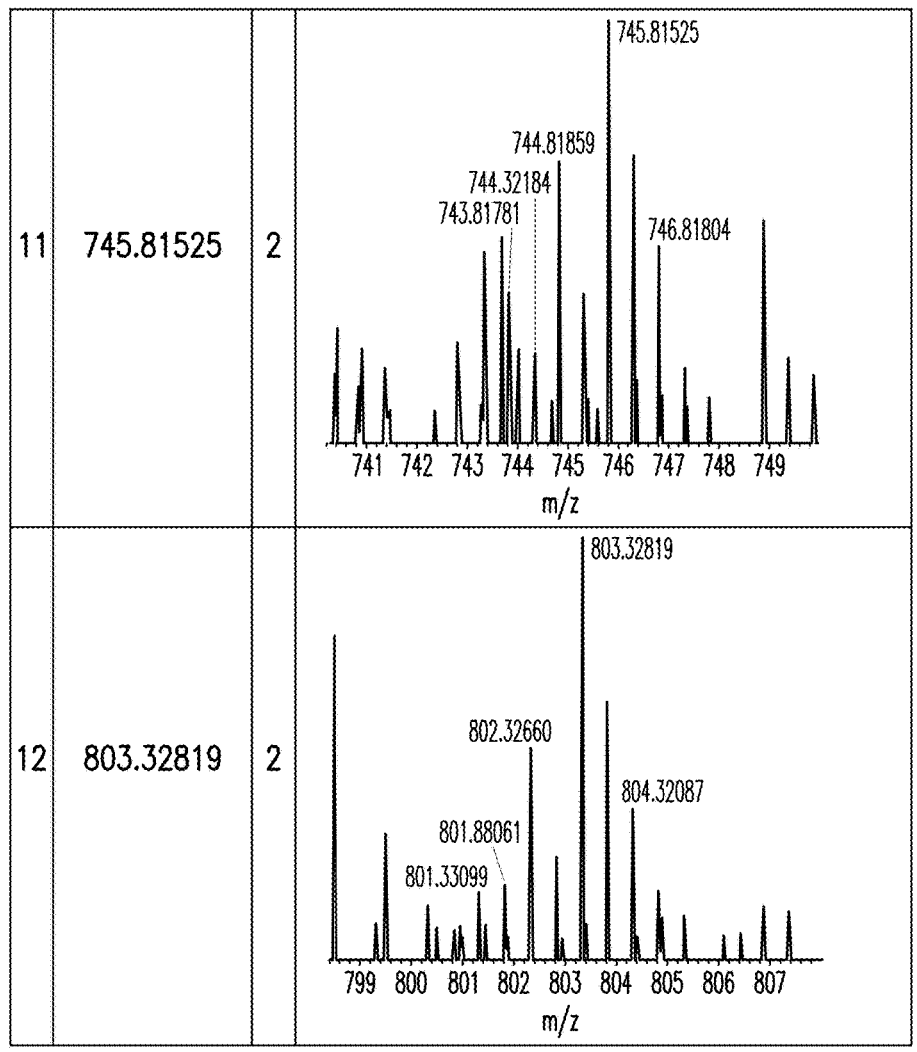
Figure 11:
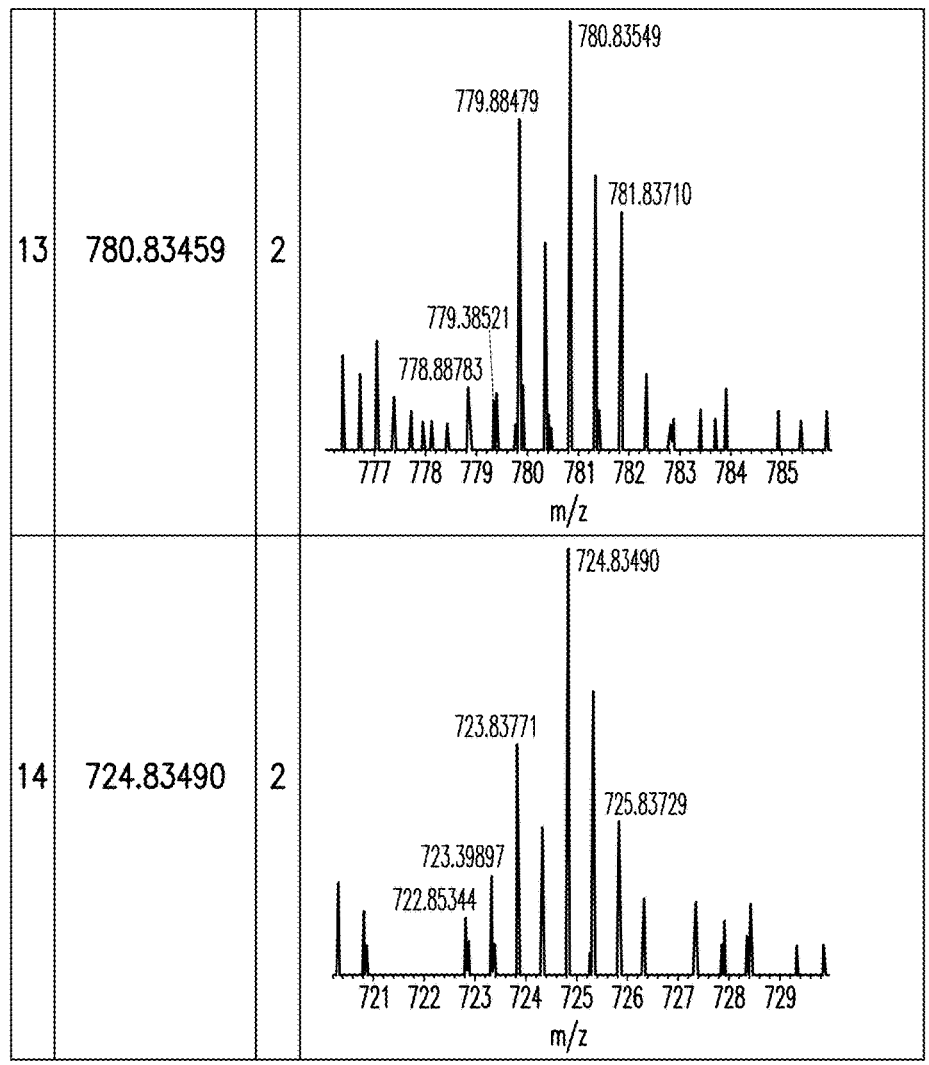
Figure 11:
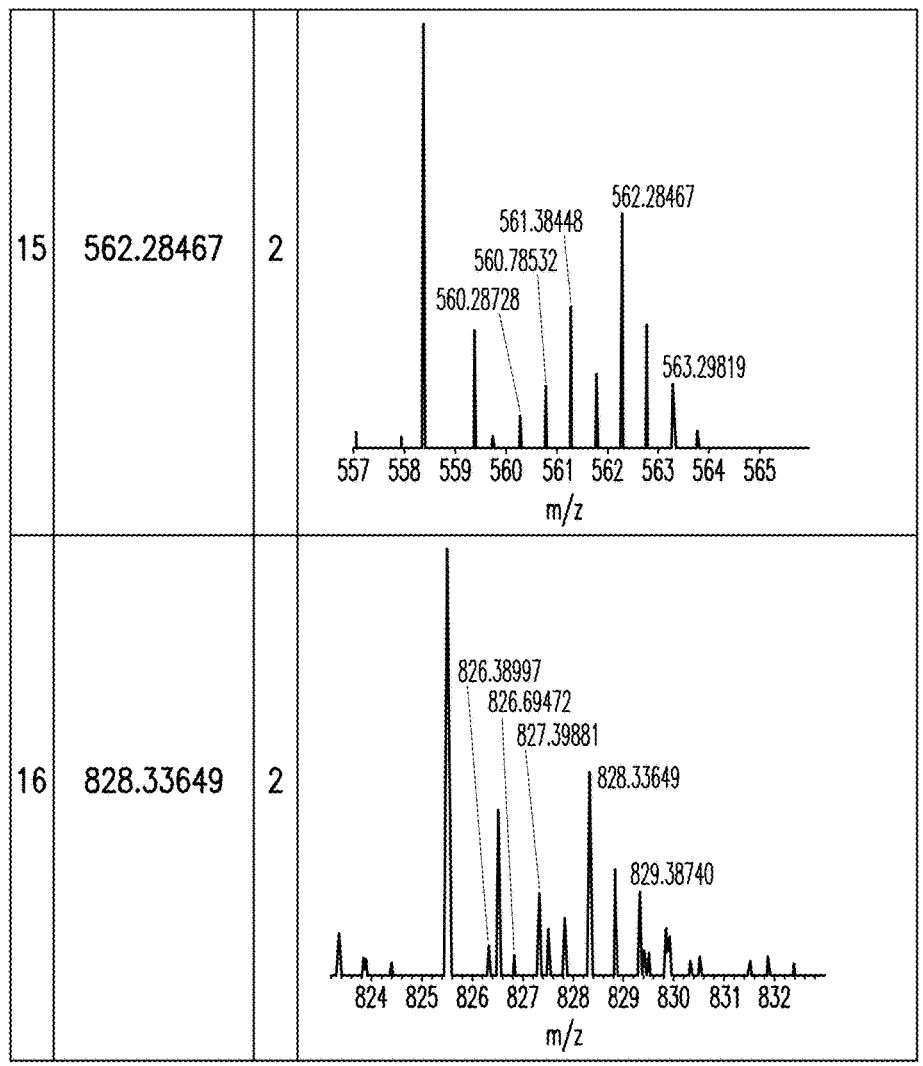
Figure 11:
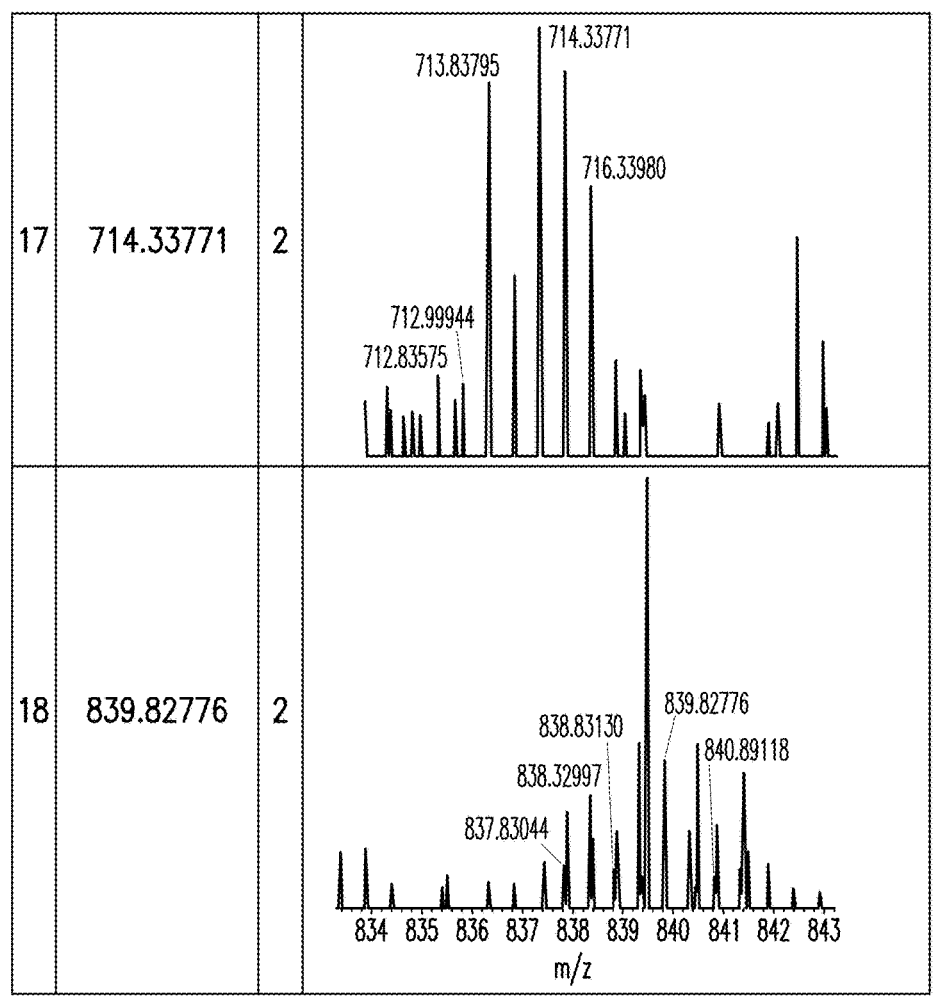
Figure 11:
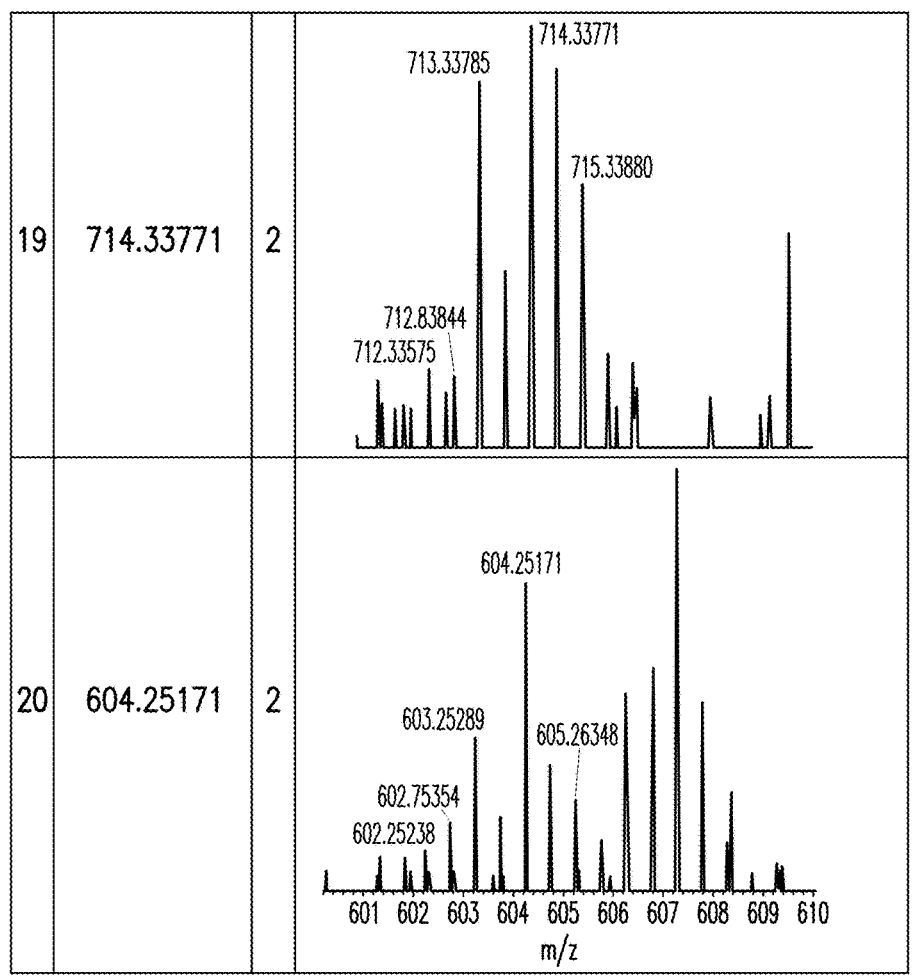
Figure 11:
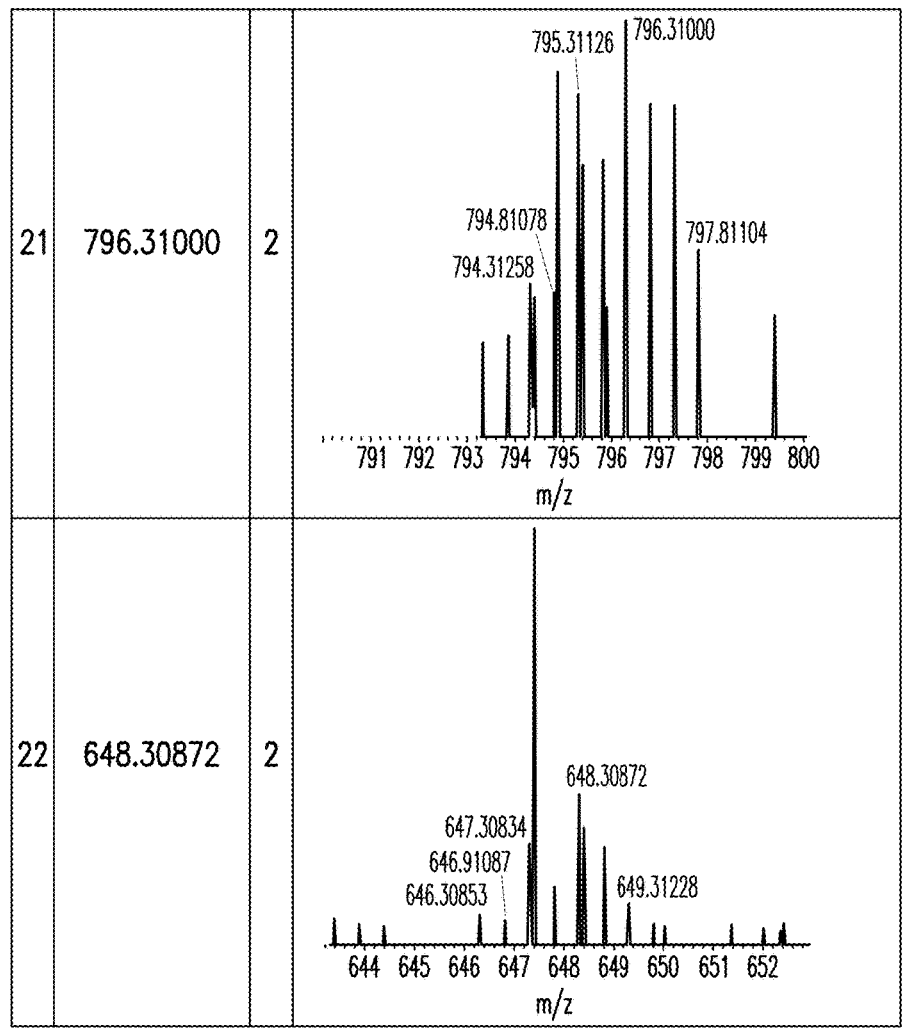
Figure 11:
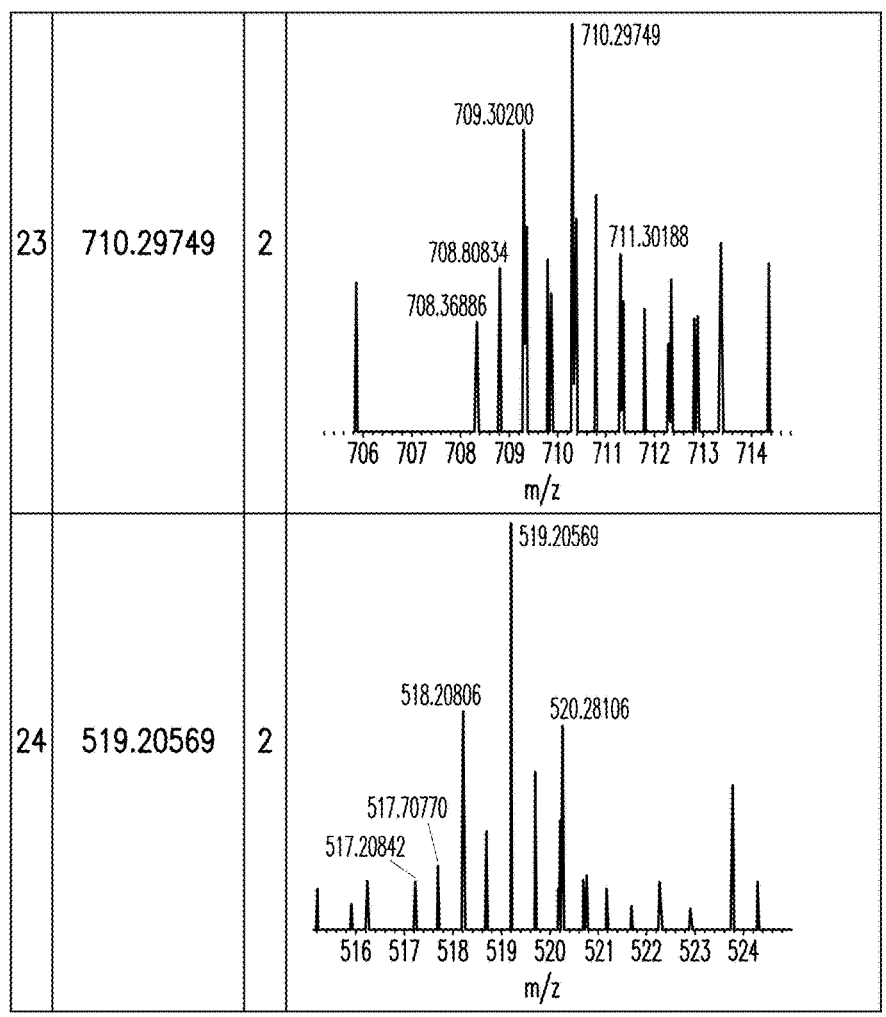
Figure 11:
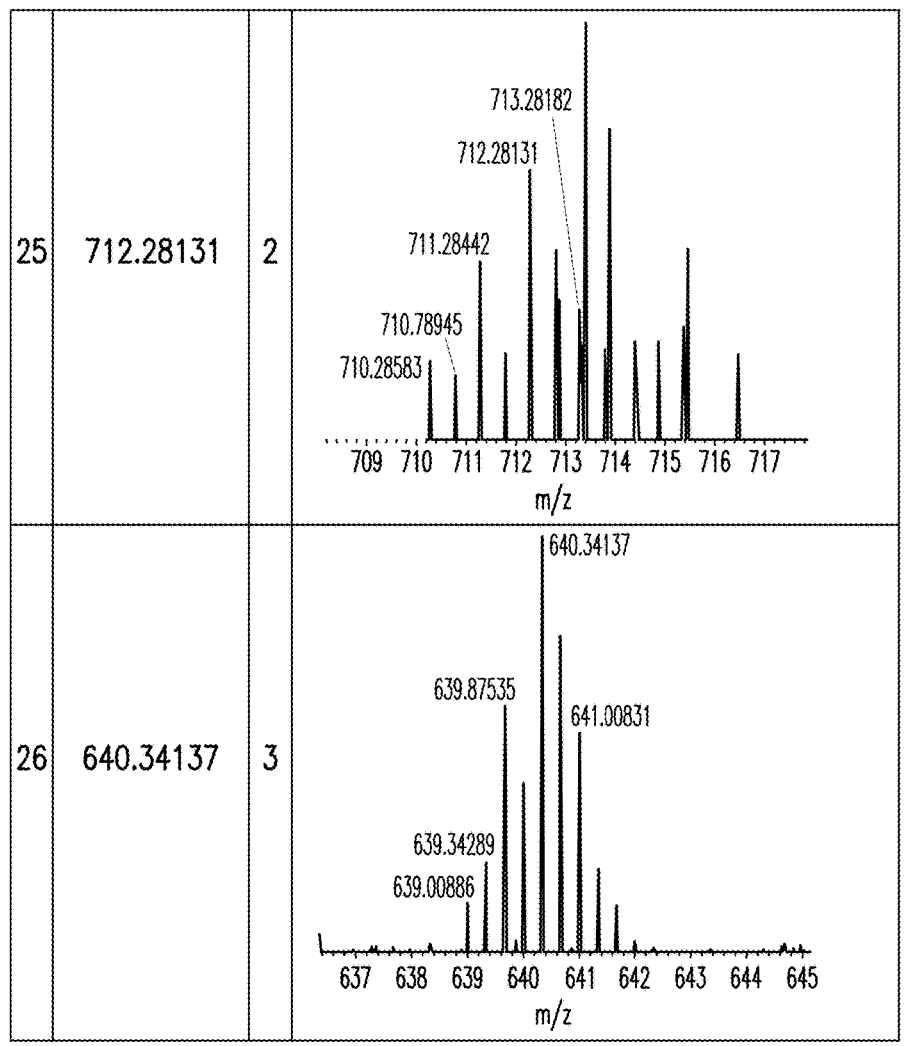
Figure 11:
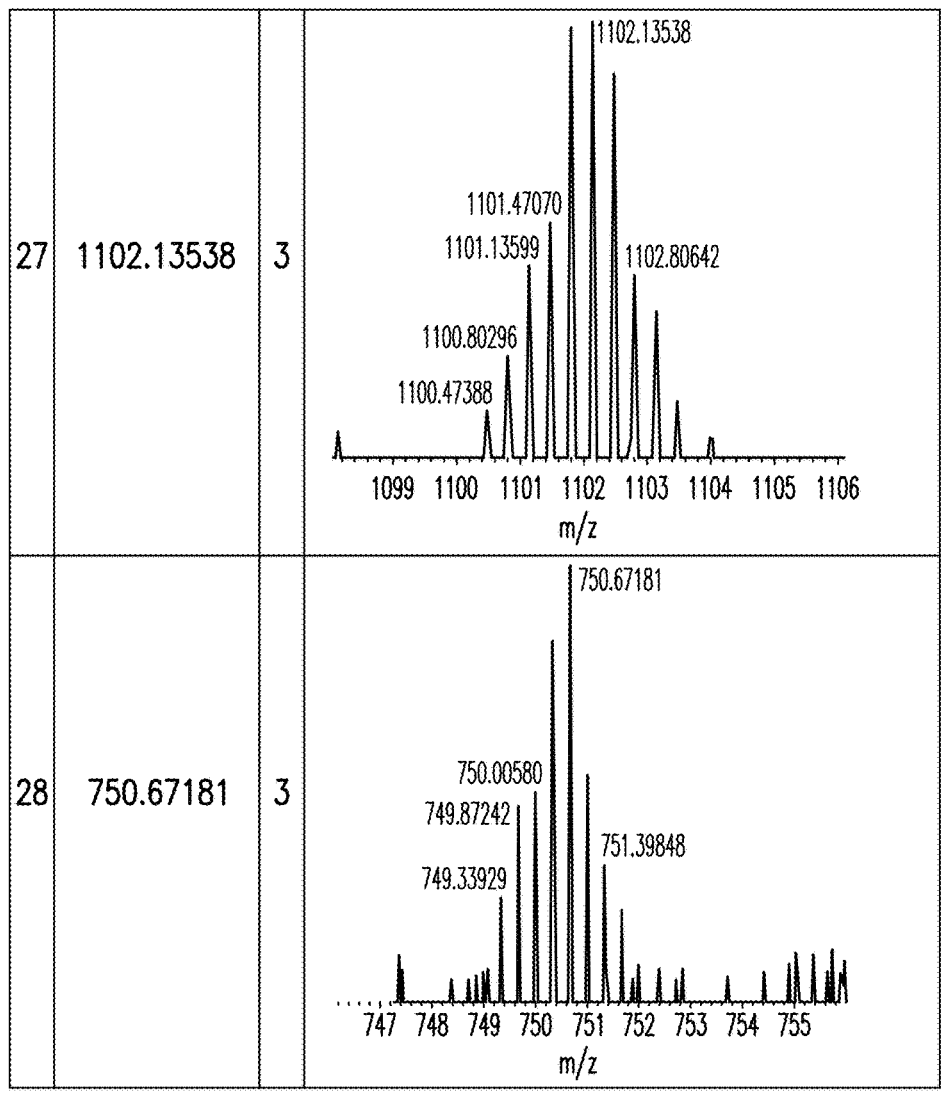
Figure 11:
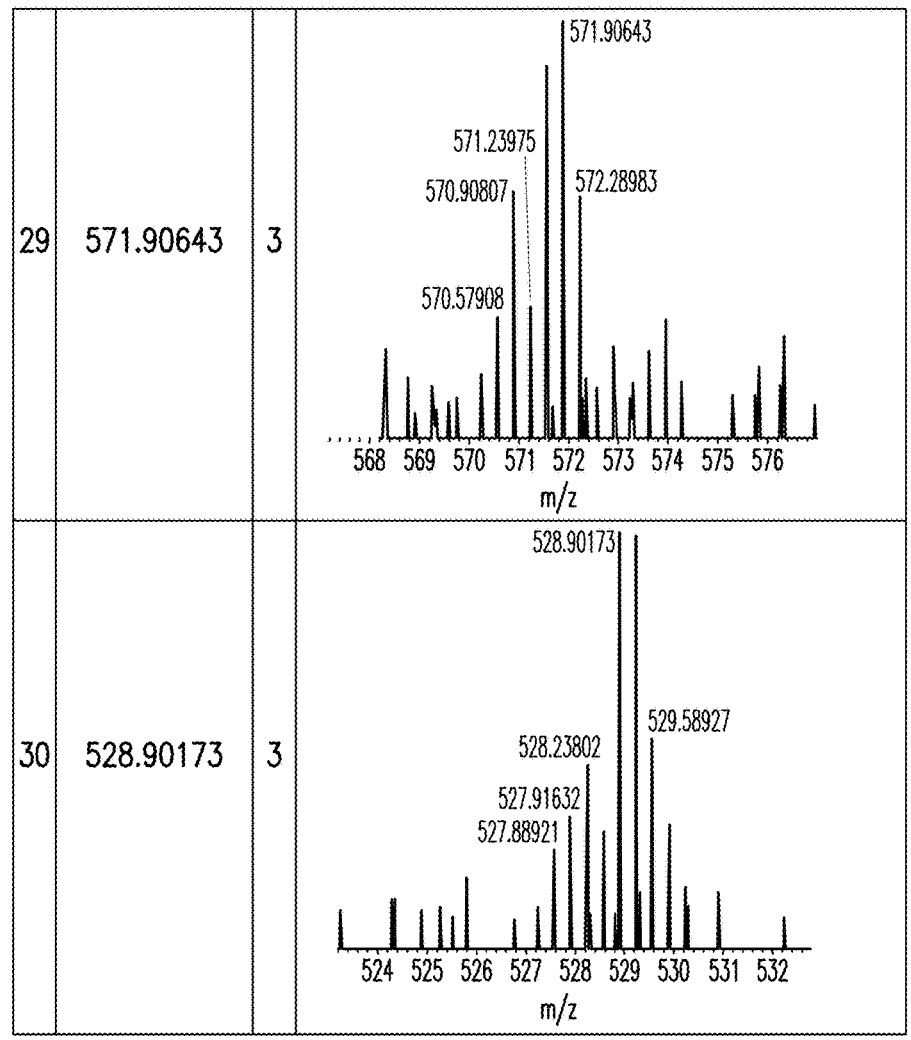
Figure 11:
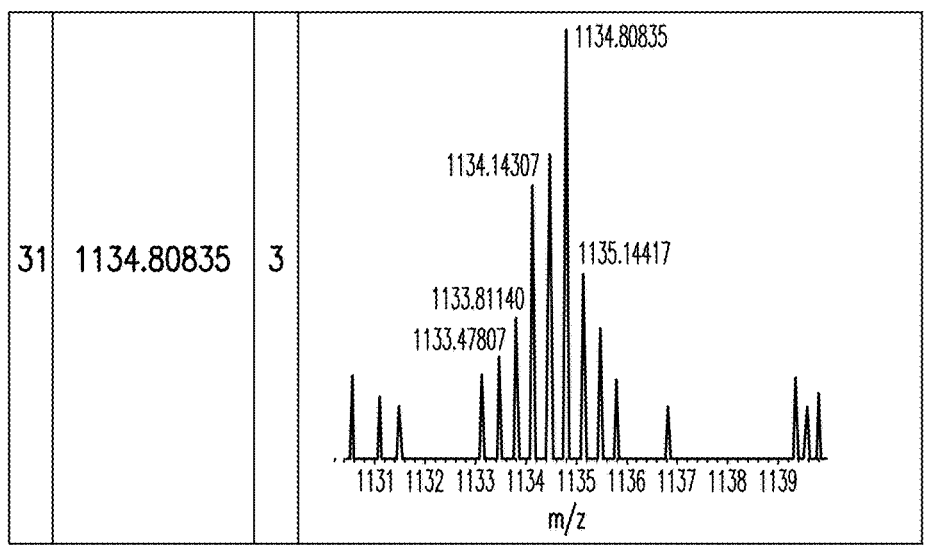
Figure 15:
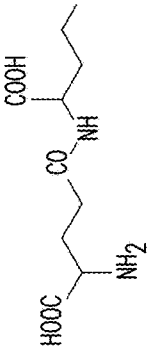
FIG. 15 shows a list of selenium containing compounds identified in SELPLEX utilizing mass spectroscopy and Orbitrap.
Figure 15:
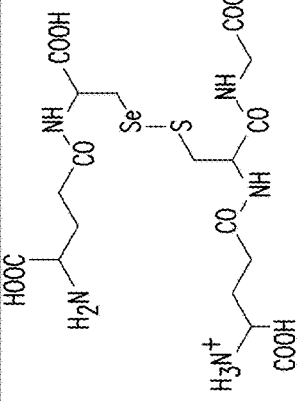

Samples were analyzed and a list of 170 compounds obtained for sub-fraction 8 with selenium patterns is given in Table 1 below. In addition, table 5 provides exemplary spectra of these compounds. All peptides identified in the undigested fraction were in the mass range between 1 and 3.4 kDa. The selenium containing compounds identified are much smaller than the original proteins from which they were derived. FIG. 11 provides a list of selenium containing peptides identified in subfraction 8 of the sample. Accordingly, in some embodiments, the present application provides one or more selenium containing compounds (e.g., identified in Table 2, FIG. 11, FIG. 13 and FIG. 15, described below), compositions comprising the same and methods of using the same (e.g., for human and/or animal use as described herein).

TABLE 2

List of masses of selenium containing compounds found in subfraction 8.

| No | Mass |
|---|---|
| 1 | 504.22677 |
| 2 | 517.59942 |
| 3 | 519.20538 |
| 4 | 528.90197 |
| 5 | 531.75903 |
| 6 | 532.67706 |
| 7 | 539.25262 |
| 8 | 539.33910 |
| 9 | 540.67584 |
| 10 | 541.24383 |
| 11 | 541.26294 |
| 12 | 541.74151 |
| 13 | 542.24139 |
| 14 | 542.24725 |
| 15 | 552.71209 |
| 16 | 553.25964 |
| 17 | 562.28595 |
| 18 | 563.78735 |
| 19 | 566.25152 |
| 20 | 566.91772 |
| 21 | 567.24585 |
| 22 | 567.76349 |
| 23 | 568.64807 |
| 24 | 571.90582 |
| 25 | 573.77539 |
| 26 | 581.73694 |
| 27 | 589.32348 |
| 28 | 601.79260 |
| 29 | 601.95440 |
| 30 | 604.25134 |
| 31 | 604.41015 |
| 32 | 608.38354 |
| 33 | 614.28143 |
| 34 | 614.78192 |
| 35 | 619.25683 |
| 36 | 622.77655 |
| 37 | 623.27374 |
| 38 | 627.17450 |
| 39 | 628.17425 |
| 40 | 631.36401 |
| 41 | 632.69647 |
| 42 | 638.27905 |
| 43 | 640.34161 |
| 44 | 648.30755 |
| 45 | 648.58545 |
| 46 | 650.31329 |
| 47 | 651.35296 |
| 48 | 677.32788 |
| 49 | 683.32922 |
| 50 | 684.33172 |
| 51 | 695.28955 |
| 52 | 698.28625 |
| 53 | 702.70654 |
| 54 | 702.98858 |
| 55 | 704.29077 |

TABLE 2-continued

List of masses of selenium containing compounds found in subfraction 8.

| No | Mass |
| --- | --- |
| 56 | 707.36828 |
| 57 | 709.31628 |
| 58 | 710.30029 |
| 59 | 712.28479 |
| 60 | 714.33471 |
| 61 | 714.83740 |
| 62 | 718.80896 |
| 63 | 720.81946 |
| 64 | 721.67334 |
| 65 | 722.00866 |
| 66 | 724.69372 |
| 67 | 724.83240 |
| 68 | 726.81750 |
| 69 | 727.31964 |
| 70 | 728.32373 |
| 71 | 729.84302 |
| 72 | 734.82367 |
| 73 | 741.04901 |
| 74 | 741.05059 |
| 75 | 741.38433 |
| 76 | 741.85113 |
| 77 | 745.81677 |
| 78 | 747.29687 |
| 79 | 748.37677 |
| 80 | 750.67205 |
| 81 | 751.87048 |
| 82 | 752.39074 |
| 83 | 764.31012 |
| 84 | 775.89483 |
| 85 | 776.39734 |
| 86 | 780.83679 |
| 87 | 781.35034 |
| 88 | 785.24920 |
| 89 | 789.43182 |
| 90 | 792.33807 |
| 91 | 794.72375 |
| 92 | 796.31152 |
| 93 | 803.32995 |
| 94 | 803.80926 |
| 95 | 804.80969 |
| 96 | 814.71167 |
| 97 | 814.79699 |
| 98 | 815.04895 |
| 99 | 815.80066 |
| 100 | 821.72363 |
| 101 | 821.87463 |
| 102 | 822.37549 |
| 103 | 828.33893 |
| 104 | 833.06408 |
| 105 | 833.06604 |
| 106 | 833.39843 |
| 107 | 833.40020 |
| 108 | 833.72723 |
| 109 | 833.72827 |
| 110 | 835.41009 |
| 111 | 839.04785 |
| 112 | 839.38415 |
| 113 | 839.82940 |
| 114 | 844.36627 |
| 115 | 844.40557 |
| 116 | 849.87439 |
| 117 | 850.19653 |
| 118 | 854.69995 |
| 119 | 855.03100 |
| 120 | 861.87719 |
| 121 | 862.36950 |
| 122 | 863.74206 |
| 123 | 863.74316 |
| 124 | 863.87079 |
| 125 | 864.07483 |
| 126 | 871.40753 |
| 127 | 872.73132 |
| 128 | 878.90771 |
| 129 | 881.38879 |
| 130 | 881.88763 |
| 131 | 886.74395 |
| 132 | 891.72467 |
| 133 | 895.74530 |
| 134 | 896.07586 |
| 135 | 908.87964 |
| 136 | 909.37103 |
| 137 | 924.37268 |
| 138 | 925.08465 |
| 139 | 925.41833 |
| 140 | 929.44366 |
| 141 | 929.74249 |
| 142 | 931.39825 |
| 143 | 932.34991 |
| 144 | 955.42822 |
| 145 | 960.50860 |
| 146 | 966.89325 |
| 147 | 975.96557 |
| 148 | 990.36322 |
| 149 | 990.41070 |
| 150 | 998.92859 |
| 151 | 1003.74280 |
| 152 | 1016.45190 |
| 153 | 1021.41125 |
| 154 | 1022.39312 |
| 155 | 1037.80859 |
| 156 | 1038.13623 |
| 157 | 1043.39104 |
| 158 | 1057.86181 |
| 159 | 1076.48632 |
| 160 | 1102.13940 |
| 161 | 1123.56475 |
| 162 | 1133.01947 |
| 163 | 1134.47436 |
| 164 | 1217.36182 |
| 165 | 1221.56891 |
| 166 | 1249.09771 |
| 167 | 1249.59564 |
| 168 | 1427.01928 |
| 169 | 1486.43866 |
| 170 | 1489.46460 |

Figure 12:
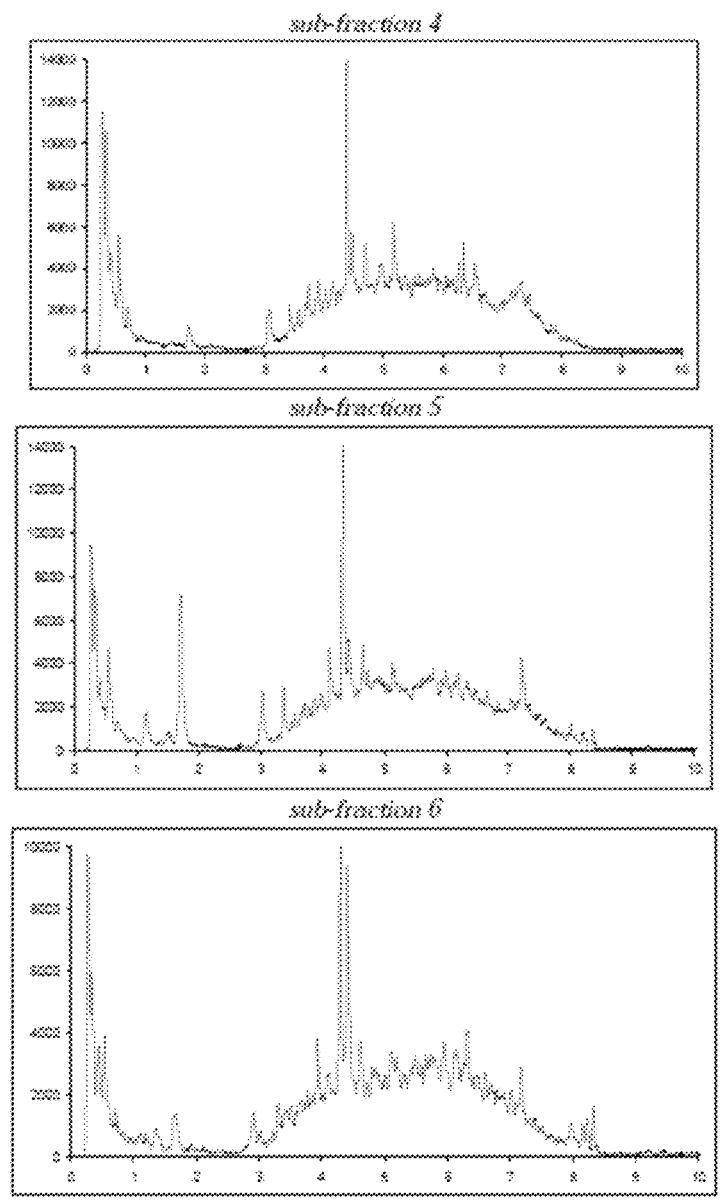
FIG. 12 shows chromatograms of subfractions of trypsin digested material. Subfractions 1-10 are shown.

Experiments were also performed in order to further characterize the sub-fractions. In particular, enzyme (e.g., tryptic) digestion of the sub-fractions was performed followed by analysis utilizing reverse phase chromatography and mass spectroscopy (e.g., HPLC-ICP MS). (FIG. 12) The UPLC-Orbitrap MS/MS analysis revealed the presence of a number of selenium containing peptides. The identity of the selenium containing peptides as well as the protein from which each of the selenium containing peptides was derived were determined and are shown in FIG. 13.

Further Analysis of Selenium Containing Compounds and/or Metabolites in Water Soluble Fractions of Selenium Rich Yeast The medium molecular size (ca. 300-1000 Da) water soluble organic selenium compounds were further targeted for identification and characterization. Unique selenometabolomes theoretically constitute fingerprints of yeasts from different sources (e.g., providing information regarding the constituent composition of the commercial products).

Water Extraction Followed by Fractionation.

0.2 g yeast (SEL-PLEX, selenium enriched yeast comprising 2% or less inorganic selenium, ALLTECH, Inc., Lexington Ky.) was extracted with 5 mL of water using an ultrasonic bath for one hour. The extract was centrifuged (2700 g, 10 min), decanted, lyophilized and stored in the freezer. The powder was then dissolved in 0.15 mL of 10 mM ammonium acetate buffer (pH 7.5) and centrifuged (14000 g, 15 min). The supernatant was fractionated on SUPERDEX peptide column (size exclusion chromatography, SEC); the elution was carried out with 100 mM ammonium acetate (pH 7.5) at 0.7 mL min-1. The eluate was collected between 20 and 30 min, frozen and lyophilized. The lyophilizate was dissolved in 0.15 mL of water and stored at −20° C. before further analyses.

HPLC-ICP MS Analysis

Lyophilized samples from SEC previously dissolved in water were diluted 20 times in buffer A and an aliquot of 10 µL was injected onto a cation-exchange PRP-X200 SCX column (150 mm×2.1 mm×10 µm; Hamilton, Reno, Nev.). Gradient elution was made with ammonium formate (buffer A: 1 mM ammonium and 10 mM formic acid in 20% methanol (pH 3), buffer B: 100 mM ammonium and 110 mM formic acid in 20% methanol (pH 6) delivered at 0.5 mL min-1. The eluate was split post-column in a way that a part of it (30%) was fed to ESI-MS and the rest (70%) went to the waste. The program was: 0-8 min up to 3% B, 8-15 3% B, 15-20 up to up to 10% B, 20-25 up to 100% B, 25-38 100% B, 38-40 up to 100% A, 40-52 100% A 4.1.3.

HPLC-ESI MS/MS Identification.

Cation-exchange HPLC-ESI MS on-line analysis of the purified Se-containing fractions was carried out with a PRP-X200 SCX column. Gradient elution was made in the same way as for ICP MS analysis. 5 µL of the sample was used for the analysis without previous dilution. The ion source was operated in the positive ion mode. The optimum settings were: ion source voltage, 2.60 kV; capillary temperature, 280° C.; source heater temperature, 120° C.; sheath gas flow, 20; auxiliary gas flow, 5; S-lens RF level, 61%; resolution, 100000. Mass spectra were acquired in the 100-1000 m/z range, and were processed with Xcalibur 2.1 software (Thermo Scientific). The instrument was mass calibrated with a mixture of caffeine, n-butylamine, Met-Arg-Phe-Ala (MRFA), Ultramark 1621 and sodium dodecyl sulfonate (SDS), dissolved in 50% acetonitrile and 0.1% formic acid solution.

The chromatographic conditions were optimized in view of compatibility with both ICP MS and ESI MS detector systems used. The cation-exchange HPLC-ICP MS profile of selenium containing compounds revealed the presence of a large number of peaks (See FIG. 14A). Experiments were also performed to generate the reversed phase ICP-MS chromatogram of the separated fractions (See FIG. 14B).

Figure 14:
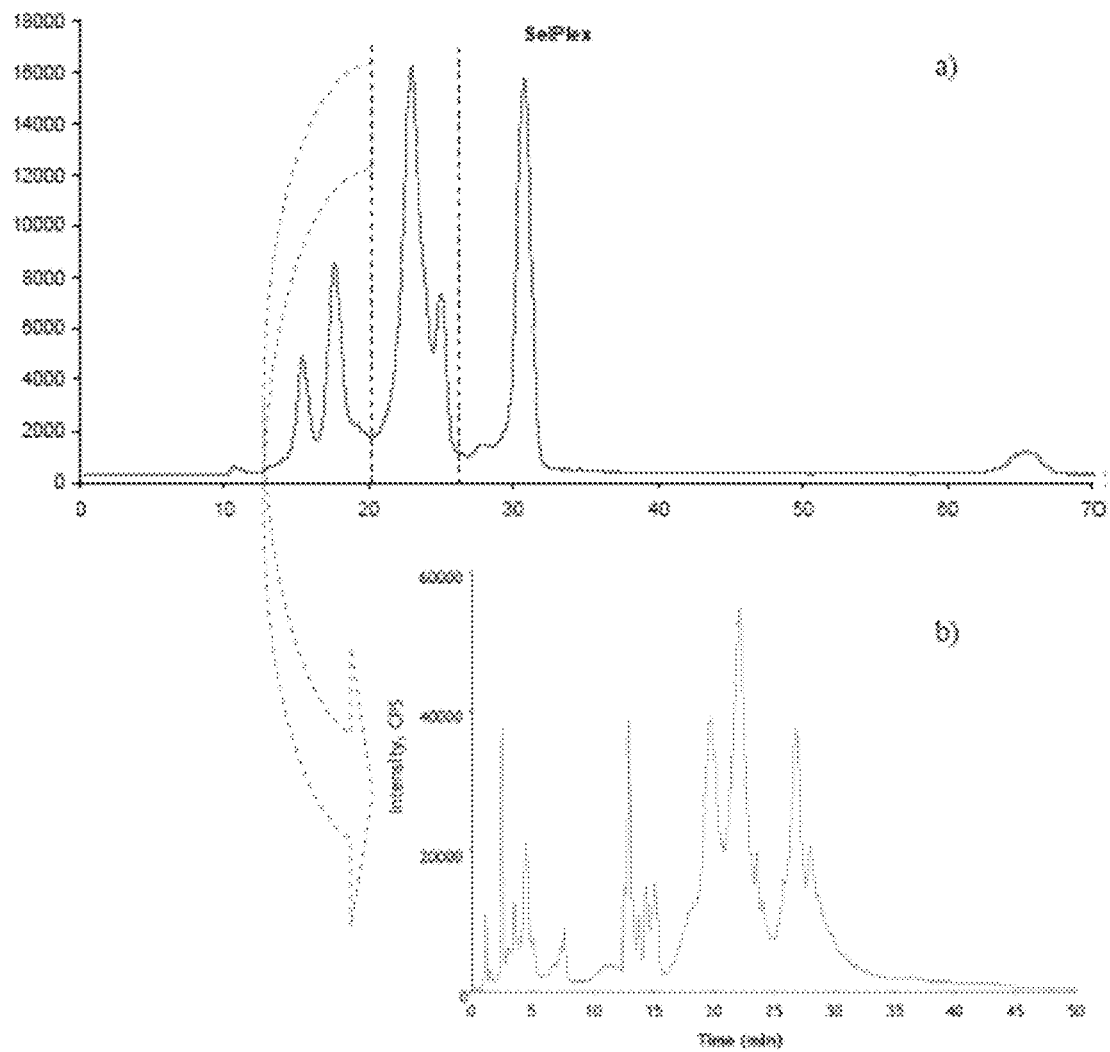
FIG. 14 shows the cation-exchange HPLC-ICP MS profile of selenium containing compounds present in SELPLEX (A) whole sample and (B) reversed phase ICP MS chromatogram of the separated fraction.

Subsequently, the same column was coupled with Orbitrap and selenium containing compounds/metabolites identified and characterized (See FIG. 14).

Additional sample preparation steps were utilized in order to fractionate and identify selenium species present in selenium enriched yeast. For example, size exclusion chromatography (e.g., utilizing a SUPERDEX column) was utilized prior to ICP-MS, with each fraction collected using size exclusion ICP MS (See, e.g., fractions encompassing each peak shown in FIG. 7A or 8A can be collected and analyzed). Analysis of the fractions was carried out according to procedures described herein (e.g., bimodal reversed-phase/hydrophilic ion interaction liquid chromatography-electrospray hybrid quadrupole trap/Orbital trap mass spectrometry, etc.). Additional selenium containing compounds identified in selenium enriched yeast (SELPLEX) using the above methods included: 2,3-DHP-selenocysteine-cysteine, N-acetylselenocysteine-selenohomocysteine, methylthioselenoglutathione, 2,3-DHP-selenocysteine-selenocysteine, 2,3-DHP-selenocysteine-cysteinylglycine, 2,3-DHP-selenocysteine-selenohomocysteine, 2,3-DHP-selenocysteine-selenohomocysteine, 2,3-DHP-selenohomocysteine-cysteinylglycine, selenomethyl-selenoglutathione, selenoglutathione-cysteine, glutathione-selenohomocysteine, 2,3-DHP-selenocysteine-γ-glutamoylcysteine, di-2,3-DHP-selenocysteine, N-acetylcysteine-selenoglutathione, Selenoglutathione-selenocysteine, 2,3-DHP-selenocysteine-2,3 DHP selenohomocysteine, glutathione-N-acetylselenohomocysteine, glutathione-selenocysteinylglycine, γ-glutamoyl selenocysteine-γ-glutamoyl cysteine, γ-glutamoylcysteine-2,3-DHP-selenocysteine, glutathione-2,3-DHP-selenocysteine, glutathione-2,3-DHP-selenohomocysteine, di-γ-glutamoylselenocysteine, selenoglutathione-γ-glutamoylcysteine, selenoglutathione-2,3-DHP-selenocysteine, selenoglutathione-2,3-DHP-selenohomocysteine, selenoglutathion-thio-2,3-DHP-selenocysteine, selenoglutathione-γ-glutamoylselenocysteine, selenoglutathione-glutathione, selenodiglutathione, diselenoglutathione, thio-diselenoglutathione, methyl dehydrohomocysteine, selenomethionine, selenohomolanthionine, N-acetylselenocystathionine, dehydroxy 5'-methylselenoadenosine, N-acetylcysteine-selenohomocysteine, 2,3-DHP-selenolanthionine, ethylselenoadenosine, N-propionylselenocystathionine, 2,3-DHP-selenocystathionine, methylselenoglutathione, γ-glutamoylselenocystathionine, selenoglutathione, seleno(hydroxyl)-selenophene-(3'-deoxy-adenosine), N-acetylcysteine-selenohomocysteine, allylselenoadenosyl homocysteine, seleno-adenosyl homocysteine, seleno-hydroxy adenosyl homocysteine, selno adenosine, seleno-adenosyl-Se(methyl)-selenoxide, adenosyl-hydroxy selenoxide, ethyl selenoadenosine, seleno-(hydroxy)-selenophene-(3'-desoxy-adenosine), adenosyl-hydroxy selnoxide, and selno-adenosyl-Se(methyl)-selenoxide. Accordingly, in some embodiments, the present application provides one or more selenium containing compounds (e.g., selenoethers, conjugates of SeCys containing di and tri peptides, selonols and selenoxides (e.g., provided in the above list) or derivatives thereof) compositions comprising the same and methods of using the same (e.g., for human and/or animal use as described herein).

Identification and Characterization of Water Insoluble Compounds and Metabolites 80-90% of selenium in SEL-PLEX prepared fractions were determined to be present in the form of selenium-containing compounds (e.g., proteins, peptides, nucleic acids, etc.) that are insoluble in water. Accordingly, experiments were conducted during development of embodiments of the present application in order to develop a method capable of extracting these compounds (e.g., extract a maximum amount of the compounds (e.g., intact or components derived therefrom) in order that the compounds be identified, characterized and/or quantified). In addition, experiments were conducted during development of embodiments of the present application in order to generate a purification process that permits ionization (e.g., efficient ionization) of the compounds (e.g., proteins, peptides, molecules, etc.) of the compounds by electrospray and/or analysis by Orbitrap. Accordingly, as described below, a method permitting the extraction of more than 50% of native compounds was developed. Solid-phase extraction fractionation was investigated. However, poor purity of the isolated compounds made analysis by Orbitrap MS non-informative. Other processes were identified that generated useful information. Size exclusion LC fractionation with and without an additional HPLC purification step were attempted that produced informative results.

Extraction of Selenium Species

Most of the selenium compounds/species (from ca. 70 to 95% of the total Se depending on the sample) present in the samples were water insoluble and required custom designed procedures to transfer them to solution prior to analysis by mass spectrometry. Twelve separate methods were tested and compared and the extraction yields (ratio of the total selenium in the extract to the total Se in the sample) obtained. The highest recovery of ca. 55% was obtained for a procedure based on extraction of proteins with 4% SDS combined with derivatization with iodoacetamide. The optimization was carried out for the SELPLEX sample for which the water soluble species represent ca. 15% of the total Se (The results are shown in the Table 3 below).

| Condition | Extraction yield, % |
|---|---|
| 4% SDS, 01M tris-HCl pH 7.5; derivitization | 55 |
| 4% SDS; 0.1M tris-HCl pH 7.5 | 40.2 |
| 5% glycerol; 2% SDS; 0.06M tris ph 8.8 | 18.9 |
| 7M urea; 0.1M tris pH 7.5 | 14.3 |
| 5M urea; 0.1M tris pH 7.5 | 11.4 |
| 7M urea; 3.3% CHAPs | 10.9 |
| 5M urea; 0.1M tris pH 7.5 | 10.6 |
| 0.1M tris pH 7.5 | 3.33 |
| 0.09M tris pH 7.5 | 2.63 |
| 5 mM MgCl$_2$; 0.1M tris pH 7.5 | 1.76 |
| 30% ethanol; 0.1M tris pH 7.5 | 1.16 |
| y-pex | 0.61 |
| * Water | 16.32 |

Extracted proteins were precipitated with acetone and digested with trypsin. Purification of the digested extracts was necessary prior to mass spectrometric analysis. In particular, the purification of the tryptic digest was optimized. The procedures tested included solid phase extraction in acidic and basic conditions (See Table 4 below) and preparative size-exclusion chromatography.

TABLE 4

Elution conditions used for solid phase extraction (SPE) purification of tryptic digestate of selenized yeast compounds.

| Acidic mode | Basic mode |
|---|---|
| H$_2$O pH 2.5 | H$_2$O pH 10.5 |
| H$_2$O 3% ACN pH 2.5 | H$_2$O 3% ACN pH 10.5 |
| H$_2$O 10% ACN pH 2.5 | H$_2$O 10% ACN pH 10.5 |
| H$_2$O 20% ACN pH 2.5 | H$_2$O 20% ACN pH 10.5 |
| H$_2$O 20% ACN pH 10.5 | H$_2$O 20% ACN pH 2.5 |
| H$_2$O 50% ACN pH 10.5 | H$_2$O 50% ACN pH 2.5 |
| H$_2$O 8% ACN pH 10.5 | H$_2$O 80% ACN pH 2.5 |

The results obtained are summarized in the Table 5 below showing the percentages of Se eluting in individual fractions.

| Condition | Percentage of Se in fraction |
|---|---|
| Water of acidic sample | 15% |
| H$_2$0 pH 2.5 | 11% |
| H$_2$0 3% ACN pH 2.5 | 11% |
| H$_2$0 10% ACN pH 2.5 | 16% |
| H$_2$0 20% ACN pH 2.5 | 18% |
| H$_2$0 20% ACN pH 10.5 | 18% |
| H$_2$0 50% ACN pH 10.5 | 8% |
| H$_2$0 80% ACN pH 10.5 | 3% |
| Water of basic sample | 5% |
| H$_2$0 pH 10.5 | 10% |
| H$_2$0 3% ACN pH 10.5 | 9% |
| H$_2$0 10% ACN pH 10.5 | 21% |
| H$_2$0 20% ACN pH 10.5 | 43% |
| H$_2$0 20% ACN pH 2.5 | 9% |
| H$_2$0 50% ACN pH 2.5 | 3% |
| H$_2$0 80% ACN pH 2.5 | 0% |

Figure 16:
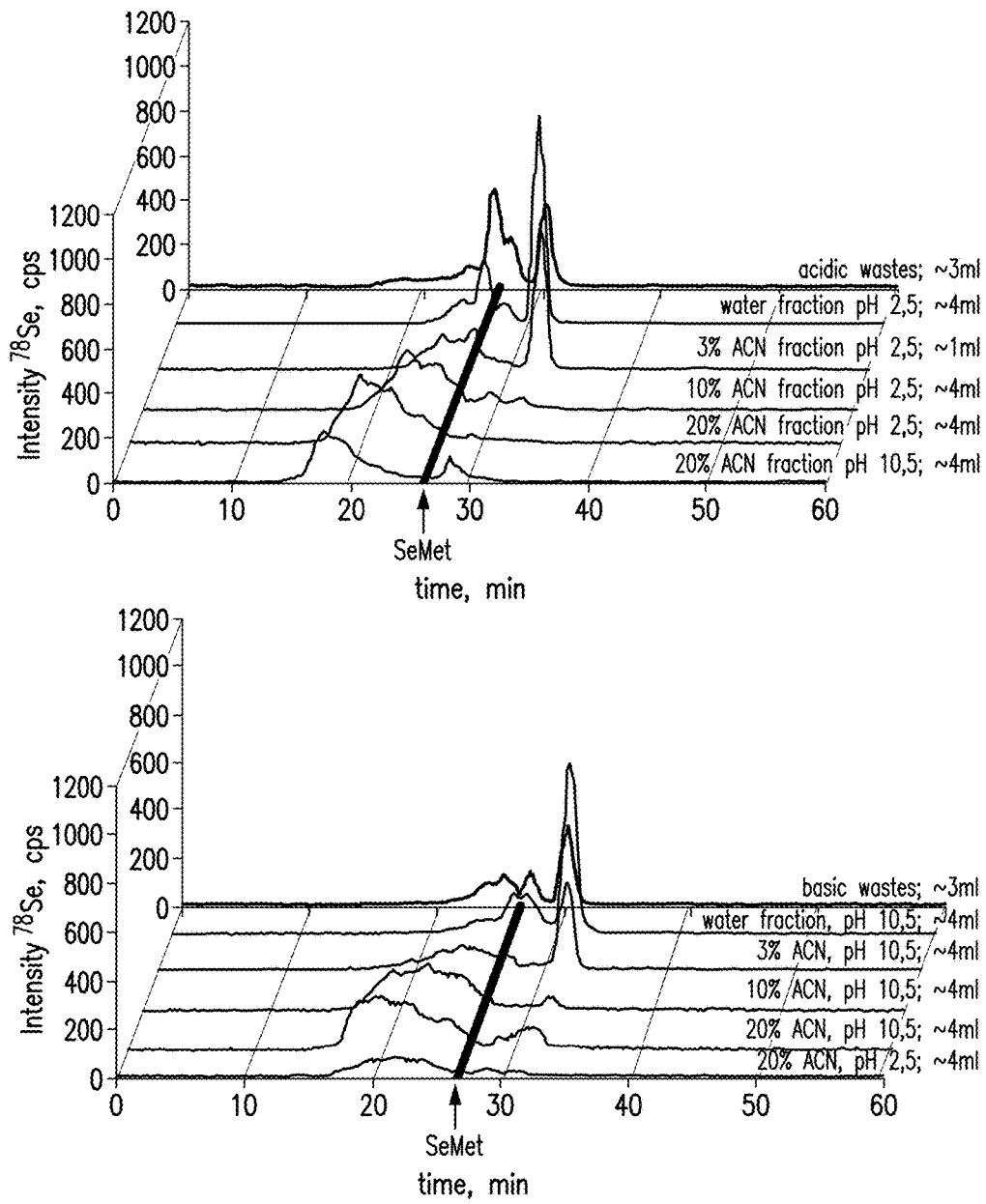
FIG. 16 shows the molecular weight (SEC-ICP MS) profiles of selenium species in individual SPE fraction eluted in the acidic (top panel) and basic (bottom panel) medium.
Figure 17:
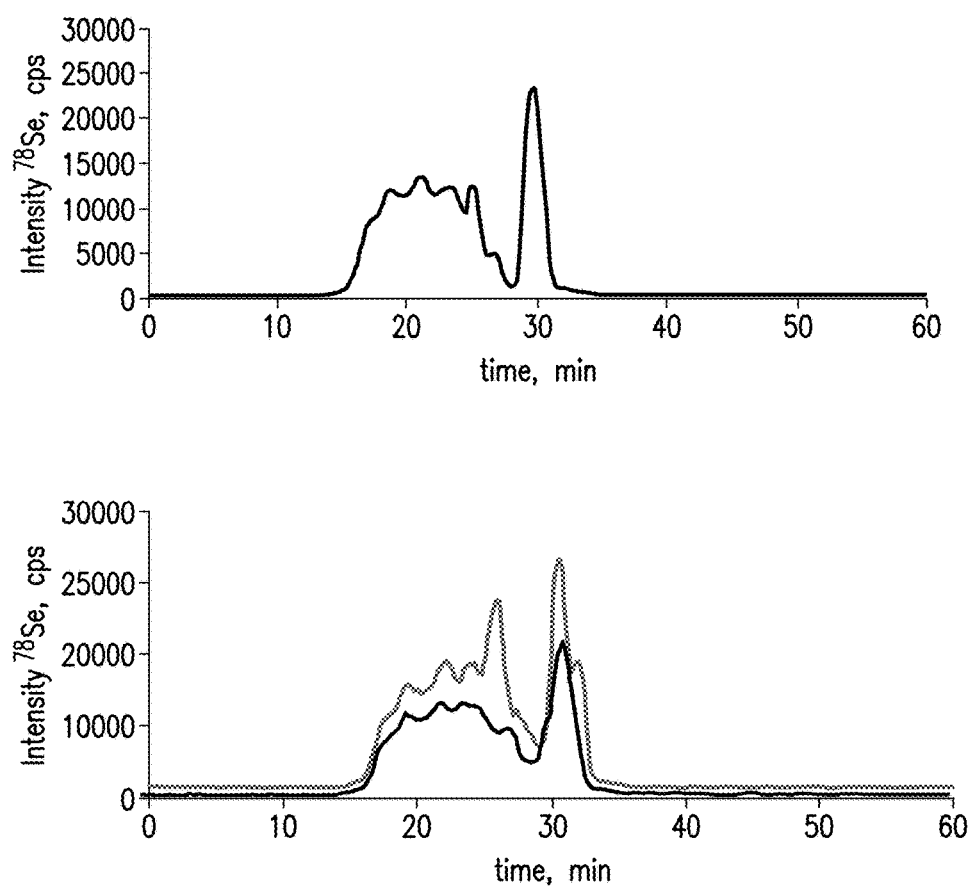
FIG. 17 shows SEC fractionation of the tryptic digest of yeast protein extract.
Figure 18:
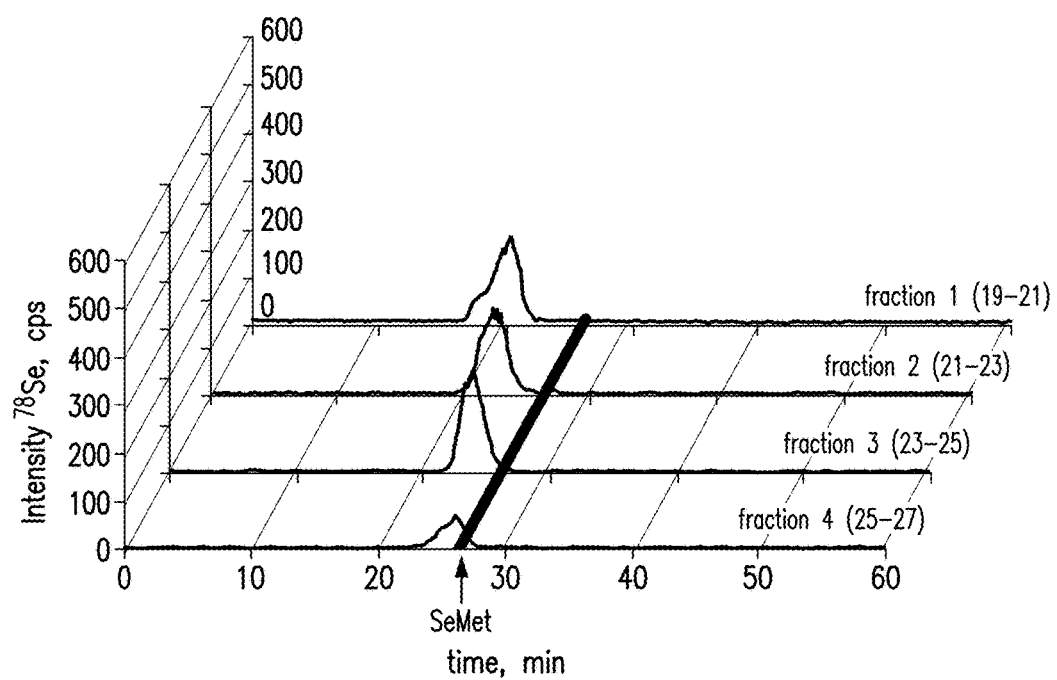
FIG. 18 shows the profiles of individual SEC fractions.

The molecular weight distribution of selenium compounds/species in individual fractions was identified by SEC-ICP MS (See FIG. 15) and the completeness of elution confirmed by the comparison of the sum of the profiles with the profile obtained for the raw digest (See FIG. 16). Unfortunately, the purity of the SPE-purified fraction proved to be insufficient for electrospray MS analysis. Finally, preparative size exclusion chromatography was chosen (See FIG. 17) which is more time consuming but provided useful material. FIG. 18 the profile of individual SEC fractions. This procedure allowed for the removal of low molecular Se fraction eluting after selenomethionine (e.g., that was not relevant for subsequent analysis).

The individual SEC fractions were analyzed by UPLC-Orbitrap MS/MS; several selenized peptides were identified. Ion-exchange HPLC fractionation can be utilized to confirm identity.

Accordingly, in some embodiments, the present application provides methods (e.g., comprising steps such as extraction of proteins with 4% SDS combined with derivatization with iodoacetamide, precipitation with acetone and enzymatic digestion (e.g., with trypsin), purification utilizing solid phase extraction in acidic and basic conditions, preparative size-exclusion chromatography, and analysis with HPLC fractionation and UPLC-Orbitrap MS/MS) for the identification of characterization of water insoluble selenium containing compounds and metabolites.

Analysis of Water Insoluble Selenium Containing Compounds by 1D Gel Electrophoresis The SDS extraction optimized and described above was identified as being highly efficient for generating fractions from SELPLEX. A separation method (1D gel electrophoresis) compatible with high concentrations of surfactant was generated. Laser ablation scanning allowed the identification of the parts of the gel with high selenium protein content that were then subsequently heartcut and subjected to enzymatic (e.g., tryptic) digestion. The tryptic digests were analysed by combined UPLC-ICP MS and UPLC-ES MS/MS. This process permitted the identification of the majority of compounds that originated from glyceryladehyde-3-phosphate dehydrogenase 3. Experiments conducted during development of embodiments of the present application identified that the protein glyceryladehyde-3-phosphate dehydrogenase 3. (35 kDa) that is found in SELPLEX is degraded during batch processing to a 10-15 kDa protein/peptide mixture accounting for over 80% of the insoluble proteins present. The data generated during development of embodiments of the present application and presented herein is the first identification and characterization of the water insoluble selenium containing compound fractions.

Water Extraction 0.1 g of the sample was weighted and washed twice with 5 mL of 30 mM Tris-HCl, pH 7.5 during 1 h in an ultrasonic bath. Supernatant was separated by centrifugation and frozen prior to analysis. Residues were taken for further analysis.

Extraction of Water Insoluble Proteins

Residue after water extraction was washed with 5 mL of 4% SDS solution in 0.1M Tris-HCl buffer. Samples were sonicated twice during 2 minutes with use of an ultrasonic probe and later on after addition of 50 μL of 0.2M DTT for 1 h in the ultrasonic bath. Samples were centrifuged and supernatant was taken for analysis.

Gel Electrophoresis

SDS extracts were analyzed for content of protein before and after electrophoresis for each sample four parallel analysis were performed (samples introduced to a gel in 4 different concentration). Gels were prepared in duplicate in order to make a transfer to blot membrane later on.

Blot Digestion Prior to HPLC Analysis

Based on the analysis by LA ICP MS, gel samples (samples L09-4531 and 0087-16) were chosen to be analyzed by HPLC ICP MS and HPLC MS/MS. Blots were cut according to visible bands as marked/described in FIG. 6 and FIG. 7 (described above). Pieces of blot were placed in separated tubes, extracted with TRITON X-100/CAN/Tris buffer, derivatized with IAM and DTT and digested with trypsin.

Figure 19:
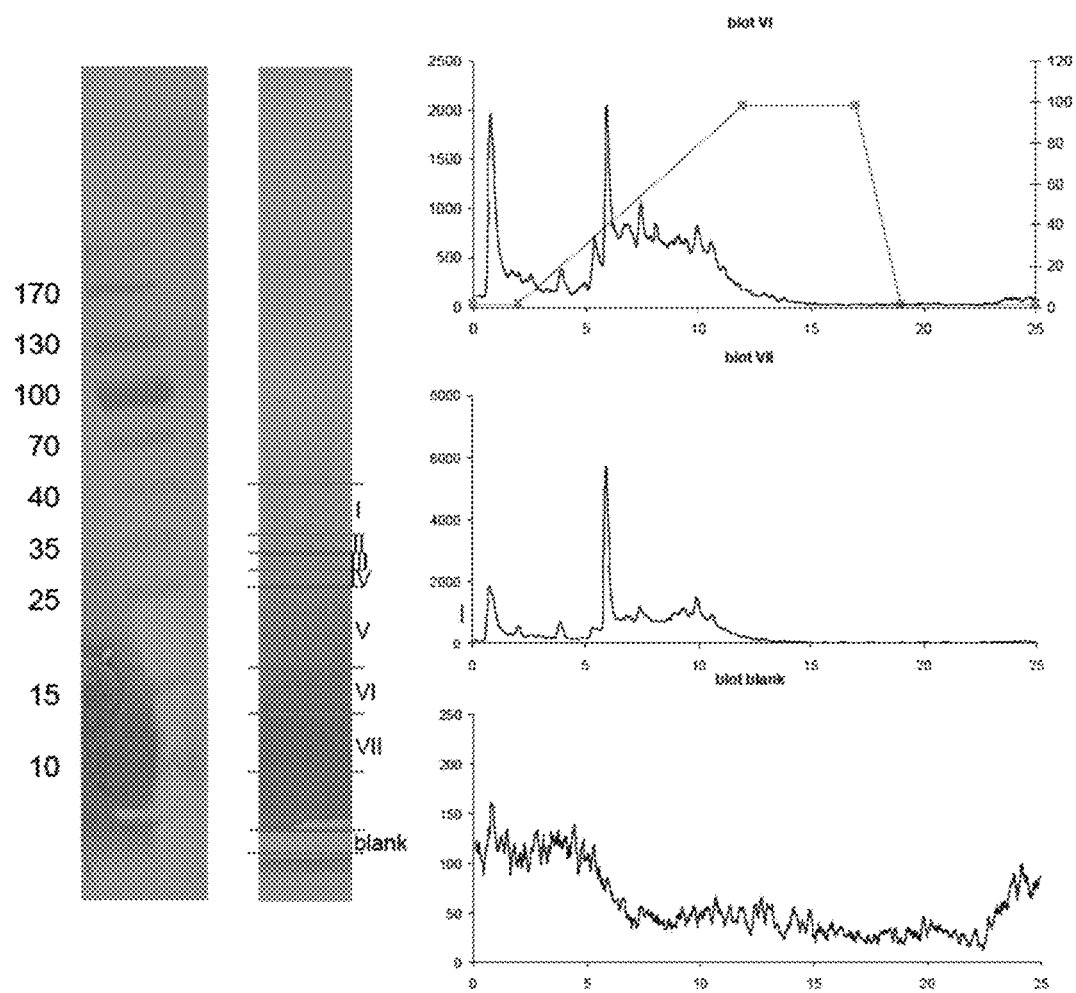
FIG. 19 shows blot of sample L09-4531 and RP ICP MS chromatograms of blot pieces number VI and VII.

ICP MS analysis of blot samples Two blot lines were chosen to be analyzed: one of yeast and the one of sample prepared for digest at pH 3. They were analyzed using C18 Phenomenex column using gradient elution program and water/methanol/formic acid solutions as eluents (See FIG. 19). From 7 bands cut out for sample L09-4531, two representative chromatograms are shown in FIG. 19 and were used for analysis with Orbitrap.

MS/MS Analysis of Blot Samples

Figure 20:
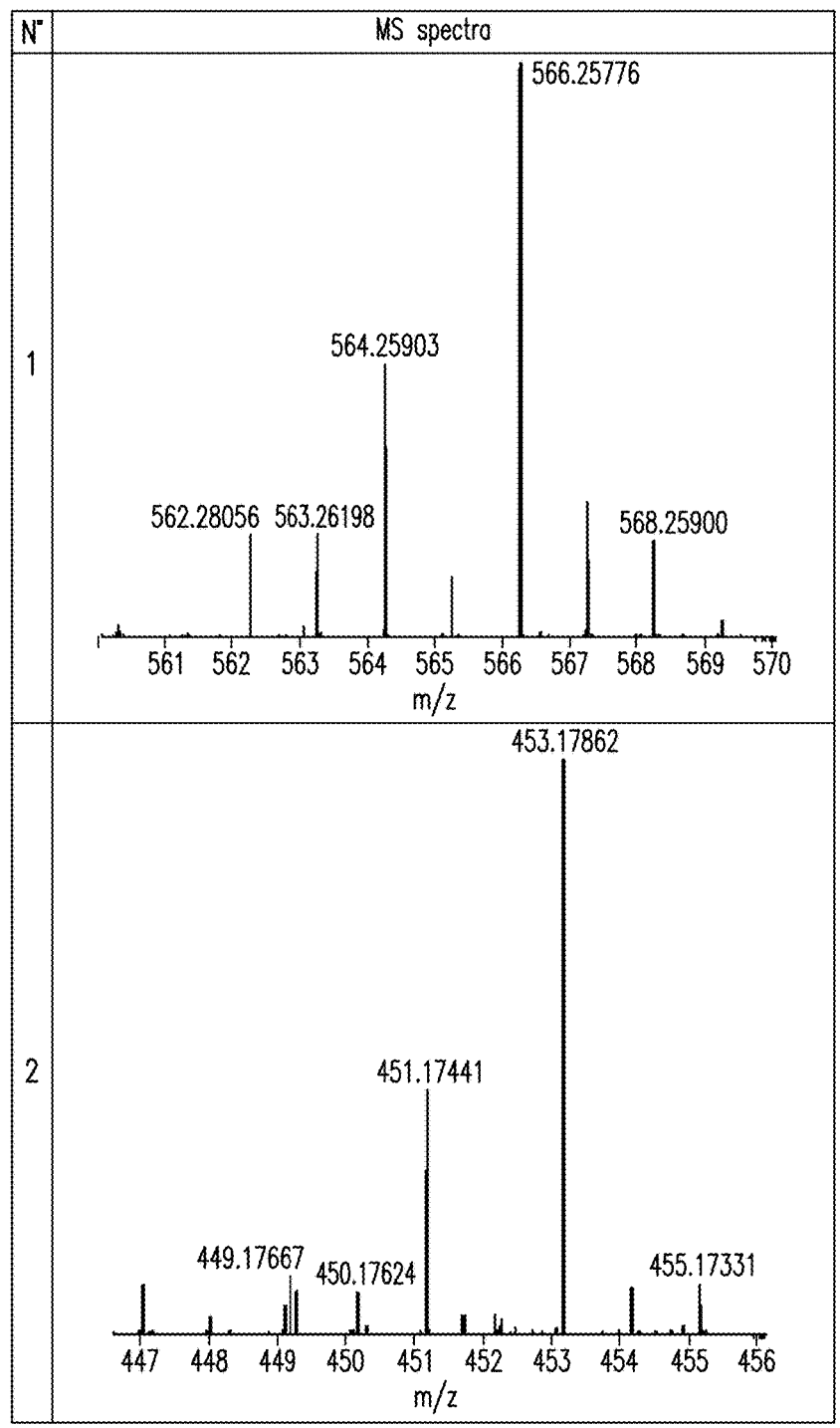
FIG. 20 shows exemplary MS spectra of selenium containing compounds found in blot samples extracts (water insoluble).
Figure 20:
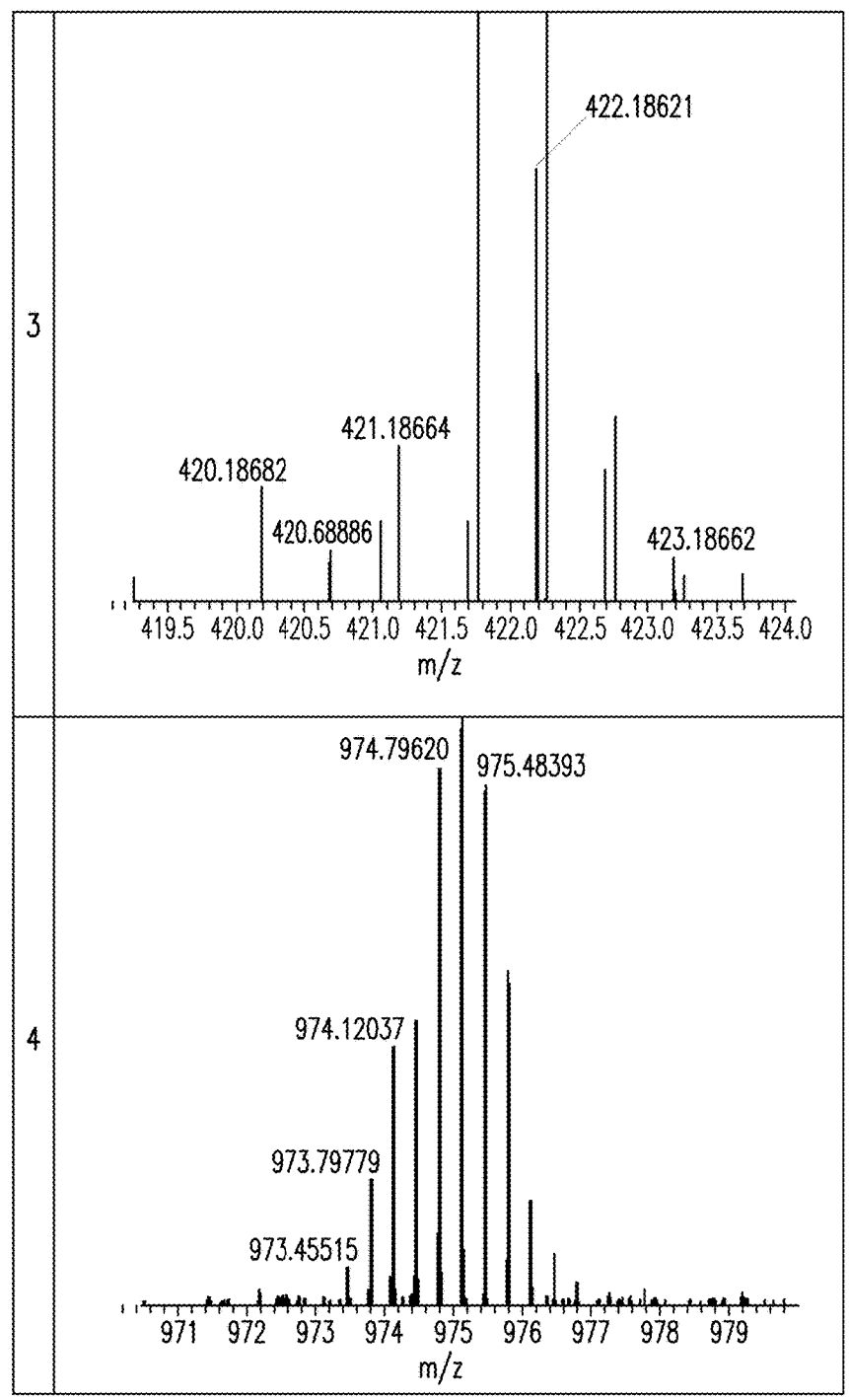
Figure 20:
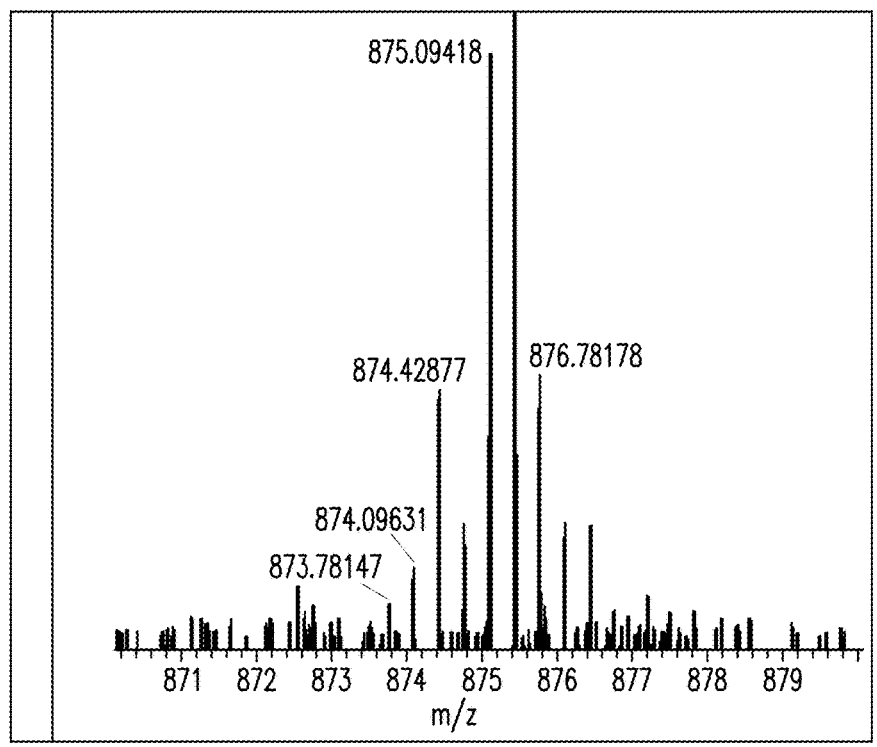

Full mass spectra was obtained. Searches for and identification of selenium containing compounds was performed as follows: MetWorks software was used to look for mono, double and triple charged compounds with selenium patterns; The list of compounds was checked manually in an effort to eliminate false positive identification; Once a list of compounds was identified and verified, a second run with Orbitrap was performed in order to obtain MS2 spectra for selected masses. MS spectras for 5 selenium containing compounds identified according to the described methods (and for which sequencing was performed) are presented in FIG. 20. Blot of yeast sample was divided into 10 parts. All of the 10 parts were analyzed with ICP MS. An interesting chromatogram was obtained from sample 6 which corresponded to the band at mass 35 kDa. The chromatogram was very similar to one obtained from a previous blot that identified peptides coming from glyceraldehyde-3-phosphate dehydrogenase 3. Thus, the present application provides that preparing a water insoluble extract at pH 3 lead to the digestion of glyceraldehyde-3-phosphate dehydrogenase 3.

MS2 analysis sequencing was performed manually. Sequence data was obtained and characterized by comparing and crosschecking with online proteomic databases (UNI-PROT, BLAST, etc.). FIG. 21 provides a list of selenium containing peptides identified by the described methods. It was concluded that each selenium containing peptide identified were derived from glyceraldehyde-3-phosphate dehydrogenase. Accordingly, in some embodiments, the present application provides one or more selenium containing compounds (e.g., identified in FIGS. 20 and 21), compositions comprising the same and methods of using the same (e.g., for human and/or animal use as described herein).

Example 2

Selenium Containing Compositions Inhibit Cardiac Muscle Cell Hypertrophy and Aging Materials and Methods Animals and Treatment.

Male PolG$^{(D257A)}$ mice expressing the homozygous mutation in the exonuclease encoding domain of mitochondrial DNA polymerase gamma at the genetic background of C57/BL6 were provided by Dr. Tomas A. Prolla (University of Wisconsin, Madison, Wis.). Mice were housed singly and maintained in the Shared Aging Rodent Facility at the William S. Middleton Memorial Veterans Administration Medical Center (Madison, Wis.). Temperature and humidity were maintained at constant levels. Room light was controlled to provide 12-hr cycles of light and dark. Mice were provided with water and fed experimental diets ad libitum which were stored in the dark at 4° C. Fresh diet was added to feeder twice weekly.

Immediately after weaning, mice were randomly assigned to one of three treatment groups. One group of mice received a basal diet having a selenium concentration of <0.01 mg/kg (SD) and a second group received a diet identical to the SD diet but with 1.0 mg/kg of selenium added thereto in the form of selenium enriched yeast comprising 2% or less inorganic selenium ((SP), SELPLEX, ALLTECH, Inc. Lexington, Ky.). The final selenium concentration of the SP diet was one (1) part per million. The selenium concentration in dietary premixes was evaluated by atomic absorption spectroscopy (See, e.g., Connolly, Power, Hynes, 2004); in the experimental diets, by Covance Inc. (Madison, Wis.). The basal SD diet contained 15 g/100 g total fat, as well as 538.6 g/kg sucrose, 300 g/kg Torula yeast, 140 g/kg corn oil, 3.0 g/kg DL methionine, 15.4 g/kg mineral mix (containing, on a g/kg diet basis, calcium carbonate, 2.02; sodium chloride, 2.6; potassium citrate (monohydrate), 7.7; potassium sulfate, 1.82; magnesium oxide, 0.84; ferric citrate, 0.21; manganous carbonate, 0.12; zinc carbonate, 0.056; chromium potassium sulfate, 0.019; cupric carbonate, 0.011; potassium iodate, 0.0004) and 3.0 g/kg vitamin mix (containing, on a mg/kg diet basis, choline bitartrate, 2800; niacin, 30; calcium pantothenate, 16; pyridoxine HCl, 7; thiamin HCl, 6; riboflavin, 6; folic acid, 2; biotin, 0.2; vitamin B-12 (0.1% in manniton, 25; dl-α-tocopheryl acetate (500 ug), 100; vitamin A palmitate (500,000 u/g), 8; cholecalciferol (500,000 u/g), 0.4; phylloquinone, 3).

From each treatment group, six mice were sacrificed after 60 days, and six after 400 days (referred to as POLG-young and POLG-old, respectively). Both groups of mice were sacrificed by cervical dislocation and tissue was collected. Experiments were performed at least in duplicate.

Tissue Preparation.

For cross-tissue gene expression studies, heart, liver, and gastrocnemius specimens were collected, flash frozen in liquid nitrogen and stored at −80° C. For brain-specific expression studies, the cerebral cortex was separated from the surrounding brain tissue, flash frozen in liquid nitrogen and stored at −80° C.

RNA Extraction.

Frozen tissue samples were homogenized using a QIA-GEN Tissue Ruptor (QIAGEN, Valencia, Calif.) and total RNA was extracted using an RNEASY Mini kit (QIAGEN) under protocols recommended by the company. Integrity and purity of isolated RNA was assessed using a NanoDrop ND-1000 spectrophotometer (Thermo Scientific, Wilmington, Del.) and further confirmed with an AGILENT 2100

Bioanalyzer System (AGILENT Technologies, Santa Clara, Calif.). Purified RNA was converted into double-stranded cDNA using GENECHIP Expression 3'-Amplification Reagents One-Cycle cDNA Synthesis Kit (AFFYMETRIX, Santa Clara, Calif.) with a T7-(dT)$_{24}$ primer and a T7 RNA polymerase promoter. Double-stranded cDNA was converted to biotin-labeled cRNA using the AFFYMETRIX GENECHIP Expression 3'-Amplification One-Cycle Target Labeling Kit (AFFYMETRIX) according to the manufacturer's recommended procedures. Biotin-labeled cRNA and cleaned using the GENECHIP Sample Cleanup Module and fragmented by heating (35 min at 94° C.).

Microarray and Bioinformatics Pathway Analyses.

Labeled cRNA was hybridized to mouse genome MG-430_2.0 GENECHIP arrays (AFFYMETRIX) for 16 h at 45° C., followed by washing, streptavidin-phycoerythrin (SAPE) staining and finally scanning in an GENECHIP Scanner 3000 7G (AFFYMETRIX). GENESPRING GX 12.5 (AGILENT) was used to validate and normalize microarray data and to perform statistical and gene expression pattern analyses. Briefly, normalization was done by first scale the intensity of probesets of the arrays to a mean target intensity of 500, followed by baseline transformation to median of all samples of this study. Background corrections were done by MASS based on its' Perfect Match (PM) and Mis-Match (MM) probe design of the microarray. To minimize the possibility of misleading findings, probe sets with low signal intensity and which were labeled as 'Absent' by the AFFYMETRIX MASS algorithm across samples were excluded from further analysis. The differentially expressed genes were filtered using the volcano plot method where genes with P<0.05 and corresponding signal intensity fold change (FC)>1.2 or FC<−1.2 were defined as significantly different.

To dissect the biological themes represented by altered transcription profiles, two independent pathway analysis approaches were applied. First, parametric analysis of gene set enrichment (PAGE) was performed, a computational method that allows determination of significant changes in defined gene set (See, e.g., Kim & Volsky, 2005) to identify significantly altered biological processes and signaling pathways by diet. Only those gene ontology (GO) terms those have at least 10 and at most 1,000 genes and have level 3 and below were analyzed. To further identify functional clusters that characterize the transcriptional alterations associated with dietary Se status, significantly changed genes were further grouped into networks, functions and canonical pathways using Ingenuity Pathways Analysis software (IPA, Ingenuity Systems, Redwood City, Calif.). Fischer's exact test was used to determine the significance of the association between the genes and the given network, biological function or canonical pathway.

Real-Time PCR Analysis:

Real-time PCR analysis was performed using the Applied-Bioscience's predesigned TAQMAN probes and primers (INVITROGEN) according to the manufacturer's recommended procedures. Data were normalized by Actb levels in each sample, and presented as mean±sem of the number of samples.

Total Protein Determination:

Cardiac tissue weights were determined using an electronic balance and then homogenized as described (See, e.g., Lan et al., Biol Reprod, 1998. 58(1): p. 197-206). Protein levels in the homogenates were determined using the Pierce 660 nm protein assay kit (Thermo Scientific-Pierce Biotechnology, Rockford, Ill.) according to the manufacturer protocol. Total protein level in each sample was normalized by the tissue weight.

Western Blot Analysis:

For Western blot analysis, equal amounts of cardiac protein from SD- or SP-treated PolG mice were subjected to SDS-PAGE gel separation, and then transferred to PVDF membranes, as described previously (See, e.g., Lan et al., Biol Reprod, 1998. 58(1): p. 197-206; Adhikari et al, Hum Mol Genet, 2010. 19(3): p. 397-410); Reddy et al., Science, 2008. 319(5863): p. 611-3). Membrane blots were then blocked in a phosphate-buffered saline containing 5% (w/v) of bovine serum albumin (Sigma, St. Louis, Mo.), followed by the incubation with specific antibodies against Myh7 (Santa Cruz), Ankrd1 (Santa Cruz), GSK3β (Cell Signaling), Foxo3a (Cell signaling), calcineurin A (Abcam), phosphorylated NFATc2, phosphorylated NFATc3 (Santa Cruz), Actb or beta-tubulin (Li-COR). Positive signals on the membrane blots were detected using the Amersham's enhanced chemiluminescence Western Blotting Detection reagents (GE healthcare) or fluorescent-labeled secondary antibodies (LI-COR). Images of these signals were recorded using the LI-COR Odyssey Fc Image system. Protein band densities were determined using the Li-COR Image studio software or NIH ImageJ software, and then normalized by Actb or beta-tubulin levels in each sample. Data are presented as mean±sem of the number of samples denoted in the figure legends. Experiments were repeated at least twice.

Statistical Analysis.

For real-time PCR and Western blot analyses, Student's t-test was performed to determine the statistical difference between two groups, while one-way ANOVA followed by Student's t-test were performed to determine the difference among multiple groups. A p-value less than 0.05 was considered significant.

Figure 22:
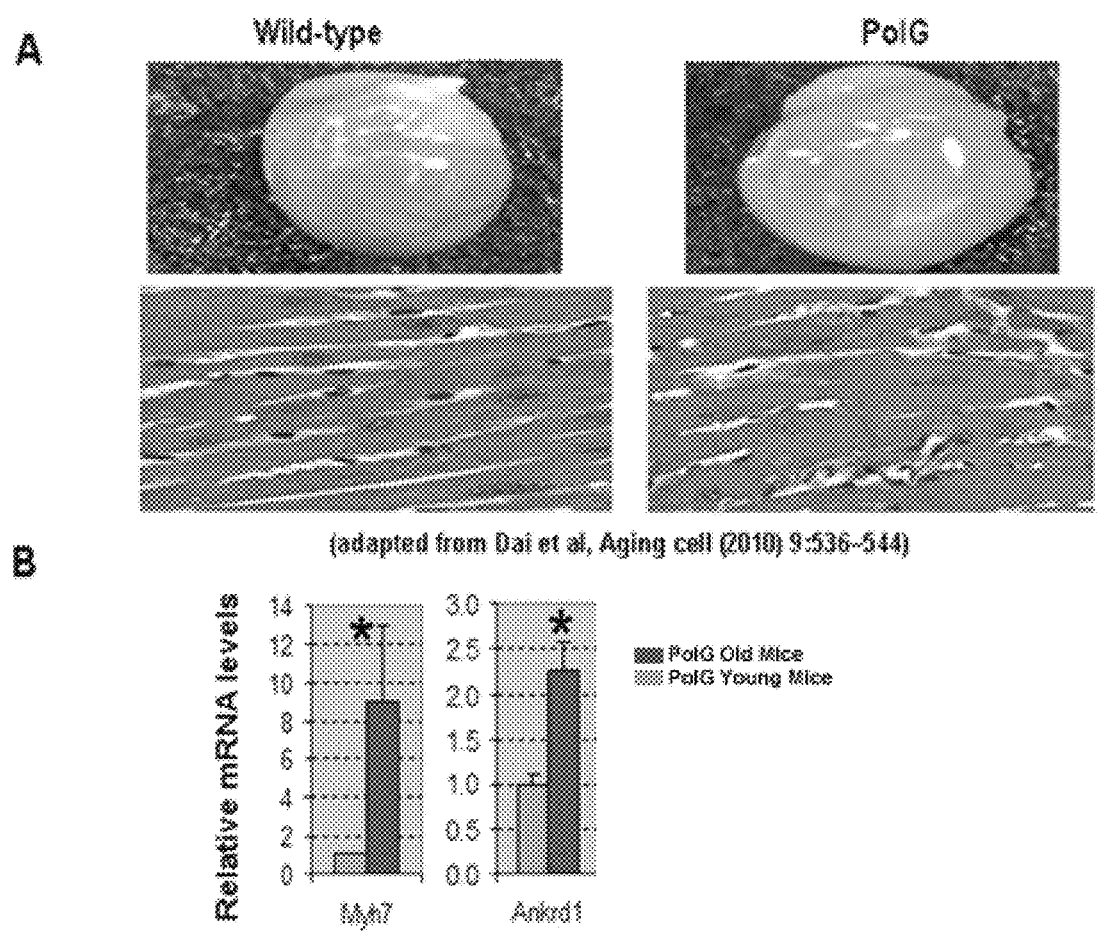
FIG. 22 shows heart hypertrophy with elevated hypertrophic marker genes including Myh7 and Ankrd1 in 13-month-old PolG mice. (A) enlarged heart size and cardiomyocytes from 13-14-month-old PolG mice. Photos are adapted from Dai et at (2010). (B) elevated Myh7 and Ankrd1 expression in 13-month-old PolG hearts (dark bars). Expression levels were normalized by Actb mRNA, and presented as mean±SEM (n=6). *$P<0.01$, when compared to their expression in 2-month-old PolG hearts (light bars).

Administration of Selenium in the Form of Selenium Enriched Yeast Inhibits Myh7 and Ankrd1 Expression in Cardiac Muscle of Aged PolG Mice Nucleus-encoded DNA polymerase c (POLG) is the only known DNA polymerase in animal cell mitochondria. Mutations in the human POLG gene are connected to numerous diseases associated with a variety of symptoms, including ophthalmoplegia, cataracts, progressive muscle weakness, parkinsonism, premature ovarian failure, male infertility, hearing loss (presbycusis), and cardiac dysfunction (See, e.g., Kujoth et al., PLoS Genetics, 2007. 3(2)). The PolG$^{(D257A)}$ mouse model displays progressive decline in respiratory function of mitochondrially encoded complexes at 12 weeks, resulting in decreased oxygen consumption and reduced ATP production (See, e.g., Kujoth et al., PLoS Genetics, 2007. 3(2)). It has been reported that PolG mice display accelerated cardiac aging phenotypes with marked cardiac hypertrophy indicated by enlarged heart size and cardiomyocytes by the ages of 13-14 months (See, e.g., Dai et al 2010, Kujoth et al., 2005 and FIG. 22A).

Hypertrophic cardiomyopathy (HCM) is the most-common monogenically inherited form of heart disease and is the most-common cause of sudden cardiac death in individuals younger than 35 years of age (See, e.g., Frey et al., Nat Rev Cardiol, 2012. 9(2): p. 91-100). Genetic mutations that are the basis for HCM have been well characterized, with a majority of mutations encoding sarcomeric proteins, such as myosin-7 (also known as cardiac muscle β-myosin heavy chain; MYH7) (See, e.g., Frey et al., Nat Rev Cardiol, 2012. 9(2): p. 91-100).

Cardiac ankyrin repeat protein (CARP) is encoded by the ANKRD1 gene and expression of the ANKRD1 gene and CARP nuclear factor is involved in left ventricular hypertrophy, human heart failure, dilated cardiomyopathy (DCM), and adriamycin-induced cardiomyopathy (See, e.g., Duboscq-Bidot et al., Archives of Cardiovascular Diseases, 2009. 102, Supplement 1(0): p. S73). Consistent with documented phenotypes, age-dependent expression of cardiac hypertrophy markers Myh7 and Aknrd1 were elevated in heart tissue of POLG old mice when compared to POLG young mice (See FIG. 22B).

Figure 23:
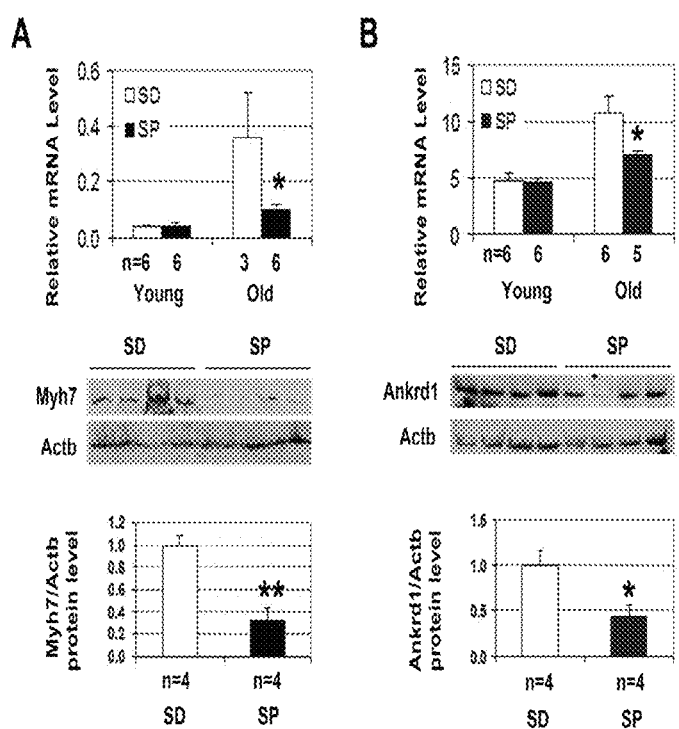
FIG. 23 shows attenuated expression of hypertrophic markers Myh7 and Ankrd1 in mouse cardiac muscle from mice administered selenium in the form of selenium rich yeast by real-time PCR and Western blot analysis. A. Cardiac expression of Myh7 mRNA (top panel) in control (SD) and treated (SP) young and old PolG mice by real-time PCR, and of Myh7 protein (middle panel) of control (SD) and treated (SP) older PolG mice by Western blot analyses. Relative Myh7 protein expression (normalized by Actb protein in each sample) is shown in the bottom panel. B. Cardiac expression of Ankrd1 mRNA (top panel) in control (SD) and treated (SP) young and old PolG mice, and Ankrd1 protein (middle panel) in control (SD) and treated (SP) older PolG mice. Quantitative Myh7 protein expression (normalized by Actb protein in each sample) is shown in the bottom panel. For both A and B, data are presented as mean±sem of indicated numbers of mice. *$P<0.05$, **$P<0.01$, vs the control at the same age.

Experiments were conducted during development of embodiments of the present application in order to determine if the administration of selenium could alter the expression of hypertrophic molecules. It was observed that the expression of hypertrophic markers myosin heavy chain beta (Myh7) and cardiac ankyrin repeat protein (Ankrd1) were down-regulated in PolG old mice administered selenium in the form of selenium rich yeast comprising 2% or less inorganic selenium when compared to PolG old mice administered the SD control diet. In order to confirm this observation, quantitative real time (QRT)-PCR was performed and the expression of Myh7 (FIG. 23A, top panel) and Ankrd1 (FIG. 23B, top panel) were significantly down-regulated in PolG old mice administered selenium in the form of selenium rich yeast comprising 2% or less inorganic selenium when compared to PolG old mice administered the SD control diet. Western blot analysis was performed using Myh7 and Ankrd1 specific antibodies and cardiac Myh7 and Ankrd1 protein levels in PolG old mice administered selenium in the form of selenium enriched yeast comprising 2% or less inorganic selenium were significantly lower than PolG mice fed with SD control diet (See FIG. 23A-B, bottom panels). Thus, the present application provides that selenium enriched yeast comprising 2% or less inorganic selenium (or one or more selenium containing compounds present therein), when administered to a subject inhibits the accumulation of hypertrophic proteins Myh7 and Ankrd1 (e.g., thereby inhibiting and/or preventing cardiac muscle aging and hypertrophy).

Figure 24:
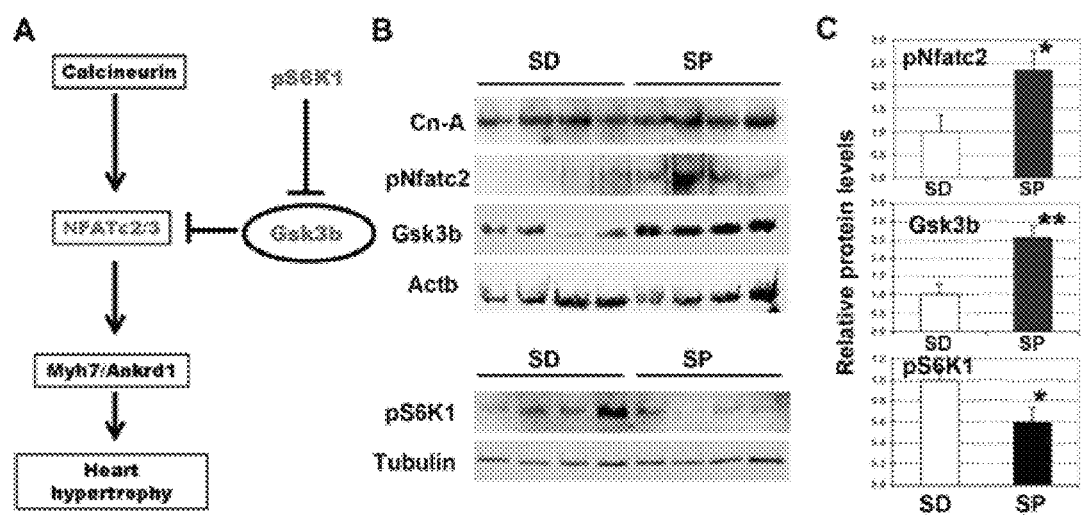
FIG. 24 shows regulation of Nfat signaling in mouse heart via administration of selenium in the form of selenium rich yeast. A. Schematic representation of Cn/Nfat signaling in cardiac hypertrophy. Nfat activity is regulated by pathways involving calcineurin; S6K and Gsk3b. Grey text represent the molecular targets in the heart identified during experiments conducted during development of embodiments of the present application to be regulated by selenium in the form of selenium rich yeast. B. Western blot analyses of Cn-A, pNfatc2, Gsk3b and pS6K1 in the hearts from control (SD) and treated (SP) mice at the age of 13 months. C. Quantitative analysis of pNfatc2, Gsk3b and pS6K1 protein levels (normalized by Actb or tubulin) in Western blots. In C, data are presented as mean±sem of four mice per group. *$P<0.05$, **$P<0.01$.

Administration of Selenium in the Form of Selenium Enriched Yeast Alters Signaling Pathways Known to Induce Cardiac Hypertrophy by Regulating Phosphorylation and Protein Levels of NFATs, Gsk3β and S6K in PolG Old Mice Calcineurin-NFAT signaling is activated in pathological cardiac hypertrophy and heart failure (See, e.g., Molkentin, Cardiovascular Research, 2004. 63(3): p. 467-475). Calcineurin was originally implicated as a hypertrophic signaling factor based on its over expression in the hearts of transgenic mice. Mice expressing an activated mutant of calcineurin demonstrated a profound hypertrophic response (2-3-fold increase in heart size) that rapidly progressed to dilated heart failure within 2-3 months (See, e.g., Molkentin, Cardiovascular Research, 2004. 63(3): p. 467-475). The main mechanism of Cn action is to stimulate the dephosphorylation of nuclear factor of activated T cells (NFAT) in the cytosol, which results in the elevation of unphosphorylated NFAT in the nuclei. Once in the nucleus, NFAT family members participate in the transcriptional induction of various immune response genes in T cells (See FIG. 24A). There are four calcineurin-regulated NFAT transcription factors, NFATc1-c4, each of which are only activated by calcineurin and are expressed in the myocardium (See, e.g., Molkentin, Cardiovascular Research, 2004. 63(3): p. 467-475). Thus, further experiments were performed in order to determine if selenium in the form of selenium enriched yeast comprising 2% or less inorganic selenium could reduce expression of Cn and thus alter Cn/NFAT signaling (e.g., so as to prevent or reduce cardiac hypertrophy).

Western blot analysis was performed to compare the protein levels of calcineurin-A (Cn-A) as well as the phosphorylation status of four NFAT subunits (NFATC1, C2, C3 and C4) in the heart of PolG old mice administered selenium in the form of selenium enriched yeast comprising 2% or less inorganic selenium compared to PolG old mice fed with SD control diet. As shown in FIG. 24B, Cn-A levels in PolG old mice were not altered; however, phosphorylated-NFATc2 (pNFATc2) levels were elevated in the heart of PolG old mice administered selenium in the form of selenium enriched yeast comprising 2% or less inorganic selenium compared to POLG old mice administered the SD control diet (FIGS. 24B and 24C). Elevated levels of phosphorylated NFATc3 were also detected in subjects administered selenium in the form of selenium enriched yeast comprising 2% or less inorganic selenium, while phosphorylated NFATc1 and C4 were not detected.

The action of calcineurin and the nuclear shuttling of NFAT are antagonized by GSK3β as it directly phosphorylates the N-terminal regulatory domain of NFATc1 (See, e.g., Crabtree et al., 2002). Increased expression of GSK3β reduced cardiac myocyte hypertrophic growth and in transgenic mice in which constitutive or inducible GSK3 f3 expression in the heart was generated, cardiac hypertrophy in response to the activated calcineurin was reduced (See, e.g., Molkentin, Cardiovascular Research, 2004. 63(3): p. 467-475). Experiments were conducted during development of embodiments of the present application to identify what role administration of selenium in the form of selenium enriched yeast comprising 2% or less inorganic selenium might have on cardiac GSK3β levels. As shown in FIGS. 24B and 24C, it was discovered that POLG old mice administered selenium in the form of selenium enriched yeast comprising 2% or less inorganic selenium had significantly enhanced cardiac expression of GSK3β compared to POLG old mice administered the SD control diet.

Recent studies have shown that inhibition of mammalian target of rapamyin (mTor) and loss of S6K can prolong mouse lifespan even though the latter is only observed in male mice (See, e.g., Selman et al., Science, 2009. 326 (5949): p. 140-4); Harrison et al., Nature, 2009. 460(7253): p. 392-5). S6K has been reported to inhibit GSK3β activity in other cells (See, e.g., Cohen and Frame, Nat Rev Mol Cell Biol, 2001. 2(10): p. 769-76). Therefore experiments were conducted in order to test whether protein levels of phosphorylated S6K (pS6K1), mTor and its downstream target in protein synthesis p4E-BP, and PI3K signaling molecules pPDK1 and pAkt, were altered in POLG old mice administered selenium in the form of selenium enriched yeast comprising 2% or less inorganic selenium compared to POLG old mice administered the SD control diet. It was discovered that pS6K1 levels, but not mTOR nor other phosphorylated PDK1/Akt/4E-BP, were significantly reduced in PolG old mice administered selenium in the form of selenium enriched yeast comprising 2% or less inorganic selenium compared to POLG old mice administered the SD control diet (See FIGS. 24A and 24B).

Administration of Selenium in the Form of Selenium Enriched Yeast Augments Foxo3, but not Foxo1 or Foxo4, Expression Recent studies have shown that forkhead box transcription factors (Foxo) family genes Foxo1, Foxo3 and Foxo4 are critical for cardiac hypertrophy and/or survival against oxidative stress (See, e.g., Ni et al, Circulation, 2006. 114(11): p. 1159-68; Sengupta et al, J Biol Chem, 2011. 286(9): p. 7468-78).

Accordingly, experiments were conducted to determine what role administration of selenium in the form of selenium enriched yeast comprising 2% or less inorganic selenium might have, if any, on Foxo family transcription factors. Utilizing real time PCR, it was determined that there was no age-dependent up- or down-regulation in the expression of each Foxo gene analyzed in heart tissue of POLG mice. Furthermore, although there was no significant effect on Foxo1 or Foxo4 expression, there was a significant increase in the expression of Foxo3 (both mRNA and protein) in POLG old mice administered selenium in the form of selenium enriched yeast comprising 2% or less inorganic selenium compared to POLG old mice administered the SD control diet (See FIG. 25). Heart hypertrophy has been documented Foxo3 null mutant mice, but not in Foxo4 null mutant mice (See, e.g., Ni et al, Circulation, 2006. 114(11): p. 1159-68). Thus, the present application provides that an increase in expression of Foxo3 functions to positively control transcriptional activity in the heart.

Figure 26:
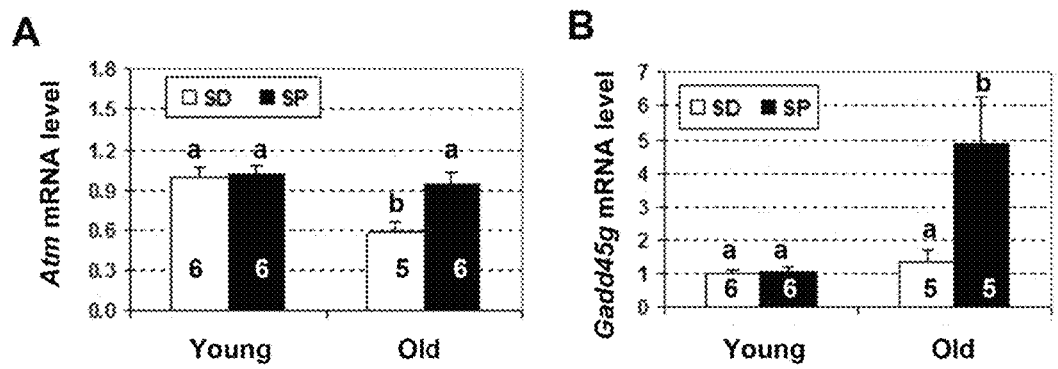
FIG. 26 shows regulation of Atm and Gadd45g expression at the mRNA level in PolG mice. A. QRT-PCR showing the age-dependent reduction of cardiac Atm expression in PolG mice, and the abolishment of this reduction via administration of selenium in the form of selenium enriched yeast. B. Elevated Gadd45g mRNA expression in PolG mice after administration of selenium in the form of selenium enriched yeast treatments for 374 days. Data are presented as mean±sem of indicated numbers of mice per group. Different letters in the bar graphs represent a significant difference as determined by ANOVA analysis followed by Student's t-test.

Administration of Selenium in the Form of Selenium Enriched Yeast Regulates Cardiac Atm/Gadd45g Signaling in Old PolG Mice Atm/Gadd45 signaling is a critical pathway in cell cycle arrest and DNA repair [13, 14]. Experiments were conducted during development of embodiments of the present application in order to characterize Atm and Gadd45 expression in heart of PolG old mice administered selenium in the form of selenium enriched yeast comprising 2% or less inorganic selenium compared to POLG old mice administered the SD control diet. It was discovered, utilizing QRT-PCR, that there was an age-dependent decrease of Atm expression in PolG mouse heart (See FIG. 26A). Interestingly, administration of selenium in the form of selenium enriched yeast comprising 2% or less inorganic selenium abolished the age-dependent decrease of Atm expression in the heart of PolG old mice (See FIG. 26A). In addition, the expression of heart Gadd45, a downstream target of the Atm/Trp53(p53, a well-known tumor suppressor key for cell cycle arrest and DNA repair), was significantly up-regulated in PolG old mice administered selenium in the form of selenium enriched yeast comprising 2% or less inorganic selenium compared to POLG old mice administered the SD control diet (See FIG. 26B).

Figure 27:
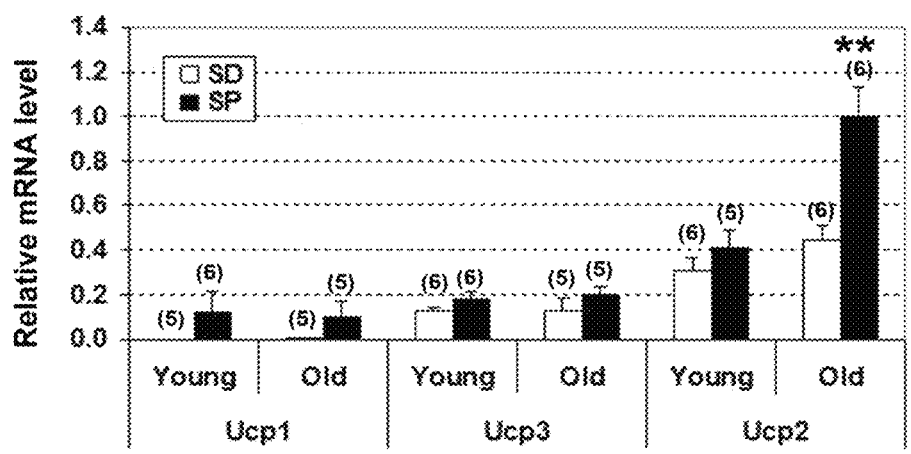
FIG. 27 shows regulation of Ucp1-3 mRNA expression by selenium treatment in PolG hearts by QRT-PCR. Data are presented as mean±sem of indicated numbers of mice per group. **P<0.01 when compared to Ucp2 expression in controls.

Administration of Selenium in the Form of Selenium Enriched Yeast Regulates Mitochondrial Ucp2 in Cardiomyocytes Uncouple proteins in mitochondria (MT) are critical for themogenesis and maintenance of MT potentials or integrity (See, e.g., Sena et al., Mol Cell, 2012. 48(2): p. 158-67; Krauss et al., Nat Rev Mol Cell Biol, 2005. 6(3): p. 248-61). Loss of Ucp2 has been documented to cause shorter lifespan and elevated production of reactive oxygen species (ROS) in MT (See, e.g., Andrews et al. Am J Physiol Endocrinol Metab, 2009. 296(4): p. E621-7; Andrews et al., Curr Aging Sci, 2010. 3(2): p. 102-12). Experiments were conducted during development of embodiments of the present application in order to characterize Ucp1, 2 and Ucp3 expression in POlG old mice administered selenium in the form of selenium enriched yeast comprising 2% or less inorganic selenium compared to POLG old mice administered the SD control diet. It was discovered, utilizing QRT-PCR, that Ucp2 was significantly elevated in PolG old mice administered selenium in the form of selenium enriched yeast comprising 2% or less inorganic selenium compared to POLG old mice administered the SD control diet (See FIG. 27).

Administration of Selenium in the Form of Selenium Enriched Yeast Downregulates Expression of Lipocalin 2 (Lcn2) a Marker of Heart Failure and Important Molecule for Heart Muscle Contractility Lcn2 is a biomarker of heart failure, and is critical for cardiac muscle contraction (See, e.g., Yang et al., Am J Transl Res. 4(1): p. 60-71; Xu et al., J Biol Chem. 287(7): p. 4808-17)).

Figure 28:
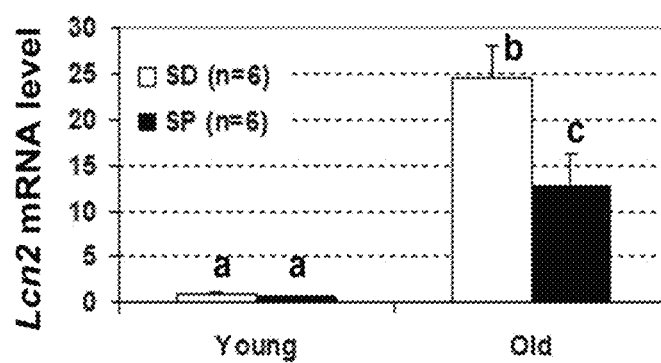
FIG. 28 shows QRT-PCR showing the age-dependent increase of cardiac Lcn2 expression in PolG mice and the inhibition of the age-dependent increased expression via administration of selenium in the form of selenium enriched yeast. Data are presented as mean±sem of six mice per group. Different letters in the bar graph represent a significant difference as determined by ANOVA analysis followed by Student's t-test.

When a human ages, the heart becomes stiff with enlarged cardiomyocytes and reduced muscle cell contractility, both leading causes of heart failure. Experiments were conducted during development of embodiments of the present application in order to characterize Lcn2 expression in heart tissue of PolG old mice administered selenium in the form of selenium enriched yeast comprising 2% or less inorganic selenium compared to POLG old mice administered the SD control diet. A significant and dramatic increase in Lcn2 expression was discovered, utilizing QRT-PCR, in PolG old mice administered selenium in the form of selenium enriched yeast comprising 2% or less inorganic selenium (See FIG. 28). This observation is consistent with the other finding disclosed herein with regard to increased pNFAT2/3 levels (e.g., inactivation of NFAT activity in gene transcription) (See FIG. 24) as Lcn2 is a NFAT target (See e.g., Gaudineau et al., J Cell Sci, 2012. 125(Pt 19): p. 4475-86).

Example 3

Selenium Containing Compositions Abate Sarcopenia

Materials and Methods

Animals and Treatment

Male C57BL/6J mice were housed singly and maintained in the Shared Aging Rodent Facility at the William S. Middleton Memorial Veterans Administration Medical Center (Madison, Wis.). Temperature and humidity were maintained at constant levels. Room light was controlled to provide 12-hr cycles of light and dark. Mice were provided with water and fed their experimental diets ad libitum. Experimental diets (manufactured by Harlan Teklad, Madison, Wis.) were stored in the dark at 4° C. and fresh diet was added to feeder twice weekly.

One group of mice received a basal diet having a selenium concentration of <0.01 mg/kg (SD); a second group received a diet identical to the SD diet but with 1.0 mg/kg of selenium added thereto in the form of sodium selenite (SS); a third group received a diet identical to the SD diet but with 1.0 mg/kg of selenium added thereto in the form of selenomethionine (SM); and a fourth group received a diet identical to the SD diet but with 1.0 mg/kg of selenium added thereto in the form of selenium enriched yeast comprising 2% or less inorganic selenium ((SP), SELPLEX, ALLTECH, Inc. Lexington, Ky.). The final selenium concentrations of each of the SS, SM and SP diets was one (1) part per million. The selenium concentration in dietary premixes was evaluated by atomic absorption spectroscopy (Connolly, Power, Hynes, 2004); in the experimental diets, by Covance Inc. (Madison, Wis.). The basal SD diet contained 15 g/100 g total fat, as well as 538.6 g/kg sucrose, 300 g/kg Torula yeast, 140 g/kg corn oil, 3.0 g/kg DL methionine, 15.4 g/kg mineral mix (containing, on a g/kg diet basis, calcium carbonate, 2.02; sodium chloride, 2.6; potassium citrate (monohydrate), 7.7; potassium sulfate, 1.82; magnesium oxide, 0.84; ferric citrate, 0.21; manganous carbonate, 0.12; zinc carbonate, 0.056; chromium potassium sulfate, 0.019; cupric carbonate, 0.011; potassium iodate, 0.0004) and 3.0 g/kg vitamin mix (containing, on a mg/kg diet basis, choline bitartrate, 2800; niacin, 30; calcium pantothenate, 16; pyridoxine HCl, 7; thiamin HCl, 6; riboflavin, 6; folic acid, 2; biotin, 0.2; vitamin B-12 (0.1% in manniton, 25; dl-α-tocopheryl acetate (500 u!g), 100; vitamin A palmitate (500,000 u/g), 8; cholecalciferol (500,000 u/g), 0.4; phylloquinone, 3).

After the administration of the above described diets (SD, SM, SS or SP) for three months, mice were sacrificed by cervical dislocation prior to tissue collection.

Tissue Preparation:

For cross-tissue gene expression studies, heart, liver, and gastrocnemius specimens were collected, flash frozen in liquid nitrogen and stored at −80° C. For brain-specific expression studies, the cerebral cortex was separated from the surrounding brain tissue, flash frozen in liquid nitrogen and stored at −80° C.

RNA Extraction.

Frozen tissue samples were homogenized using a QIAGEN Tissue Ruptor (QIAGEN, Valencia, Calif.) and total RNA was extracted using an RNEASY Mini kit (QIAGEN) under protocols recommended by the company. Integrity and purity of isolated RNA was assessed using a NANODROP ND-1000 spectrophotometer (Thermo Scientific, Wilmington, Del.) and further confirmed with an AGILENT 2100 Bioanalyzer System (AGILENT Technologies, Santa Clara, Calif.).

Purified RNA was converted into double-stranded cDNA using GeneChip Expression 3'-Amplification Reagents One-Cycle cDNA Synthesis Kit (AFFYMETRIX, Santa Clara, Calif.) with a T7-(dT)$_{24}$ primer and a T7 RNA polymerase promoter. Double-stranded cDNA was converted to biotin-labeled cRNA using the AFFYMETRIX GeneChip Expression 3'-Amplification One-Cycle Target Labeling Kit (AFFYMETRIX) according to the manufacturer's recommended procedures. Biotin-labeled cRNA and cleaned using the Genechip Sample Cleanup Module and fragmented by heating (35 min at 94° C.).

Microarray and Bioinformatics Pathway Analyses.

Labeled cRNA was hybridized to mouse genome MG-430_2.0 GeneChip arrays (AFFYMETRIX) for 16 h at 45° C., followed by washing, streptavidin-phycoerythrin (S APE) staining and finally scanning in an GeneChip Scanner 3000 7G (AFFYMETRIX).

GeneSpring GX 12.5 (Agilent) was used to validate and normalize microarray data and to perform statistical and gene expression pattern analyses. Briefly, normalization was done by first scale the intensity of probesets of the arrays to a mean target intensity of 500, followed by baseline transformation to median of all samples of this study. Background corrections were done by MASS based on its' Perfect Match (PM) and Mis-Match (MM) probe design of the microarray. To minimize the possibility of misleading findings, probe sets with low signal intensity and which were labeled as 'Absent' by the AFFYMETRIX MASS algorithm across samples were excluded from further analysis. The differentially expressed genes were filtered using the volcano plot method where genes with P<0.05 were defined as significantly different.

To dissect the biological themes represented by altered transcription profiles, two independent pathway analysis approaches were applied. First, parametric analysis was performed utilizing gene set enrichment (PAGE), a computational method that allows determination of significant changes in defined gene set (See, e.g., Kim & Volsky, 2005) to identify significantly altered biological processes and signaling pathways by diet. Only those gene ontology (GO) terms that have at least 10 and at most 1,000 genes and have level 3 and below were analyzed. To further identify functional clusters that characterize the transcriptional alterations associated with dietary Se status, significantly changed genes were further grouped into networks, functions and canonical pathways using Ingenuity Pathways Analysis software (IPA, Ingenuity Systems, Redwood City, Calif.). Fischer's exact test was used to determine the significance of the association between the genes and the given network, biological function or canonical pathway.

Total Protein Determination.

Gastrocnemius tissue weights were determined using an electronic balance and then homogenized as described (See, e.g., Lan et al., 1998). Protein levels in the homogenates were determined using the Pierce 660 nm protein assay kit (Thermo Scientific-Pierce Biotechnology, Rockford, Ill.) according to the manufacturer protocol. Total protein level in each sample was normalized by the tissue weight. Data are presented as mean±sem of the number of samples. Experiments were repeated twice.

Statistical Analysis

Student's t-test was performed to determine the statistical difference between two groups, while one-way ANOVA followed by Student's t-test were performed to determine the difference among multiple groups. A p-value less than 0.05 was considered significant.

Figure 29:
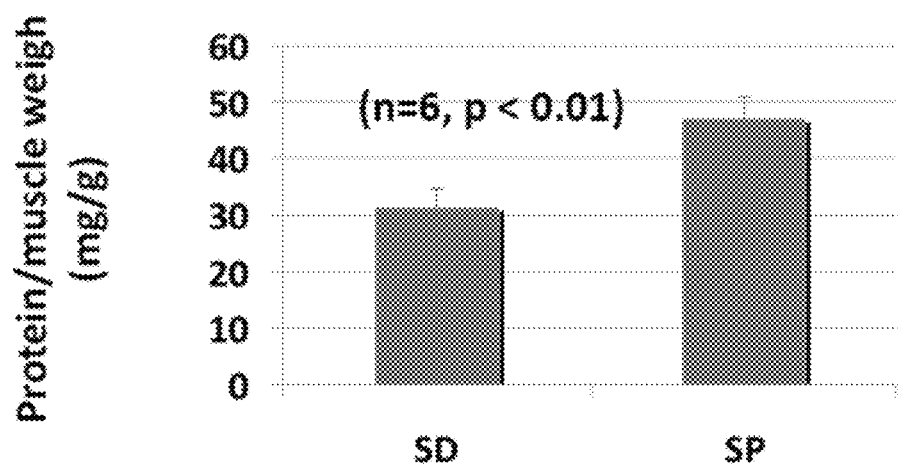
FIG. 29 shows elevated total protein levels in skeletal muscle from normal mice fed a diet supplemented with selenium in the form of selenium enriched yeast comprising 2% or less inorganic selenium (SP, SELPLEX) or not supplemented with selenium (SD) for 3 months. Data are presented as mean±sem of indicated number of samples per group. P<0.01.

Subjects Treated with Selenium in the Form of Selenium Enriched Yeast Display Elevated Skeletal Muscle Protein In order to investigate whether administration of selenium in the form of selenium enriched yeast could affect skeletal muscle composition and/or mass, total skeletal muscle protein in mice fed a diet supplemented with selenium in the form of selenium enriched yeast (SP) versus mice fed a diet not supplemented with selenium (SD) over a period three months was monitored. As shown in FIG. 29, total protein in skeletal muscle was significantly elevated in mice that were administered the SP diet compared to mice administered the SD diet. This data indicates that selenium supplementation in the form of selenium enriched yeast increases total protein levels in skeletal muscle.

Figure 34:
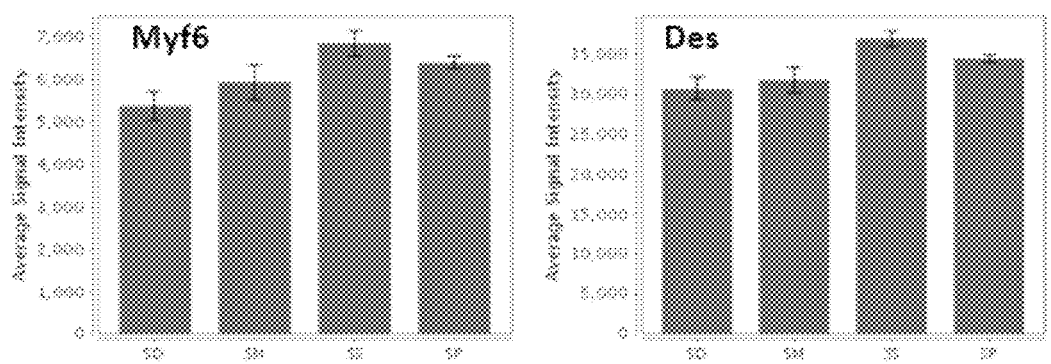
FIG. 34 shows elevated expression of differentiated muscle satellite (stem) in skeletal muscle of normal mice fed for three months with a diet supplemented with selenium in the form selenium enriched yeast comprising 2% or less inorganic selenium (SP) compared to control diets supplemented with selenium in the form of selenomethionine (SM), supplemented with selenium in the form of sodium selenite (SS) or a diet not supplemented with selenium (SD). Data are presented as mean±sd (n=6).
Figure 35:
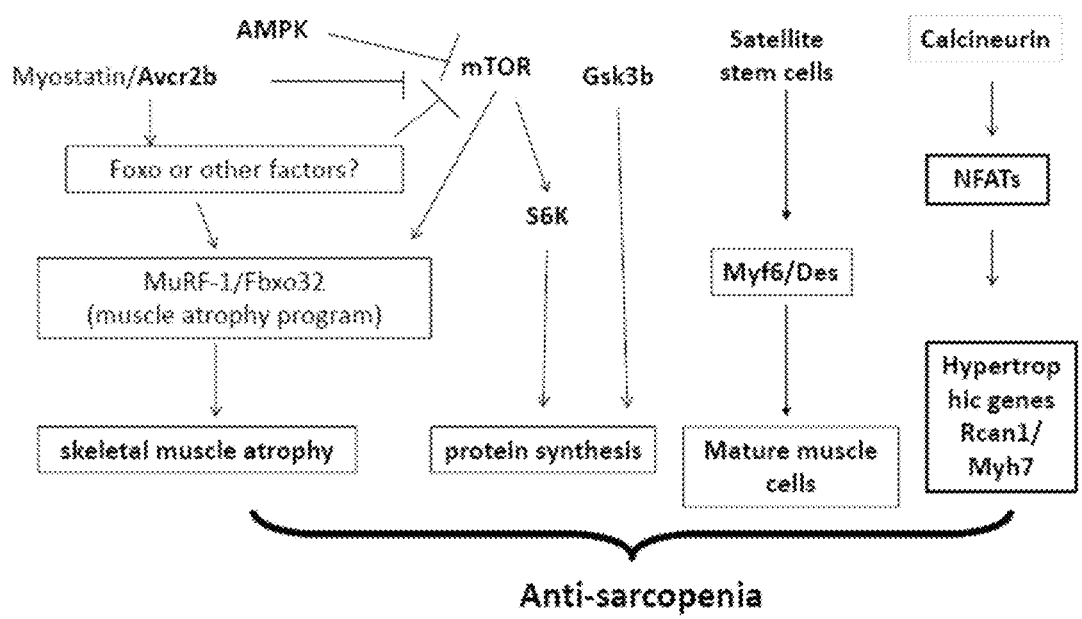
FIG. 35 shows several non-limiting examples of pathways regulated by selenium in the form of selenium enriched yeast comprising 2% or less inorganic selenium (or one or more selenium containing compounds present therein) resulting in an increase in total skeletal muscle protein mass in a subject administered the same discovered during experiments conducted during development of embodiments of the present application.

Administration of Selenium in the Form of Selenium Enriched Yeast Activates Muscle Satellite Cell Maturation and/or Production and Skeletal Muscle Regeneration The lack of activation of muscle satellite (stem) cells to produce mature muscle cells in response to nutritional signals is one cause of sarcopenia (See, e.g., Ryall et al., 2008). Experiments were conducted during the development of embodiments of the present application in order to characterize muscle satellite (stem) cell activation in the skeletal muscle of selenium treated versus control subjects by measuring the expression of activated satellite marker genes, myogenic factor 6 (Myf6) and desmin (Des). It was discovered that expression of these activated satellite marker genes were significantly upregulated in the skeletal muscle of mice administered selenium in the form of selenium enriched yeast containing 2% or less inorganic selenium (SP) and sodium selenite (SS) compared to controls (See FIG. 34). Thus, the present application provides that selenium in the form of selenium enriched yeast comprising 2% or less inorganic selenium (or one or more selenium containing compounds present therein) promotes the maturation of muscle satellite cells (e.g., to produce mature muscle cells) thereby attenuating sarcopenia.

Administration of Selenium in the Form of Selenium Enriched Yeast Alters Signaling Pathways that Control Protein Synthesis in Skeletal Muscle mTOR/S6K and the MAPK/S6K Signaling Signaling by mTOR impacts several major cellular functions that can both positively and negatively regulate cellular behaviors such as growth (mass accumulation) and proliferation (See, e.g., Laplante, Cell. 2012, 149(2):274-93). Protein synthesis is one of the best characterized processes controlled by mTOR. The activation of S6K by mTOR is an important step for protein synthesis via the mTOR signaling pathway (See, e.g., Laplante, Cell. 2012, 149(2):274-93). In addition to the activation of S6K by the mTOR-pathway, protein synthesis can also be stimulated by activating S6K via the MAPK/ERK2-mediated pathway (See, e.g., Kenessey and Ojamaa, J Biol Chem, 2006, 281(30) 20666-20672). Mitogen-activated protein kinase kinase 2 (MAP2K2) is an enzyme that activates the MAPK1/ERK2 pathway and in humans, is encoded by the MAP2K2 gene (See, e.g., Biochim Biophys Acta. 2007, 1773(8):1150-60). MAPK then activates RSK, which, in turn, phosphorylates ribosomal protein S6K (See, e.g., Pende et al. Mol Cell Bio, 2004. 24(8): p. 3112-3124). A negative regulator of pathways associated with proteins synthesis is GSK3β Inhibition of GSK3β blocks the eukaryotic initiation factor 2B (eIF2B), which is involved in protein synthesis. Expression of the inactive form of GSK3β was shown to induce a dramatic increase in hypertrophy in skeletal myotubes and over expression of wild-type GSK3β in the heart induces a 30% decrease in heart size (See, e.g., Santri, Physiology (Bethesda). 2008; 23:160-70.

Figure 31:
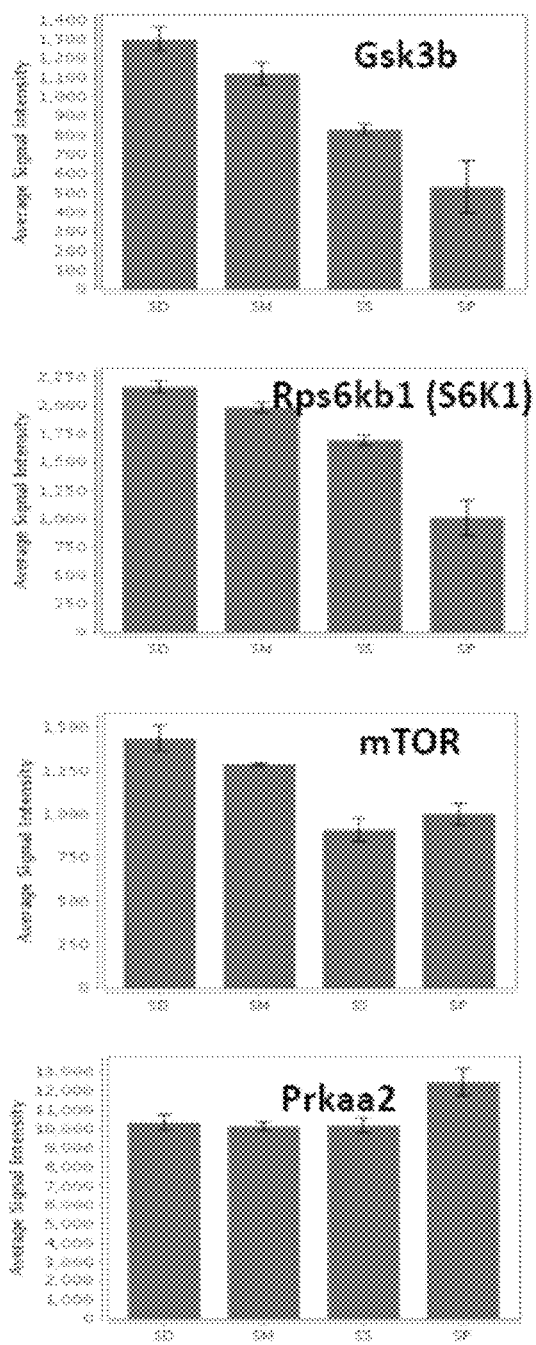
FIG. 31 shows data obtained from microarray analysis indicating the presence of reduced expression of molecules involved in protein synthesis (Gsk3b, mTor, S6K1) and enhanced expression of a key signaling molecule for protein synthesis (Prkaa2) in skeletal muscle of normal mice fed for three months with a diet supplemented with selenium in the form selenium enriched yeast comprising 2% or less inorganic selenium (SP) compared to control diets supplemented with selenium in the form of selenomethionine (SM), supplemented with selenium in the form of sodium selenite (SS) or a diet not supplemented with selenium. Data are presented as mean±sd (n=6).
Figure 36:
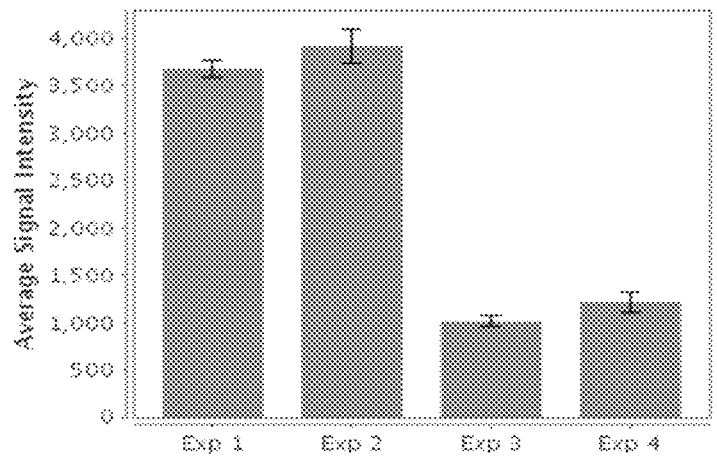
FIG. 36 shows reduced expression of MAP2K2 in the skeletal muscle of mice administered selenium in the form of selenium enriched yeast (Exp 4) compared to control (Exp 1, no selenium supplementation, Exp 2, supplementation with selenomethionine). Sodium selenite (Exp 3) also reduced expression of MAP2K2 in the skeletal muscle of mice.

A significant reduction was observed in the gene expression levels of mTOR in the skeletal muscle of mice administered selenium in the form of selenium enriched yeast (SP) compared to controls (See FIG. 31). An even more dramatic reduction in MAP2K2 gene expression was observed in the skeletal muscle of mice administered selenium in the form of selenium enriched yeast (SP), demonstrating a −3.03 fold change when compared to mice administered the SD diet (FIG. 36).

The finding that administration of selenium enriched yeast comprising 2% or less inorganic selenium (SELPLEX) down-regulated S6K expression when compared to controls (See, e.g., FIG. 31) correlated with the discovery that SELPLEX reduced mTOR and MAPK2K expression in the skeletal muscle of mice. However, the finding that SELPLEX significantly down-regulated GSK3β expression in the gastrocnemius tissue of mice administered SELPLEX was surprising considering that inactivation of GSK-3β can stimulate protein synthesis. These results indicate that despite the down-regulation of genes that are known to promote protein synthesis in muscle (e.g., mTOR, MAPK2K, and S6K), selenium enriched yeast comprising 2% or less inorganic selenium (or one or more selenium containing compositions present therein) increases total skeletal muscle protein (e.g., skeletal muscle mass) via other pathway(s).

Ampk, an inhibitor of mTor, is also involved in protein synthesis (See, e.g., Gordon et al., 2008; Thomson et al., 2008). Consistent with reduced expression of S6k and mTOR, elevated expression of Prkaa2, a subunit of Ampk, was also observed in the skeletal muscle of mice administered selenium in the form of selenium enriched yeast compared to controls (See FIG. 31). Accordingly, in some embodiments, selenium in the form of selenium enriched yeast comprising 2% or less inorganic selenium (or a selenium containing compound component thereof) is utilized as described herein to increase skeletal muscle mass in a subject.

Administration of Selenium in the Form of Selenium Enriched Yeast Up-Regulates the Expression of Calcinerin in the Formation of Skeletal Muscle Mass The Calcinurin/NFAT Network Calcineurin/Nuclear factor of activated T-cells (NFAT) signaling is a key pathway associated with the increase of skeletal muscle mass in response to exercise and calcium signaling (See, e.g., Glass, 2003). Experiments were conducted during the development of embodiments of the present application in order to characterize the expression of the calcineurin/NFAT signaling molecules that control hypertrophic genes. It was discovered that expression of the genes that encode the catalytic subunits of calcineurin (Ppp3cb and Ppp3cc, and calcineurin B subunit Ppp3r1) were all significantly elevated in the skeletal muscle of mice administered selenium in the form of selenium enriched yeast containing 2% or less inorganic selenium compared to controls (See Table 6, below). In addition, a trend of increased expression of Ppp3r2, the other subunit of calcineurin B, was also observed (See Table 6, below).

TABLE 6

Elevated calcineurin in skeletal muscle of normal mice fed for three months with a diet supplemented with selenium in the form selenium enriched yeast comprising 2% or less inorganic selenium (SP) compared to control diet not supplemented with selenium.

|  | Genes | SP (vs SD group) |
| --- | --- | --- |
| Calcineurin | Ppp3ca | No |
|  | Ppp3cb | ↑ |
|  | Ppp3cc | ↑ |
|  | Ppp3r1 | ↑ |
|  | Ppp3r2 | ↑ (trend) |
| NFATs | Nfatc1 (NFAT2) | No |
|  | Nfatc2 (NFAT1) | No |
|  | Nfatc3 (NFAT4) | No |
|  | Nfatc4 (NFAT3) | No |
|  | Nfat5 | No |
| Calcineurin | Ppp3ca | No |
|  | Ppp3cb | ↑ |
|  | Ppp3cc | ↑ |
|  | Ppp3r1 | ↑ |
|  | Ppp3r2 | ↑ (trend) |

Figure 30:
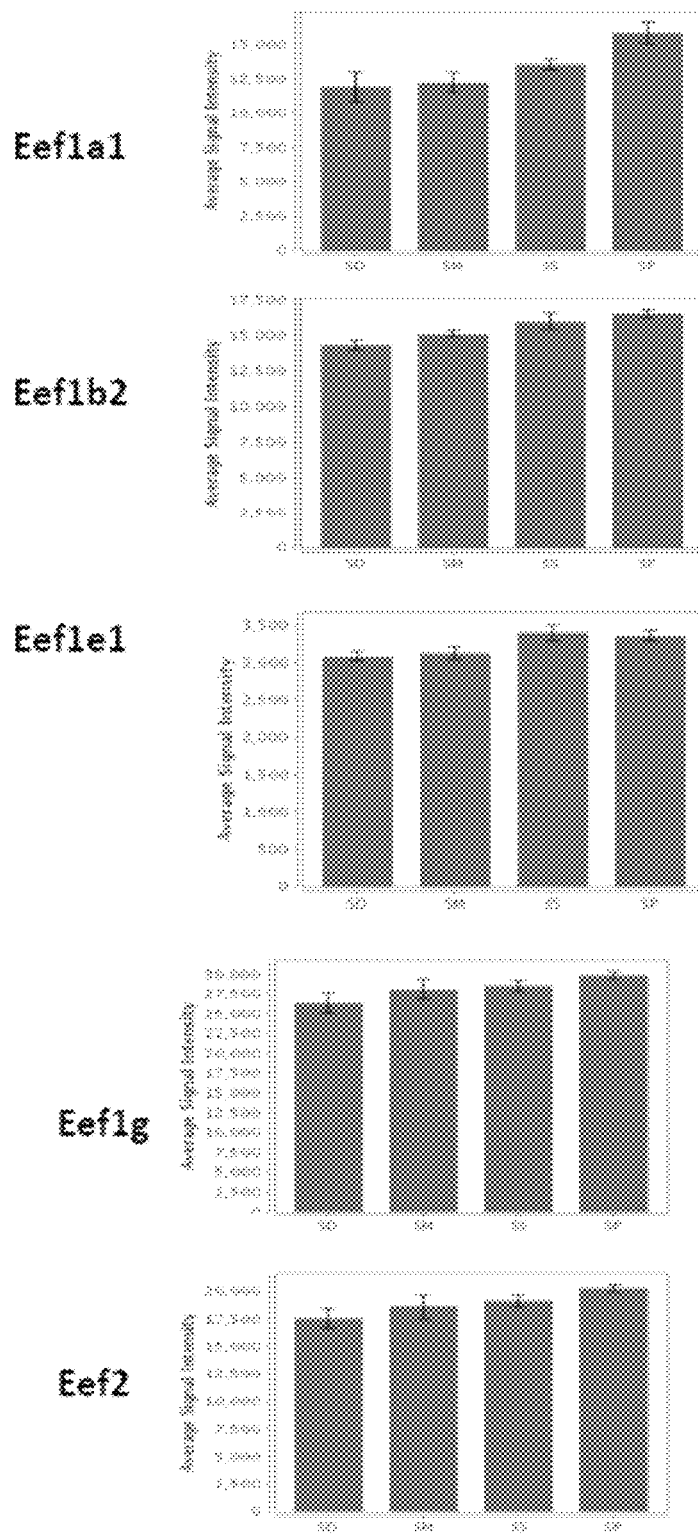
FIG. 30 shows data obtained from microarray analysis indicating the presence of elevated expression of genes involved in protein elongation for protein synthesis in skeletal muscle of normal mice fed for three months with a diet supplemented with selenium in the form selenium enriched yeast comprising 2% or less inorganic selenium (SP) compared to control diets supplemented with selenium in the form of selenomethionine (SM), supplemented with selenium in the form of sodium selenite (SS) or a diet not supplemented with selenium. Data are presented as mean±sd (n=6).

It was also observed that multiple genes encoding protein elongation factors (Eef1a1, Eef1b2, Eef1e1, Eef1g, Eef2) that contribute to increased protein levels and skeletal muscle growth were up-regulated in the skeletal muscle of mice administered selenium in the form of selenium enriched yeast compared to controls (See FIG. 30).

Administration of Selenium in the Form of Selenium Enriched Yeast Alters Signaling Networks that Inhibit Protein Synthesis in Skeletal Muscle Myostatin/Acvr2b Network Myostatin and its receptor, activin A, are another important pathway that control muscle atrophy. The genetic ablation of Acvr2b (specifically in myofibers), is sufficient to induce muscle hypertrophy even in the absence of satellite cell activation (See, e.g., Lee et al, PNAS 2012). In addition, the Myostatin/Acvr2b complex inhibits protein synthesis by disrupting the Akt/mTOR signaling pathway (See, e.g., Sakuma and Yamaguchi, J Aging, 2012).

Accordingly, experiments were conducted during the development of embodiments of the present application in order to characterize Acvr expression in skeletal muscle from subjects administered a control diet versus a diet containing selenium. It was determined that Acvr2b expression was significantly downregulated in subjects administered selenium in the form of selenium enriched yeast comprising 2% or less inorganic selenium (See FIG. 33).

Administration of Selenium in the Form of Selenium Enriched Yeast Down-Regulates Atrophic Gene Expression and Inhibits Protein Degradation in Skeletal Muscle It has been documented that elevated expression of atrophic genes such as tripartite motif-containing 63 (Trim63) and ubiquitin E3 ligase atrogin-1 (Fbxo32) lead to protein degradation in sarcopenia (See, e.g., Sakuma and Yamaguchi, 2012). Thus, experiments were performed during the development of embodiments of the present application in order to characterize atrophic gene expression in skeletal muscle in subjects administered selenium containing experimental diets versus those administered a selenium deficient diet. It was discovered that both Trim63 and Fbxo32 were down-regulated in the skeletal muscle of mice administered selenium in the form of selenium enriched yeast containing 2% or less inorganic selenium compared to controls (See FIG. 32). Reduced expression of Trim53 and Fbxo32 was also documented in skeletal muscle from normal mice administered selenium in the form of selenium enriched yeast comprising 2% or less inorganic selenium for two years compared to controls.

Accordingly, in some embodiments, selenium in the form of selenium enriched yeast comprising 2% or less inorganic selenium (or a selenium containing compound component thereof) is utilized as described herein to inhibit skeletal muscle atrophy.

Example 4

Administration of Compositions Comprising Selenium Significantly Attenuate Expression of Molecules Associated with Obesity Sarcopenia and obesity are two independent yet interconnected conditions that have a growing impact on life expectancy and health care costs in developed nations. The combination of diminished muscle mass with increased fat mass is referred to as "sarcopenic obesity" (See, e.g., Parr, E., Maturitas, 2013. 74: p. 109-113). Obesity exacerbates sarcopenia as it promotes an increase in fat mass and lipid accumulation that prevents amino acid incorporation and reduces protein synthesis in skeletal muscle (See, e.g., Parr, E., Maturitas, 2013. 74: p. 109-113). In turn, because skeletal muscle mass is critical to metabolic health with fundamental roles in whole-body glucose disposal and insulin sensitivity, sarcopenia exacerbates obesity (See, e.g., Parr, E., Maturitas, 2013. 74: p. 109-113). In addition to sarcopenia, obesity is often a side effect associated with other metabolic diseases such as, type II diabetes, hyperglycemia, and others. It is well understood that genetic predisposition and the expression of obesity associated molecules are also a contributing factor. Obesity has a growing impact on life expectancy and health care costs in developed nations (See, e.g., Parr, E., Maturitas, 2013. 74: p. 109-113).

The fat mass and obesity related gene (FTO), commonly referred to as the "obesity gene", is powerfully associated with increased body mass index and predisposition to obesity in children and adults (See, e.g., Gulati et al, PNAS, 2013. 110(7): p. 2557-2562). The FTO gene is ubiquitously expressed, but in the brain, mRNA levels are particularly high within the hippocampus, cerebellum and hypothalamus suggesting a potential role of brain FTO in the control of food intake, whole body metabolism and obesity (See, e.g., Church, PLoS Genetics, 2009).

Experiments were conducted during development of embodiments of the present application in order to determine if administration of selenium to a subject might alter the expression of FTO.

Figure 37:
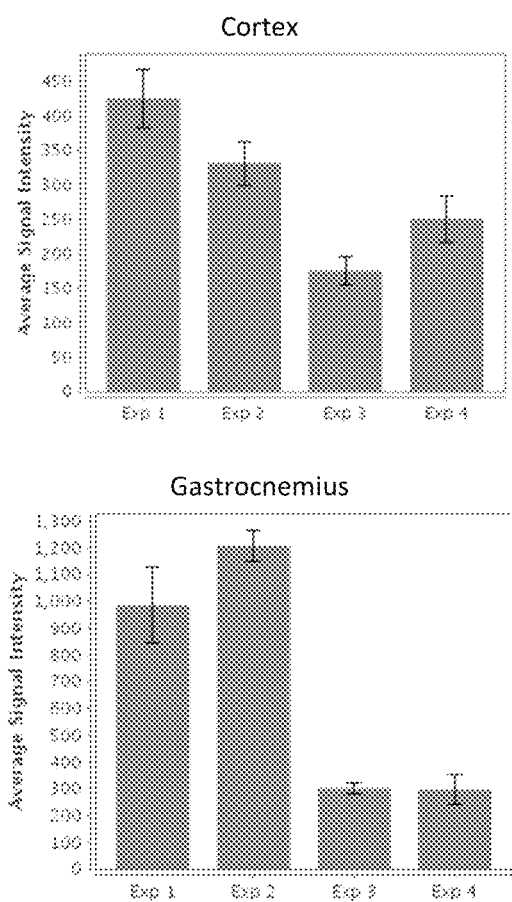
FIG. 37 shows that subjects administered selenium in the form of selenium enriched yeast comprising 2% or less inorganic selenium displayed markedly reduced levels of FTO gene expression in cortex tissue and in gastrocnemius tissue. Exp 1 shows FTO expression in control (SD) mice, Exp 2 shows FTO expression in mice fed selenomethionine, Exp 3 shows FTO expression in mice fed sodium selenite, and Exp 4 shows FTO expression in mice fed selenium enriched yeast comprising 2% or less inorganic selenium (SELPLEX).

Utilizing the animal model described in Example 3, it was determined that subjects administered selenium in the form of selenium enriched yeast comprising 2% or less inorganic selenium displayed markedly reduced levels of FTO gene expression, not only in cortex tissue, (fold change=−1.70) but also in gastrocnemius tissue (fold change=−3.33) when compared to subjects administered a SD diet (See FIGS. 36 and 37).

Example 5

Inverse Relationship Between Skeletal Muscle Versus Liver Expression of Peroxisome Proliferator-Activated Receptor Gamma (PPARg) Coactivator 1 Alpha (PGC-1α) Expression Upon Administration of Selenium Enriched Yeast Comprising 2% or Less Inorganic Selenium Materials and Methods Animals and Treatment Male C57BL/6J mice were housed singly and maintained in the Shared Aging Rodent Facility at the William S. Middleton Memorial Veterans Administration Medical Center (Madison, Wis.). Temperature and humidity were maintained at constant levels. Room light was controlled to provide 12-hr cycles of light and dark. Mice were provided with water and fed their experimental diets ad libitum. Experimental diets (manufactured by Harlan Teklad, Madison, Wis.) were stored in the dark at 4° C. and fresh diet was added to feeder twice weekly.

One group of mice received a basal diet having a selenium concentration of <0.01 mg/kg (SD); a second group received a diet identical to the SD diet but with 1.0 mg/kg of selenium added thereto in the form of sodium selenite (SS); a third group received a diet identical to the SD diet but with 1.0 mg/kg of selenium added thereto in the form of selenomethionine (SM); and a fourth group received a diet identical to the SD diet but with 1.0 mg/kg of selenium added thereto in the form of selenium enriched yeast comprising 2% or less inorganic selenium ((SP), SELPLEX, ALLTECH, Inc. Lexington, Ky.). The final selenium concentrations of each of the SS, SM and SP diets was one (1) part per million. The selenium concentration in dietary premixes was evaluated by atomic absorption spectroscopy (Connolly, Power, Hynes, 2004); in the experimental diets, by Covance Inc. (Madison, Wis.). The basal SD diet contained 15 g/100 g total fat, as well as 538.6 g/kg sucrose, 300 g/kg Torula yeast, 140 g/kg corn oil, 3.0 g/kg DL methionine, 15.4 g/kg mineral mix (containing, on a g/kg diet basis, calcium carbonate, 2.02; sodium chloride, 2.6; potassium citrate (monohydrate), 7.7; potassium sulfate, 1.82; magnesium oxide, 0.84; ferric citrate, 0.21; manganous carbonate, 0.12; zinc carbonate, 0.056; chromium potassium sulfate, 0.019; cupric carbonate, 0.011; potassium iodate, 0.0004) and 3.0 g/kg vitamin mix (containing, on a mg/kg diet basis, choline bitartrate, 2800; niacin, 30; calcium pantothenate, 16; pyridoxine HCl, 7; thiamin HCl, 6; riboflavin, 6; folic acid, 2; biotin, 0.2; vitamin B-12 (0.1% in manniton, 25; dl-α-tocopheryl acetate (500 u!g), 100; vitamin A palmitate (500,000 u/g), 8; cholecalciferol (500,000 u/g), 0.4; phylloquinone, 3).

Mice were sacrificed by cervical dislocation prior to tissue collection.

Tissue Preparation:

For cross-tissue gene expression studies, heart, liver, and gastrocnemius specimens were collected, flash frozen in liquid nitrogen and stored at −80° C. For brain-specific expression studies, the cerebral cortex was separated from the surrounding brain tissue, flash frozen in liquid nitrogen and stored at −80° C.

RNA Extraction.

Frozen tissue samples were homogenized using a QIAGEN Tissue Ruptor (QIAGEN, Valencia, Calif.) and total RNA was extracted using an RNEASY Mini kit (QIAGEN) under protocols recommended by the company. Integrity and purity of isolated RNA was assessed using a NANODROP ND-1000 spectrophotometer (Thermo Scientific, Wilmington, Del.) and further confirmed with an AGILENT 2100 Bioanalyzer System (AGILENT Technologies, Santa Clara, Calif.).

Purified RNA was converted into double-stranded cDNA using GeneChip Expression 3'-Amplification Reagents One-Cycle cDNA Synthesis Kit (AFFYMETRIX, Santa Clara, Calif.) with a T7-$(dT)_{24}$ primer and a T7 RNA polymerase promoter. Double-stranded cDNA was converted to biotin-labeled cRNA using the AFFYMETRIX GeneChip Expression 3'-Amplification One-Cycle Target Labeling Kit (AFFYMETRIX) according to the manufacturer's recommended procedures. Biotin-labeled cRNA and cleaned using the Genechip Sample Cleanup Module and fragmented by heating (35 min at 94° C.).

Microarray and Bioinformatics Pathway Analyses.

Labeled cRNA was hybridized to mouse genome MG-430_2.0 GeneChip arrays (AFFYMETRIX) for 16 h at 45° C., followed by washing, streptavidin-phycoerythrin (SAPE) staining and finally scanning in an GeneChip Scanner 3000 7G (AFFYMETRIX).

GeneSpring GX 12.5 (Agilent) was used to validate and normalize microarray data and to perform statistical and gene expression pattern analyses. Briefly, normalization was done by first scale the intensity of probesets of the arrays to a mean target intensity of 500, followed by baseline transformation to median of all samples of this study. Background corrections were done by MASS based on its' Perfect Match (PM) and Mis-Match (MM) probe design of the microarray. To minimize the possibility of misleading findings, probe sets with low signal intensity and which were labeled as 'Absent' by the AFFYMETRIX MASS algorithm across samples were excluded from further analysis. The differentially expressed genes were filtered using the volcano plot method where genes with P<0.05 and corresponding signal intensity fold change (FC)>1.2 or FC<−1.2 were defined as significantly different.

To dissect the biological themes represented by altered transcription profiles, two independent pathway analysis approaches were applied. First, parametric analysis was performed utilizing gene set enrichment (PAGE), a computational method that allows determination of significant changes in defined gene set (See, e.g., Kim & Volsky, 2005) to identify significantly altered biological processes and signaling pathways by diet. Only those gene ontology (GO) terms that have at least 10 and at most 1,000 genes and have level 3 and below were analyzed. To further identify functional clusters that characterize the transcriptional alterations associated with dietary Se status, significantly changed genes were further grouped into networks, functions and canonical pathways using Ingenuity Pathways Analysis software (IPA, Ingenuity Systems, Redwood City, Calif.). Fischer's exact test was used to determine the significance of the association between the genes and the given network, biological function or canonical pathway.

Real-Time PCR Analysis.

Real-time PCR analysis was performed using the Applied-Bioscience's predesigned TAQMAN probes and primers (INVITROGEN) according to the manufacturer's recommended procedures. Data were normalized by Actb levels in each sample, and presented as mean±sem of the number of samples.

Statistical Analysis

For real-time PCR and Western blot analyses, Student's t-test was performed to determine the statistical difference between two groups, while one-way ANOVA followed by Student's t-test were performed to determine the difference among multiple groups. A p-value less than 0.05 was considered significant.

Background

Skeletal muscle and liver are two key insulin-responsive organs in the maintenance of glucose homeostasis. The transition of these organs to an insulin-resistant state accounts for most of the changes in glucose metabolism seen in patients with Type II diabetes (See, e.g., Lowell and Shulman, 2005). Of these two organs, skeletal muscle is the more important in terms of consequences accruing from insulin resistance development. This is because skeletal muscle has been found to dispose of or metabolize 80 to 90% of daily ingested glucose (See, e.g., DeFronzo et al., 1985).

It has been documented that mitochondrial oxidative phosphorylation (OXPHOS) genes exhibit reduced expression in pre-diabetic and diabetic individuals when compared to healthy controls and that s significant number of OXPHOS genes are regulated by the transcriptional coactivator, PGC1-α (See, e.g., Mootha et al., 2003). In these studies, the typical decrease in expression for OXPHOS genes was modest (approximately 20%) but extremely consistent, with 89% of the genes studied showing lower expression in individuals with either impaired glucose tolerance or Type II diabetes relative to those with normal glucose tolerance. In support of the importance of OXPHOS molecule expression, aerobic exercise, which is the best non-pharmacological intervention for treating diabetes, increases mitochondrial number and promotes OXPHOS molecule expression.

Accordingly, experiments were conducted during development of embodiments of the present application in order to investigate if administration of selenium to subjects could alter OXPHOS activity in the subject's liver and/or skeletal muscle (e.g., as a therapeutic for Type II diabetes mellitus). Empirical data generated during development of embodiments of the present application discovered that administration of selenium in the form of selenium enriched yeast comprising 2% or less inorganic selenium (Trt) resulted in significant enhancement of PGC1-α expression in skeletal muscle compared to control subjects (Con) (See FIG. 38).

As described herein, PGC1-α is a powerful transcriptional coactivator which enhances mitochondrial activity in skeletal muscle. However, expression of elevated PGC1-α levels in tissues other than skeletal muscle may have a deleterious and/or harmful effect in a subject. For example, in liver, PGC1-α performs a different role than the role it performs in skeletal muscle. In particular, elevated levels PGC1-α in liver leads to increased gluconeogenesis (glucose production; See, e.g., Liang and Ward, 2006), an extremely unfavorable event to occur in a diabetic subject with impaired insulin sensitivity that is unable to metabolize glucose.

Thus, experiments were conducted during development of embodiments of the present application in order to investigate what activity, if any, administration of selenium to subjects may have regarding the expression of PGC1-α in non-skeletal muscle tissues. Unexpectedly, it was discovered that administration of selenium in the form of selenium enriched yeast comprising 2% or less inorganic selenium (Trt) resulted in significant reduction of PGC1-α expression in liver tissue compared to control subjects (control) (See FIG. 39). This discovery was surprising based upon the observation that administration of selenium in the form of selenium enriched yeast comprising 2% or less inorganic selenium resulted in significant enhancement of PGC1-α expression in skeletal muscle compared to control subjects. Thus, the present application provides compositions comprising selenium enriched yeast comprising 2% or less inorganic selenium (or one or more selenium containing compounds present therein or derived therefrom) for use in methods of enhancing PGC1-α expression in skeletal muscle of a subject while concurrently decreasing PGC1-α expression in liver in the subject (e.g., thereby providing a subject with enhanced glucose disposal in skeletal muscle (e.g., via enhanced OXPHOS) and suppressed glucose production in liver).

In order to further characterize and verify the ability of a composition comprising a selenium enriched yeast comprising 2% or less inorganic selenium to have such a disparate impact on the expression of the same molecule (e.g., PGC1-α) in different tissues of a subject, experiments were conducted to analyze expression of COUP transcription factor 2 (also known as nuclear receptor subfamily 2, group F, member 2 (Nr2F2)) in subjects administered a composition comprising selenium. Nr2F2 is a putative direct inhibitor of PGC1-α (See, e.g., Lin et al., 2011).

Figure 38:
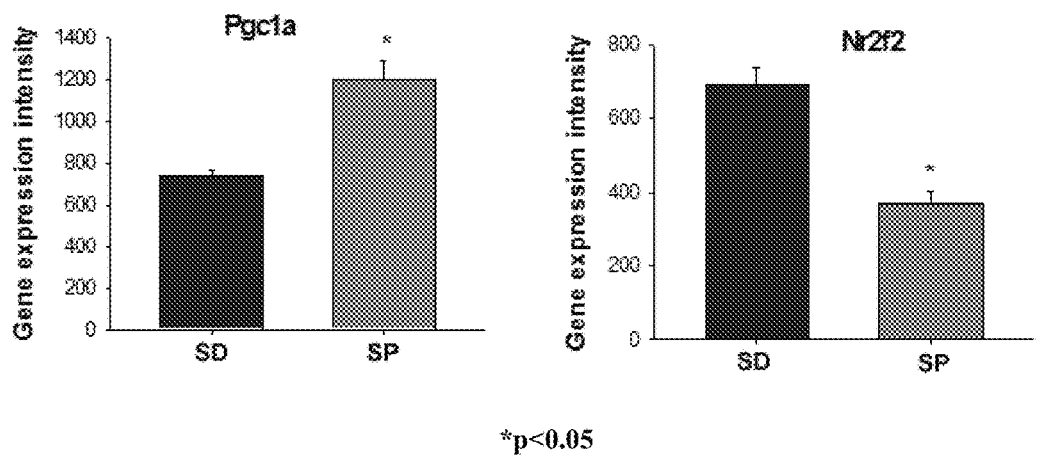
FIG. 38 shows that administration of selenium in the form of selenium enriched yeast comprising 2% or less inorganic selenium (SP) resulted in a significant enhancement of PGC1-α expression and a significant reduction of Nr2F2 expression in skeletal muscle compared to control subjects (SD). *p<0.05.
Figure 39:
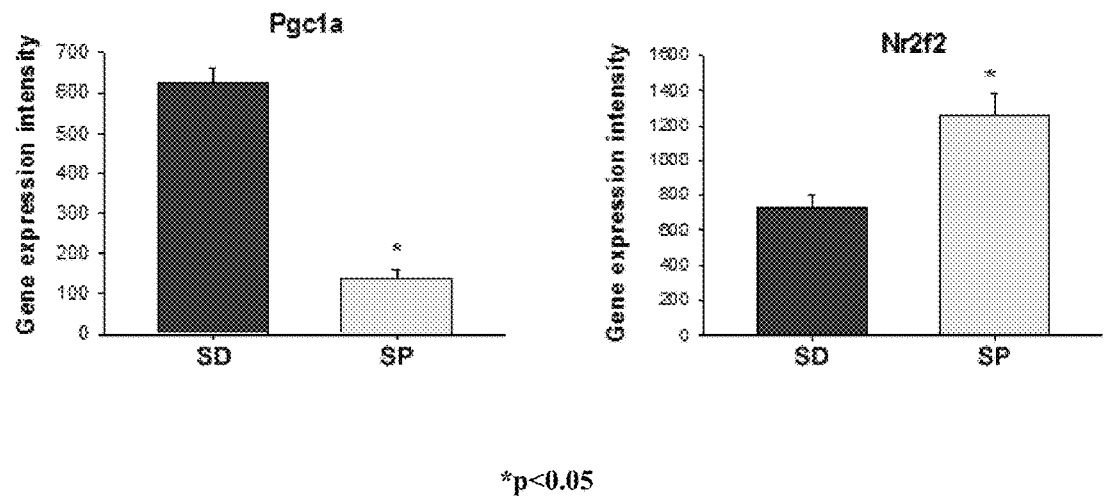
FIG. 39 shows that administration of selenium in the form of selenium enriched yeast comprising 2% or less inorganic selenium (SP) resulted in a significant reduction of PGC1-α expression and a significant enhancement of Nr2F2 expression in liver compared to control subjects (SD). *p<0.05.

Again, it was surprising to find that administration of selenium in the form of selenium enriched yeast comprising 2% or less inorganic selenium (Trt) resulted in a significant reduction of Nr2F2 expression in skeletal muscle compared to control subjects (Con) (See FIG. 38, whereas there was a significant enhancement of Nr2F2 in liver tissue compared to control (See FIG. 39). This data provides the first evidence regarding the utility of a composition comprising selenium in the form of selenium enriched yeast comprising 2% or less inorganic selenium (or one or more water soluble fractions thereof or one or more water insoluble fractions thereof or one or more selenium containing compounds present therein or derived therefrom) for use in regulating glucose homeostasis in multiple tissues (e.g., skeletal muscle tissue and liver tissue) in a subject.

Example 6

Administration of Selenium in the Form of Selenium Enriched Yeast Enhances Expression of Molecules Involved in Glucose Utilization Utilizing the animal model described in Example 2, experiments were conducted to analyze the expression of molecules that regulate oxidative phosphorylation (OXPHOS) in the liver of subjects administered a composition comprising selenium. It was discovered that it is possible to preferentially and differentially regulate liver specific mitochondrial activity via administration of selenium enriched yeast comprising 2% or less inorganic selenium, whereas administration of selenium selenite or selenomethionine were significantly less effective. In particular, it was observed that mice administered selenium enriched yeast comprising 2% or less inorganic selenium displayed a significant increase in expression of ATP synthase; ATPase, H+ transporting, V1 subunit A; cytochrome c oxidase, subunit Va; cytochrome c-1, NADH dehydrogenase (ubiquinone) 1 alpha subcomplex 10; NADH dehydrogenase (ubiquinone) 1 alpha subcomplex 1; NADH dehydrogenase (ubiquinone) 1 alpha subcomplex 3; NADH dehydrogenase (ubiquinone) 1 alpha subcomplex 4; NADH dehydrogenase (ubiquinone) 1 alpha subcomplex aase; NADH dehydrogenase (ubiquinone) 1 beta subcomplex 4; NADH dehydrogenase (ubiquinone) 1 beta subcomplex 8; NADH dehydrogenase (ubiquinone) 1 beta subcomplex 10; NADH dehydrogenase (ubiquinone) Fe—S-protein 4; NADH dehydrogenase (ubiquinone) Fe—S-protein 6; and succinate dehydrogenase complex, subunit C; and also significantly reduced the expression of ATPase inhibitory factor 1; ATPase, H+ transporting lysosomal, V1 subunit H; NADH dehydrogenase (ubiquinone) 1 alpha subcomplex 4; and zinc finger CCHC domain containing 2.

In contrast, mice administered sodium selenite displayed a significant increase in expression of ATPase, H+ transporting, V1 subunit A; ATPase, H+ transporting, V1 subunit D; cytochrome c oxidase, subunit Va; NADH dehydrogenase (ubiquinone) 1 alpha subcomplex 10; NADH dehydrogenase (ubiquinone) 1 alpha subcomplex 1; NADH dehydrogenase (ubiquinone) 1 beta subcomplex 10; and succinate dehydrogenase complex, subunit C; and also significantly reduced the expression of ATPase inhibitory factor 1; ATPase, H+ transporting lysosomal, V1 subunit H; and NADH dehydrogenase (ubiquinone) 1 alpha subcomplex 4.

Mice administered selenomethionine displayed a significant increase in expression ATP synthase and cytochrome c oxidase subunit Va; and also significantly reduced the expression of ATPase inhibitory factor 1; ATPase, H+ transporting lysosomal, V1 subunit H; and ATPase, H+ transporting, V1 subunit A.

Example 7

Isolated Selenium Containing Compounds Regulate Mitochondrial Activity

In any complex biological mixture, it is possible that groups of molecules present therein may not act additively; rather, they may act synergistically or, even, antagonistically to temper the activity of the final preparation. For example, the biological activity of selenium enriched yeast comprising 2% or less inorganic selenium described herein may be due to a sum of the effects of some or all of the selenium species/selenium containing compounds therein.

As described in Example 1 above, experiments were conducted during development of embodiments of the present application in order to characterize the Se metabolome and proteome of selenium rich yeast. Provided in Example 1 is the identification and characterization of Se-containing compounds (e.g., molecules, metabolites and proteins/peptides) whose identification and characterization have heretofore remained unknown.

Thus, experiments were conducted during development of embodiments of the present application in order to determine if specific selenium containing compounds identified in Example 1 possessed biological activity(ies) (e.g., to determine whether a selenium containing compound would display biological activity and/or whether a selenium containing compound might be more (or less) biologically active if isolated and purified from the constraints of the yeast cell and/or the internal mélange of other, non-selenium-containing, cellular components). A number of the most abundant selenium containing compounds and molecules identified from selenium enriched yeast in Example 1 were synthesized or obtained. One focus of the experiments was on the water-soluble extract which as described in Example 1 accounted for up to 25% of the total selenium present in the selenium enriched yeast. It was postulated that selenium containing compounds from the water soluble extract would be the first to be liberated/digested from the selenium enriched yeast upon consumption by a subject and its passage through the intestinal tract. Also described in Example 1 above, selenium-containing proteins present in the selenium enriched yeast were identified using computer-assisted prediction modeling. Moreover, experiments identified small, selenium containing peptides that are liberated by the action of digestive enzymes (e.g., trypsin).

A panel of nine of the selenium-containing compounds were obtained for analysis and characterization. This panel included the following selenium containing compounds: LVSe-MR ($C_{16}H_{33}N_6O_4Se$) (#5); LVSe-MR ($C_{22}H_{44}N_7O_5Se$) (#6); LTGSe-MAFR ($C_{35}H_{59}N_{10}O_9Se$) (#7); Selenoglutathionine dimer ($C_{20}H_{32}N_6O_{12}Se_2$) (#8); Methylselenoadenosine ($C_{11}H_{15}N_5O_3Se$) (#9); Glutamylselenocysteine ($C_{16}H_{26}N_2O_{10}Se_2$) (#10); Yeast pH 6.0 (#25); (3×) Glutathione, oxidized (obtained from Sigma Aldrich) (#28); and Glutamylcysteine (obtained from Sigma Aldrich) (#30).

Selenium containing compounds used (and arbitrarily assigned numbers for each) were as follows: (#1) L-Selenocystine ($C_6H_{12}N_2O_4Se_2$) was purchased from Sigma-Aldrich Cat#545996, purity 97%;
(#2) L-Selenohomocystine ($C_8H_{16}N_2O_4Se_2$). The synthesis scheme and methodology was:

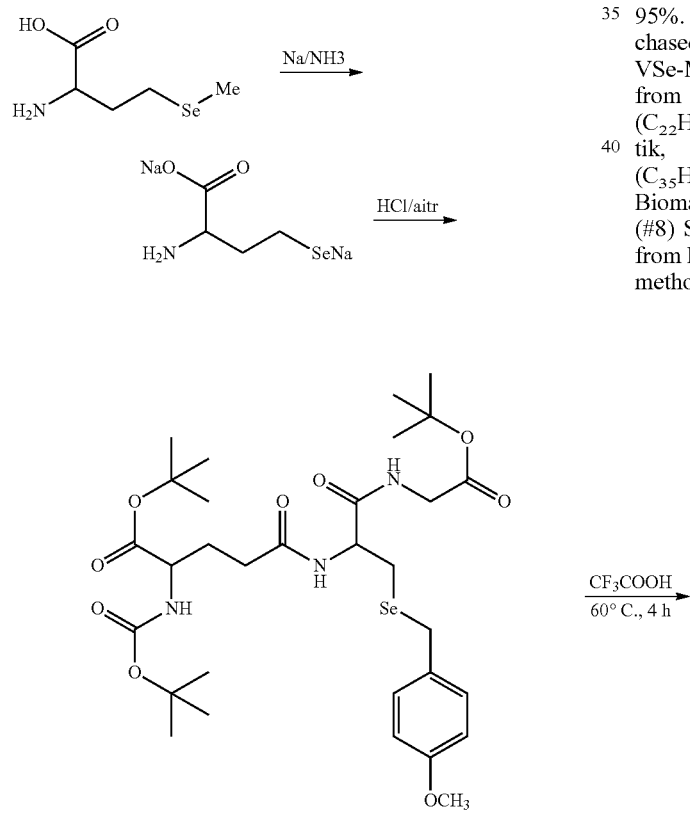

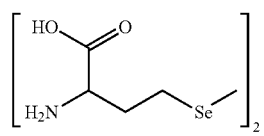

To a solution of L-(+)-selenomethionine (1.96 g, 10.0 mM) in liquid ammonia (80 mL, 60 g) at −78° C. (dry ice-acetone bath) under stirring, small pieces of metallic sodium (0.575 g, 25.0 mM) were carefully added within 80 min until the solution remained blue for 15 min. The solution was stirred for another 50 min at −78° C. and solid ammonium chloride (3.0 g, 56 mM) were added to neutralize sodium amide. The reaction mixture was opened to air and slowly wormed up to ambient temperature overnight. The resulted yellow solid was mixed with 100 mL of water and the pH~9.0 was adjusted to 6.7 by the addition of 1N HCl (6.0 mL). Methanol (50 mL) was added and the mixture was vigorously stirred under air flow from 9 am (Apr. 28, 2011) to 9 am (Apr. 29, 2011). The pale yellow precipitate collected by filtration (1.652 g, 91.2% yield) constituted for clean selenohomocystine (Rf=0.52) without selenomethionine ($R_f$=0.8) contamination. TLC: $SiO_2$; $MeOH:H_2O$: $NH_4OH$/ 18:2:0.2). Yellow spots after treatment with 5% $KMnO_4$ and heating. MS (M+H$^+$)=433. NMR, 400 MHz, 1N DCl in $D_2O$, δ=0.0 ppm ($Me_3Si-CD_2CD_2CO_2Na$): 5.238 br. S all $ND_3^+$, 7.13 H/D; 4.259 t, J=6.4 Hz, 1H, C-1; 3.058 dt, J=3.2&6.4 Hz, 2H, C-3; 2.446 dp, J=6.4&13.6&6.4, 2H, C-2 (optically active).

(#3) Methylseleno-L-cysteine ($C_4H_9NO_2Se$), was purchased from Sigma-Aldrich as hydrochloride, Cat# M6680, purity 95%. (#4) L-Selenomethionine ($C_5H_{11}NO_2Se$), was purchased from Sigma-Aldrich, Cat#53132, purity 98%. (#5) VSe-MR ($C_{16}H_{33}N_6O_4Se$), synthesized by and obtained from Biomatik, Wilmington, Del.). (#6) LVSe-MR ($C_{22}H_{44}N_7O_2Se$), synthesized by and obtained from Biomatik, Wilmington, Del.). (#7) LTGSe-MAFR ($C_{35}H_{59}N_{10}O_9Se$), synthesized by and obtained from Biomatik, Wilmington, Del.).

(#8) Selenoglutathione dimer ($C_{20}H_{32}N_6O_{10}Se_2$), obtained from Biomatik, Willington, Del.). The synthesis scheme and methodology was:

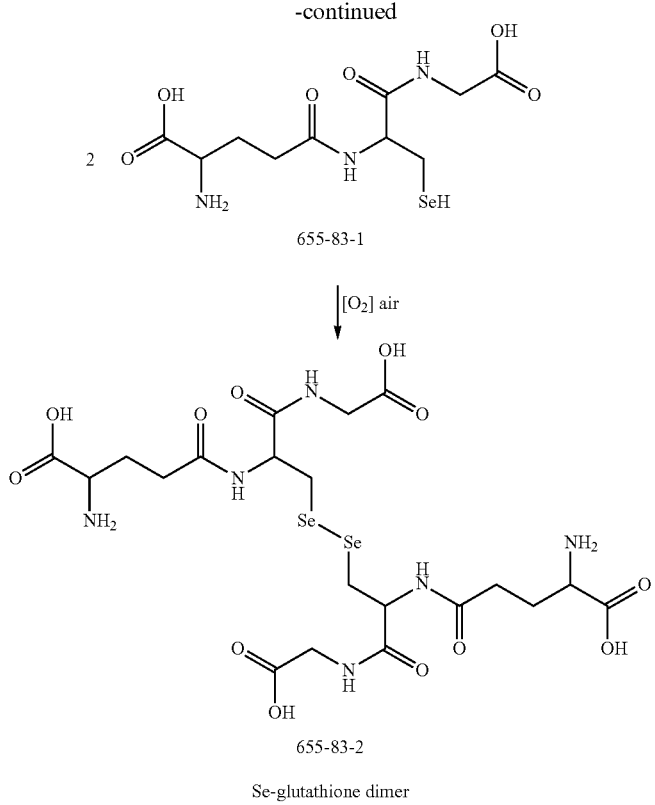

Se-glutathione dimer

Synthesis of MOB-Selenocysteine (665-71)

Selenocystine 3.341 g (10 Mm01) is dissolved in 10 mL of 0.5N sodium hydroxide (ice bath, Ar°, 30 min, yellow coloration of the solution), followed by portion wise addition of 1.35 g (30 Mmol) of sodium borohydride until complete discoloration. 2N sodium hydroxide (30 mL) is added to the reaction mixture with strong-magnetic agitation and neat p-methoxybenzyl chloride 7.831 g (50 Mmol) is added with ice cooling. Stirring, cooling and Ar° flow is maintained for 4 h. After this time ~7.0 mL of conc. hydrochloric acid is added to adjust the reaction mixture pH to 8.5. The white precipitate which forms is filtered off and washed with 2×10 mL and 5×10 mL of ethyl ether. The product is dried for 20 h over $P_2O_5$ under high vacuum resulting with 8.29 g of amorphous white precipitate which is used in the next stage of the synthesis without any further purification.

Synthesis of Boc-Glu(OtBu)-Se(MOB)CysOH (655-72)

A solution of 6.55 g (16.357 Mmol) of Boc-Glu(OtBu)-NHS ester in 50 mL of 1,4-dioxane is added with magnetic stirring to a suspension of 4.68 g (16.25 Mmol) of MOB-Selenocysteine in a mixture of 12.5 mL of water and 2.3 mL (16.5 Mmol) of triethylamine at ambient temperature (22° C.) and left for 50 h with efficient agitation. After this time the mixture is cooled in an ice bath and a mixture of 1.4 mL of conc. hydrochloric acid with 8.6 mL of water is added drop-by-drop. The excess of solvent is removed by vacuum rotary evaporation at T<25° C., the solution is diluted with 20 mL of water (pH 6.5) and extracted with 3×50 mL of ethyl ether, 3×50 mL of ethyl acetate and 3×50 mL of dichloromethane. The solutions are evaporated to dryness yielding 9.2 g of crude product which is used in the next stage of the synthesis without any further purification.

Synthesis of Boc-Glu(OtBu)-Se(MOB)Cys-NHS ester (655-75)

Boc-Glu(OtBu)-Se(MOB)CysOH 9.2 g (16.0 Mmol), N-hydroxysuccinimide 1.841 g (16.0 Mmol) and N.N-dimethybenzylamine 130 µL are dissolved/suspended in 200 mL of anhydrous ethyl ether. Than the solution of dicyclohexyldicarboimide 3.404 g (16.5 Mmol) in 100 mL of anhydrous ethyl ether is added with a good stirring by the means of a dropping funnel (with air equilibration) to the solution in the ambient temperature (22° C.). The reaction is left with stirring for 24 h and the white precipitate that is formed is filtered off, washed with 3×20 mL of anhydrous ethyl ether and discarded. The filtrates are concentrated yielding 12.95 g of yellow viscous oil which is used in the next step of the synthesis without any further purification. Synthesis of fully protected Selenoglutathione (see scheme, 655-77)

All of Boc-Glu(OtBu)-Se(MOB)Cys-NHS ester from the previous step, 12.97 g (~16. Mmol), 3.2 g (19.1 Mmol) of glycine hydrochloride-O-tBu ester and 4.2 mL of triethylamine are dissolved in 130 mL of anhydrous ethyl ether and left with stirring at ambient temperature (22° C.) over weekend. The white precipitate that formed (triethylamine hydrochloride) was separated by filtration and washed on the filter with 2×25 mL of anhydrous ether. The filtrate was concentrated under vacuum using rotary evaporator yielding 12.9 g of oil which was diluted with 11 mL of solvents mixture:toluene:ethylacetate:

Acetonitrile (7:2:1) and applied to the top of $SiO_2$ LC column (50 cm bed) prepared from the suspension of 350 mL $SiO_2$ in 400 mL of the same solvents mixture. The low polarity impurities were collected in the first 500 mL of the eluent. The product was collected by eluting column with 5:2:1 toluene:ethylacetate:acetonitrile 500 mL followed by 400 mL of the same solvents mixture 4:2:1. The product $R_f$ 0.55 in 4:2:1 mixture of solvents. Spots were revealed by dipping plate in 5% of $KMnO_4$ (yellow). All of the fractions containing product were combined and concentrated under vacuum using rotary evaporator and finally dried under high vacuum to yield 4,658 g of the product with MW=686.7 m/e that was in full agreement with the calculated value for the Selenoglutathione formula of: $C_{31}H_{49}N_3O_9Se$.

Synthesis of Selenoglutathione Dimer (655-83)

The oily, LC purified product from the former step was dissolved in a mixture of 30 mL thioanisol with 50 mL of trifluoroacetic acid. The resulted solution was stirred and heated to 60° C. for 5 h. After this time the gasses evolution ceased. Then the mixture is stirred over night at ambient temperature. The next morning trifluoroacetic acid is removed under vacuum at T<37° C. using rotary evaporation. The oily residue is added in ~1.5 mL portions into a very well mechanically stirred 400 mL of anhydrous ethyl ether. The supernatant is discarded while the precipitate is washed with 4×50 mL portions of anhydrous ethyl ether and finally dried under high vacuum. The white precipitate (3.16 g) that was obtained was purified by preparative HPLC to yield 1.1 g of pure Selenoglutathione dimer (MW 594.87) m/e.

(#9) Methylselenoadenosine ($C_{11}H_{15}N_5O_3Se$). The synthesis scheme and methodology was:

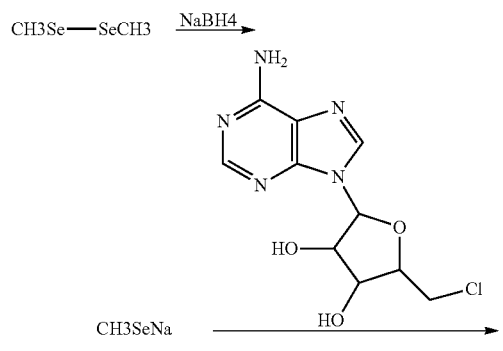

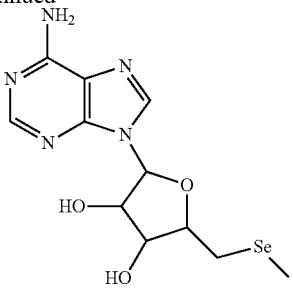

Place sodium borohydride (227 mg, 6.0 mM, under Ar°) in a 200 mL round-bottom flask containing 20 mL of anhydrous ethyl alcohol, equipped in a magnetic stirrer and located in an ice cooling bath. Add from a syringe dimethyldiselenide (190 uL, 376 mg, 2.0 mM), with cooling, stirring and under Ar flow. After discoloration of a yellowish solution add solid 5'-chloro-5'-deoxyadenosine (1,143 g, 4.0 mM). The 5-Cl-Ade is very poorly soluble in ethyl alcohol. 100 mL more ethyl alcohol was added to dissolve the precipitate. Stirring of the mixture at r.t. was continued for the following four days. MS was used to monitor the conversion. ~75% conversion accomplished after 5 days. The solvents were evaporated and the product 3.22 g (with ~20% of SM) was collected and purified by the reverse phase (C-8) preparative chromatography to yield 1.1 g of pure product which molecular weight was confirmed by mass spectrometry.

(#10) Glutamylselenocysteine dimer ($C_{16}H_{26}N_2O_{10}Se_2$). The synthesis scheme and methodology was:

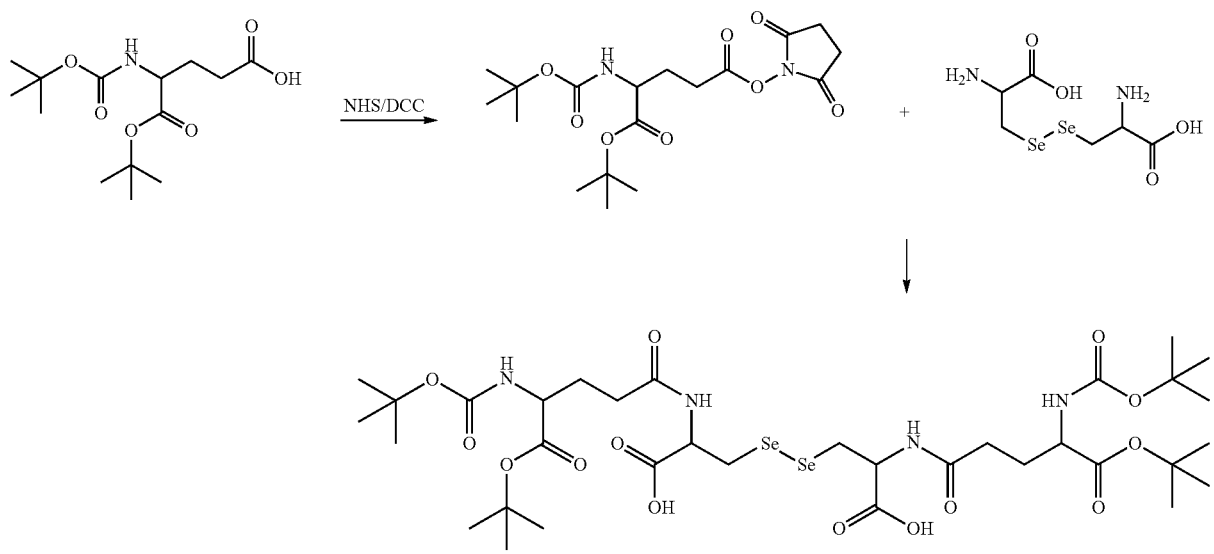

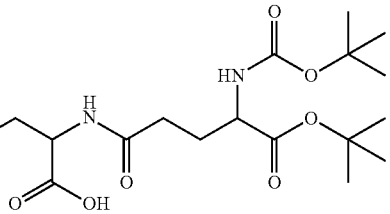

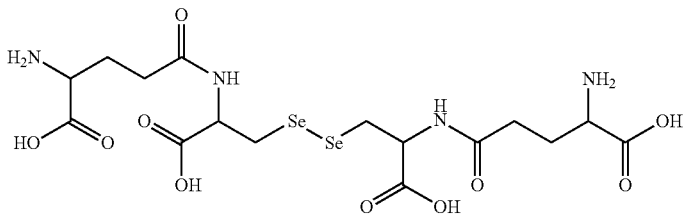

Synthesis of N-Boc-(O-tBu)-L-Glu-OSu (639-37)

N-Boc-(O-tBu)-L-Glu-OH (2.712 g, 9.0 mM), N-hydroxysuccinimide (1.047 g, 9.1 mM) and dicyclohexyl carbodiimide (1.888 g, 9.15 mM) were suspended/dissolved in 300 mL of anhydrous ethyl ether and 50 uL of dimethylethylbenzylamine was added from a syringe into the reaction mixture. Stirring at r.t. was maintained for 24 h. The mixture was filtered and the precipitate was washed 3×20 mL of ethyl ether. The filtrate was concentrated and dried under high vacuum yielding white crystalline product (3.6 g, 100% yield). MS (M+Na$^+$)=423.17; NMR 400 MHz Varian, CDCl$_3$, ppm: 5.152 2H, d, J=7.6 Hz, NH; 4.255 1H, q, J=4.4 Hz; 2.838 4H, br s; 2.734 1H, ddd (?) 7 lines; 2.673 1H, ddd (?) 7 lines; 2.272 1H, octet, J=5.2 Hz; 2.021 1H, m; 1.478 9H, s; 1.450 9H, s.

Synthesis of N-Boc-(O-tBu)-L-Glu-L-Secys-OH dimer (639-39)

Dissolve/suspend selenocystine (1.5 g, 4.49 mM) in water (25 mL). Magnetically agitate and cool the mixture in an ice bath and add into the mixture triethylamine (1.324 mL, 0.961 g, 9.5 mM). Prepare and add drop-by-drop a solution of N-Boc-(O-tBu)-L-Glu-OSu (3.6 g, 8.99 mM) in 50 mL of 1,4-dioxane into a stirred and cooled reaction mixture. Leave the reaction mixture with stirring overnight at r.t. Some of the yellow precipitate separated from the solution and was filtered out. The filtrate was evaporated under vacuum and dried under high vacuum to yield white solid (5.388 g). This material was dissolved in 8 mL of methyl alcohol and submitted to chromatography on SiO$_2$ using 2:1→1:2/AcOEt:MeOH+0.5% AcOH. The N-Boc-(O-tBu)-L-Glu-L-Secys-OH dimer (1.212 g, after KOH/high vacuum drying) was separated as a single fraction (R$_f$=0.32, 1:1/ AcOEt:MeOH+0.5% AcOH). MS (M+H$^+$)=909.11; NMR 400 MHz Varian, DMSO d$^6$, ppm: 7.658 1H, d, J=6.4 Hz, NH; 7.206 1H, d, J=7.2 Hz, NH; 4.20 1H, m; 3.759 1H, m; 3.455 1H, part A of ABX$_2$; 3.404 part B of ABX$_2$; 2.18 2H, br pent; 1.877 1H, m; 1.75 1H, m; 1.391 9H, s; 1.379 9H, s.

Synthesis of L-Glu-Secys-OH dimer (639-46)

A mixture of TFA:CH$_2$Cl$_2$:thioanisole:H$_2$O/47:47:3:3 (25 mL) is added into solid N-Boc-(O-tBu)-L-Glu-L-Secys-OH dimer (1.21 g) at r.t. The resulted solution is stirred for 3.5 h at r.t. and poured into water (50 mL). The water (upper) layer is separated and washed with 5×50 mL of ethyl ether. The water layer is vacuum evaporated at the temperature below 40° C. and high vacuum dried over NaOH pellets. L-Glu-Se-Cys-OH dimer (0.717 g, 99.8% yield). MS (M+H$^+$)=592.92.

(#11) Selenoadenosylhomocysteine (C$_{14}$H$_{20}$N$_6$O$_5$Se). The synthesis scheme and methodology was:

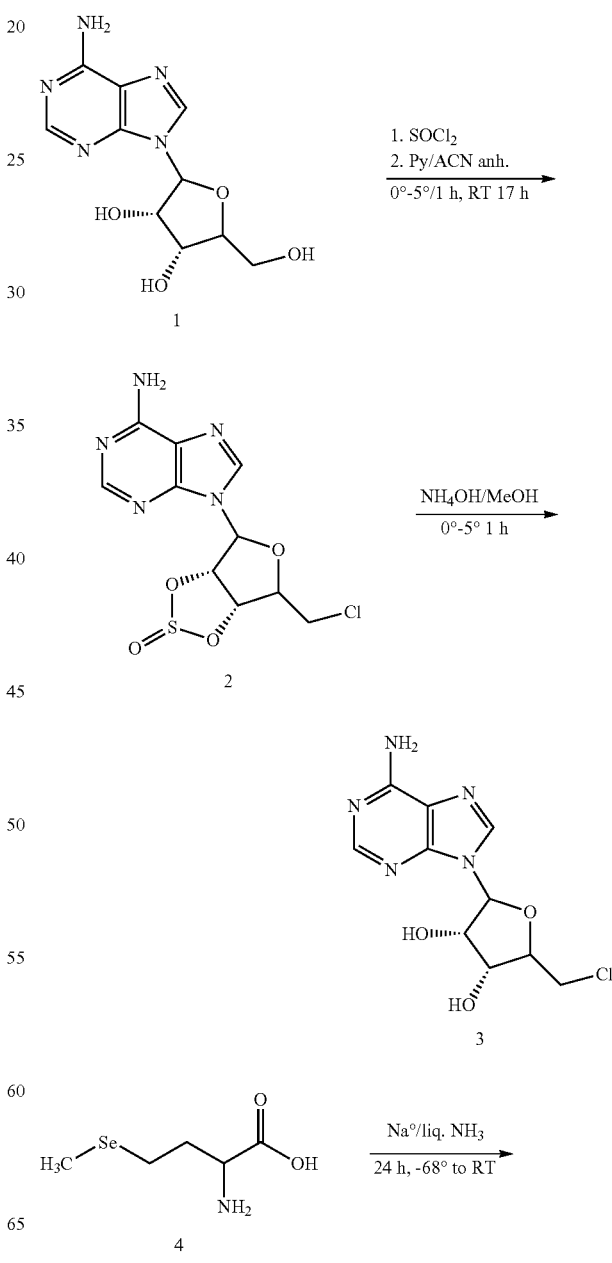

-continued

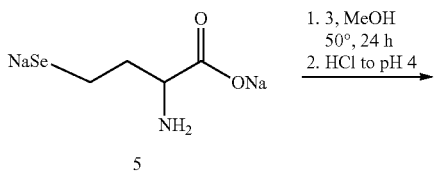

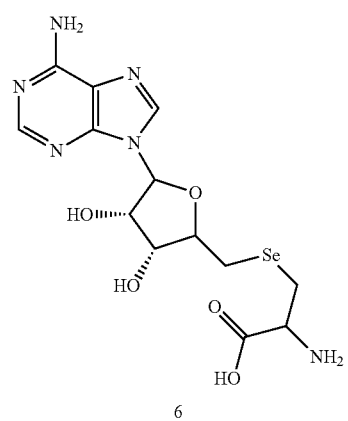

5'-Chloro-5'-deoxyadenosine (639-62)

Place 89 G (0.366 mole, 1 eq.) adenosine, 59.3 ML (58 G, 1.833 mole, 2 eq.) anhydrous pyridine and 1 L anhydrous acetonitrile in an oven dried, 2 L, 4 neck flask, equipped in a dropping funnel, a stirrer, gas inlet/outlet and a thermometer. The reaction set is placed in an ice/salt bath. Initiate agitation and when the temperature of the solution drops below 3° C. start a very slow addition of thionyl chloride (strong exotherm!). The temperature of the reaction mixture needs to be maintained below 5° C. during thionyl chloride addition and for 4 h more (at this time the solution is yellow with white-yellow precipitate on the bottom. Then the reaction is left overnight at ambient temperature. The next morning the voluminous precipitate is filtered off using sintered glass filter and washed on the filter with three 100 ML volumes of dry acetonitrile during which the precipitate color changes into white. The wet precipitate is then transferred back into the 2 L reaction flask, containing a mixture of 800 ML of methanol and 160 ML of water into which, 80 ML of concentrated ammonium hydroxide solution is added drop-by-drop with mechanical stirring and cooling with water bath. The mixture is agitated for 45 min at ambient temperature and a white precipitate that is formed is separated from the liquid by vacuum filtration. The filtrate is concentrated to dryness using vacuum rotary-evaporator, while the precipitate is crystallized from ~560 ML hot water, cooled in an ice-water bath, and the first crop of the crystals is filtered off and freeze-dried. Then this filtrate is used as a solvent in the crystallization of solids resulted from the rotary evaporation of the first filtrate to obtain second crop of the product which is also freeze-dried (2 days). Both crops of crystals are finally dried for two days over phosphorous pentoxide in a vacuum dessicator. 84 G of white crystals, 80.5% yield are obtained. MS (286-M+H), mp. 187° C.

Selenoadenosylhomocysteine (655-40)

9.806 G (50 mM, 1 eq.) of L-selenomethionine are charged into a 2 L, three neck flask equipped in a thermometer, a large cooling finger (with bubble-meter at the outlet), ammonia gas inlet (reaching bottom of the flask) and a magnetic stirring bar and placed in a 2.5 L duar vessel containing $CO_2$-Aceton cooling bath. Ar° is passed through the flask before adding solid $CO_2$ to acetone bath and the cooling finger. When the temperature inside the flask drops below −35° C. the flow of anhydrous ammonia (gas) is started and when liquid ammonia level reaches the volume of 800 ML the gas flow is stopped. At this time small pieces of metallic sodium are added to a well stirred solution until blue-violet coloration of the solution persists for ~30 sec. Total of 2.645 G (115 mM, 2.3 eq.) of sodium are added within 45 min. Agitation and cooling is maintained for 30 min more. At this time all of the components are in the solution. 14.856 G (52 mM, 1.04 eq.) of anhydrous 5'-chloro-5'-deoxyadenosine are added in a single portion and the reaction mixture is left with stirring and very slow Ar° flow overnight. The next morning (if all of ammonia is gone) 350 ML of anhydrous methanol are added to the white solids which are present in the flask. The flask is placed in an oil bath, a reflux condenser is installed, Ar° gas flow is maintained and an oil bath is heated to 50° C. for the subsequent 24 h. At this time 1 ML of the solution is acidified to pH 3.5 with few drops of 0.1N HCl and the sample is analyzed for the presence of substrates using mass spectrometry. If they are below 5% the mixture can be acidified with 1N HCl to pH 3.5, filtered from salts, concentrated to dryness using vacuum rotary-evaporator and the crude product can be purified by crystallization from water-ethanol mixture. 15.98 G (74% yield) of the first crop of Selenoadenosylhomocysteine crystals is ~95% clean, and can be used in biological studies without further purification.

(#39) γ-Glutamyl-methylselenocysteine ($C_9H_{16}N_2O_5Se$). The synthesis scheme and methodology was:

Se atom in it. Calcd. Ms for $C_{18}H_{32}N_2O_7Se$=468.42. Found 469.24 m/e (M+H$^+$) and 491.24 m/e (M+Na$^+$).

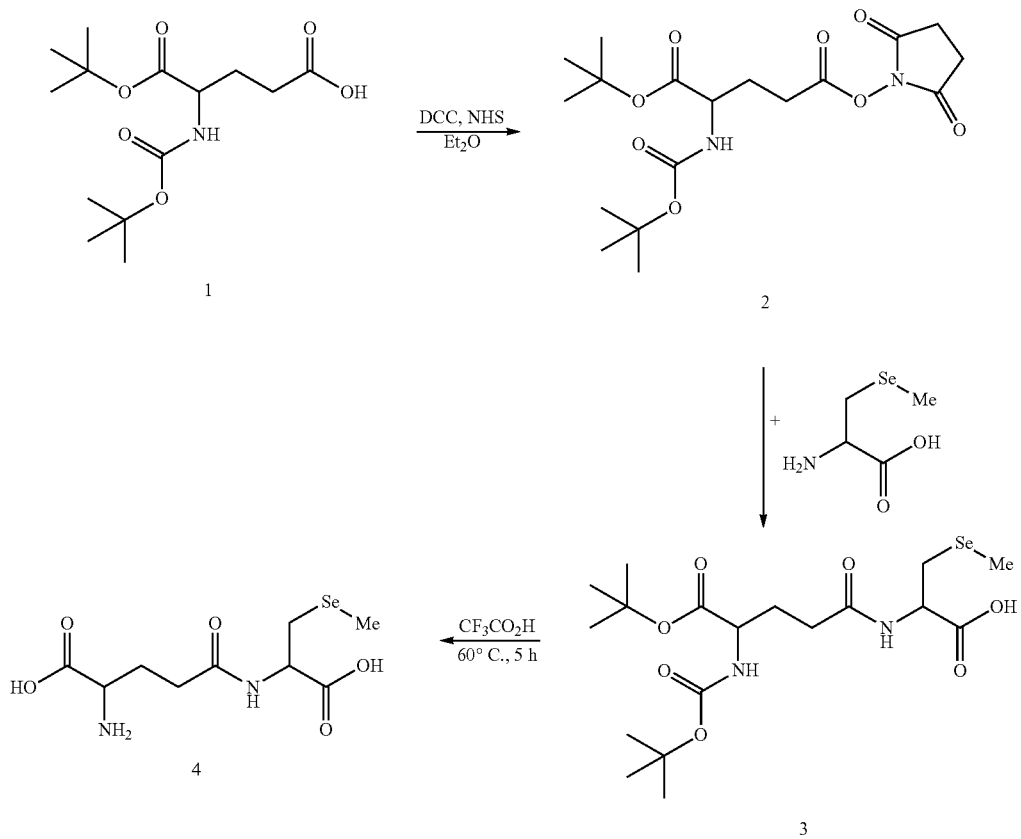

Synthesis of N-Boc-(O-tBu)-L-Glu-OSu (655-90)

N-Boc-(O-tBu)-L-Glu-OH (303 mg, 1.0 Mmol), N-hydroxysuccinimide (121 mg, 1.05 Mmol) and dicyclohexyl carbodiimide (227 mg, 1.1 Mmol) were suspended/dissolved in 15 mL of anhydrous ethyl ether and 10 uL of dimethylethylbenzylamine was added from a syringe into the reaction mixture. Stirring at ambient temperature (22° C.) was maintained for 48 h. The mixture was filtered and the precipitate was washed 10×10 mL of ethyl ether. The filtrate was concentrated and dried under high vacuum yielding white crystalline product (570 mg, ~90% yield). MS (M+Na$^+$)=423.17;

Synthesis of N-Boc-(O-tBu)-L-Glu-MeSe-Cys-OH (655-90)

N-Boc-(O-tBu)-L-Glu-OSu (570 mg, 0.9 Mmol), methylselenocysteine (175 mg, 0.8 Mmol), triethylamine (152 mg, 209 μL, 1.5 Mmol) were added into a mixture of 6 mL of 1,4-Dioxane and 2 mL of water. Magnetic stirring of the reaction mixture was maintained for 100 h. After this time 1.21N HCl (1.65 mL) were added and the post-reaction mixture was extracted with 3×20 mL of ethyl ether and the extract was concentrated to dryness using vacuum rotary-evaporator yielding 649 mg of waxy product that was submitted to preparative HPLC. 283 mg of the product were collected (75.6% Yield). The mass spectrum confirmed the molecular weight of the product and the presence of a single

Synthesis of γ-Glutamyl-methylselenocysteine (655-92)

A mixture of 283 mg (0.6 Mmol) of N-Boc-(O-tBu)-L-Glu-MeSe-Cys-OH, 2 mL of thioanisol and 5 mL of trifluoroacetic acid were heated with magnetic stirring in an oil bath, for 6 h and at 63° C. and left over night at ambient temperature (22° C.). After this time the reaction mixture was added (drop-by-drop) into vigorously stirred ethyl ether (20 mL). The precipitate that formed was washed with 2×20 mL of ethyl ether yielding 138.3 mg of creamy precipitate which was then purified by preparative HPLC.

(#25) Extract of non-selenium enriched yeast prepared as described in U.S. Patent Publication No. 20120164234A1, at pH 6.0. (#28) (3×) Glutathione, oxidized. Obtained from Sigma Aldrich.

(#30) Glutamylcysteine. Obtained from Sigma Aldrich.

The selenium containing compounds are identified by number in FIG. 40 and Table 7, below.

In order to determine what potential effects, if any, the individual selenium containing compounds had on mitochondrial bioenergetics, the selenium containing compounds were tested directly using isolated mitochondria. Mitochondria isolated from rat brain were chosen for this purpose for a number of reasons, including a) the ease with which mitochondria can be isolated from soft tissue, such as brain and b) the fact that brain tissue has a high demand for glucose and oxygen.

Experiments were conducted as follows: a variety of concentrations of selenium containing compounds were tested ranging from low (50 ppb), mid (500 ppb) and high (1 ppm). Based on no observable toxicity against mitochondria in the mid-range, a concentration of 500 ppb (5 uM) was utilized for performing screening/activity assays using mitochondrial bioenergetics as the primary outcome measure. Adult rat brain ficoll purified mitochondria were isolated and incubated with the individual selenium containing compounds for 30 minutes at 37 C prior to being loaded into a Seahorse Biosciences flux analyzer in triplicate. OCR (Oxygen Consumption Rates) parameters were measured in three respiratory states including ATP synthesis (State III), Complex I dependent (NADH-driven) Maximum Respiratory Capacity (State $V_{FCCP}$) and Complex II (FADH-driven) dependent Maximum Respiratory Capacity (State $V_{succ}$). Sea Horse assay was performed as described (See, e.g., Sauerbeck et al., J Neurosci Methods. 2011 May 15; 198(1): 36-43; Seahorse XF, Seahorse Bioscience Inc).

The mitochondrial bioenergetic results are provided in FIG. 40. It was observed that two of the nine compounds (the selenium containing peptide LVSe-MR ($C_{22}H_{44}N_7O_5Se$) (#6) and methylselenoadenosine ($C_{11}H_{15}N_5O_3Se$) (#9)) demonstrated positive increases in all three states of respiration and increased mitochondrial bioenergetics profiles (See FIG. 40A, an equal number of isolated mitochondria incubated without a selenium containing compound were used as controls). In particular, LVSe-MR ($C_{22}H_{44}N_7O_5Se$) increased State III (10.3%), State $V_{FCCP}$ (21.2%) and State $V_{succ}$ (7.6%) compared to controls. Methylselenoadenosine increased State III (17.3%), State $V_{FCCP}$ (15.6%) and State $V_{succ}$ (25%) compared to control.

The bioactivities of selenium containing peptide LVSe-MR ($C_{22}H_{44}N_7O_5Se$) (#6) and methylselenoadenosine ($C_{11}H_{15}N_5O_3Se$) (#9) were analyzed utilizing oxytherm (Clark-type electrode) (See, e.g., Chance and Williams, J Biol Chem, 1955, 217, 383-393; Sullivan et al., J. Bioenerg. Biomembr. 36, 353-356.). Oxytherm analysis allows the determination of oxygen uptake or evolution measurements across a broad range of applications including mitochondrial and cellular respiration. For this experiment, 60 μg mitochondrial protein was co-incubated with either compound LVSe-MR ($C_{22}H_{44}N_7O_5Se$) or methylselenoadenosine (500 ppb) or their corresponding equivalent concentrations of respective controls (LVMR and methylthioadenosine, respectively) for 30 minutes prior to injection into the oxytherm chamber. Mitochondrial activity (measured and presented as the rate of mitochondrial respiration observed as % change in nmols $O_2$/min/mg of mitochondrial protein) was measured in the presence of each compound. As presented in FIG. 40B, the selenium containing peptide LVSe-MR increased State III (7.7%), State $V_{FCCP}$ (13.3%) and State $V_{succ}$ (9.6%) compared to control. Methylselenoadenosine ($C_{11}H_{15}N_5O_3Se$) (#9) increased State III (29.9%), State $V_{FCCP}$ (17.3%) and State $V_{succ}$ (15.3%) compared to control.

Accordingly, the present application provides selenium containing compounds (e.g., LVSe-MR ($C_{22}H_{44}N_7O_5Se$), methylselenoadenosine ($C_{11}H_{15}N_5O_3Se$), and other compounds identified in Example 1 above) and compositions comprising the same for use in modulating mitochondrial activity/bioenergetics in a subject (e.g., a subject in need thereof (e.g., a type 2 diabetic subject)).

The data and information generated during development of embodiments of the present application are unique and unprecedented findings. In particular, the present application provides new compositions and methods for the treatment (e.g., prophylactic and/or therapeutic treatment) of mitochondrial dysfunction or insufficiency (e.g., related to diabetes (e.g., type II diabetes), obesity, insulin resistance, diabetic cardiomyopathy, etc.).

TABLE 7

Selenium containing compounds effects on mitochondrial bioenergetics (rat brain purified mitochondria 5 μg/well).

| CTRL | STATE III 432.6 | % change | STATE V 182.1 | % change | STATE Vsucc 350.1 | % change |
|---|---|---|---|---|---|---|
| #5[2] | 445.9 | 3.0 | 187.8 | 3.2 | 292.5 | −16.4 |
| #6[1] | 477.5[1] | 10.3[1] | 220.6[1] | 21.2[1] | 376.4[1] | 7.6[1] |
| #7[3] | 372.5 | −14.0 | 147.1 | −19.2 | 288.0 | −17.7 |
| #8[4] | 424.0 | −2.1 | 192.3 | 5.7 | 371.0 | 6.0 |
| #9[1] | 507.8[1] | 17.3[1] | 210.3[1] | 15.6[1] | 437.1[1] | 24.9[1] |
| #10[3] | 352.1 | −18.7 | 112.7 | −38.1 | 254.4 | −27.3 |
| #25[3] | 419.0 | −3.2 | 136.2 | −25.2 | 309.3 | −11.6 |
| #28[2] | 451.6 | 4.3 | 149.6 | −17.8 | 319.3 | −8.8 |
| #30[2] | 423.2 | −2.3 | 153.8 | −15.5 | 305.4 | −12.7 |

[1]Positive Trend
[2]Positive/Negative trend
[3]Negative Trend
[4]No Change

Another surprising finding was the fact that while certain selenium containing compounds (e.g., LVSe-MR ($C_{22}H_{44}N_7O_5Se$) (#6) and methylselenoadenosine ($C_{11}H_{15}N_5O_3Se$) (#9)) had mitochondrial activity-enhancing properties when incubated with mitochondria, this was not the case for a number of the other selenium containing compounds identified and characterized. For example, as shown in Table 7, three of the selenium containing compounds (e.g., LTGSe-MAFR ($C_{35}H_{59}N_{10}O_9Se$) (#7); Glutamylselenocysteine ($C_{16}H_{26}N_{24}O_{10}Se_2$)(#10); and Yeast pH 6.0 (#25) displayed a negative effect on mitochondrial activity when assessed using the Seahorse instrument.

In particular, it was surprising to find that several selenium containing compounds that share some similarity in overall structure displayed vastly different outcomes with regard to activation of mitochondrial activity. For example, glutamylselenocysteine ($C_{16}H_{26}N_{24}O_{10}Se_2$)(#10) decreased ATP synthesis (State III) by almost 19% even though its overall structure is similar to/not vastly different from methylselenoadenosine ($C_{11}H_{15}N_5O_3Se$) (#9) which increased ATP synthesis by 17.3%; a greater than 36% swing in effect on mitochondrial activity between these two selenium containing compounds present in selenium enriched yeast (See Table 7). Accordingly, in some embodiments, the present application provides a composition comprising two or more selenium containing compounds (e.g., a water soluble fraction of selenium enriched yeast, a water insoluble fraction of selenium enriched yeast, a selenium containing compound present in selenium enriched yeast and/or derived therefrom) that are combined to generate a composition comprising a desired, specific mitochondrial activity enhancing ability.

Example 8

Isolated Selenium Containing Compounds Present in Selenium Enriched Yeast Comprising 2% or Less Inorganic Selenium Significantly Increases Pyruvate Dehydrogenase Enzyme Complex Activity and Mitochondrial Complex I Activity Experiments conducted during development of embodiments of the present application discovered and characterized (e.g., using mitochondrial bioenergetics) selenium containing compounds present in selenium enriched yeast that, when isolated, display biological activity capable of positively modulating energy metabolism (e.g., increasing mitochondrial respiration and/or mitochondrial ATP production) (See Examples 1 and 7). For example, and as describe herein, both of the selenium containing compounds LVSe-MR ($C_{22}H_{44}N_7O_5Se$) (#6) and methylselenoadenosine ($C_{11}H_{15}N_5O_3Se$) (#9), at a concentration of 500 ppb, could remarkably increase mitochondrial bioenergetics profiles.

Thus, additional experiments were performed during development of embodiments of the present application to further characterize the ability of selenium containing compounds isolated and/or derived from selenium enriched yeast to alter mitochondrial activity. For example, further experiments using methylselenoadenosine ($C_{11}H_{15}N_5O_3Se$) (#9) are described below.

In order to measure pyruvate dehydrogenase complex (PDHC) activity as well as mitochondrial Complex I activity, cortical mitochondria were isolated from adult SD rats using a ficoll gradient method. Methylselenoadenosine was tested at four concentration ranges (0, 50, 500 and 1000 PPB). All assays were done in triplicate with co-incubation of the individual compounds with mitochondria (60 µg mitochondrial protein/well) in 100 µl assay system using standard techniques in a 96-well fluorescence plate reader.

Figure 41:
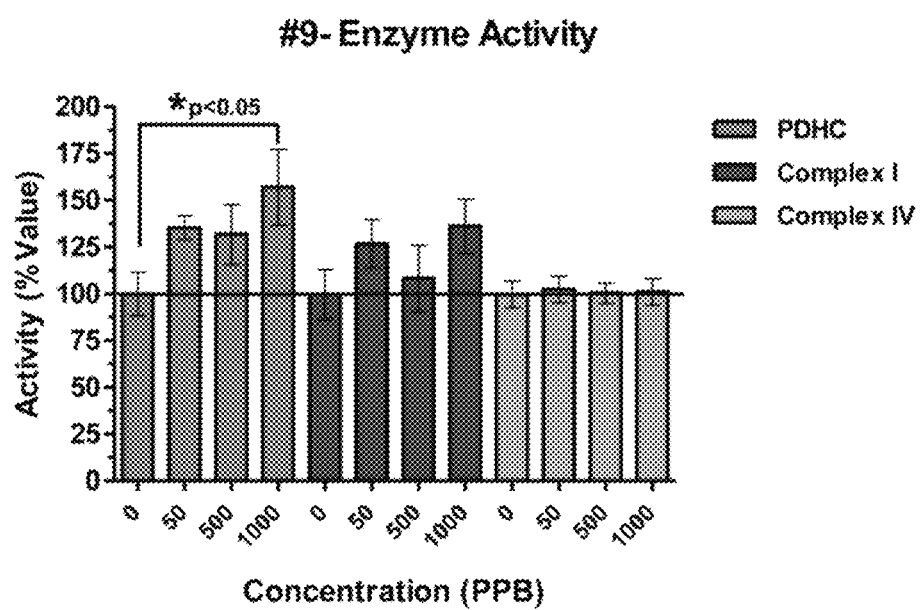
FIG. 41 shows mitochondrial enzyme activity (PDHC activity, Complex I activity, and Complex IV activity) in the presence of 0, 50, 500, and 1000 parts per billion (PPB) of methylselenoadenosine ($C_{11}H_{15}N_5O_3Se$) (#9).

Mitochondrial enzyme activity in the presence of 0, 50, 500, and 1000 parts per billion (PPB) of either methylselenoadenosine ($C_{11}H_{15}N_5O_3Se$) (#9), or the control compound methylthioadenosine (#31) is shown in FIG. 41. Compound #9 (0-1000 PPB) significantly enhanced PDHC enzyme activity~30-57% compared to not PDHC enzyme activity in the absence of methylselenoadenosine, depending upon the concentration ($p<0.05$ at concentration of 1000 PPB). No changes in Complex IV enzyme activities were detected with the tested concentrations. Methylthioadenosine did not alter PDHC, complex I or complex IV activity.

These experiments documented that methylselenoadenosine increased mitochondrial Complex I and PDHC activity. Thus, in some embodiments, the present application provides a composition (e.g., a pharmaceutical composition) comprising a selenium containing compound (e.g., identified in Example 1). In some embodiments, the present application provides a method of increasing PDHC enzyme activity and/or increasing mitochondrial Complex I activity in a subject comprising administering to a subject in need thereof (e.g., a type II diabetic subject) an effective amount of a composition (e.g., a pharmaceutical composition) comprising a selenium containing compound (e.g., described in Example 1) to the subject to that increases mitochondrial Complex I and/or PDHC activity (e.g., thereby increasing mitochondrial respiration in the subject (e.g., in skeletal muscle and or liver).

Example 9

Isolated Selenium Containing Compounds Present in Selenium Enriched Yeast Comprising 2% or Less Inorganic Selenium Significantly Increase Antioxidant Potential and Mitochondrial Activity Experiments conducted during development of embodiments of the present application discovered that certain, isolated selenium containing compounds present within selenium enriched yeast or derived therefrom enhanced mitochondrial activity (e.g., increased ATP production, increased mitochondrial Complex I activity and/or PDHC activity) (See Examples 1, 6-8). Thus, additional experiments were performed in order to further characterize selenium containing compounds disclosed and described herein (e.g., to identify bioactivity, if any, of the compounds (e.g., stimulatory activity, inhibitory activity, synergistic activity, antagonistic activity, etc. (e.g., in order to identify selenium containing compounds that display a desired effect on mitochondrial activity))).

Due to the fact that several of the selenium containing compositions of the present application displayed the ability to enhance the activity of mitochondrial Complex I, experiments were conducted in order to determine if mitochondrial stimulation might take place through removal of damaging reactive oxygen species (ROS) by the selenium containing compounds. Thus, experiments were conducted during development of embodiments of the present application in order to assess the antioxidant potential of selenium containing compounds.

Thus, a kit-based antioxidant assay (oxygen radical absorbance capacity (ORAC) was utilized to identify selenium containing compounds of the present application that possessed/displayed antioxidant potential. In the ORAC assay kit used (BioTek, VT, USA), the antioxidant properties of Trolox are the standard against which the antioxidant capacity of a range of substances are related. Thus, ORAC results are commonly referred to as Trolox Equivalents (TE) as calculated from comparison to a Trolox calibration curve. In the assays performed, Quercetin (a known potent antioxidant) was included as an internal reference standard.

Briefly, samples of selenium containing compounds (e.g., identified in Example 1) were analyzed using the Trolox assay kit, according to the manufacturer's instructions. Compounds were tested singly or in combination (at concentrations ranging from 0.05 to 5 µM) to examine for potential synergies, antagonisms or purely additive effects. Representative results are shown in Table 8.

TABLE 8

Antioxidant Activities of various selenium containing compounds.

| Compound | TE Value | Quercetin TE | Theoretical Additive Effect | Synergy Ration Exp/Theor |
|---|---|---|---|---|
| #3 L-Methylselenocysteine | 1.075 | 6.451 | 4.014 | 1.72 |
| #26 Selenoadenosyl-homocysteine | 2.939 | | | |
| #3 + #26 | 6.899 | | | |
| #9 Methylselenoadenosine | 0.722 | 3.87 | 1.95 | 1.2 |
| #4 Selenomethionine | 1.228 | | | |
| #9 + #4 | 2.332 | | | |
| #26 Selenoadenosyl-homocysteine | 2.012 | 3.222 | 2.961 | −1.14 |
| #39 Gamma Glutamylmethylcysteine | 0.949 | | | |
| #26 + #39 | 2.592 | | | |

As the data in Table 8 indicates, it was discovered that some of the selenium containing compounds possess/display antioxidant capacity (e.g., a positive TE value). Moreover, some of the selenium containing compounds possess/display antioxidant capacity that is additive or mildly synergistic (e.g., #9 and #4 in combination); mildly antagonistic (#26 and #39 in combination) or synergistic (#3 and #26 in combination) (e.g., in terms of oxygen radical-scavenging ability). In the case of the combination of #3 and #26, the increase was approximately 70% greater than had the effect of these compounds just been additive.

All publications and patents mentioned in the present application are herein incorporated by reference. Various modification and variation of the described methods and compositions of the present application will be apparent to those skilled in the art without departing from the scope and spirit of the present application. Although the present application has been described in connection with specific preferred embodiments, it should be understood that the present application as claimed should not be unduly limited to such specific embodiments. Indeed, various modifications of the described modes for carrying out the present application that are obvious to those skilled in the relevant fields are intended to be within the scope of the following claims.

What is claimed is:

1. A method of increasing mitochondrial function in a cell in a subject comprising administering an effective amount of a composition, the composition comprising a compound selected from the group consisting of isolated 5'methylselenoadenosine, selenoadenosyl homocysteine, leucyl-valyl-selenomethionyl-arginine, and combinations thereof to the subject, wherein the effective amount increases mitochondrial function in a cell as compared to a cell not exposed to the composition, wherein the administering of the composition administers a dose of between 25 and 800 µg of selenium to the subject per day.

2. The method of claim 1, wherein the composition further comprises an isolated compound selected from the group consisting of seleno(hydroxyl)-selenophene-(3'-deoxy-adenosine), N-acetylcysteine-selenohomocysteine, allylselenoadenosyl homocysteine, seleno-hydroxyadenosyl homocysteine, selenoadenosine, seleno-adenosyl-Se(methyl)-selenoxide, adenosyl-hydroxy selenoxide, ethyl selenoadenosine, seleno-(hydroxy)-selenophene-(3'-desoxy-adenosine), adenosyl-hydroxyselenoxide, seleno-adenosyl-Se(methyl)-selenoxide, methylselenocysteine, and combinations thereof.

3. The method of claim 1, wherein the administering of the composition administers a dose of between 200 and 500 µg of selenium to the subject per day.

4. The method of claim 1, wherein the composition is administered orally.

5. The method of claim 1, wherein the composition comprises a carrier.

6. The method of claim 1, wherein the composition is formulated as a powder, tablet, pill, capsule, gel, syrup, solution, powder, sachet, dragee, or suspension.

\* \* \* \* \*